(12) United States Patent
Graczyk et al.

(10) Patent No.: US 7,432,375 B2
(45) Date of Patent: Oct. 7, 2008

(54) JNK INHIBITORS

(75) Inventors: Piotr Graczyk, London (GB); Afzal Khan, London (GB); Gurpreet Bhatia, London (GB); Yoichi Iimura, London (GB)

(73) Assignee: Eisai R & D Management Co., Ltd. (JP)

( * ) Notice: Subject to any disclaimer, the term of this patent is extended or adjusted under 35 U.S.C. 154(b) by 0 days.

(21) Appl. No.: 10/548,163

(22) PCT Filed: Mar. 5, 2004

(86) PCT No.: PCT/GB2004/000944

§ 371 (c)(1),
(2), (4) Date: May 9, 2006

(87) PCT Pub. No.: WO2004/078756

PCT Pub. Date: Sep. 16, 2004

(65) Prior Publication Data

US 2006/0270646 A1    Nov. 30, 2006

(30) Foreign Application Priority Data

| Mar. 6, 2003 | (GB) | ................................. 0305144.8 |
| Jul. 17, 2003 | (GB) | ................................. 0316814.3 |
| Jul. 18, 2003 | (GB) | ................................. 0316952.1 |

(51) Int. Cl.
*C07D 471/02* (2006.01)
*C07D 491/02* (2006.01)
*C07D 498/02* (2006.01)
*C07D 513/02* (2006.01)
*C07D 515/02* (2006.01)

(52) U.S. Cl. ........................................ 546/113; 546/113
(58) Field of Classification Search .................. 546/113
See application file for complete search history.

(56) References Cited

U.S. PATENT DOCUMENTS

| 5,714,495 A | 2/1998 | Viaud et al. |
| 2002/0013354 A1 | 1/2002 | Cheng et al. |

FOREIGN PATENT DOCUMENTS

| WO | 98/47899 | * 10/1998 |
| WO | WO-98/47899 | 10/1998 |
| WO | WO-99/21859 | 5/1999 |
| WO | WO-99/51233 | 10/1999 |
| WO | WO-00/43393 | 7/2000 |
| WO | WO-01/49288 | 7/2001 |
| WO | WO-03/028724 | 4/2003 |
| WO | WO-03/082868 | 10/2003 |
| WO | WO-03/082869 | 10/2003 |
| WO | WO-2004/016609 | 2/2004 |
| WO | WO-2004/016610 | 2/2004 |

OTHER PUBLICATIONS

Tamao et al., "Palladium-Catalyzed Cross-Coupling REaction of Alkenylalkosysilanes with Aryl and Alkenyl Halides in the Presence of a Fluoride Ion" *Tetrahedron Letters*, vol. 30, No. 44 pp. 6051-6054 (1989).
Stille, J.K., "The Palladium-Catalyzed Cross-Coupling Reactions of Organotin REagents with Organic Electrophiles" *Angew. Chem. Int. Ed. Engl.* 25 pp. 508-524 (1986).
Hatanaka et al., "Cross-Coupling of Organosilanes with Organic Halides Mediated by Palladium Catalyst and Tris(diethylamino)sulfonium Difluorotrimethylsilicate" *J. Org. Chem* 53 pp. 918-920 (1988).
Littke et al., "Pd/P(t-Bu)$_3$: A Mild and General Catalyst for Stille Reactions of Aryl Chlorides and Aryl Bromides" *J. Am. Chem. Soc.* 124 pp. 6343-6348 (2002).
Hatanaka et al., "Highly Selective Cross-Coupling Reactions of Organosilicon Compounds Mediated by Fluoride Ion and a Palladium Catalyst", *Synlett* pp. 845-853 (1991).
Littke et al., "Versatile Catalysts for the Suzuki Cross-Coupling of Arylboronic Acids with Aryl and Vinyl Halides and Triflates under Mild Conditions" *J. Am. Chem. Soc.* 122 pp. 4020-4028 (2000).
Denmark et al., "Highly Stereospecific, Palladium-Catalyzed Cross-Coupling of Alkenylsilanols" *Organic Letters* vol. 2, No. 4, pp. 565-568 (2000).
Suzuki, A. "Synthetic Studies via the Cross-Coupling REaction of Organoboron Derivatives with Organic Halides" *Pure Appl. Chem* vol. 63, No. 3 pp. 419-422 (1991).
Mitchell, T. "Palladium-Catalysed Reactions of Organotin Compounds" *Synthesis* pp. 803-815 (1992).
Denmark et al., "Convergence of Mechanistic Pathways in the Palladium(0)-Catalyzed Cross-Coupling of Alkenylsilacyclobutanes and Alkenylsilanols"*Organic Letters*. vol. 2, No. 16, pp. 2491-2494. (2000).
Corey, E.Jr., et. al.., A synthetic Method for Formyl-Ethynyl Conversion (RCHO-RC=CH or RC=CR'), Tetrahedron Letters No. 36, (Aug. 1972).

(Continued)

*Primary Examiner*—D. Margaret Seaman
*Assistant Examiner*—Niloofar Rahmani
(74) *Attorney, Agent, or Firm*—Wilmer Cutler Pickering Hale & Dorr LLP

(57) ABSTRACT

The present invention provides novel compounds of formula (I) and their use in the inhibition of c-Jun N-terminal kinases. The present invention further provides the use of these compounds in medicine, in particular in the prevention and/or treatment of neurodegenerative disorders related to apoptosis and/or inflammation.

(I)

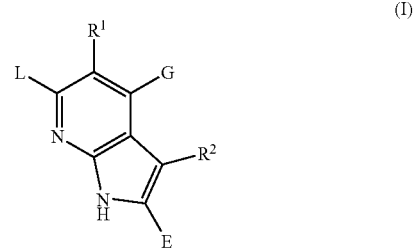

34 Claims, No Drawings

OTHER PUBLICATIONS

Dhar, et al., "The TosMIC Approach to 3-(Oxazol-5-yl) Indoles: Application to the Synthesis of Indole-Based IMPDH Inhibitors," Bioorganic & Medicinal Chemistry Letters, (2002).

Houwing, et al., Preparation of N-Tosylmethylimino Compounds and their Use in the Synthesis of Oxazoles, Imidazoles and Pyrroles, Tetrahedron Letters No. 2, (1976).

Van Leusen, et al., Chapter 3: Synthetic Uses of Tosylmethyl Isocyanide (TosMIC), Organic Reactions, vol. 57, (2001).

Guillard, et al. "Synthesis of New Maltonin Analogues from Dimers of Azaindole and Indole by Use of Suzuki Monocoupling", Heterocycles, vol. 60, No. 4, pp. 865-877 (2003).

Database Beilstein, Beilstein Institute for Organic Chemistry, Citation No. 5563002 (1987).

Mettey, et al., "Aloisines, a New Family of CDK/GSK-3 Inhibitors. SAR STudy, Crystal Structure in Complex with CDK2, Enzyme Selectivity and Cellular Effects", J. Med. Chem, 46, pp. 222-236 (2003).

Pisano et al, "Bis-indols: a Novel Class of Molecules Enhancing the Cytodifferentiating Properties of Retinoids in Myeloid Leukemia Cells", Blood, vol. 100, No. 10 (2002).

Harper, et al., "Inhibitors of the JNK Sinaling Pathway", Drugs of the Future, vol. 26, No. 10 (2001).

Kumar et al, "Synthesis of 7-Azaindole and 7-Azaoxindole Derivatives through a Palladium-Catalyzed Cross Coupling Reaction", J. Org. Chem, 57, pp. 6995-6998 (1992).

Witherington et al., "5-Aryl-pyrazolo [3,4-b]pyridines: Potent Inhibitors of Glycogen Synthase Kinase-3 (GSK-3)", Bioorganic & Medicinal Chemistry Letters 13, pp. 1577-1580 (2003).

Park et al, "A FAcile Synthesis of 2,3-Disubstitute Pyrrolo[2,3-b]pyridines via Palladium-Catalyzed Heteroannulation with Internal Alkynes", Tetrahedron Letters 39, pp. 627-630 (1998).

* cited by examiner

JNK INHIBITORS

The present invention relates to novel compounds, their use in the inhibition of c-Jun N-terminal kinases, their use in medicine and particularly in the prevention and/or treatment of neurodegenerative disorders related to apoptosis and/or inflammation. The invention also provides processes for manufacture of said compounds, compositions containing them and processes for manufacturing such compositions.

c-Jun N-terminal kinases (hereinafter referred to as "JNKs") are members of the mitogen-activated protein kinase (MAPK) family. JNKs are involved in response to various stimuli, including proinflammatory cytokines and environmental stress. JNKs, and JNK3 in particular, play an important role during apoptotic death of cells and therefore have been implicated in various disorders including stroke, traumatic brain injury and other neurodegenerative diseases such as Parkinson disease, Alzheimer disease and others. Since JNK activity is a physiological regulator of AP-1 transcriptional activity, JNK inhibitors are expected to reduce inflammatory response.

Apoptosis is a form of cell death in which the cell actively participates in its own destruction in a process involving a characteristic series of biochemical and morphological changes, which are regulated by specific cell death genes. Apoptotic cell death is a process that has been observed in the developing mammalian nervous system. In mice, the inactivation by homologous recombination of genes that encode proteins that promote apoptosis, such as the caspase-3 or the Bax protein, prevents developmental neuronal cell death. The destruction of genes that encode cell death suppressors such as Bcl-x, leads to enhanced neuronal cell death. There is increasing evidence that apoptosis plays an important role in the pathology of acute and chronic neurodegenerative diseases. For example, in transgenic mice overexpressing the anti-apoptotic Bcl-2 protein in the nervous system there is a decrease in infarct volume following cerebral ischemia. Similarly, injection of the caspase inhibitor BAF reduces neuronal cell death following hypoxia/ischaemia in neonatal rats. Another example is spinal muscular atrophy (a motor neuron disease) where loss of function mutations in the SMN gene is associated with the disease. Recent data has shown that the wild type SMN protein binds to Bcl-2 and co-operates with it to inhibit apoptosis. These results suggest that inhibitors of neuronal apoptosis could be beneficial in the treatment of human neurodegenerative diseases. There is increasing evidence that neuronal apoptosis is an important pathological feature of stroke, traumatic brain injury and other neurodegenerative diseases. Therefore, pharmacotherapy using inhibitors of neuronal apoptosis may provide a therapeutic benefit in neurodegenerative conditions.

A number of groups have studied the mechanisms of neuronal cell death using in vitro cell culture systems and the results suggest that in some systems the transcription factor c-Jun is activated by the removal of survival signals and promotes cell death.

Antibodies specific for c-Jun protected NGF-deprived rat sympathetic neurones from apoptosis. Analogous neuroprotection due to expression of a c-Jun dominant negative mutant has been demonstrated, whereas overexpression of wild type c-Jun protein was sufficient to induce apoptosis in the presence of NGF. Estus and co-workers recently showed that an increase in c-Jun RNA levels occurs in cortical neurones undergoing apoptosis after treatment with β-amyloid peptide. It has also been shown that c-Jun is required for apoptosis in cerebellar granule neurones deprived of survival signals.

c-Jun is activated by JNKs, which phosphorylate its transcriptional activation domain. In humans there are three JNK genes: JNK1, JNK2 and JNK3. The RNAs encoding JNK1 and JNK2 are expressed in many tissues, including the brain, but JNK3 is restricted to the nervous system and to a smaller extent the heart and testes.

JNKs are strongly activated in cellular responses to various stresses such as UV radiation, heat shock, osmotic shock, DNA-damaging agents, and proinflammatory cytokines such as TNFα, IL-1β and others. Upstream regulators of the JNK pathway include kinases such as SEK1, MKK7 and MEKK1. There is evidence that Jun kinase activity is required for neuronal apoptosis in vitro. Overexpression of MEKK1 in sympathetic neurones increased c-Jun protein levels and phosphorylation and induced apoptosis in the presence of NGF indicating that activation of the Jun kinase pathway can trigger neuronal cell death. The Jun kinase pathway has been shown to be necessary for the death of differentiated PC12 cells deprived of NGF. Furthermore, compound CEP-1347, which inhibits the c-Jun pathway (upstream of Jun kinase), protects motor neurones against cell death induced by survival factor withdrawal.

In JNK3 homozygous (−/−) knockout mice, epileptic seizures and death of hippocampal CA3 neurones induced by injection of kainic acid is blocked. This indicates that JNK3 is involved in certain forms of neuronal cell death in vivo. It is also a critical component of GluR6-mediated excitotoxicity. Furthermore, JNK3 (−/−) mice appear to develop normally and are viable suggesting that JNK3 is not essential for development or viability.

Strong nuclear JNK3 immunoreactivity in the brain CA1 neurones of patients with acute hypoxia suggests that JNK3 is involved in hypoxia-related neurodegeneration. Transient hypoxia may also trigger apoptosis through JNK signaling pathway in developing brain neurons.

Furthermore, JNK3 immunoreactivity is colocalized with Alzheimer disease-affected neurones. Moreover JNK3 is related to neurofibrillary pathology of Alzheimer disease. In particular, JNK3 induces robust phosphorylation of amyloid precursor protein (APP) thus affecting its metabolism in disease state.

The present inventors have provided compounds, which are inhibitors of c-Jun N-terminal kinases.

The first aspect of the invention therefore relates to a compound of formula (I) as illustrated below:

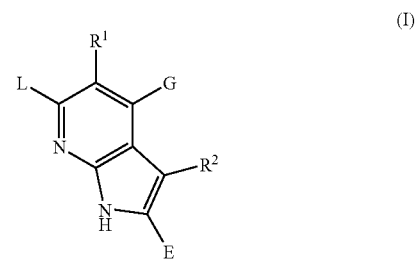

(I)

wherein $R^1$ is an optionally substituted carbocyclyl or heterocyclyl group, $R^2$ is an optionally substituted five or six membered heterocyclyl group or an optionally substituted six membered carbocyclyl group, E is hydrogen, halogen, cyano, $C_{1-6}$ alkoxy or $C_{1-6}$ alkyl, G is hydrogen, halogen, cyano, $C_{1-6}$ alkoxy or $C_{1-6}$ alkyl, and L is hydrogen, halogen, cyano, $C_{1-6}$ alkoxy or $C_{1-6}$ alkyl;

wherein the optionally substituted carbocyclyl or heterocyclyl group of $R^1$ is optionally fused to a partially saturated, unsaturated or fully saturated five to seven membered ring containing zero to three heteroatoms, and each substitutable carbon atom in $R^1$, including the optional fused ring, is optionally and independently substituted by one or more of halogen, $C_{1-12}$ alkyl, $C_{2-12}$ alkenyl, $C_{2-12}$ alkynyl, haloalkyl, carbocyclyl, heterocyclyl, $(CH_2)_nOR^3$, $(CH_2)_nNR^3{}_2$, $OR^3$, $SR^3$, $NO_2$, $CN$, $NR^3{}_2$, $NR^3COR^3$, $NR^3CONR^3{}_2$, $NR^3COR^3$, $NR^3CO_2R^3$, $CO_2R^3$, $COR^3$, $CONR^3{}_2$, $S(O)_2R^3$, $SONR^3{}_2$, $S(O)R^3$, $SO_2NR^3{}_2$, or $NR^3S(O)_2R^3$ wherein the $C_{1-12}$ alkyl group optionally contains one or more insertions selected from —O—, —N($R^3$)— —S—, —S(O)— and —S($O_2$)—; and each saturated carbon in the optional fused ring is further optionally and independently substituted by =O, =S, $NNR^4{}_2$, =N—$OR^4$, =$NNR^4COR^4$, =$NNR^4CO_2R^4$, =$NNSO_2R^4$, or =$NR^4$; and each substitutable nitrogen atom in $R^1$ is optionally substituted by $R^5$, $COR^5$, $SO_2R^1$ or $CO_2R^5$;

wherein n is 1 to 6, preferably n is 1, 2 or 3;

wherein $R^3$ is hydrogen, $C_{1-12}$ alkyl, carbocyclyl or heterocyclyl, optionally substituted by one or more of $C_{1-6}$ alkyl, carbocyclyl, heterocyclyl, halogen, $C_{1-6}$ haloalkyl, $OR^6$, $SR^6$, $NO_2$, $CN$, $NR^6R^6$, $NR^6COR^6$, $NR^6CONR^6R^6$, $NR^6COR^6$, $NR^6CO_2R^6$, $CO_2R^6$, $COR^6$, $CONR^6{}_2$, $S(O)_2R^6$, $SONR^6{}_2$, $S(O)R^6$, $SO_2NR^6R^6$, $NR^6S(O)_2R^6$, wherein the $C_{1-12}$ alkyl group optionally incorporates one or two insertions selected from the group consisting of —O—, —N($R^6$)—, —S(O)— and —S($O_2$)—, wherein each $R^6$ may be the same or different and is as defined below;

wherein two $R^3$ in $NR^3{}_2$ may optionally form a partially saturated, unsaturated or fully saturated four to seven membered ring containing one to three heteroatoms, optionally and independently substituted by one or more of $C_{1-6}$ alkyl, halogen, $C_{1-6}$ haloalkyl, $OR^6$, $SR^6$, $NO_2$, $CN$, $NR^6R^6$, $NR^6COR^6$, $NR^6CONR^6R^6$, $NR^6COR^6$, $NR^6CO_2R^6$, $CO_2R^6$, $COR^6$, $CONR^6{}_2$, $S(O)_2R^6$, $SONR^6{}_2$, $S(O)R^6$, $SO_2NR^6R^6$, $NR^6S(O)_2R^6$, wherein the $C_{1-6}$ alkyl group optionally incorporates one or two insertions selected from the group consisting of —O—, —N($R^6$)—, —S(O)— and —S($O_2$)—, wherein each $R^6$ may be the same or different and is as defined below;

wherein $R^4$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^6$, $SR^6$, $NO_2$, $CN$, $NR^6R^6$, $N^6COR^6$, $NR^6CONR^6R^6$, $NR^6COR^6$, $NR^6CO_2R^6$, $CO_2R^6$, $COR^6$, $CONR^6{}_2$, $S(O)_2R^6$, $S(O)R^6$, $SO_2NR^6R^6$, $NR^6S(O)_2R^6$, wherein the $C_{1-12}$ alkyl group optionally incorporates one or two insertions selected from the group consisting of —O—, —N($R^6$)-, —S(O)— and —S($O_2$)—, wherein each $R^6$ may be the same or different and is as defined below;

wherein $R^5$ is hydrogen, $C_{6-12}$ aryl, $C_{1-6}$ alkyl or $C_{1-6}$ haloalkyl;

wherein $R^6$ is hydrogen, $C_{1-6}$ alkyl, or $C_{1-6}$ haloalkyl;

and wherein $R^2$ is a six-membered carbocycyl group or a five or six-membered heterocyclyl group containing from 1 to 4 heteroatoms independently selected from N, S or O, wherein the optionally substituted six-membered carbocyclyl or five or six-membered heterocyclyl group is optionally fused to a partially saturated, unsaturated or fully saturated five to seven membered ring containing zero to three heteroatoms, and each substitutable carbon or hetero-atom in $R^2$ including the optional fused ring, is optionally and independently substituted by one or more of halogen, $C_{1-12}$ alkyl, $C_{2-12}$ alkenyl, $C_{2-12}$ alkynyl, haloalkyl, carbocyclyl, heterocyclyl, $(CH_2)_nOR^7$, $(CH_2)_nNR^7{}_2$, $OR^7$, $SR^7$, $NO_2$, $CN$, $NR^7{}_2$, $NR^7COR^7$, $NR^7CONR^7{}_2$, $NR^7COR^7$, $NR^7CO_2R^7$, $CO_2R^7$, $COR^7$, $CONR^7{}_2$, $S(O)_2R^7$, $SONR^7{}_2$, $S(O)R^7$, $SO_2NR^7{}_2$, or $NR^7S(O)_2R^7$ wherein the $C_{1-12}$ alkyl group optionally contains one or more insertions selected from —O—, —N($R^7$)— —S—, —S(O)— and —S($O_2$)—; and each saturated carbon in the optional fused ring is further optionally and independently substituted by =O, =S, $NNR^8{}_2$, =N—$OR^8$, =$NNR^8COR^8$, =$NNR^8CO_2R^8$, =$NNSO_2R^8$, or =$NR^8$; and each substitutable nitrogen atom in $R^2$ is optionally substituted by $R^9$, $COR^9$, $SO_2R^9$ or $CO_2R^9$; wherein n is 1 to 6, preferably n is 1, 2 or 3; preferably, wherein each substitutable carbon or hetero-atom in $R^2$ is optionally and independently substituted by one or more of $C_{1-6}$ alkyl, $OR^{10}$, $SR^{10}$, $NO_2$, $CN$, $NR^{10}{}_2$, $NR^{10}COR^{10}$, $NR^{10}CONR^{10}{}_2$, $NR^{10}COR^{10}$, $NHCO_2R^{10}$, $CO_2R^{10}$, $COR^{10}$, $CONR^{10}{}_2$, $S(O)_2R^{10}$, $SONR^{10}{}_2$, $S(O)R^{10}$, $SO_2NR^{10}{}_2$, or $NR^{10}S(O)_2R^{10}$;

wherein $R^{10}$ is hydrogen, $C_{1-6}$ alkyl, or $C_{1-16}$ haloalkyl;

wherein $R^7$ is hydrogen, $C_{1-12}$ alkyl, carbocyclyl or heterocyclyl, optionally substituted by one or more of $C_{1-6}$ alkyl, carbocyclyl, heterocyclyl, halogen, $C_{1-6}$ haloalkyl, $OR^{11}$, $SR^{11}$, $NO_2$, $CN$, $NR^{11}R^{11}$, $NR^{11}COR^{11}$, $NR^{11}CONR^{11}R^{11}$, $NR^{11}COR^{11}$, $NR^{11}CO_2R^{11}$, $CO_2R^{11}$, $COR^{11}$, $CONR^{11}{}_2$, $S(O)_2R^{11}$, $SONR^{11}{}_2$, $S(O)R^{11}$, $SO_2NR^{11}R^{11}$, $NR^{11}S(O)_2R^{11}$, wherein the $C_{1-12}$ alkyl group optionally incorporates one or two insertions selected from the group consisting of —O—, —N($R^{11}$)—, —S(O)— and —S($O_2$)—, wherein each $R^{11}$ may be the same or different and is as defined below;

wherein two $R^7$ in $NR^7{}_2$ may optionally form a partially saturated, unsaturated or fully saturated four to seven membered ring containing one to three heteroatoms, optionally and independently substituted by one or more of $C_{1-6}$ alkyl, halogen, $C_{1-6}$ haloalkyl, $OR^{11}$, $SR^{11}$, $NO_2$, $CN$, $NR^{11}R^{11}$, $NR^{11}COR^{11}$, $NR^{11}CONR^{11}R^{11}$, $NR^{11}COR^{11}$, $NR^{11}CO_2R^{11}$, $CO_2R^{11}$, $COR^{11}$, $CONR^{11}{}_2$, $S(O)_2R^{11}$, $SONR^{11}{}_2$, $S(O)R^{11}$, $SO_2NR^{11}R^{11}$, $NR^{11}S(O)_2R^{11}$, wherein the $C_{1-6}$ alkyl group optionally incorporates one or two insertions selected from the group consisting of —O—, —N($R^{11}$)—, —S(O)— and —S($O_2$)—, wherein each $R^{11}$ may be the same or different and is as defined below;

wherein $R^8$ is hydrogen, $C_{1-12}$ alkyl, carbocyclyl or heterocyclyl, optionally substituted by one or more of $C_{1-6}$ alkyl, halogen, $C_{1-6}$ haloalkyl, $ORO^{11}$, $SR^{11}$, $NO_2$, $CN$, $NR^{11}R^{11}$, $NR^{11}COR^{11}$, $NR^{11}CONR^{11}R^{11}$, $NR^{11}COR^{11}$, $NR^{11}CO_2R^{11}$, $CO_2R^{11}$, $COR^{11}$, $CONR^{11}{}_2$, $S(O)_2R^{11}$, $S(O)R^{11}$, $SO_2NR^{11}R^{11}$, $NR^{11}S(O)_2R^{11}$, wherein the $C_{1-12}$ alkyl group optionally incorporates one or two insertions selected from the group consisting of —O—, —N($R^{11}$)—, —S(O)— and S($O_2$)—, wherein each $R^{11}$ may be the same or different and is as defined below;

wherein $R^9$ is hydrogen, $C_{6-12}$ aryl, $C_{1-6}$ alkyl or $C_{1-6}$ haloalkyl;

wherein $R^{11}$ is hydrogen, $C_{1-6}$ alkyl, or $C_{1-6}$ haloalkyl;

and the pharmaceutically acceptable salts, and other pharmaceutically acceptable biohydrolyzable derivatives thereof, including esters, amides, carbamates, carbonates, ureides, solvates, hydrates, affinity reagents or prodrugs thereof.

For the avoidance of doubt when a group as defined above contains two or more radicals eg the radical $R^3$ as for example in the groups $SO_2NR^3R^3$ and $NR^3COR^3$, the two or more radicals such as $R^3$ may be the same or different.

For the purposes of this invention, alkyl relates to both straight chain and branched alkyl radicals of 1 to 12 carbon atoms, preferably 1 to 8 carbon atoms and most preferably 1 to 4 carbon atoms including but not limited to methyl, ethyl, n-propyl, isopropyl, n-butyl, sec-butyl, isobutyl, tert-butyl n-pentyl, n-hexyl, n-heptyl, n-octyl. The term alkyl also encompasses cycloalkyl radicals of 3 to 12 carbon atoms, preferably 4 to 8 carbon atoms, and most preferably 5 to 6 carbon atoms including but not limited to cyclopropyl, cyclobutyl, $CH_2$-cyclopropyl, $CH_2$-cyclobutyl, cyclopentyl or cyclohexyl. Cycloalkyl groups may be optionally substituted or fused to one or more carbocyclyl or heterocyclyl group. Haloalkyl relates to an alkyl radical preferably having 1 to 8 carbon atoms, preferably 1 to 4 carbon atoms substituted with one or more halide atoms for example $CH_2CH_2Br$, $CF_3$ or $CCl_3$.

The term "alkenyl" means a straight chain or branched alkylenyl radical of 2 to 12 carbon atoms, preferably 2 to 6 carbon atoms and most preferably 2 to 4 carbon atoms, and containing one or more carbon-carbon double bonds and includes but is not limited to ethylene, n-propyl-1-ene, n-propyl-2-ene, isopropylene, etc. The term "alkynyl" means a straight chain or branched alkynyl radical of 2 to 12 carbon atoms, preferably 2 to 6 carbon atoms and most preferably 2 to 4 carbon atoms, and containing one or more carbon-carbon triple bonds and includes but is not limited to ethynyl, 2-methylethynyl etc.

"Carbocyclyl" relates to a saturated, partly unsaturated or unsaturated 3 to 12 membered hydrocarbon ring, including cycloalkyl and aryl.

"Aryl" means an aromatic 3 to 12 membered hydrocarbon containing one ring or being fused to one or more saturated or unsaturated rings including but not limited to phenyl, napthyl, anthracenyl or phenanthracenyl.

"Heteroaryl" means an aromatic 3 to 12 membered aryl containing one or more heteroatoms selected from N, O or S and containing one ring or being fused to one or more saturated or unsaturated rings and;

"Heterocyclyl" means a 3 to 12 membered ring system containing one or more heteroatoms selected from N, O or S and includes heteroaryl. The heterocyclyl system can contain one ring or may be fused to one or more saturated or unsaturated rings; the heterocyclyl can be fully saturated, partially saturated or unsaturated and includes but is not limited to heteroaryl and heterocarbocyclyl.

Examples of carbocyclyl or heterocyclyl groups include but are not limited to cyclohexyl, phenyl, acridine, benzimidazole, benzofuran, benzothiophene, benzoxazole, benzothiazole, carbazole, cinnoline, dioxin, dioxane, dioxolane, dithiane, dithiazine, dithiazole, dithiolane, furan, imidazole, imidazoline, imidazolidine, indole, indoline, indolizine, indazole, isoindole, isoquinoline, isoxazole, isothiazole, morpholine, napthyridine, oxazole, oxadiazole, oxathiazole, oxathiazolidine, oxazine, oxadiazine, phenazine, phenothiazine, phenoxazine, phthalazine, piperazine, piperidine, pteridine, purine, pyran, pyrazine, pyrazole, pyrazoline, pyrazolidine, pyridazine, pyridine, pyrimidine, pyrrole, pyrrolidine, pyrroline, quinoline, quinoxaline, quinazoline, quinolizine, tetrahydrofuran, tetrazine, tetrazole, thiophene, thiadiazine, thiadiazole, thiatriazole, thiazine, thiazole, thiomorpholine, thianaphthalene, thiopyran, triazine, triazole, and trithiane.

Halogen means F, Cl, Br or I, preferably F.

$R^1$ is preferably an optionally substituted five or six membered carbocyclyl or heterocyclyl group wherein the carbocyclyl or heterocyclyl group is optionally fused to one or more unsaturated rings.

$R^1$ is preferably selected from optionally substituted phenyl, acridine, benzimidazole, benzofuran, benzothiophene, benzoxazole, benzothiazole, cyclohexyl furan, imidazole, indole, isoindole, isoquinoline, isoxazole, isothiazole, morpholine, napthaline, oxazole, phenazine, phenothiazine, phenoxazine, piperazine, piperidine, pyrazole, pyridazine, pyridine, pyrrole, quinoline, quinolizine, tetrahydrofuran, tetrazine, tetrazole, thiophene, thiazole, thiomorpholine, thianaphthalene, thiopyran, triazine, triazole or trithiane.

More preferably $R^1$ is optionally substituted phenyl, thiophene or pyridinyl.

As discussed above, $R^1$ can be optionally substituted at any position on the carbocyclyl, heterocyclyl or optional fused ring.

Substitution can occur at the ortho, meta or para positions relative to the pyridine ring. When $R^1$ is a six-membered ring, subsitution is preferably at the ortho and/or para positions, more preferably at the para position.

$R^1$ is preferably substituted with one or more of $OR^{12}$, halogen, $C_{1-6}$ alkyl, $C_{2-6}$ alkenyl, $C_{2-6}$ alkynyl, haloalkyl, $C_{1-6}$ alkylaryl, $C_{1-6}$ alkylheterocyclyl, $(CH_2)_nOR^{12}$, $(CH_2)_nNR^{12}{}_2$, $SR^{12}$, $NO_2$, $CN$, $NR^{12}{}_2$, $O_2R^{12}$, $NR^{12}C(O)R^{12}$, $NR^{12}S(O)_2R^{12}$, $COR^{12}$, $CONR^{12}{}_2$, $S(O)_2R^{12}$, $S(O)R^{12}$ or $SO_2NR^{12}{}_2$;

wherein $R^{12}$ is hydrogen, $C_{1-4}$ alkyl or aryl preferably phenyl, or heterocyclyl preferably pyridine, and n is 1, 2, 3, 4, 5 or 6.

wherein two $R^{12}$ in $NR^{12}{}_2$ may optionally form a partially saturated, unsaturated or fully saturated four to seven membered ring containing one to three heteroatoms, said ring is preferably independently substituted with one or more of halogen, $C_{1-12}$ alkyl, $C_{2-12}$ alkenyl, $C_{2-12}$ alkynyl, haloalkyl, carbocyclyl, heterocyclyl, $OR^{13}$, $SR^{13}$, $NO_2$, $CN$, $NR^{13}{}_2$, $NR^{13}COR^{13}$, $NR^{13}CONR^{13}{}_2$, $NR^{13}COR^{13}$, $NR^{13}CO_2R^{13}$, $CO_2R^{13}$, $COR^{13}$, $CONR^{13}{}_2$, $S(O)_2R^{13}$, $SONR^{13}{}_2$, $S(O)R^{13}$, $SO_2NR^{13}{}_2$, or $NR^{13}S(O)_2R^{13}$; and each saturated carbon in the optional ring is further optionally and independently substituted by =O, =S, $NNR^{14}{}_2$, =N—$OR^{14}$, =$NNR^{14}COR^{14}$, =$NNR^{14}CO_2R^{14}$, =$NNSO_2R^{14}$, or =$NR^{14}$; and each substitutable nitrogen atom is optionally substituted by $R^{15}$, $COR^{15}$, $SO_2R^{15}$ or $CO_2R^{15}$;

wherein $R^{13}$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^{16}$, $SR^{16}$, $NO_2$, $CN$, $NR^{16}R^{16}$, $NR^{16}COR^{16}$, $NR^{16}CONR^{16}R^{16}$, $NR^{16}COR^{16}$, $NR^{16}CO_2R^{16}$, $CO_2R^{16}$, $COR^{16}$, $CONR^{16}{}_2$, $S(O)_2R^{16}$, $SONR^{16}{}_2$, $S(O)R^{16}$, $SO_2NR^{16}R^{16}$, $NR^{16}S(O)_2R^{16}$, wherein the $C_{1-12}$ alkyl group optionally incorporates one or two insertions selected from the group consisting of —O—, —N($R^{16}$)—, —S(O)— and —S($O_2$)—, wherein each $R^{16}$ may be the same or different and is as defined below;

wherein $R^{14}$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^{16}$, $SR^{16}$, $NO_2$, $CN$, $NR^{16}R^{16}$, $NR^{16}COR^{16}$, $NR^{16}CONR^{16}$, $NR^{16}COR^{16}$, $NR^{16}CO_2R^{16}$, $CO_2R^{16}$, $COR^{16}$, $CONR^{16}{}_2$, $S(O)_2R^{16}$, $S(O)R^{16}$, $SO_2NR^{16}R^{16}$, $NR^{16}S(O)_2R^{16}$, wherein the $C_{1-12}$ alkyl group optionally incorporates one or two insertions selected from the group consisting of —O—, —N($R^{16}$)—, —S(O)— and —S($O_2$)—, wherein each $R^{16}$ may be the same or different and is as defined below;

wherein $R^{15}$ is hydrogen, $C_{1-6}$ alkyl, $C_{1-6}$ haloalkyl or $C_{6-12}$ aryl;

wherein $R^{16}$ is hydrogen, $C_{1-6}$ alkyl, or $C_{1-6}$ haloalkyl.

$R^2$ is preferably selected from phenyl, cyclohexyl, acridine, benzimidazole, benzofuran, benzothiophene, benzoxazole, benzothiazole, indole, isoindole, indolizine, indazole, isoindole, isoquinoline, morpholine, napthalene, phenazine, phenothiazine, phenoxazine, piperazine, piperidine, pyridazine, pyridine, pyridinyl, pyrimidinyl, pyrazinyl, pyridazinyl, quinoline, quinolizine, tetrazine, thiomorpholine, thianaphthalene, thiopyran, triazine, trithiane, furan, imidazole, isoxazole, isothiazole, oxazole, oxadiazole, oxathiazole, pyrazole, pyrrole, tetrazole, thiophene, thiadiazole, thiatriazole, thiazole or triazole.

As discussed above, $R^2$ can be optionally substituted at any position on the carbocyclyl, heterocyclyl or optional fused ring. Preferably, each substitutable carbon or hetero-atom in $R^2$ is optionally and independently substituted by one or more of $C_{1-6}$ alkyl, $OR^{10}$, $SR^{10}$, $NO_2$, $CN$, $NR^{10}_2$, $NR^{10}COR^{10}$, $NR^{10}CONR^{10}_2$, $NR^{10}COR^{10}$, $NHCO_2R^{10}$, $CO_2R^{10}$, $COR^{10}$, $CONR^{10}_2$, $S(O)_2R^{10}$, $SONR^{10}_2$, $S(O)R^{10}$, $SO_2NR^{10}_2$, or $NR^{10}S(O)_2R^{10}$;

wherein $R^{10}$ is hydrogen, $C_{1-6}$ alkyl, or $C_{1-6}$ haloalkyl.

When $R^2$ is a six-membered carbocyclyl or heterocyclyl group, $R^2$ is preferably substituted with one or more of $OR^{17}$, $NR^{17}_2$, $SR^{17}$, $(CH_2)_nOR^{17}$, $(CH_2)_nNR^{17}_2$, halogen, $C_{1-6}$ alkyl, $C_{2-6}$ alkenyl, $C_{2-6}$ alkynyl, haloalkyl, $NO_2$, $CN$, $NR^{17}C(O)R^{17}$, $NR^{17}S(O)_2R^{17}$, $CO_2R^{17}$, $COR^{17}$, $CONR^{17}_2$, $S(O)_2R^{17}$, $S(O)R^{17}$ or $SO_2NR^{17}_2$;

wherein $R^{17}$ is hydrogen, $C_{1-4}$ alkyl, heterocyclyl or aryl preferably phenyl, and n is 1, 2, 3, 4, 5 or 6.

wherein two $R^{17}$ in $NR^{17}_2$ may optionally form a partially saturated, unsaturated or fully saturated five to seven membered ring containing one to three heteroatoms, optionally and independently substituted with one or more of halogen, $C_{1-12}$ alkyl, $C_{2-12}$ alkenyl, $C_{2-12}$ alkynyl, haloalkyl, carbocyclyl, heterocyclyl, $OR^{18}$, $SR^{18}$, $NO_2$, $CN$, $NR^{18}_2$, $NR^{18}COR^{18}$, $NR^{18}CONR^{18}_2$, $NR^{18}COR^{18}$, $NR^{18}CO_2R^{18}$, $CO_2R^{18}$, $COR^{18}$, $CONR^{18}_2$, $S(O)_2R^{15}$, $SONR^{18}_2$, $S(O)R^{18}$, $SO_2NR^{18}_2$, or $NR^{18}S(O)_2R^{18}$; and each saturated carbon in the optional ring is further optionally and independently substituted by $=O$, $=S$, $NNR^{19}_2$, $=N-OR^{19}$, $=NNR^{19}COR^{19}$, $=NNR^{19}CO_2R^{19}$, $=NNSO_2R^{19}$, or $=NR^{19}$; and each substitutable nitrogen atom is optionally substituted by $R^{20}$, $COR^{20}$, $SO_2R^{20}$ or $CO_2R^{20}$;

wherein $R^{18}$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^{21}$, $SR^{21}$, $NO_2$, $CN$, $NR^{21}R^{21}$, $NR^{21}COR^{21}$, $NR^{21}CONR^{21}R^{21}$, $R^{21}COR^{21}$, $NR^{21}CO_2R^{21}$, $CO_2R^{21}$, $COR^{21}$, $CONR^{21}_2$, $S(O)_2R^{21}$, $SONR^{21}_2$, $S(O)R^{21}$, $SO_2NR^{21}R^{21}$, $NR^{21}S(O)_2R^{21}$, wherein the $C_{1-12}$ alkyl group optionally incorporates one or two insertions selected from the group consisting of $—O—$, $—N(R^{21})—$, $—S(O)—$ and $—S(O_2)—$, wherein each $R^{21}$ may be the same or different and is as defined below;

wherein $R^{19}$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^{21}$, $SR^{21}$, $NO_2$, $CN$, $NR^{21}R^{21}$, $NR^{21}COR^{21}$, $NR^{21}CONR^{21}R^{21}$, $NR^{21}COR^{21}$, $NR^{21}CO_2R^{21}$, $CO_2R^{21}$, $COR^{21}$, $CONR^{21}_2$, $S(O)_2R^{21}$, $S(O)R^{21}$, $SO_2NR^{21}R^{21}$, $NR^{21}S(O)_2R^{21}$, wherein the $C_{1-12}$ alkyl group optionally incorporates one or two insertions selected from the group consisting of $—O—$, $—N(R^{21})—$, $—S(O)—$ and $—S(O_2)—$, wherein each $R^{21}$ may be the same or different and is as defined below;

wherein $R^{20}$ is hydrogen, $C_{6-12}$ aryl, $C_{1-6}$ alkyl or $C_{1-6}$ haloalkyl;

wherein $R^{21}$ is hydrogen, $C_{1-6}$ alkyl, or $C_{1-6}$ haloalkyl.

When $R^2$ is a five-membered heterocyclyl, it is preferably a group

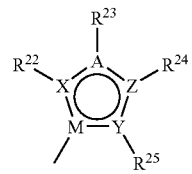

Wherein A, X, Y or Z are independently selected from N, O, C, S and M is C or N, wherein one, two, three or four of A, X, Y, Z and M is other than C, preferably $R^2$ is furan, imidazole, isoxazole, isothiazole, oxazole, oxadiazole, oxatriazole, pyrazole, pyrrole, tetrazole, thiophene, thiadiazole, thiatriazole, thiazole or triazole;

$R^{22}$, $R^{23}$, $R^{24}$ or $R^{25}$ are independently selected from a lone electron pair, hydrogen, halogen, $C_{1-12}$ alkyl, haloalkyl, $OR^{26}$, $SR^{26}$, $NO_2$, $CN$, $NR^{26}_2$, $NR^{26}COR^{26}$, $NR^{26}CONR^{26}_2$, $NR^{26}COR^{26}$, $NR^{26}CO_2R^{26}$, $(CH_2)_nOR^{26}$, $(CH_2)_nNR^{26}_2$, $CO_2R^{26}$, $COR^{26}$, $CONR^{26}_2$, $S(O)_2R^{26}$, $SONR^{26}_2$, $S(O)R^{26}$, $SO_2NR^{26}_2$, or $NHS(O)_2R^{26}$;

wherein n is 1 to 6, preferably n is 1, 2 or 3;

or wherein any two of $R^{22}$, $R^{23}$, $R^{24}$ or $R^{25}$ may optionally form a partially saturated, unsaturated or fully saturated five to seven membered ring containing zero to three heteroatoms, each saturated carbon in the optional fused ring is further optionally and independently substituted with one or more of halogen, $C_{1-12}$ alkyl, $C_{2-12}$ alkenyl, $C_{2-12}$ alkynyl, haloalkyl, carbocyclyl, heterocyclyl, $OR^{26}$, $SR^{26}$, $NO_2$, $CN$, $NR^{26}_2$, $NR^{26}CONR^{26}_2$, $NR^{26}COR^{26}$, $NR^{26}CO_2R^{26}$, $(CH_2)_nOR^{26}$, $(CH_2)_nNR^{26}_2$, $CO_2R^{26}$, $COR^{26}$, $CONR^{26}_2$, $S(O)_2R^{26}$, $SONR^{26}_2$, $S(O)R^{26}$, $SO_2NR^{26}_2$, or $NR^{26}S(O)_2R^{26}$; and each saturated carbon in the optional fused ring is further optionally and independently substituted by $=O$, $=S$, $NNR^{27}_2$, $=N-OR^{27}$, $=NNR^{27}COR^{27}$, $=NNR^{27}CO_2R^{27}$, $=NNSO_2R^{27}$, or $=NR^{27}$; and each substitutable nitrogen atom in $R^1$ is optionally substituted by $R^{28}$, $COR^{28}$, $SO_2R^{28}$ or $CO_2R^{28}$;

wherein n is 1 to 6, preferably n is 1, 2 or 3;

wherein $R^{26}$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^{29}$, $SR^{29}$, $NO_2$, $CN$, $NR^{29}R^{29}$, $NR^{29}CONR^{29}R^{29}$, $NR^{29}COR^{29}$, $NR^{29}CO_2R^{29}$, $CO_2R^{29}$, $COR^{29}$, $CONR^{29}_2$, $S(O)_2R^{29}$, $SONR^{29}_2$, $S(O)R^{29}$, $SO_2NR^{29}R^{29}$, $NR^{29}S(O)_2R^{29}$, wherein the $C_{1-12}$ alkyl group optionally incorporates one or two insertions selected from the group consisting of $—O—$, $—N(R^{29})—$, $—S(O)—$ and $—S(O_2)—$, wherein each $R^{29}$ may be the same or different and is as defined below;

wherein $R^{27}$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^{29}$, $SR^{29}$, $NO_2$, $CN$, $NR^{29}R^{29}$, $NR^{29}COR^{29}$, $NR^{29}CONR^{29}R^{29}$, $NR^{29}COR^{29}$, $NR^{29}CO_2R^{29}$, $CO_2R^{29}$, $COR^{29}$, $CONR^{29}_2$, $S(O)_2R^{29}$, $S(O)R^{29}$, $SO_2NR^{29}R^{29}$, $NR^{29}S(O)_2R^{29}$, wherein the $C^{1-12}$ alkyl group optionally incorporates one or two insertions selected from the group consisting of —O—, —N($R^{29}$)—, —S(O)— and —S(O$_2$)—, wherein each $R^{29}$ may be the same or different and is as defined below;

wherein $R^{28}$ is hydrogen, $C_{1-6}$ alkyl, $C_{1-6}$ haloalkyl or $C_{6-12}$ aryl.

wherein $R^{29}$ is hydrogen, $C_{1-6}$ alkyl, or $C_{1-6}$haloalkyl.

More preferably $R^{22}$, $R^{23}$, $R^{24}$ or $R^{25}$ are independently selected from a lone electron pair, hydrogen, halogen, $C_{1-6}$ alkyl, haloalkyl, $OR^{30}$, $SR^{30}$, CN, $NR^{30}{}_2$, $NR^{30}COR^{30}$, $CO_2R^{30}$, $COR^{30}$, $CONR^{30}{}_2$, $S(O)_2R^{30}$, or $S(O)R^{30}$;

Wherein $R^{30}$ is hydrogen, $C_{1-4}$ alkyl, preferably methyl or ethyl or carbocyclyl, preferably phenyl.

Representative compounds according to the first aspect of the invention are illustrated below;

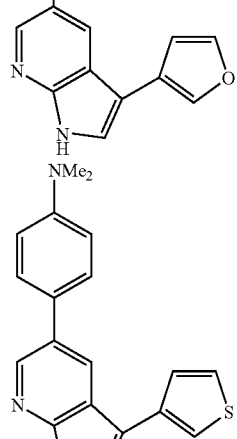
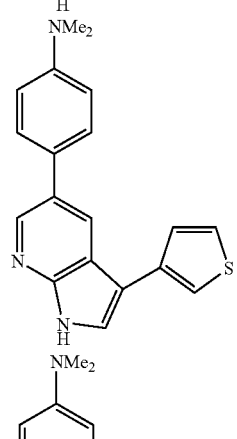
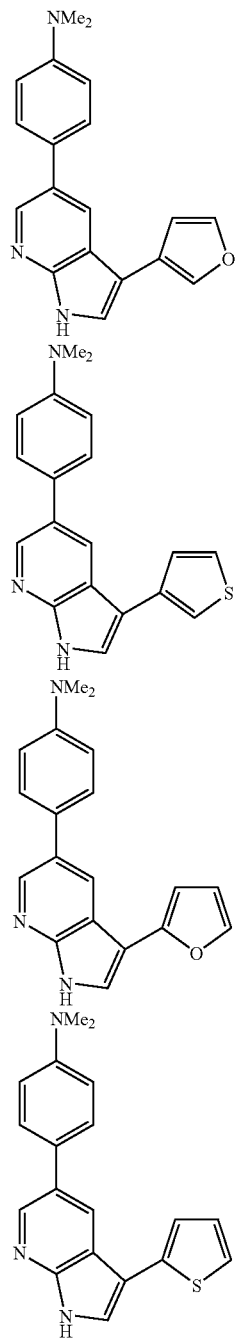
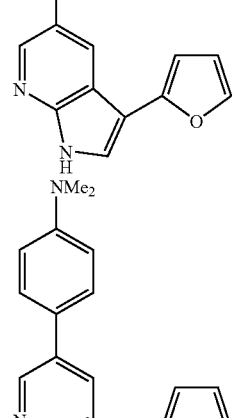
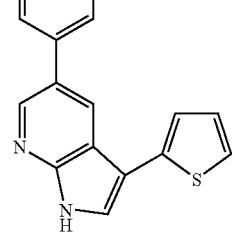

-continued

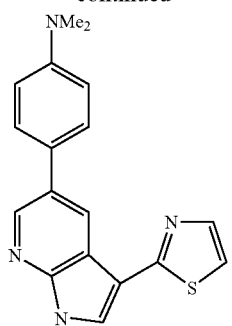
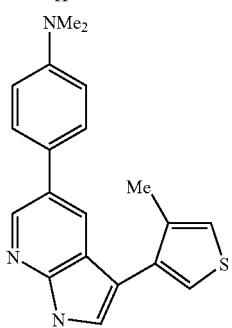
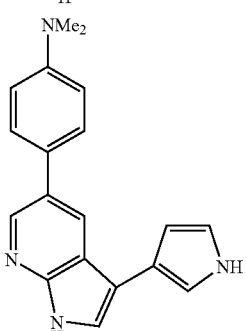
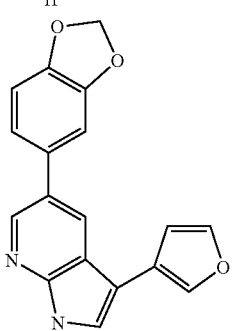
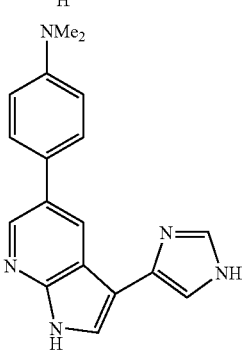

-continued
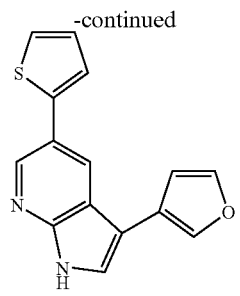
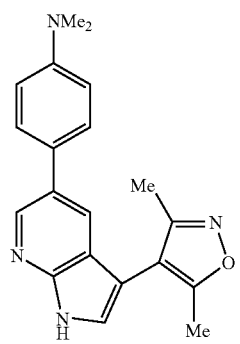
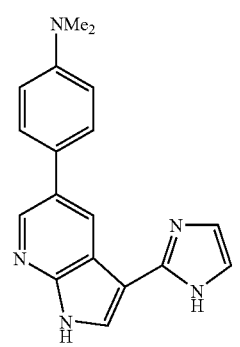
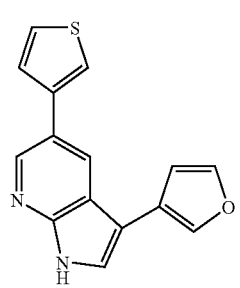
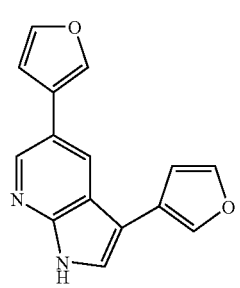
-continued
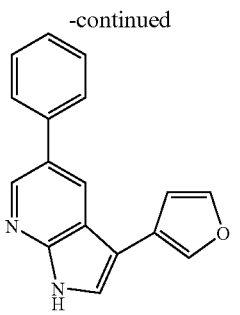
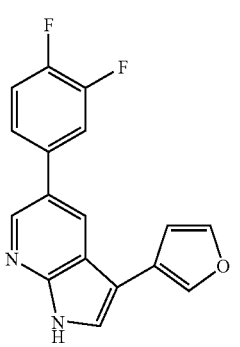
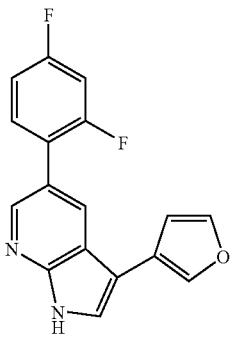
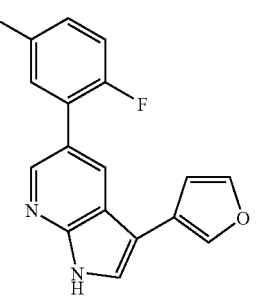
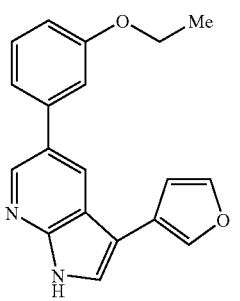

-continued
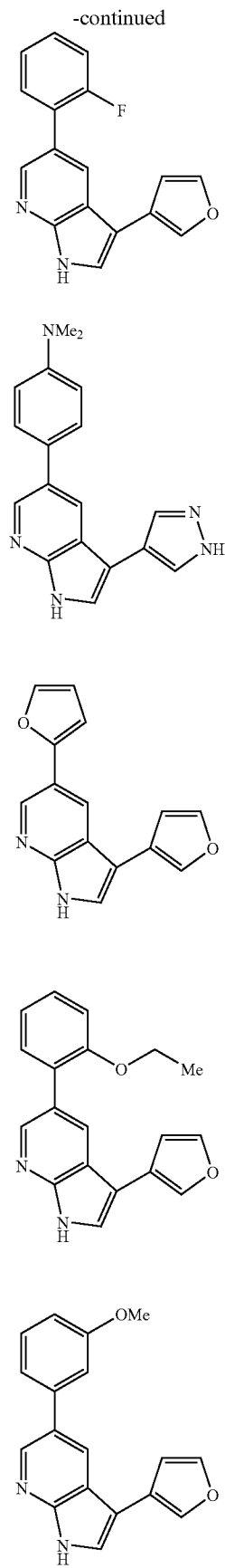
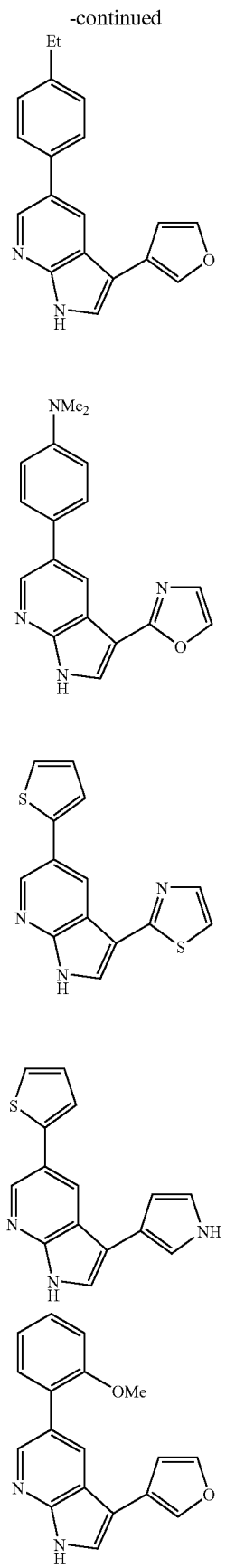

-continued
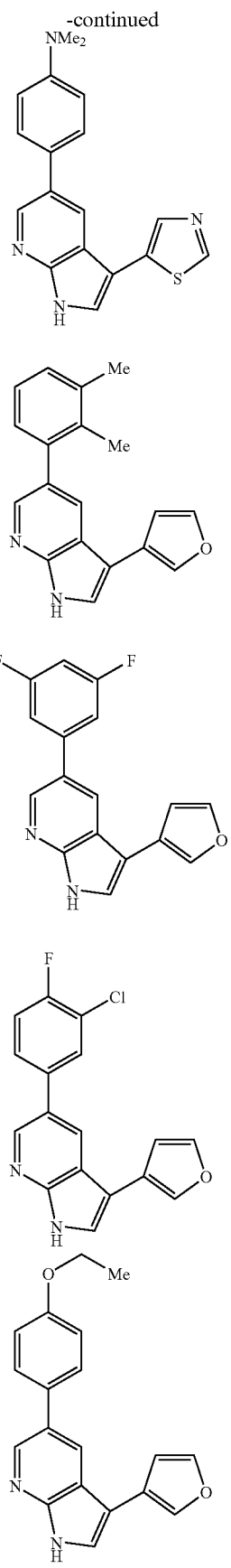
-continued
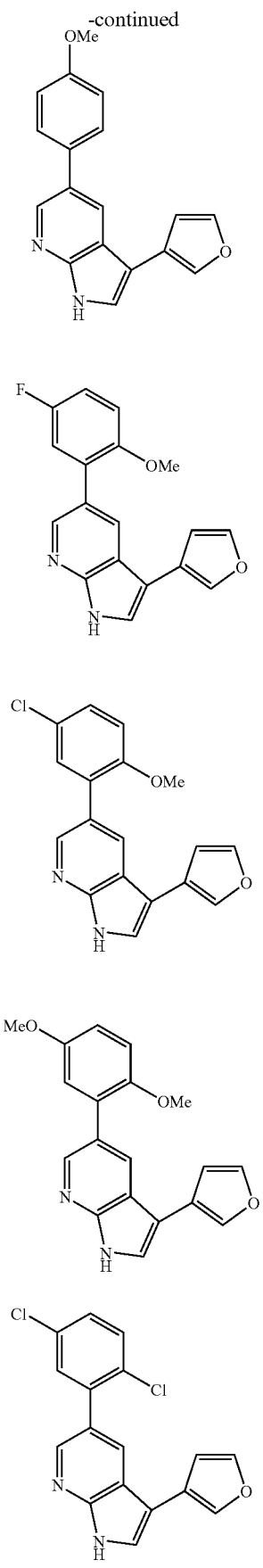

-continued
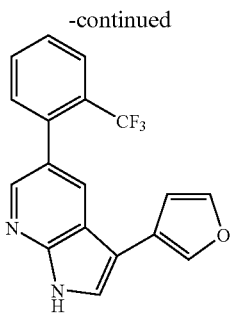
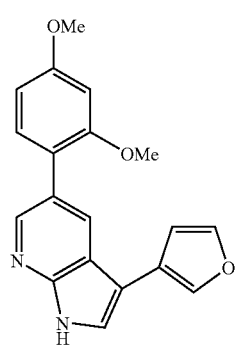
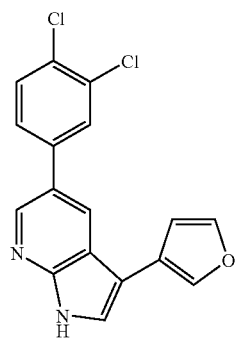
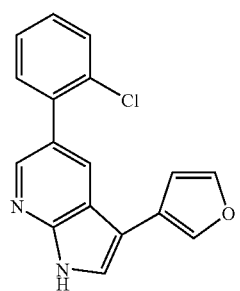
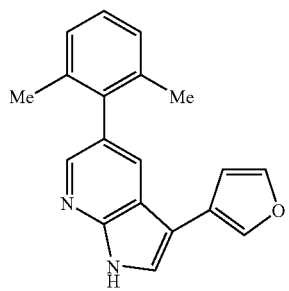
-continued
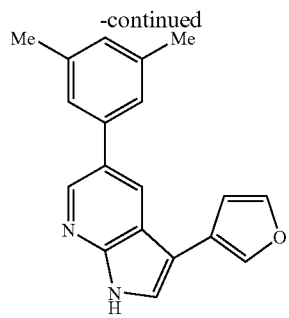
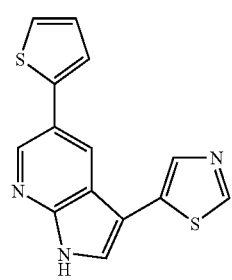
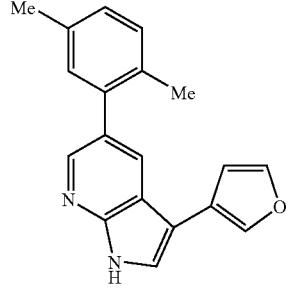
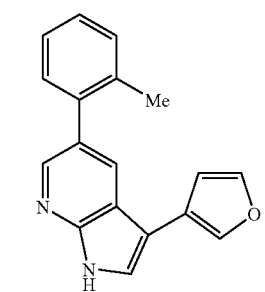
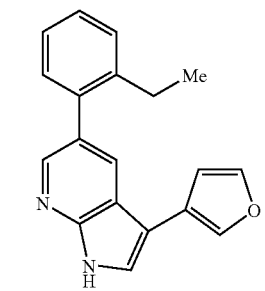

-continued
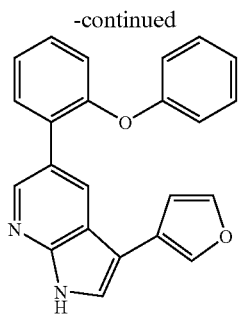
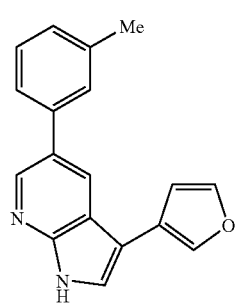
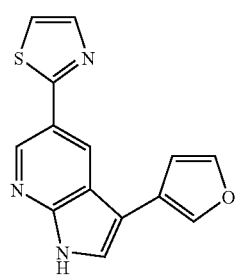
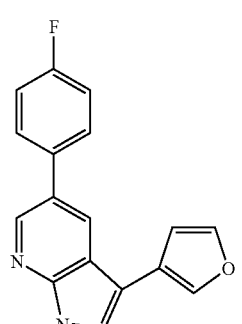
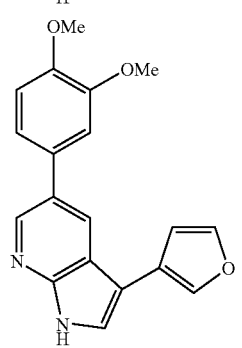
-continued
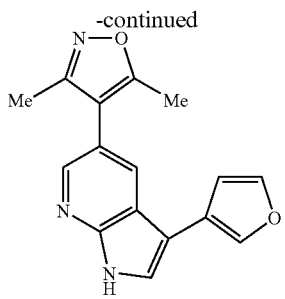
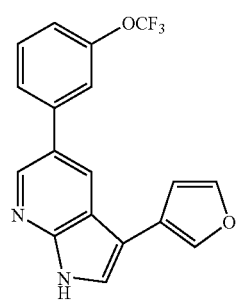
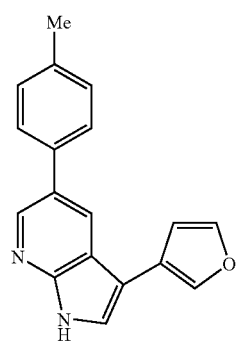
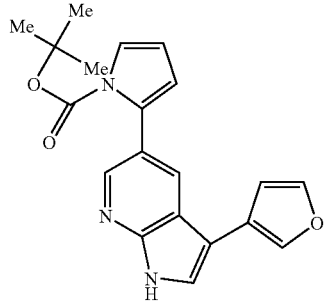
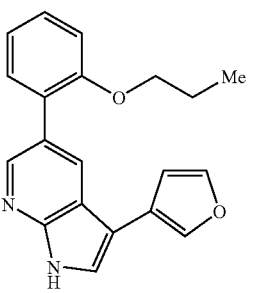

-continued
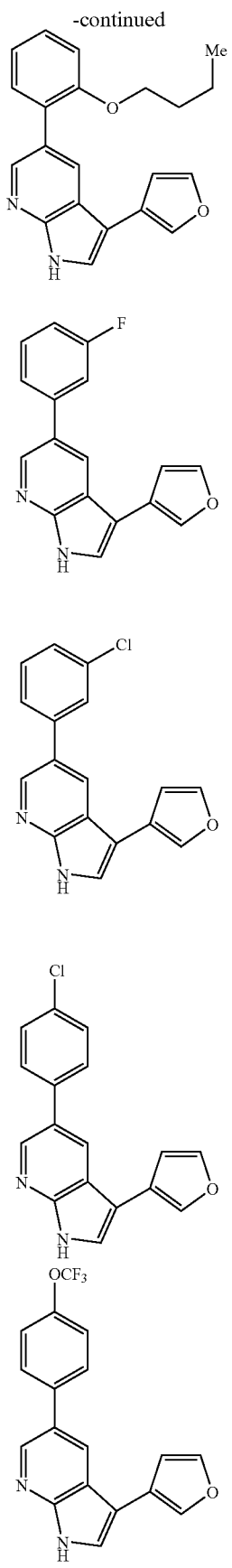
-continued
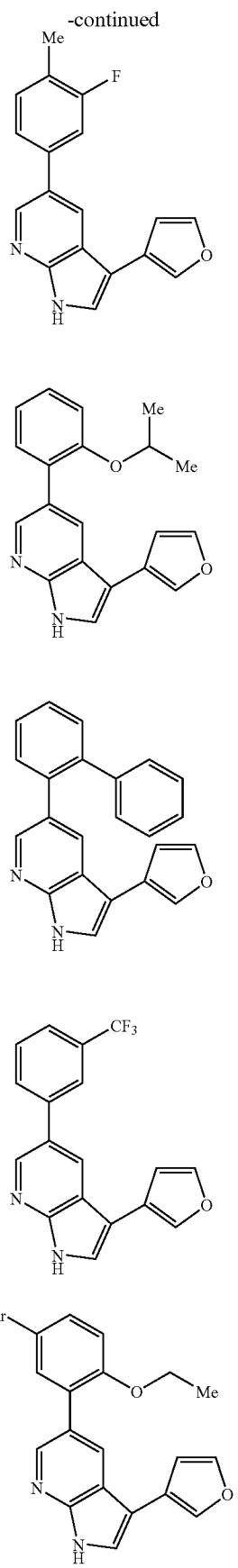

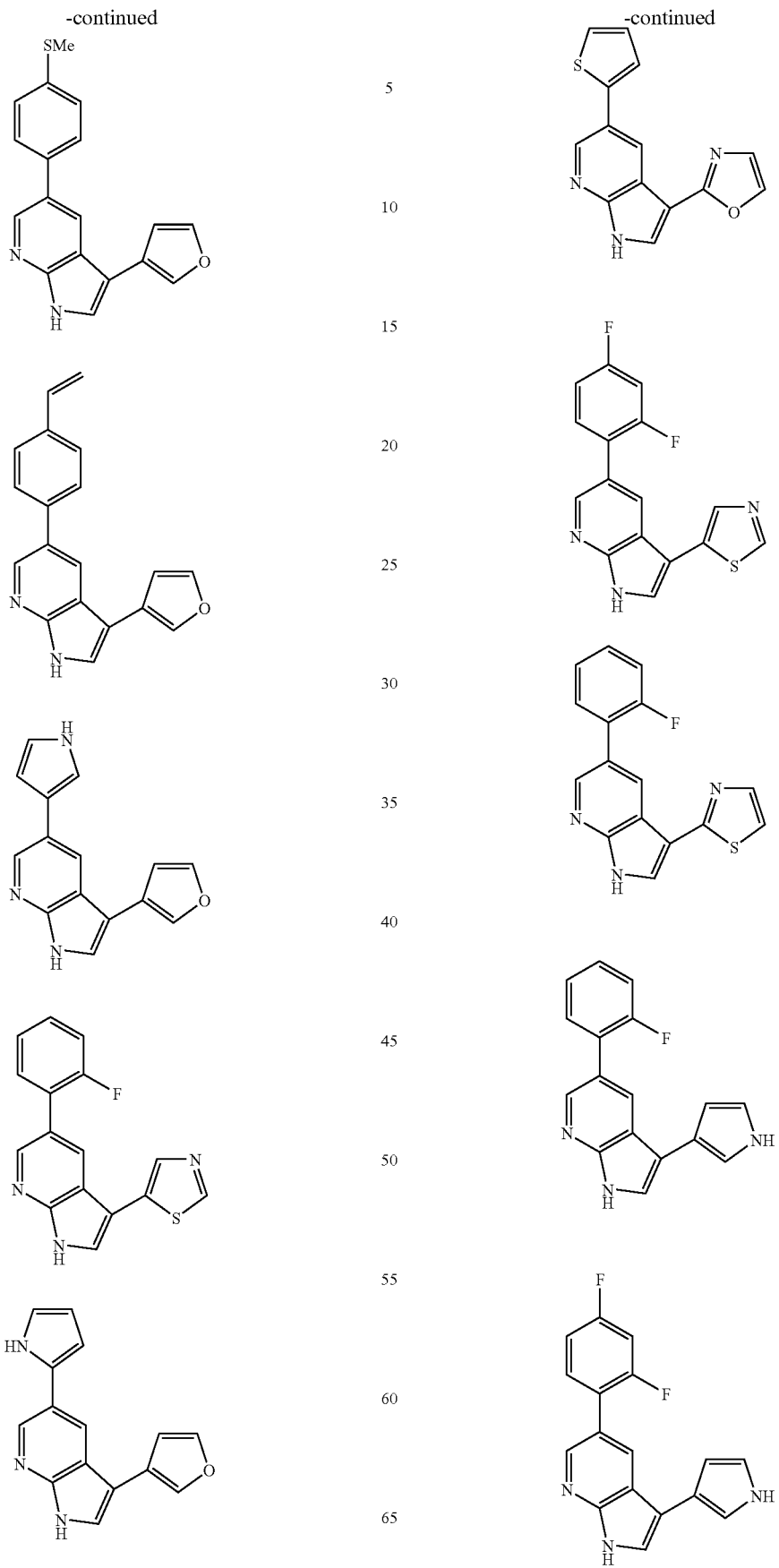

-continued
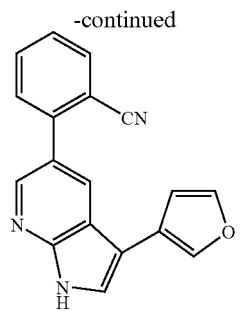
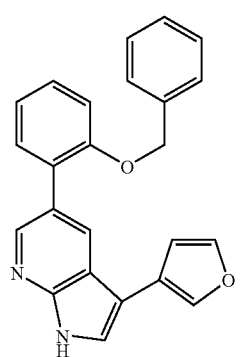
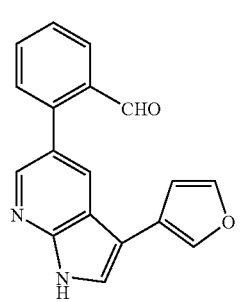
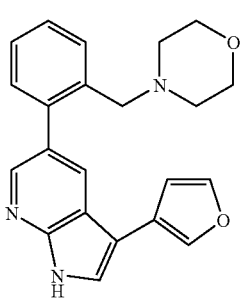
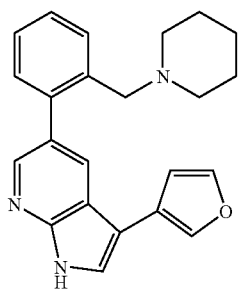
-continued
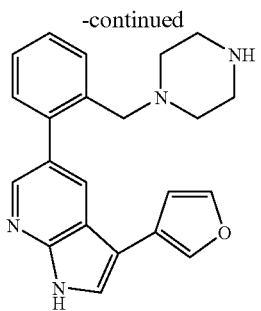
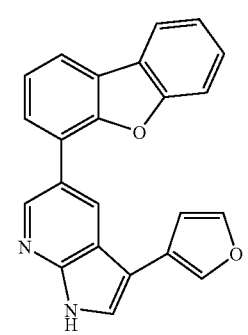
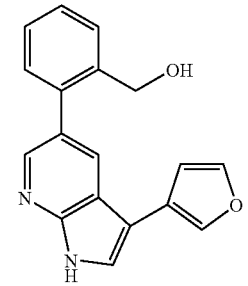
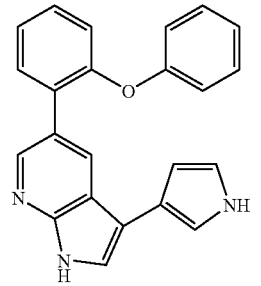
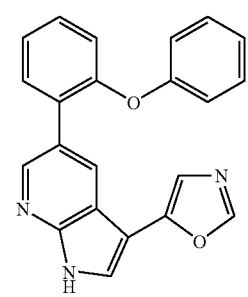

-continued
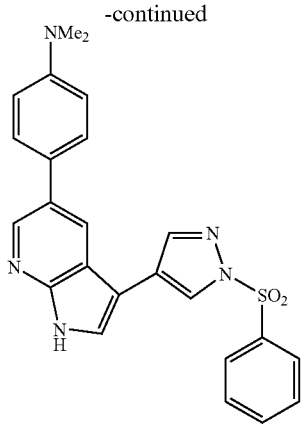
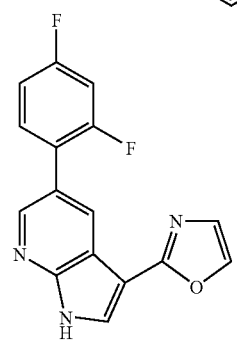
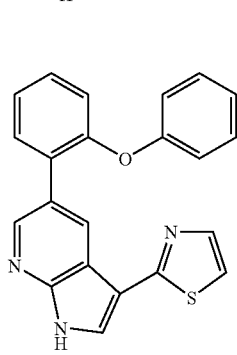
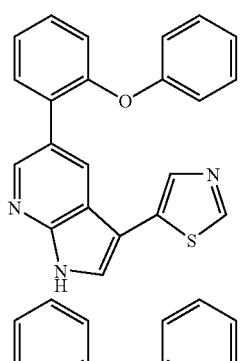
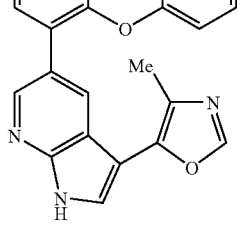
-continued
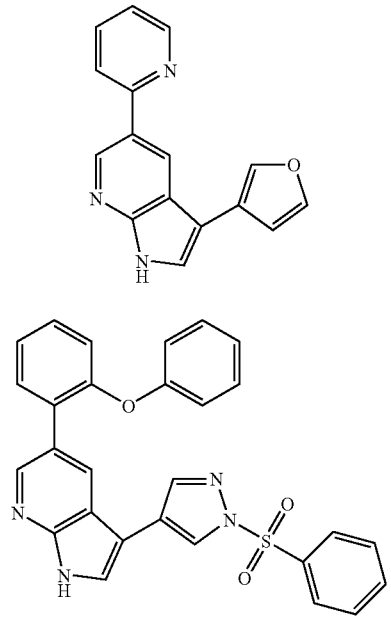
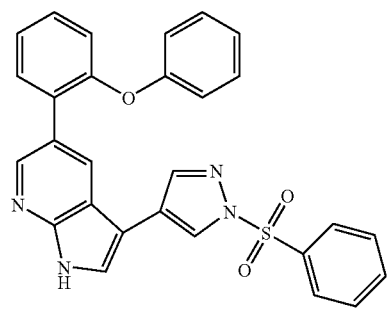

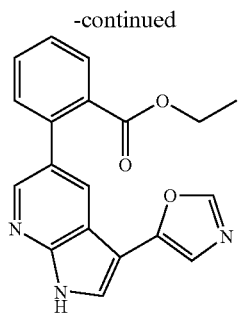
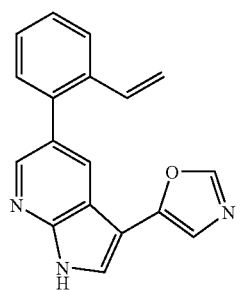
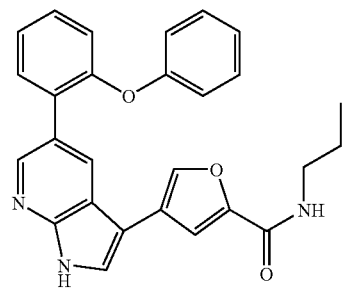
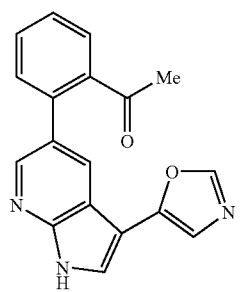
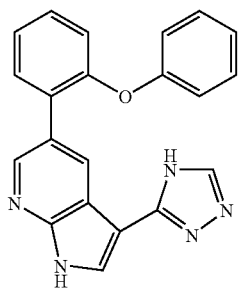
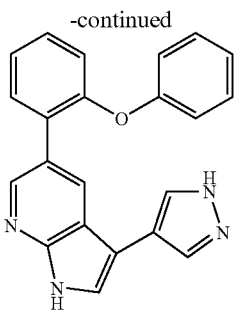
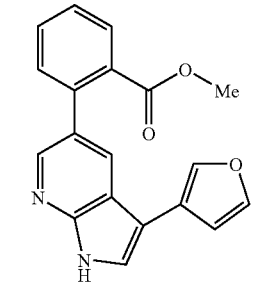
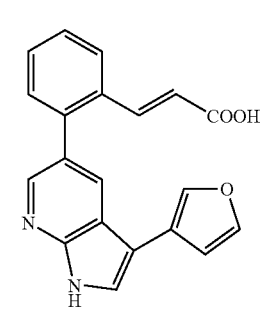
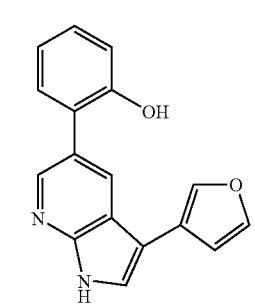
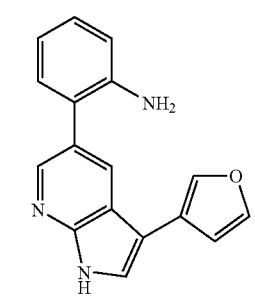

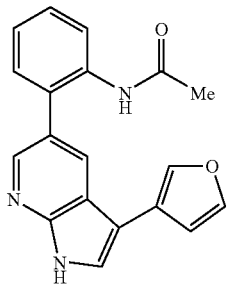
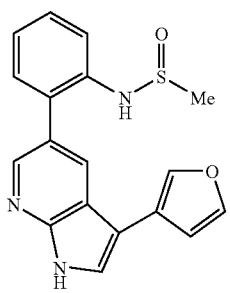
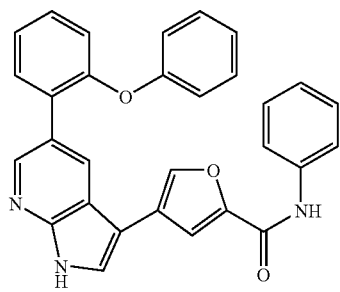
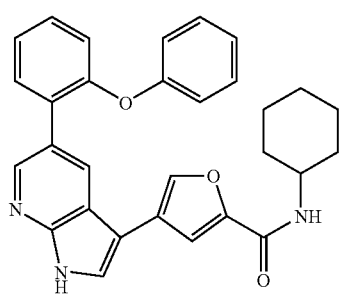
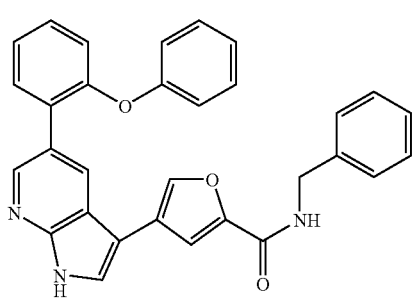
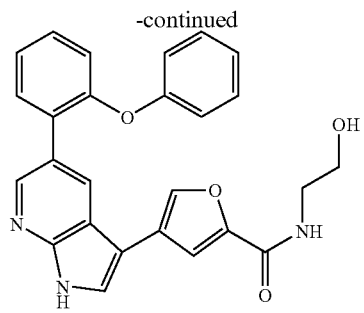
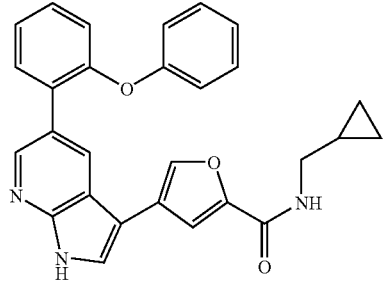
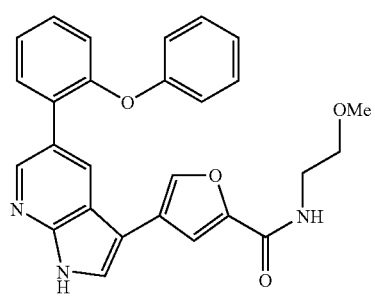
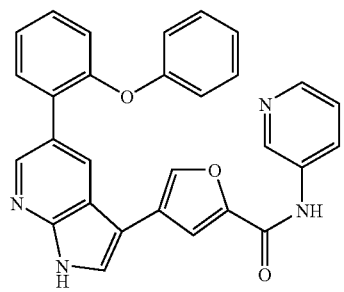
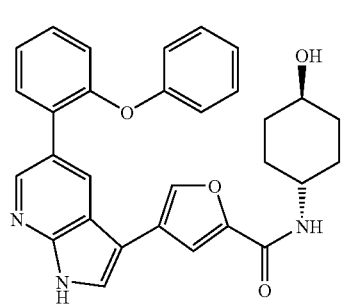

-continued
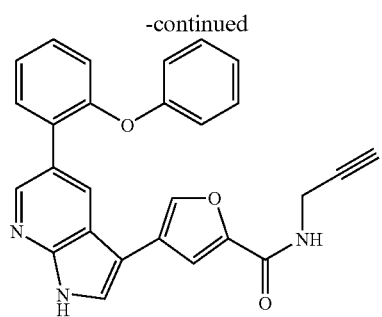
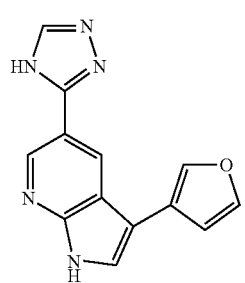
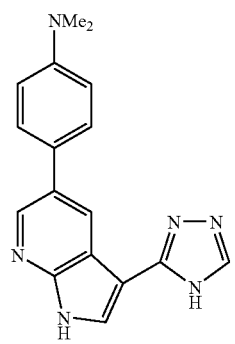
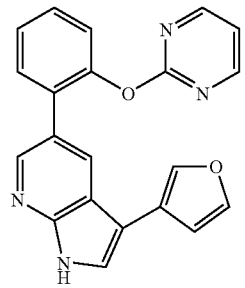
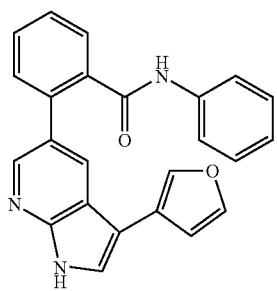
-continued
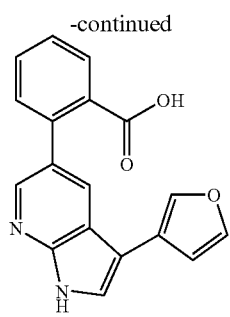
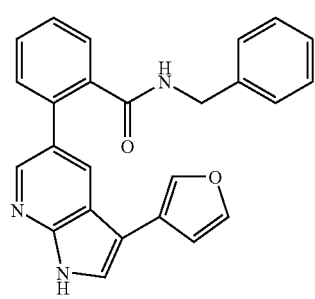
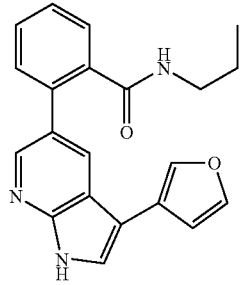
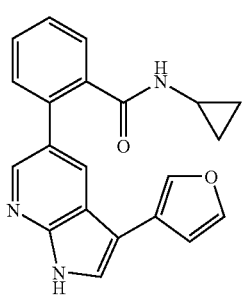
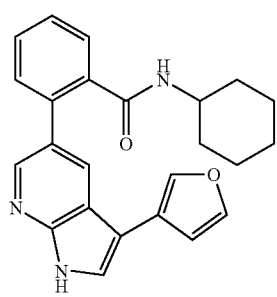

-continued
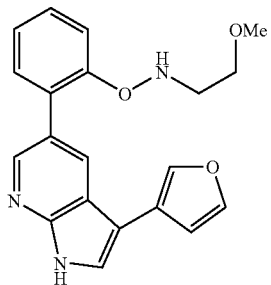
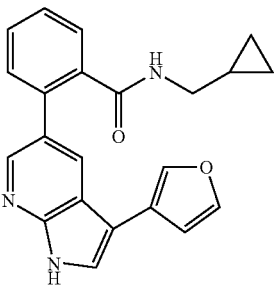
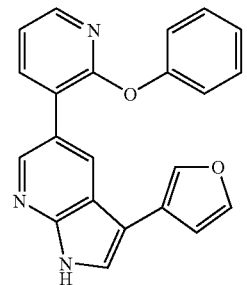
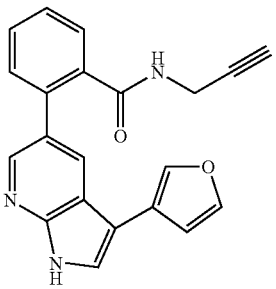
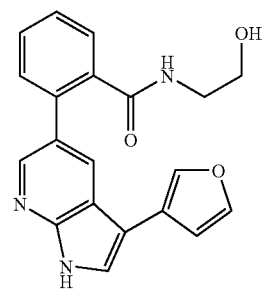
-continued
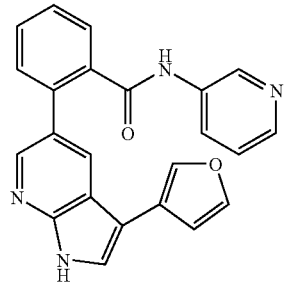
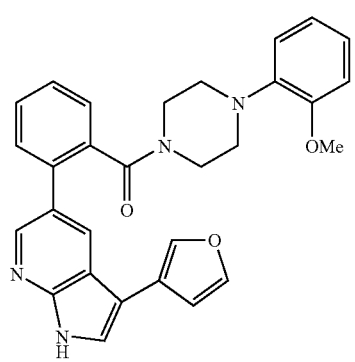
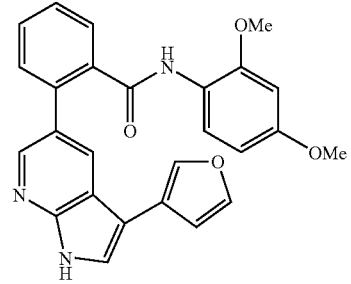
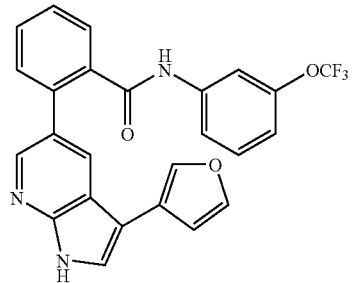
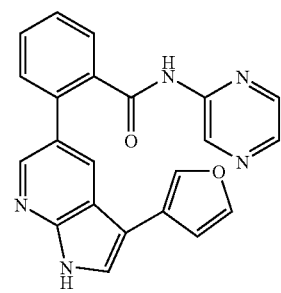

-continued
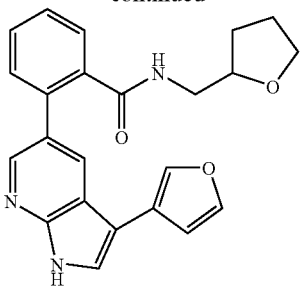
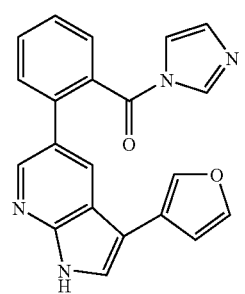
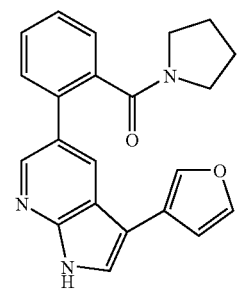
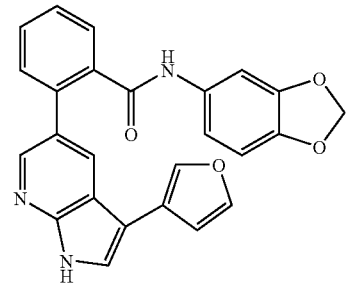
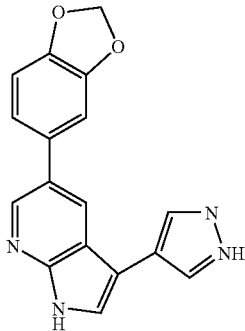
-continued
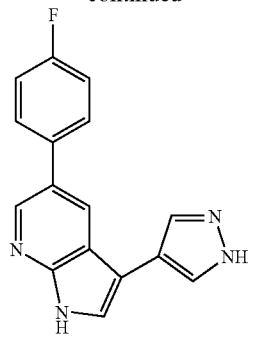
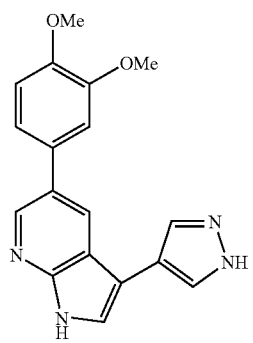
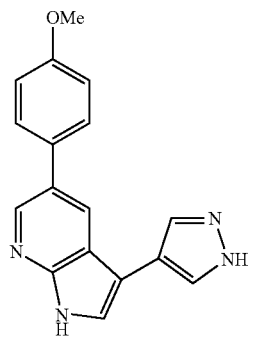
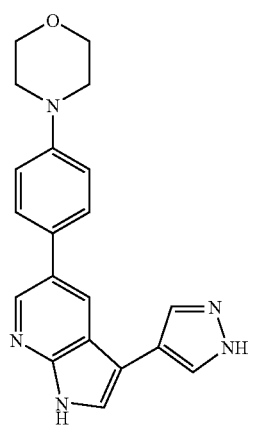

-continued
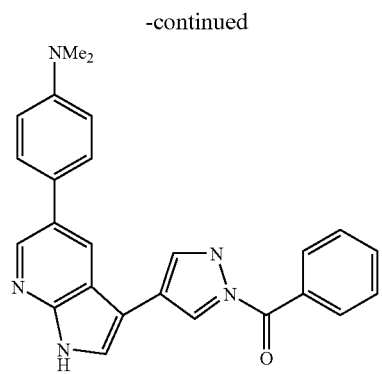
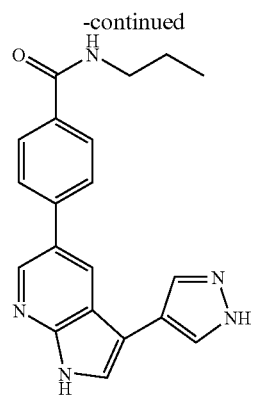
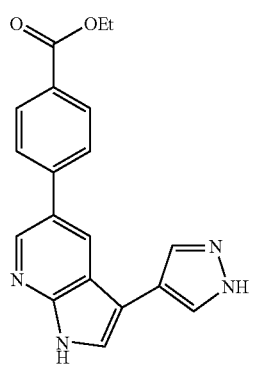
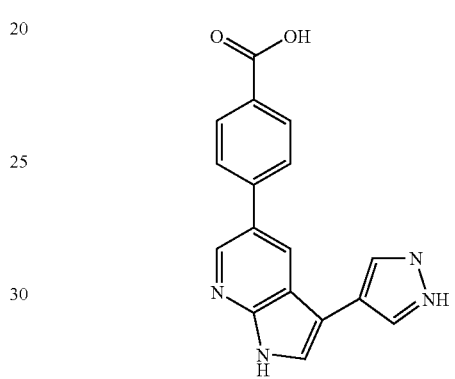
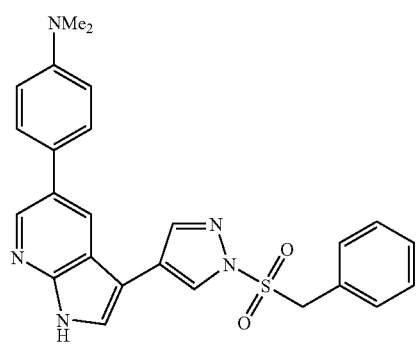
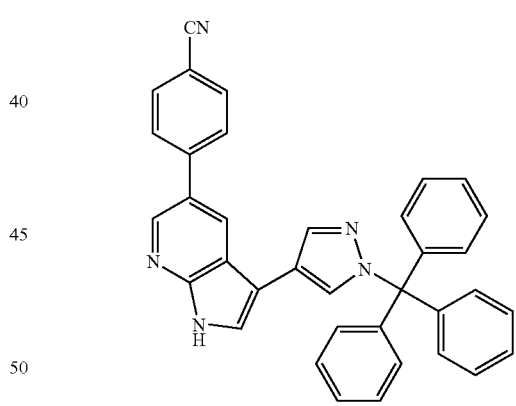
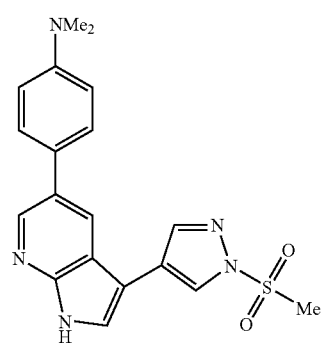
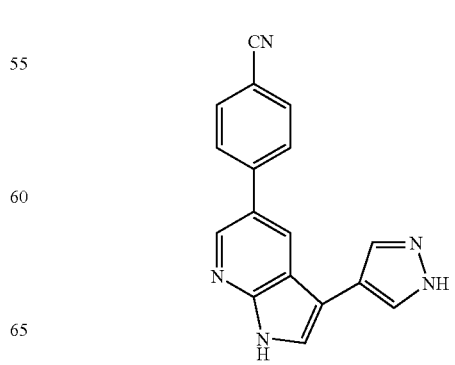

-continued
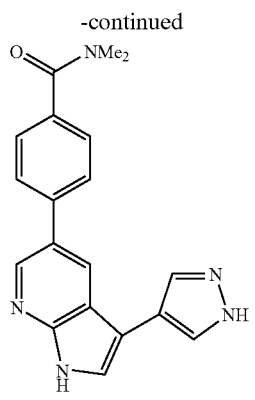
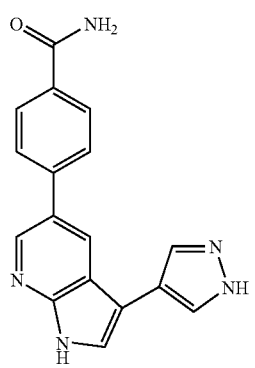
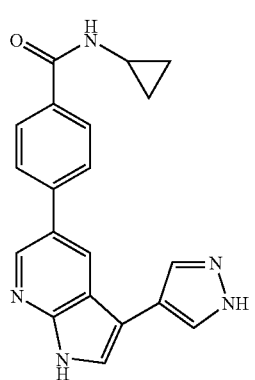
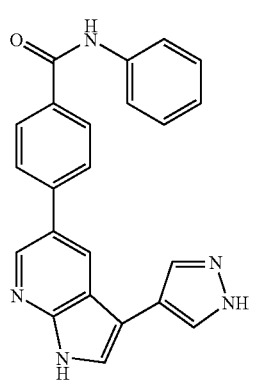
-continued
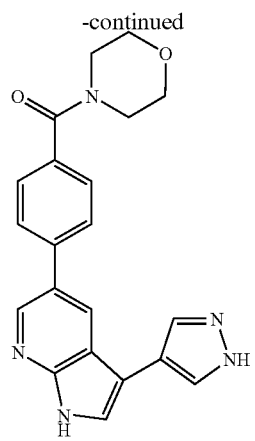
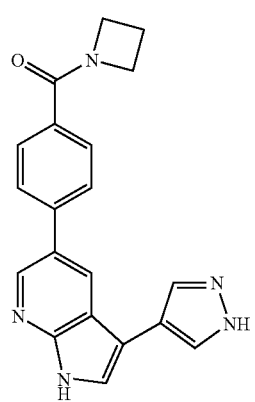
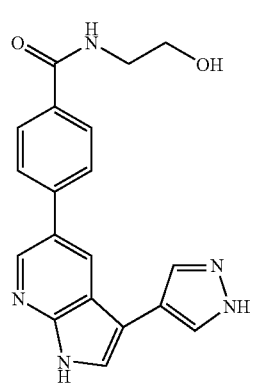
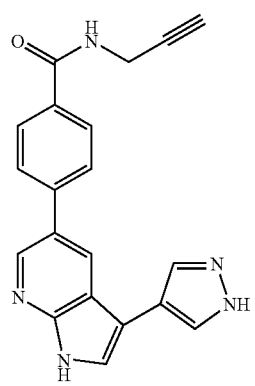

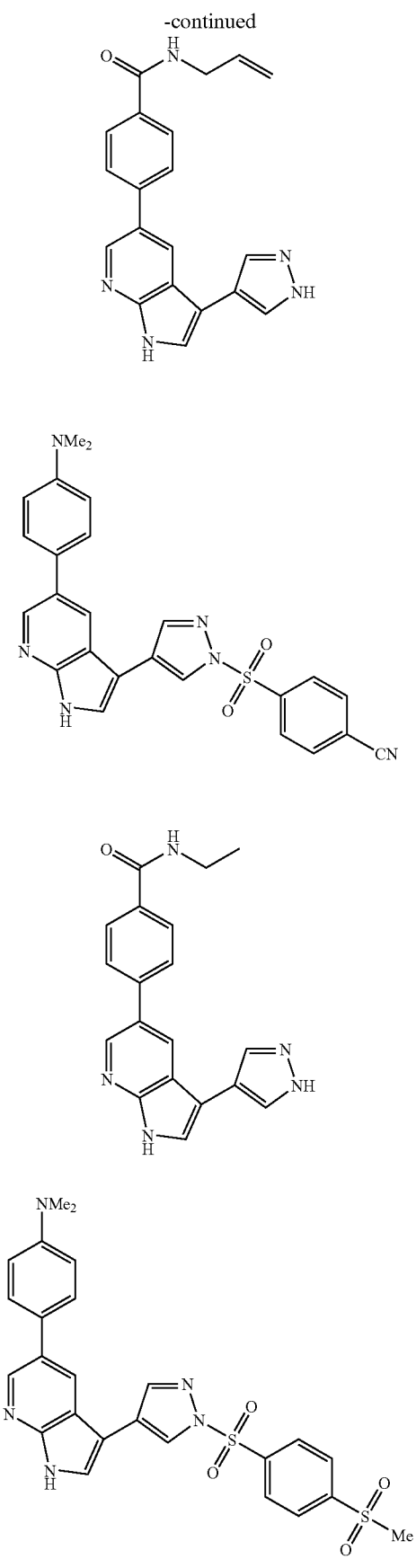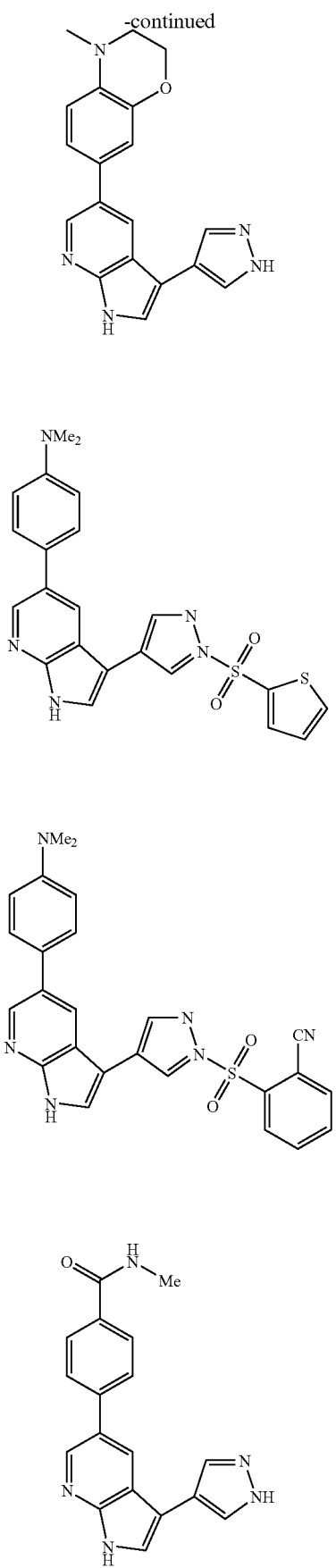

-continued
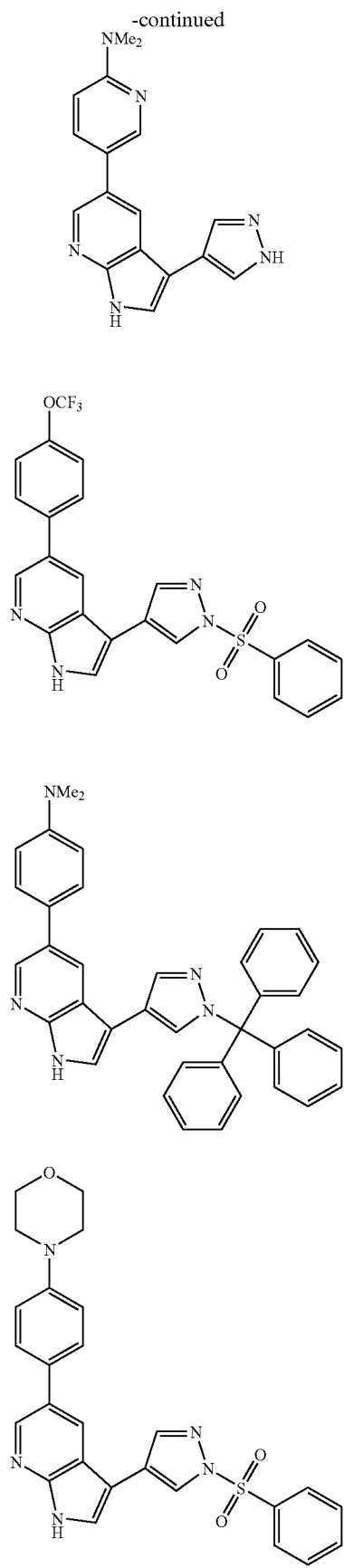
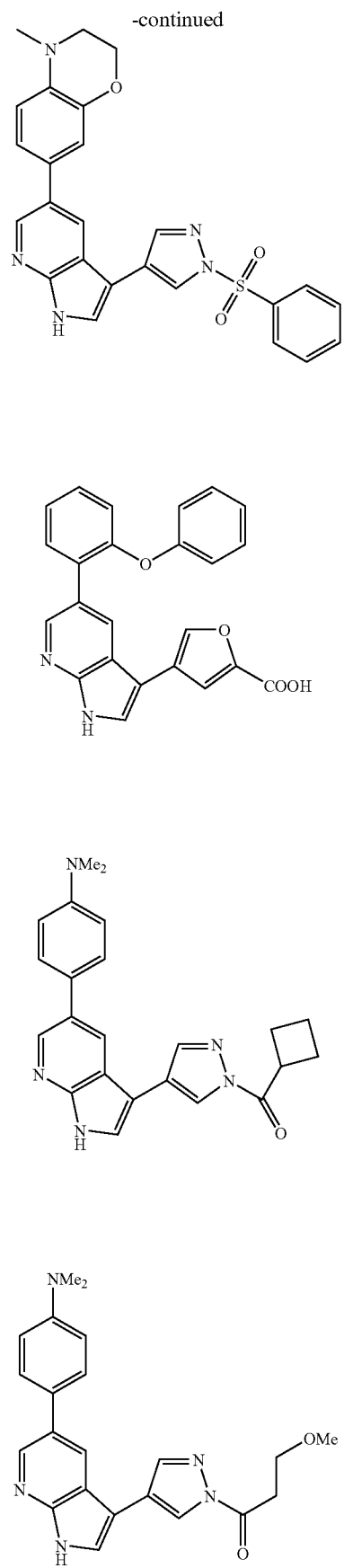

-continued
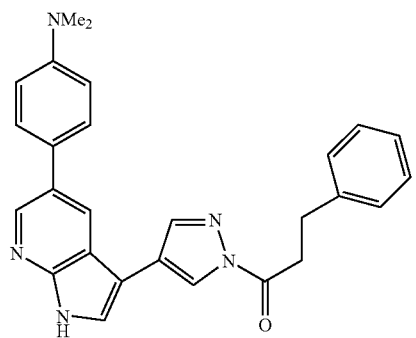
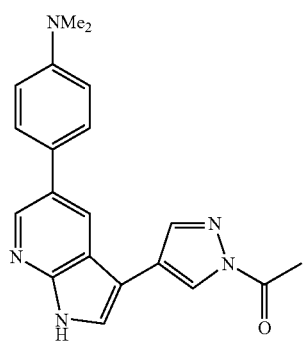
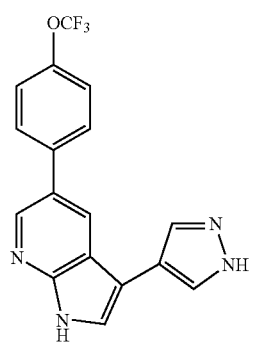
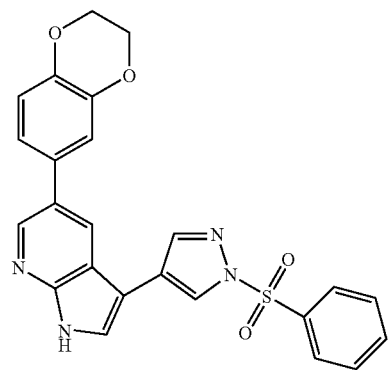
-continued
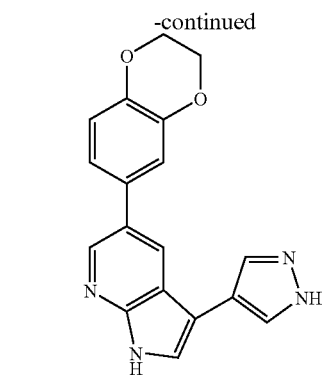
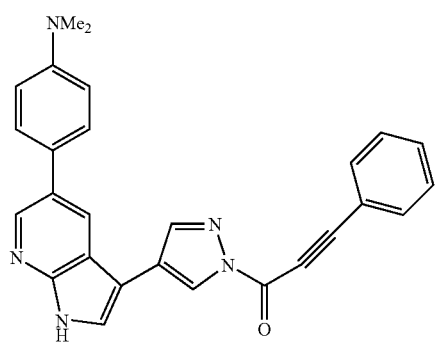
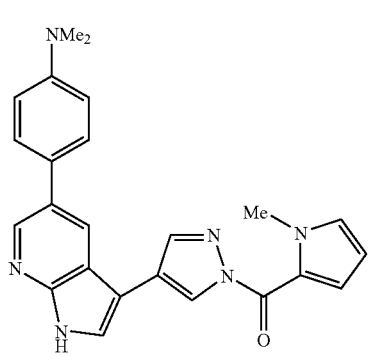
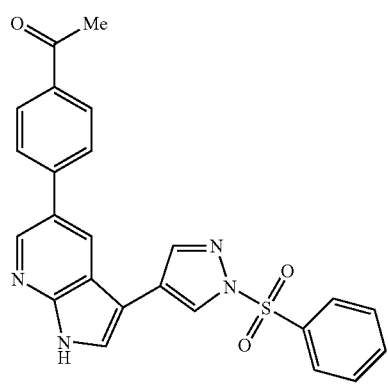

-continued
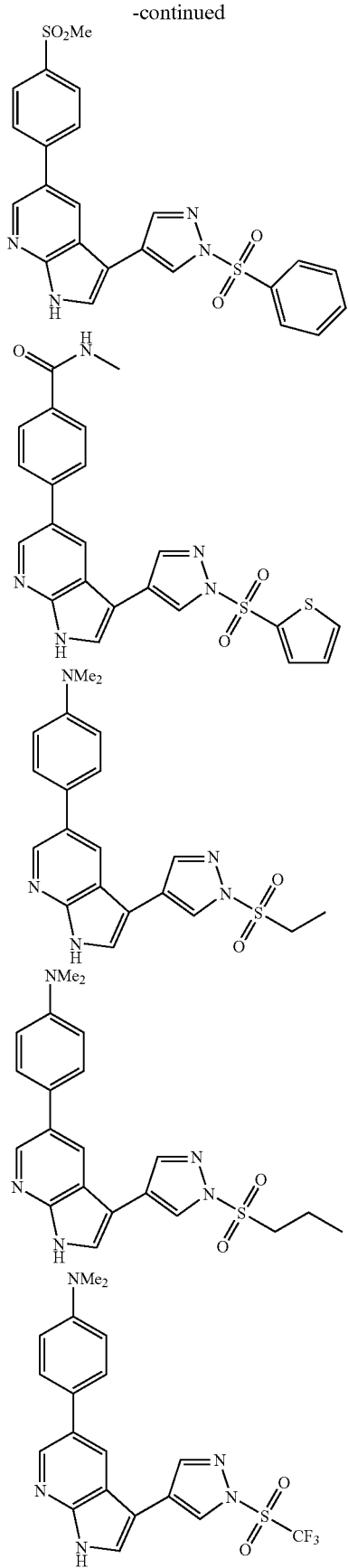
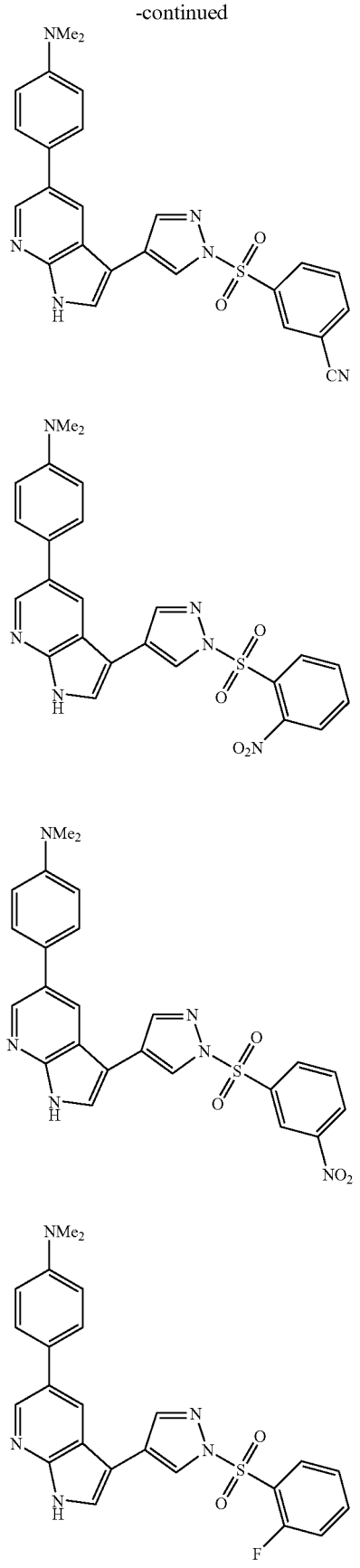

51
-continued
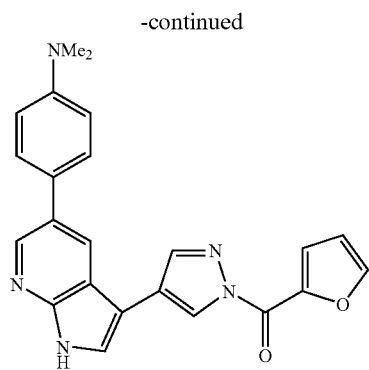
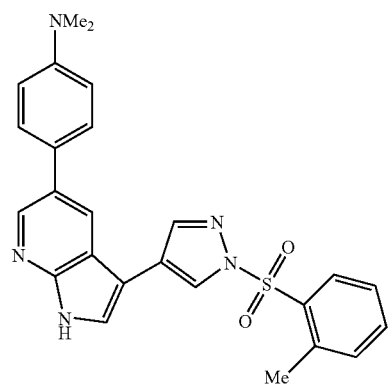
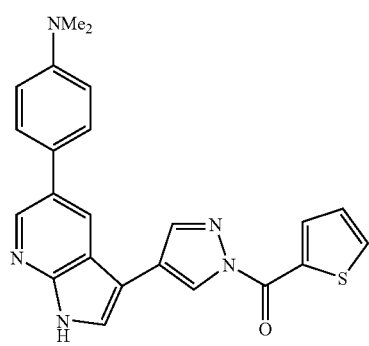
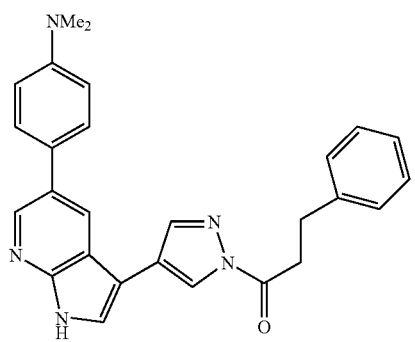
52
-continued
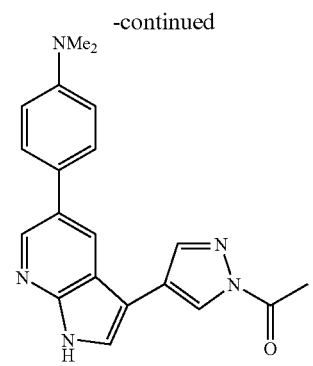
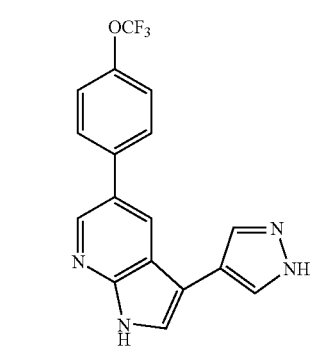
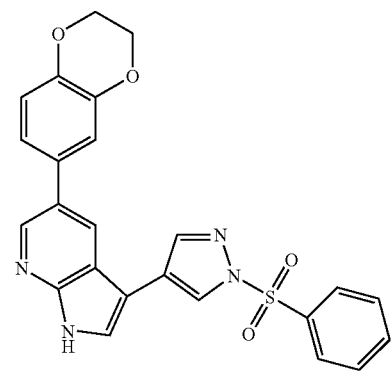
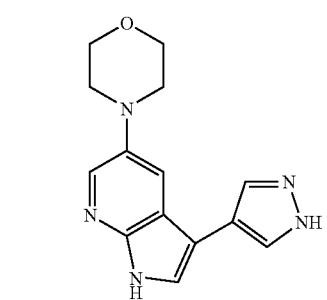

-continued
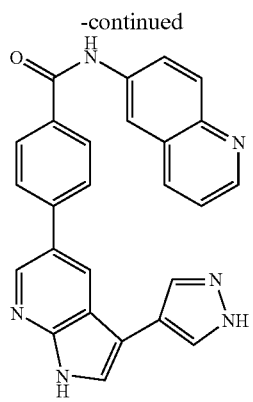
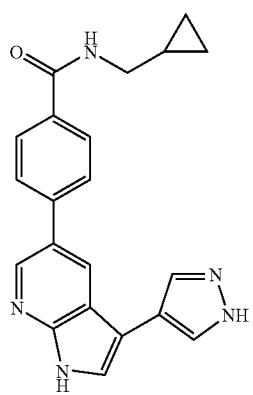
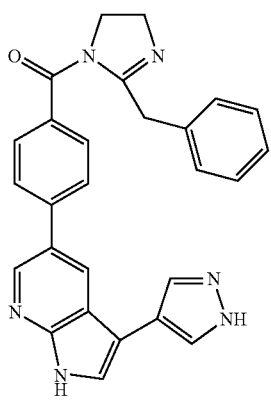
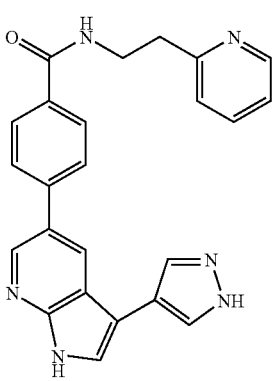
-continued
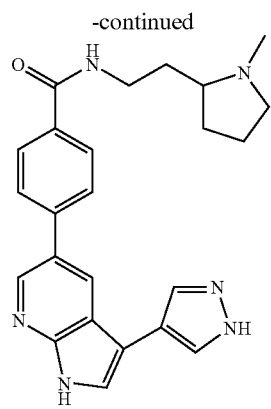
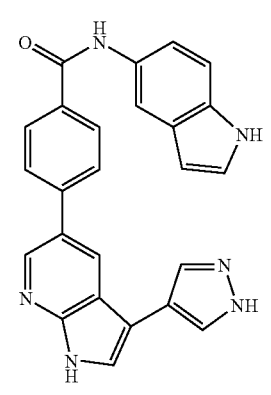
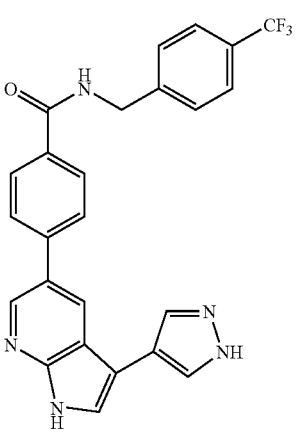
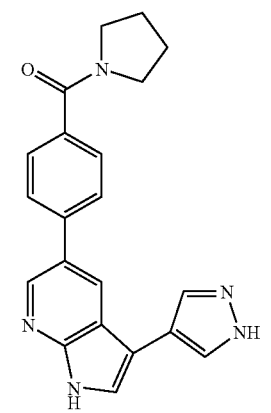

55
-continued
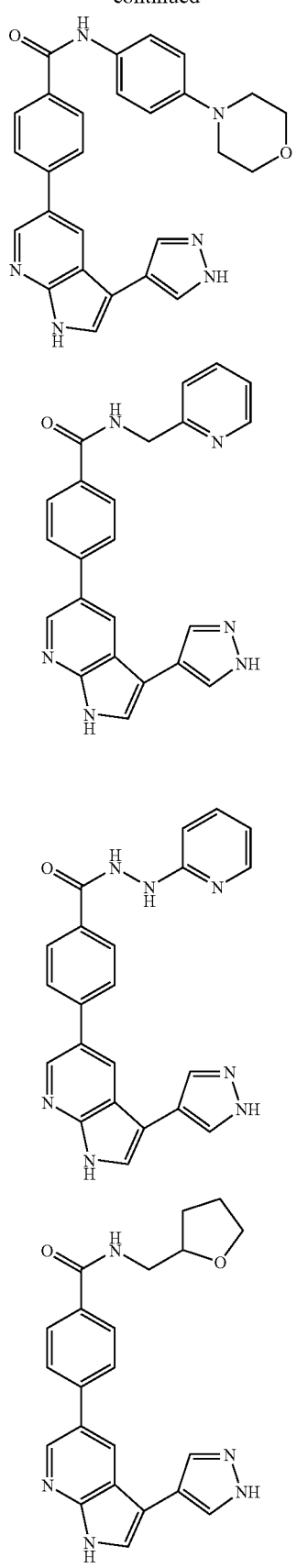
56
-continued
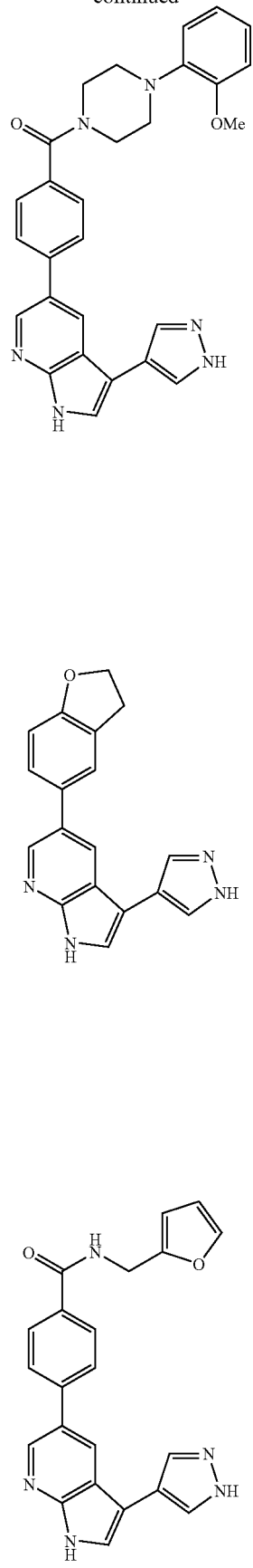

-continued
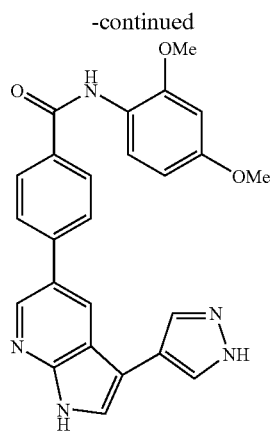
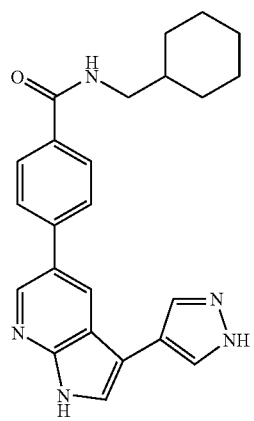
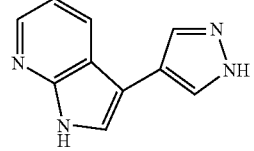
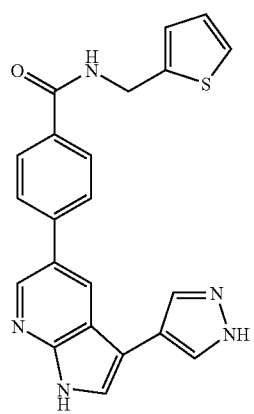
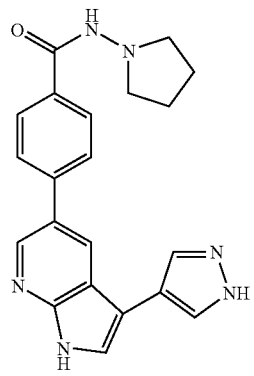
-continued
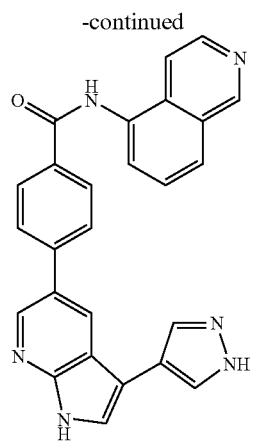
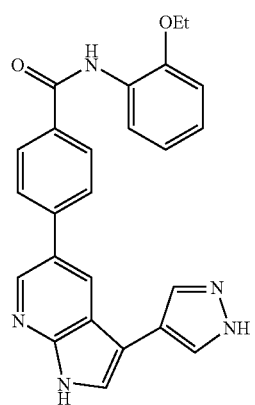
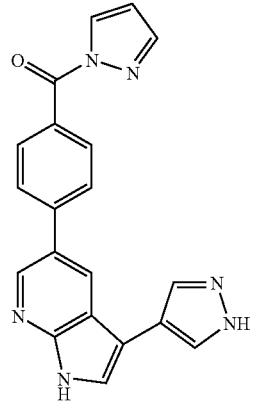
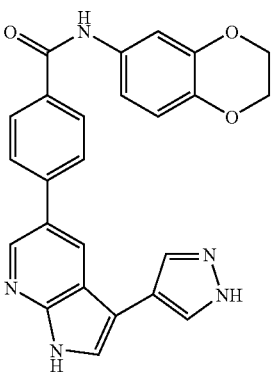

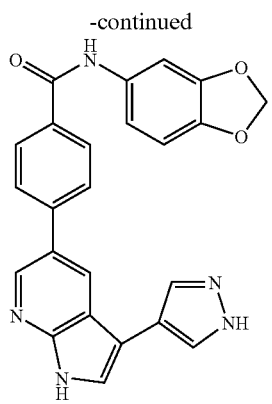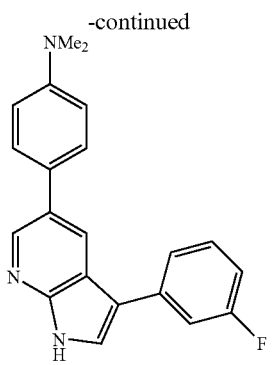

-continued
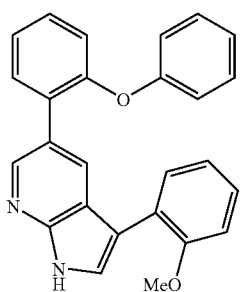
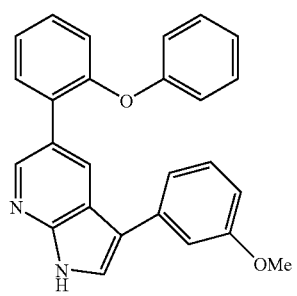
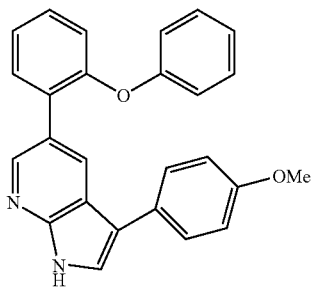
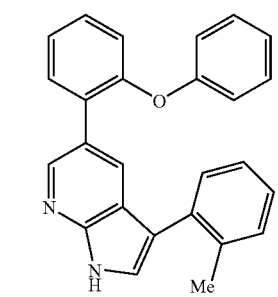
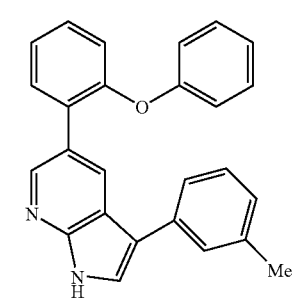
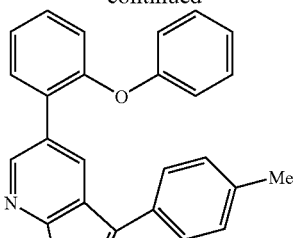
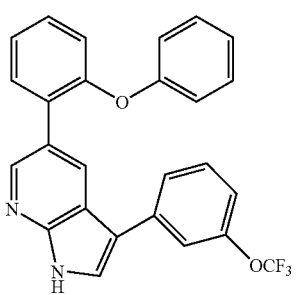
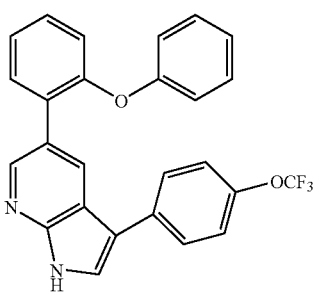
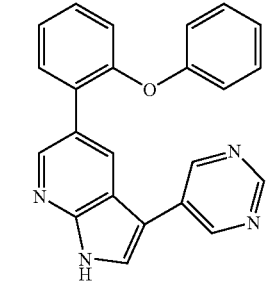
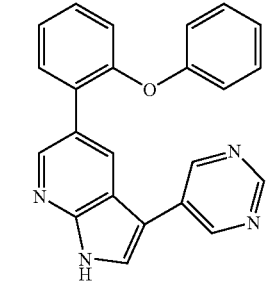

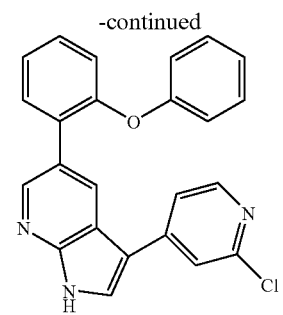
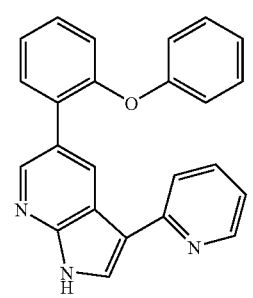
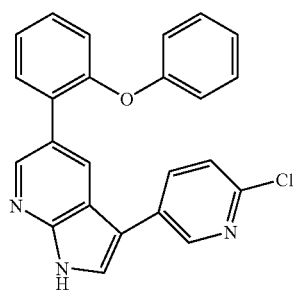
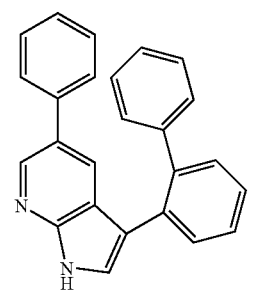
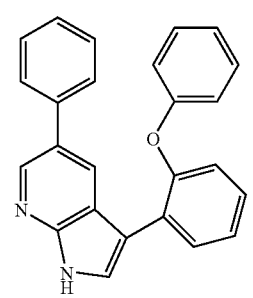
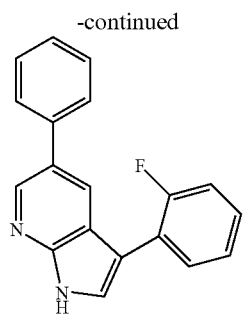
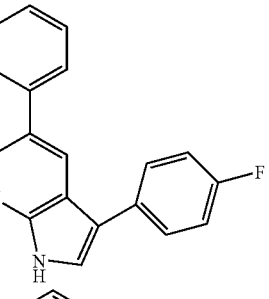
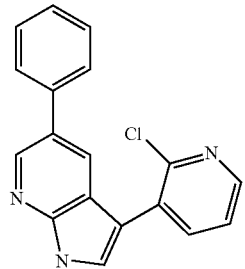
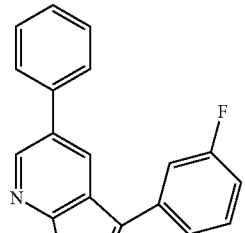
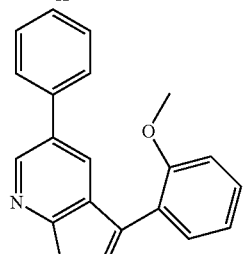
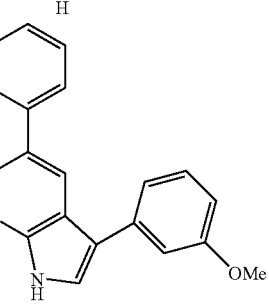

-continued
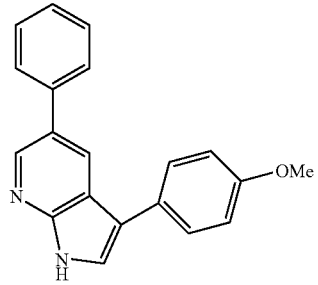
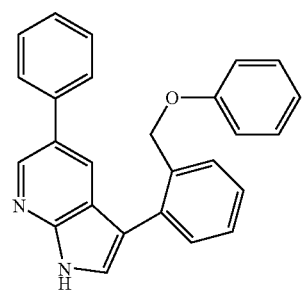
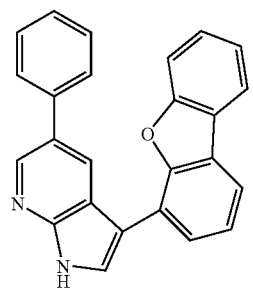
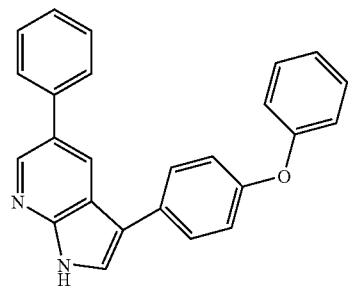
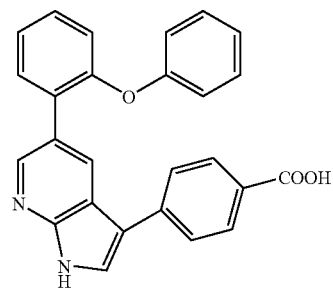
-continued
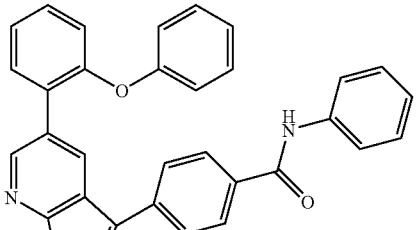
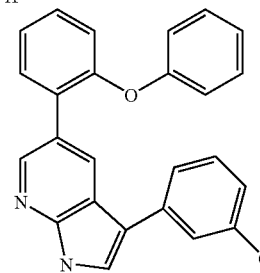
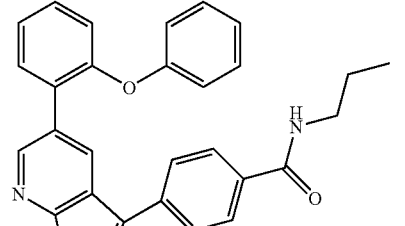
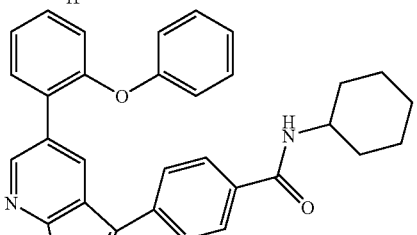
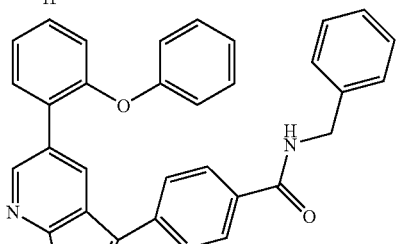
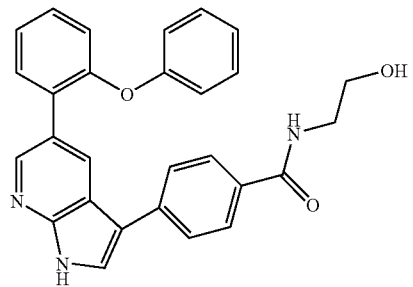

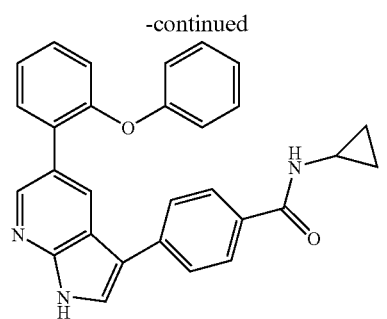
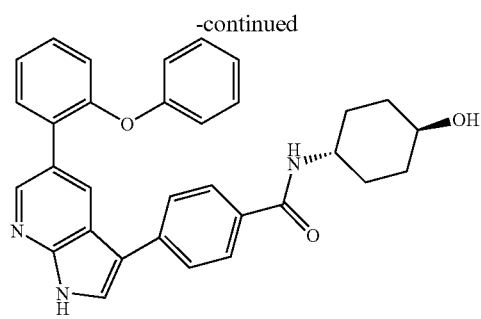
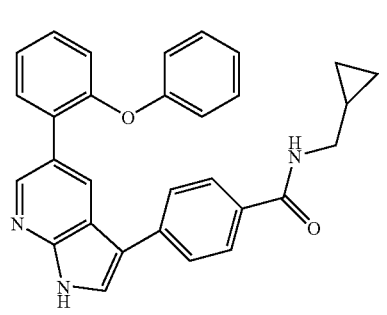
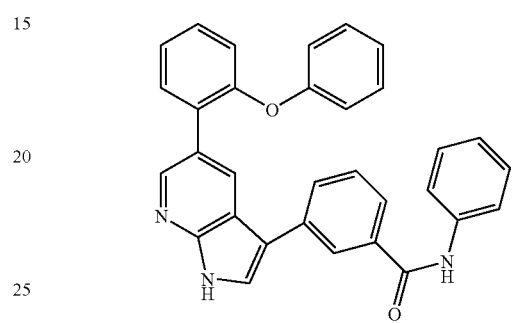
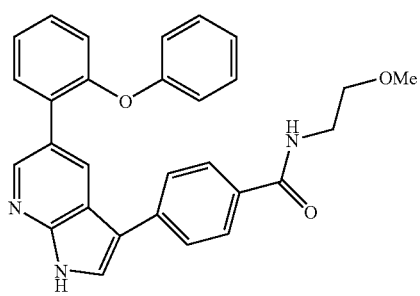
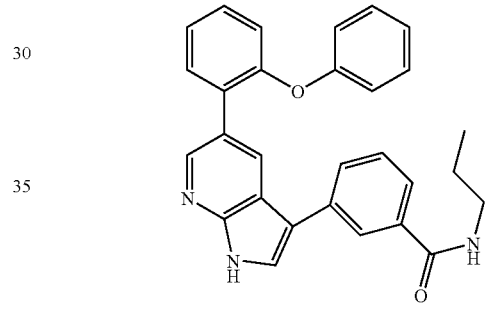
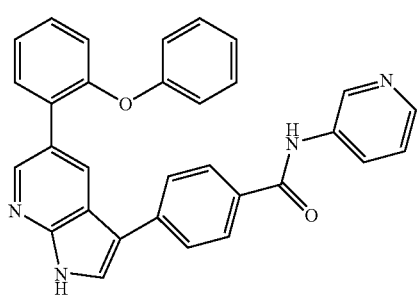
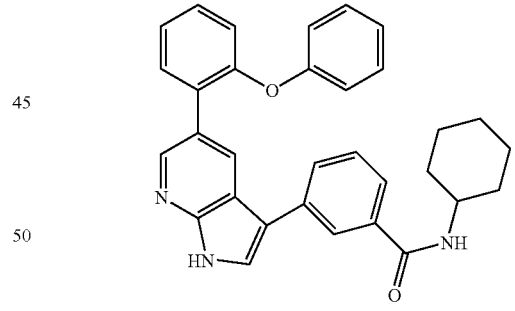
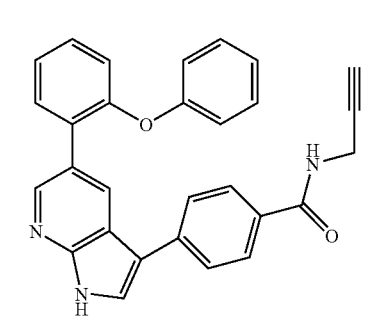
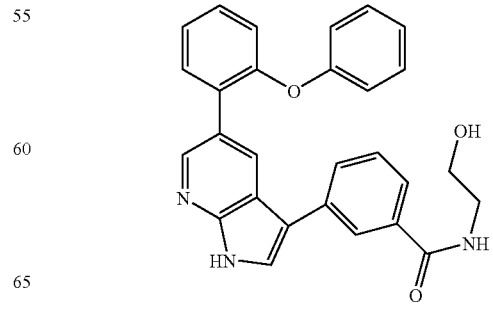

-continued

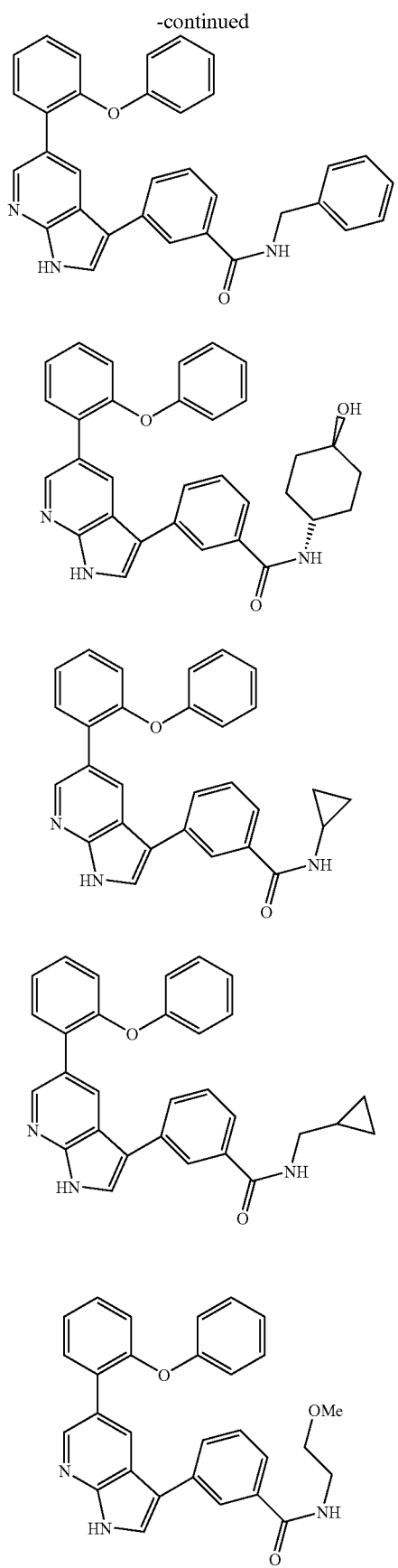

-continued

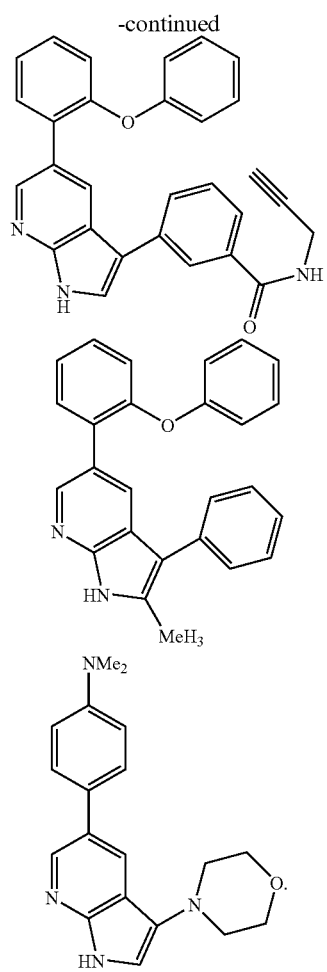

The compounds of the first aspect may be provided as a salt, preferably as a pharmaceutically acceptable salt of compounds of formula (I). Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases, which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine;

N-methylpiperazine; morpholine; ethylenediamine; N-benzylphenethylamine; tris(hydroxymethyl)aminomethane; and the like.

Salts may be prepared in a conventional manner using methods well known in the art. Acid addition salts of said basic compounds may be prepared by dissolving the free base compounds according to the first aspect of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

The invention also extends to a prodrug of the aforementioned compounds such as an ester or amide thereof. A prodrug is any compound that may be converted under physiological conditions or by solvolysis to any of the compounds of the invention or to a pharmaceutically acceptable salt of the compounds of the invention. A prodrug may be inactive when administered to a subject but is converted in vivo to an active compound of the invention.

The compounds of the invention may contain one or more asymmetric carbon atoms and may exist in racemic and optically active forms. The compounds of the invention may exist in trans or cis form. The first aspect of the invention covers all of these compounds.

The second aspect of the invention provides a process for the manufacture of a compound of formula (I) as defined in the first aspect of the invention comprising removal of group $R^{40}$ from an intermediate (III)

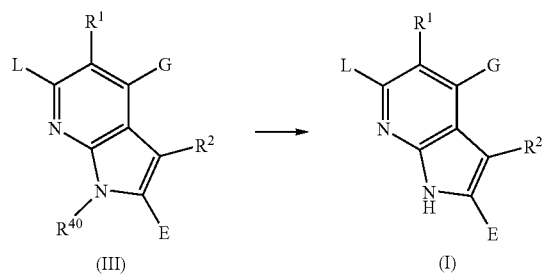

wherein $R^1$, $R^2$, E, G, and L are as defined in the first aspect, and wherein $R^{40}$ is an amino protecting group. The pyrrole nitrogen can be protected using any protection known in the art including $R^{31}SO_2$, $R^{31}C(O)$, $R^{31}{}_3Si$, $R^{31}OCH_2$, $(R^{31})_2NSO_2$, $(R^{31})_2NC(O)$, $R^{31}OC(O)$, $R^{31}(R^{31}O)CH$, $R^{31}CH_2CH_2$, $R^{31}CH_2$, $PhC(O)CH_2$, $CH_2$=CH, $ClCH_2CH_2$, $Ph_3C$, $Ph_2(4$-pyridyl$)C$, $Me_2N$, HO—$CH_2$, $R^{31}OCH_2$, $(R^{31})_3SiOCH_2$, $(R^{31}O)_2CH$, t-BuOC(O)$CH_2$, $Me_2NCH_2$, and tetrahydropyranylamine, wherein $R^{31}$ is $C_{1-6}$ alkyl or $C_{6-12}$ aryl.

More preferably $R^{40}$ is sulfonamide, most preferably benzenesulfonamide, $(R^{31})_2NSO_2$, and $(R^{31})_2NC(O)$, Removal of the protecting group can be afforded using conditions relevant to the protecting group used i.e. sulfonamide or amide protection can be removed by hydrolysis under basic conditions for example sodium hydroxide in water-ethanol, and silyl protection can be removed under acidic conditions for example TPA, HCl or using a source of fluoride, for example TBAF.

The third aspect of the invention provides a compound of formula (III)

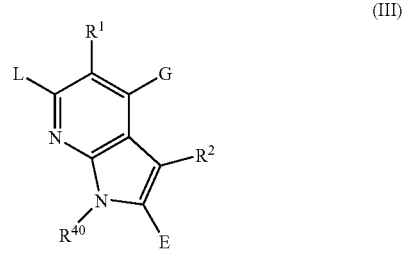

wherein $R^1$, $R^2$, E, G, and L are as defined in the first aspect and $R^{40}$ is a nitrogen protecting group as defined in the second aspect of the invention.

A compound of formula (III) may undergo one or more further reactions to provide a different compound of formula (III). For example, a compound may undergo a reduction, oxidation, elimination, substitution and/or addition reaction.

The fourth aspect of the invention provides a process for the manufacture of a compound of formula (III) as defined in the third aspect of the invention comprising a) reaction of a compound of formula (II) with stannane $R^1$—$Sn(R^{32})_3$ in the presence of a palladium catalyst or b) reaction of a compound of formula (II) with boronic acid or ester $R^1$—$B(OR^{33})_2$ in a presence of a suitable palladium catalyst or c) reaction of a compound of formula (II) with silane $R^1$—$Si(R^{34})_3$ in the presence of a palladium catalyst;

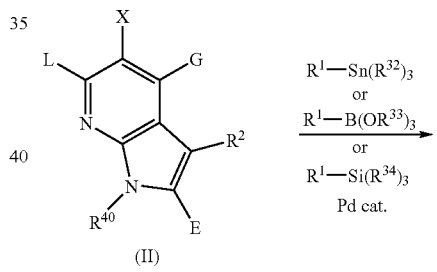

wherein $R^1$, $R^2$, E, G, and L are as defined in the first aspect, wherein $R^{40}$ is an amino protecting group as defined in the second aspect;

wherein X is F, Cl, Br I or $CF_3SO_3$ preferably I or Br, and wherein $R^{32}$ is independently $C_{1-6}$ alkyl;

wherein $R^{33}$ is independently hydrogen or $C_{1-6}$ alkyl or wherein two $R^{33}$ groups together optionally form a five, six or seven membered ring with the boron and oxygen atoms, wherein the ring is optionally substituted with one or more $C_{1-6}$ alkyl group. Preferably, $R^{33}$ is hydrogen or both $R^{33}$ groups form the group —$C(CH_3)_2$—$C(CH_3)_2$—;

and wherein $R^{34}$ is independently $C_{1-6}$ alkyl, F, OH

Suitable catalysts for the purpose of this invention include $(PPh_3)_2PdCl_2$, $(PPh_3)_4Pd$, $Pd(OAc)_2$, $[PdCl(\eta^3-C_3H_5)]_2$, $Pd_2(dba)_3$, $Pd(dba)_2$ (dba=dibenzylideneacetone), $Pd/P(t-Bu)_3$.

It will be appreciated that the reaction set out as option a) for the fourth aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343.

The reaction set out as option b) for the fourth aspect is a Suzuki reaction which can be carried out according to Suzuki Pure Appl. Chem. 1991, 63, 419 or Littke J. Am. Chem. Soc. 2000, 122, 4020

It will be appreciated that the reaction set out as option c) for the fourth aspect is a Hiyama reaction which can be carried out according to Hatanaka et al. J. Org. Chem. 1988, 53, 918, Hatanaka et al. Synlett, 1991, 845, Tamao et al. Tetrahedron Lett. 1989, 30, 6051 or Denmark et al. Org. Lett. 2000, 2, 565, ibid. 2491.

It will further be appreciated than when $R^{40}$ is replaced with hydrogen the process of the fourth aspect yields a compound of formula (I) as defined in the first aspect of the invention.

The fifth aspect of the invention provides a process for the manufacture of a compound of formula (II) comprising protection of the pyrrole nitrogen.

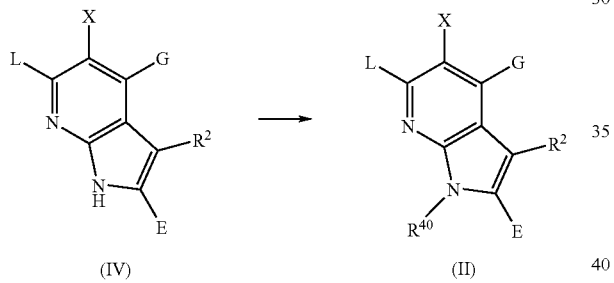

wherein $R^2$, E, G, and L are as defined in the first aspect of the invention wherein X is as defined in the fourth aspect of the invention wherein $R^{40}$ is as defined in the second aspect of the invention.

The sixth aspect of the invention provides a compound of formula (II)

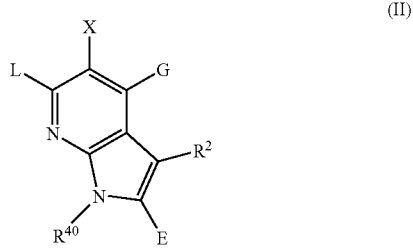

wherein $R^2$, E, G, and L are as defined in the first aspect wherein $R^{40}$ is a nitrogen protecting group defined in the second aspect of the invention; and wherein X is as defined in the fourth aspect of the invention.

The seventh aspect of the invention provides a process for the manufacture of a compound of formula (IV) comprising desilylation of a compound of formula (V)

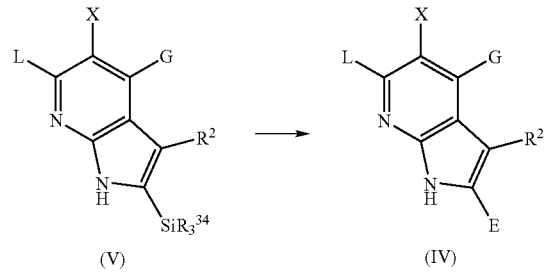

wherein $R^2$, E, G, and L are as defined in the first aspect of the invention and wherein X and $R^{34}$ are as defined in the fourth aspect Removal of the silyl group in (V) can be achieved under standard conditions by employing either a fluoride source (e.g. tetrabutylammonium fluoride) or acid (e.g. trifluoroacetic acid, HCl, etc).

The eighth aspect of the invention provides a compound of formula (IV)

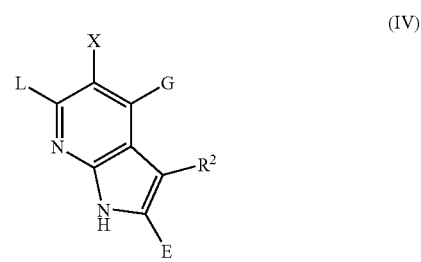

wherein $R^2$, E, G, and L are as defined in the first aspect wherein X is as defined in the fourth aspect The ninth aspect of the invention provides a process for the manufacture of a compound of formula (I) as defined in the first aspect of the invention comprising a a) reaction of a compound of formula (IV) with stannane $R^1$—$Sn(R^{32})_3$ in the presence of a palladium catalyst or b) reaction of a compound of formula (IV) with boronic acid or ester $R^1$—$B(R^{33})_2$ in a presence of a suitable palladium catalyst or c) reaction of a compound of formula (IV) with silane $R^1$—$Si(R^{34})_3$ in the presence of a palladium catalyst;

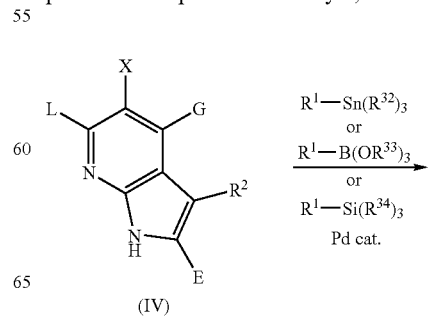

-continued

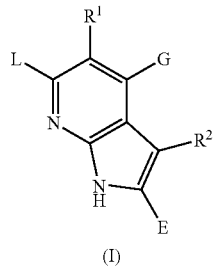

(I)

wherein $R^1$ and $R^2$, E, G, and L are as defined in the first aspect, wherein X is F, Cl, Br I or $CF_3SO_3$ preferably I or Br, and wherein $R^{32}$ is independently $C_{1-6}$ alkyl;

wherein $R^{33}$ is independently hydrogen or $C_{1-6}$ alkyl or wherein two $R^{33}$ groups together optionally form a five, six or seven membered ring with the boron and oxygen atoms, wherein the ring is optionally substituted with one or more $C_{1-6}$ alkyl group. Preferably, $R^{33}$ is hydrogen or both $R^{33}$ groups form the group —$C(CH_3)_2$—$C(CH_3)_2$—;

and wherein $R^{34}$ is independently $C_{1-6}$ alkyl, F, OH

Suitable catalysts for the purpose of this invention include $(PPh_3)_2PdCl_2$, $(PPh_3)_4Pd$, $Pd(OAc)_2$, $[PdCl(\eta^3-C_3H_5)]_2$, $Pd_2(dba)_3$, $Pd(dba)_2$ (dba=dibenzylidenacetone), $Pd/P(t-Bu)_3$.

It will be appreciated that the reaction set out as option a) for the ninth aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343.

The reaction set out as option b) for the ninth aspect is a Suzuki reaction which can be carried out according to Suzuki Pure Appl. Chem. 1991, 63, 419 or Littke J. Am. Chem. Soc. 2000, 122, 4020

It will be appreciated that the reaction set out as option c) for the ninth aspect is a Hiyama reaction which can be carried out according to Hatanaka et al. J. Org. Chem. 1988, 53, 918, Hatanaka et al. Synlett, 1991, 845, Tamao et al. Tetrahedron Lett. 1939, 30, 6051 or Denmark et al. Org. Lett. 2000, 2, 565, ibid. 2491.

The tenth aspect of the invention provides a compound of formula (V)

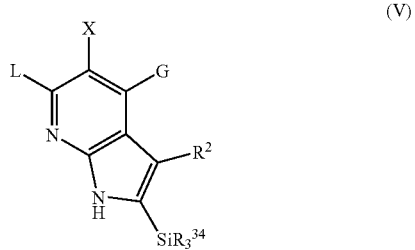

(V)

wherein $R^2$, G, and L are as defined in the first aspect wherein X and $R^{34}$ are as defined in the fourth aspect.

The eleventh aspect of the invention provides a process for the manufacture of a compound of formula (V) as defined in the tenth aspect of the invention comprising a reaction of acetylene of formula (VI) with iodoaminopyridine (VII).

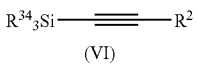
(VI)

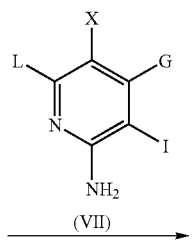
(VII)

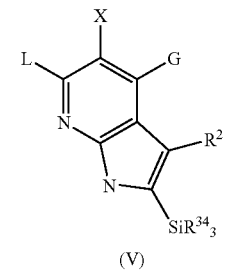
(V)

wherein $R^2$, G, and L are as defined in the first aspect of the invention wherein X is as defined in the fourth aspect wherein $R^{34}$ is as defined in the fourth aspect.

Compounds (VI) and (VII) undergo a palladium-catalyzed annulation reaction under conditions similar to those described by Park et al. (Tetrahedron Lett. 1998, 39, 627) to afford novel azaindole (V).

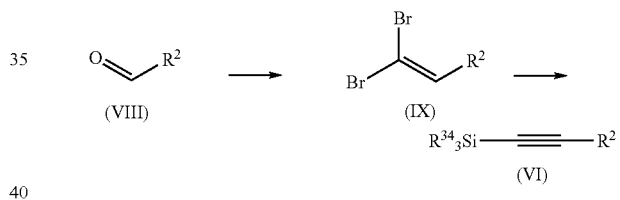

Silylated acetylene (VI) can be obtained from aldehyde (VIII), which can be converted into dibromide (IX) using the method described by Corey and Fuchs (Tetrahedron Lett. 1972, 36, 3769). Subsequent reaction of dibromide (IX) with n-BuLi followed by silylation under standard conditions affords silylated acetylene (VI).

The twelfth aspect of the invention provides an alternative process for the introduction of the group $R^1$ to obtain a compound of formula (III) as defined in the third aspect of the invention comprising reaction of a) boronic acid or ester (X) or b) stannane (XI) or c) silane (XII) with $R^1$-Hal in the presence of a suitable palladium catalyst.

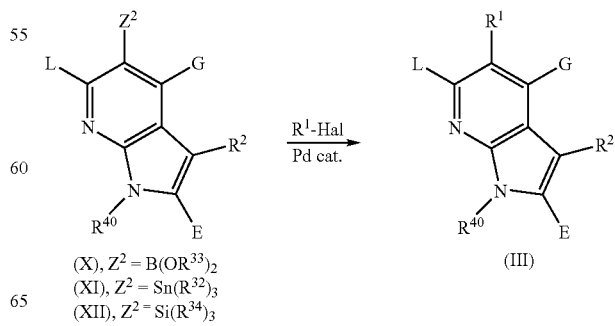

(X), $Z^2 = B(OR^{33})_2$
(XI), $Z^2 = Sn(R^{32})_3$
(XII), $Z^2 = Si(R^{34})_3$ (III)

wherein R¹, R², E, G, and L are as defined in the first aspect, wherein R⁴⁰ is as defined in the second aspect More preferably R⁴⁰ is sulfonamide, most preferably benzenesulfonamide, (R³¹)₂NSO₂, and (R³¹)₂NC(O), wherein Hal is I, Br, Cl, F or CF₃SO₃ wherein R³² is as defined in the fourth aspect wherein R³³ is as defined in the fourth aspect wherein R³⁴ is as defined in the fourth aspect Suitable catalysts for the purpose of this invention include (PPh₃)₂PdCl₂, (PPh₃)₄Pd, Pd(OAc)₂, [PdCl(η³-C₃H₅)]₂, Pd₂(dba)₃, Pd(dba)₂ (dba=dibenzylidenacetone), Pd/P(t-Bu)₃.

The reaction of R¹-Hal set out as option a) for the twelfth aspect is a Suzuki reaction which can be carried out according to Suzuki Pure Appl. Chem. 1991, 63, 419 or Littke J. Am. Chem. Soc. 2000, 122, 4020. The boronic ester (X) can then be reacted with a halide or triflate R¹-Hal, preferably iodide or bromide in the presence of a palladium catalyst. Suitable catalysts for the purpose of this invention include (PPh₃)₂PdCl₂, (PPh₃)₄Pd, Pd₂(dba)₃, Pd(dba)₂ (dba=dibenzylidenacetone), or Pd(OAc)₂

It will be appreciated that the reaction of R¹-Hal set out as option b) for the twelfth aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343. The stannyl derivative (XI) can be reacted with a halide or triflate (R¹-Hal), preferably iodide or bromide, in the presence of a palladium catalyst. Suitable catalysts for the purpose of this invention are those suitable for Stille coupling reaction for example PdCl₂(MeCN)₂, Pd/P(t-Bu)₃, or Pd₂(dba)₃, Pd(dba)₂ (dba=dibenzylidenacetone).

It will be appreciated that the reaction of R¹-Hal set out as option c) for the twelfth aspect is a Hiyama reaction which can be carried out according to Hatanaka et al. J. Org. Chem. 1988, 53, 918, Hatanaka et al. Synlett, 1991, 845, Tamao et al. Tetrahedron Lett. 1989, 30, 6051 or Denmark et al. Org. Lett. 2000, 2, 565, ibid. 2491. Compound (XII) can be reacted with a halide or triflate (R¹-Hal), preferably iodide or bromide, in the presence of a palladium catalyst. Suitable catalysts for the purpose of this invention are those suitable for Hiyama coupling reaction for example [PdCl(η³-C₃H₅)]₂, Pd₂(dba)₃, or Pd(dba)₂ (dba=dibenzylidenacetone)

Compound of formula (X) can be formed, for example, from a compound of formula (II) by reaction with a strong base such as tert-BuLi followed by trialkylborate B(OR³³)₃.

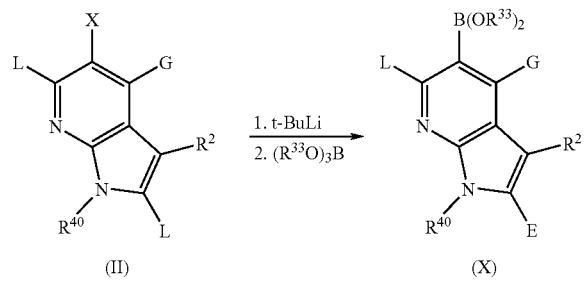

Alternatively, compound (X) can be prepared by incubating a compound of formula (II) with B(R³⁵)₃ or (R³⁵)₂B—B(R³⁵)₂ wherein each R³⁵ is independently hydrogen or OR³³, wherein R³³ is as defined in the fourth aspect. Preferably two OR³³ groups form the group —OC(CH₃)₂—C(CH₃)₂O—. Conversion of (II) to (X) can be catalysed by a palladium catalyst, such as PdCl₂ or PdCl₂(1,1'-bis(diphenylphosphino) ferrocene).

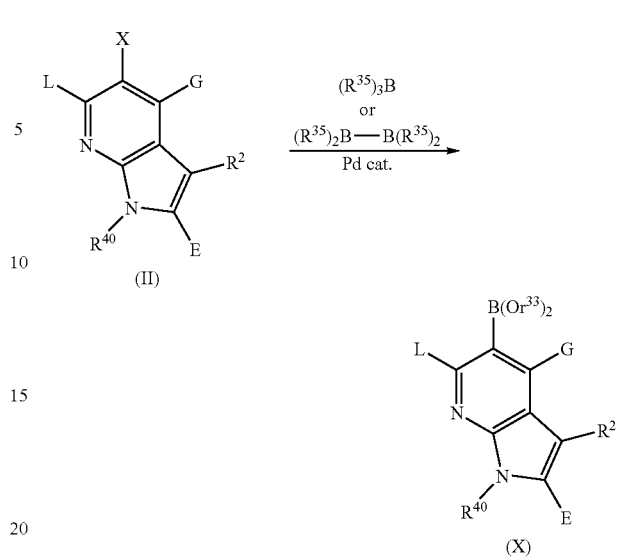

For example, compound (II) (X=Br, E=G=L=hydrogen), may be converted into the relevant pinacol boronic ester (X).

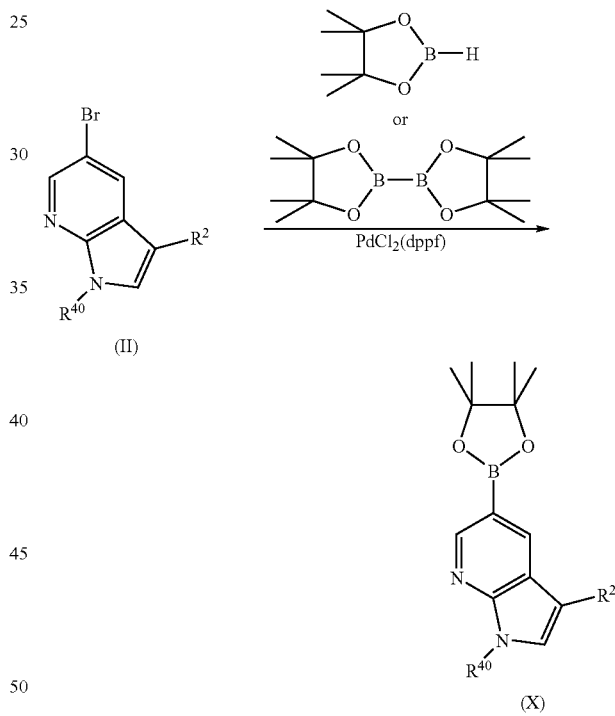

Formation of a compound of formula (XI) from a compound of formula (II) can be achieved by reaction with a strong base such as tert-BuLi followed by (R³²)₃Sn-Hal wherein each R³² is as defined in the fourth aspect of the invention

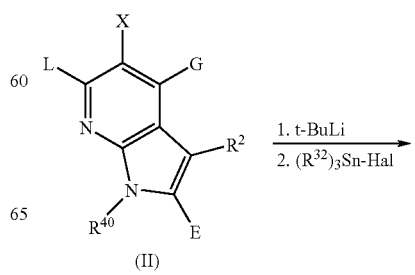

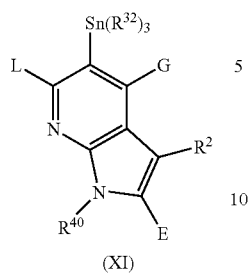

(XI)

Silicon derivative of formula (XII) may be synthesized from a compound of formula (II) by reaction with a strong base such as n-BuLi or tert-BuLi followed by halosilane $(R^{34})_3Si-Hal$ or siloxane $[(R^{34})_2SiO]_3$ wherein each $R^{34}$ is as defined in the fourth aspect of the invention

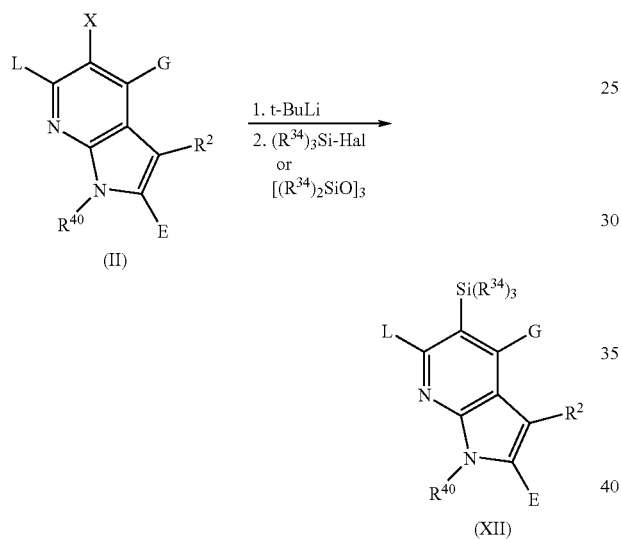

The thirteenth aspect of the invention provides a compound of formula (X)

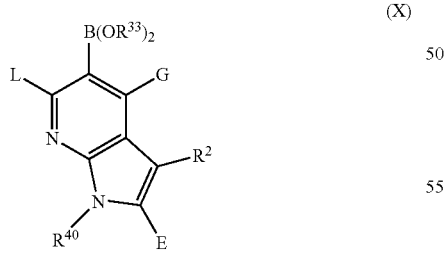

(X)

wherein $R^2$, E, G, and L are as defined in the first aspect wherein $R^{40}$ is as defined in the second aspect wherein $R^{33}$ is as defined in the fourth aspect A preferred compound of formula (X), (Xa) is illustrated below, wherein E, G, and L are hydrogen, and $R^{40}$ and $R^2$ are as defined above.

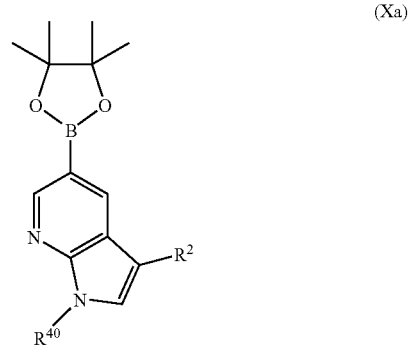

(Xa)

An intermediate of the thirteenth aspect of the invention may be converted into another intermediate of the thirteenth aspect. For example, an intermediate compound may undergo a reduction, oxidation, elimination, substitution and/or addition reaction.

The fourteenth aspect of the invention provides a compound of formula (XI)

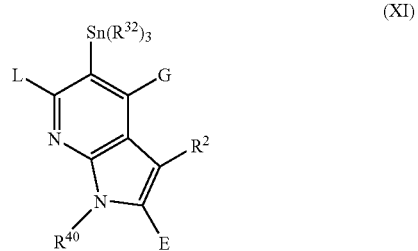

(XI)

wherein $R^2$, E, G, and L are as defined in the first aspect wherein $R^{40}$ is as defined in the second aspect wherein $R^{32}$ is as defined in the fourth aspect An intermediate of the fourteenth aspect of the invention may be converted into another intermediate of the fourteenth aspect. For example, an intermediate compound may undergo a reduction, oxidation, elimination, substitution and/or addition reaction.

The fifteenth aspect of the invention provides a compound of formula (XII)

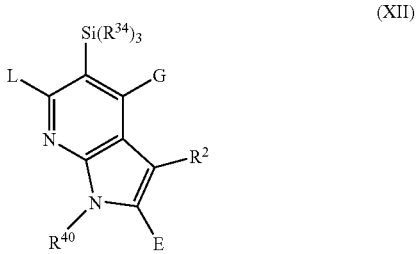

(XII)

wherein $R^2$, E, G, and L are as defined in the first aspect wherein $R^{40}$ is as defined in the second aspect wherein $R^{34}$ is as defined in the fourth aspect An intermediate of the fifteenth aspect of the invention may be converted into another intermediate of the fifteenth aspect. For example, an intermediate compound may undergo a reduction, oxidation, elimination, substitution and/or addition reaction.

The sixteenth aspect of the invention provides an alternative process for the introduction of the group $R^1$ to obtain a compound of formula (I) as defined in the first aspect of the invention comprising reaction of a) boronic acid or ester (L) or b) stannane (LI) or c) silane (LII) with $R^1$-Hal in the presence of a suitable palladium catalyst.

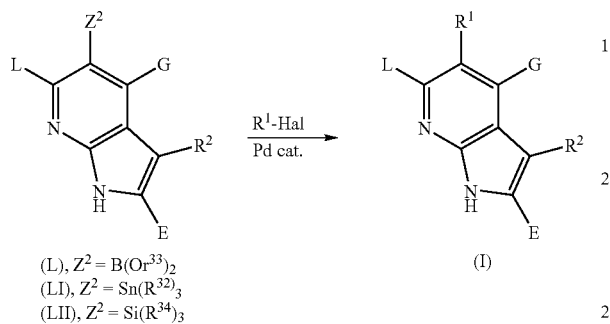

(L), $Z^2 = B(Or^{33})_2$
(LI), $Z^2 = Sn(R^{32})_3$
(LII), $Z^2 = Si(R^{34})_3$ wherein $R^1$, $R^2$, E, G, and L are as defined in the first aspect, wherein Hal is I, Br, Cl, F or $CF_3SO_3$ wherein $R^{32}$ is as defined in the fourth aspect wherein $R^{33}$ is as defined in the fourth aspect wherein $R^{34}$ is as defined in the fourth aspect Suitable catalysts for the purpose of this invention include $(PPh_3)_2PdCl_2$, $(PPh_3)_4Pd$, $Pd(OAc)_2$, $[PdCl(\eta^3-C_3H_5)]_2$, $Pd_2(dba)_3$, $Pd(dba)_2$ (dba=dibenzylidenacetone), $Pd/P(t-Bu)_3$.

The reaction of $R^1$-Hal set out as option a) for the sixteenth aspect is a Suzuki reaction which can be carried out according to Suzuki Pure Appl. Chem. 1991, 63, 419 or Littke J. Am. Chem. Soc. 2000, 122, 4020. The boronic ester (L) can then be reacted with a halide or triflate $R^1$-Hal, preferably iodide or bromide in the presence of a palladium catalyst. Suitable catalysts for the purpose of this invention include $(PPh_3)_2PdCl_2$, $(PPh_3)_4Pd$, $Pd_2(dba)_3$, $Pd(dba)_2$ (dba=dibenzylidenacetone), or $Pd(OAc)_2$ It will be appreciated that the reaction of $R^1$-Hal set out as option b) for the sixteenth aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343. The stannyl derivative (LI) can be reacted with a halide or triflate ($R^1$-Hal), preferably iodide or bromide, in the presence of a palladium catalyst. Suitable catalysts for the purpose of this invention are those suitable for Stille coupling reaction for example $PdCl_2(MeCN)_2$, $Pd/P(t-Bu)_3$, or $Pd_2(dba)_3$, $Pd(dba)_2$ (dba=dibenzylidenacetone).

It will be appreciated that the reaction of $R^1$-Hal set out as option c) for the sixteenth aspect is a Hiyama reaction which can be carried out according to Hatanaka et al. J. Org. Chem. 1988, 53, 918, Hatanaka et al. Synlett, 1991, 845, Tamao et al. Tetrahedron Lett. 1989, 30, 6051 or Denmark et al. Org. Lett. 2000, 2, 565, ibid. 2491. Compound (LII) can be reacted with a halide or triflate ($R^1$-Hal), preferably iodide or bromide, in the presence of a palladium catalyst. Suitable catalysts for the purpose of this invention are those suitable for Hiyama coupling reaction for example $[PdCl(\eta^3-C_3H_5)]_2$, $Pd_2(dba)_3$, or $Pd(dba)_2$ (dba=dibenzylidenacetone)

Compound of formula (L) can be formed, for example, from a compound of formula (IV) by reaction with a strong base such as tert-BuLi followed by trialkylborate $B(OR^{33})_3$.

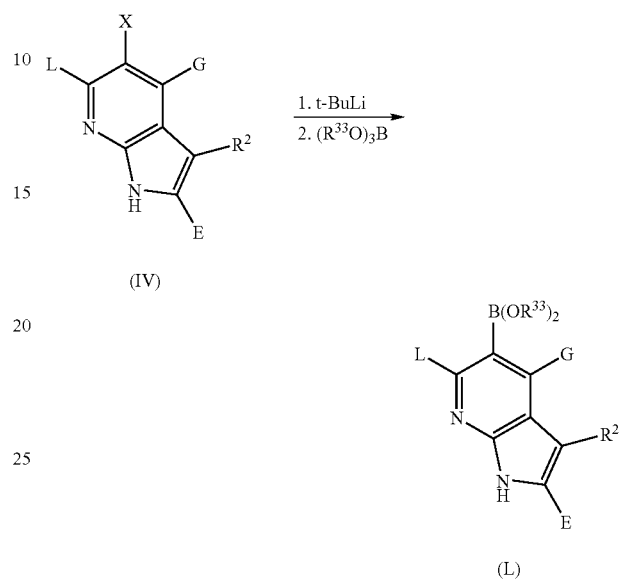

Alternatively, compound (L) can be prepared by incubating a compound of formula (IV) with $B(R^{35})_3$ or $(R_{35})_2B$—B$(R^{35})_2$ wherein each $R^{35}$ is independently hydrogen or $OR^{33}$, wherein $R^{33}$ is as defined in the fourth aspect Preferably two $OR^{33}$ groups form the group $—OC(CH_3)_2—C(CH_3)_2O—$. Conversion of (IV) to (L) can be catalysed by a palladium catalyst, such as $PdCl_2$ or $PdCl_2$(1,1'-bis(diphenylphosphino) ferrocene).

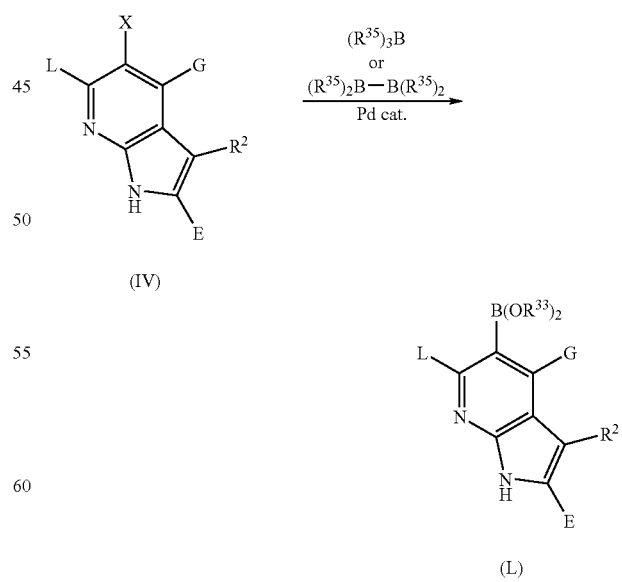

For example, compound (II) (X=Br, E=G=L=H), may be converted into the relevant pinacol boronic ester (L).

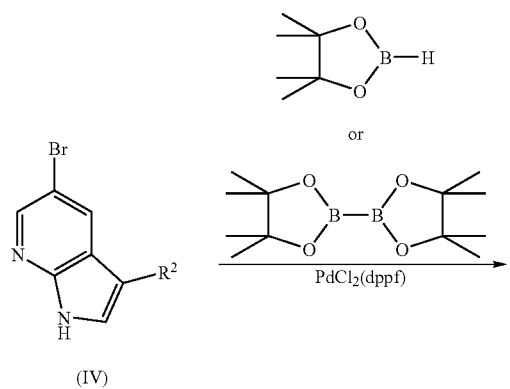

(IV)

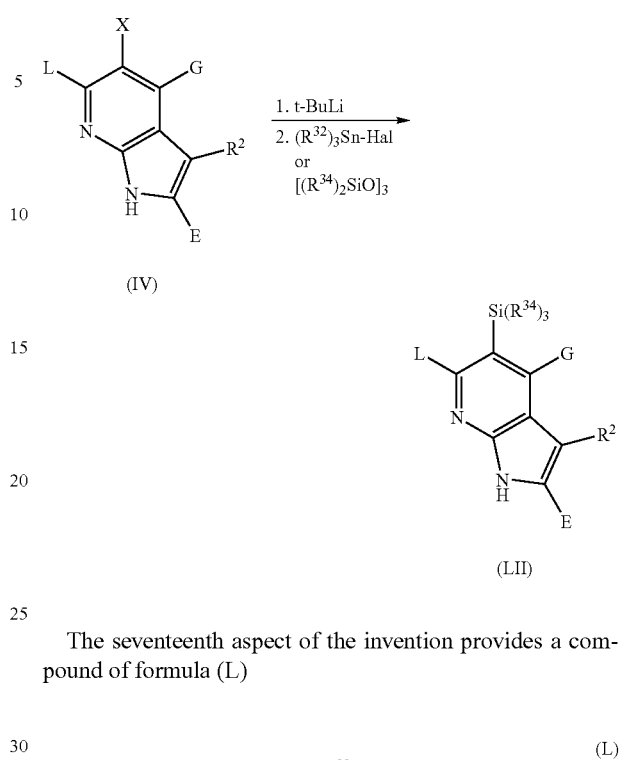

(IV)

(LII)

The seventeenth aspect of the invention provides a compound of formula (L)

(L)

Formation of a compound of formula (LI) from a compound of formula (IV) can be achieved by reaction with a strong base such as tert-BuLi followed by $(R^{32})_3$Sn-Hal wherein each $R^{32}$ is as defined in the fourth aspect of the invention

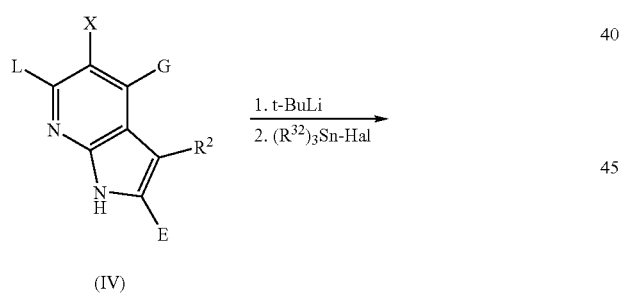

(LI)

Silicon derivative of formula (LII) may be synthesized from a compound of formula (IV) by reaction with a strong base such as n-BuLi or tert-BuLi followed by halosilane $(R^{34})_3$Si-Hal or siloxane $[(R^{34})_2SiO]_3$ wherein each $R^{34}$ is as defined in the fourth aspect of the invention

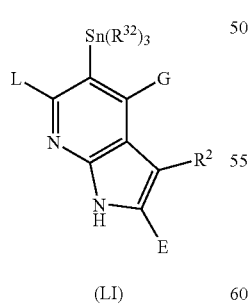

wherein $R^2$, E, G, and L are as defined in the first aspect wherein $R^{33}$ is as defined in the fourth aspect A preferred compound of formula (L), (La) is illustrated below, wherein E=G=L=hydrogen and $R^2$ is as defined above.

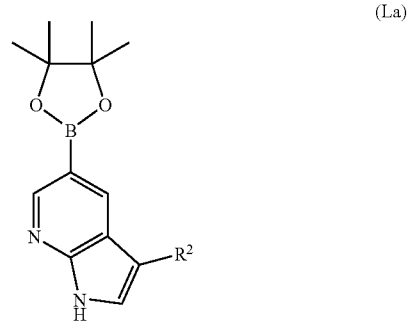

(La)

An intermediate of the seventeenth aspect of the invention may be converted into another intermediate of the seventeenth aspect. For example, an intermediate compound may undergo a reduction, oxidation, elimination, substitution and/or addition reaction.

The eighteenth aspect of the invention provides a compound of formula (LI)

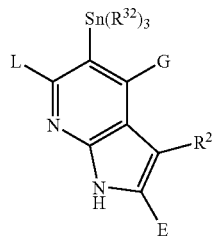

(LI)

wherein $R^2$, E, G, and L are as defined in the first aspect wherein $R^{32}$ is as defined in the fourth aspect An intermediate of the eighteenth aspect of the invention may be converted into another intermediate of the eighteenth aspect. For example, an intermediate compound may undergo a reduction, oxidation, elimination, substitution and/or addition reaction.

The nineteenth aspect of the invention provides a compound of formula (LII)

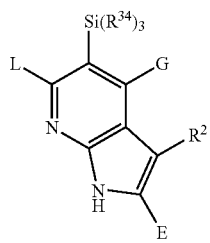

(LII)

wherein $R^2$, E, G, and L are as defined in the first aspect wherein $R^{34}$ is as defined in the fourth aspect An intermediate of the nineteenth aspect of the invention may be converted into another intermediate of the nineteenth aspect. For example, an intermediate compound may undergo a reduction, oxidation, elimination, substitution and/or addition reaction.

The twentieth aspect of the invention provides a process for the manufacture of an intermediate of formula (III) comprising a a) reaction of a compound of formula (XIII) with stannane $R^2$—$Sn(R^{32})_3$ in the presence of a palladium catalyst or b) reaction of a compound of formula (XIII) with boronic acid or ester $R^2$—$B(OR^{33})_2$ in a presence of a suitable palladium catalyst or c) reaction of a compound of formula (XIII) with silane $R^2$—$Si(R^{34})_3$ in the presence of a palladium catalyst;

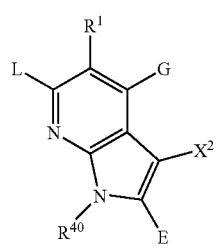 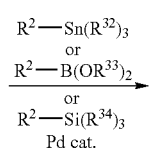

(XIII)

-continued

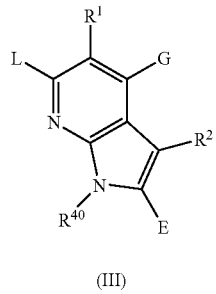

(III)

wherein $R^1$, $R^2$, E, G, and L are as defined in the first aspect, wherein $R^{40}$ is as defined in the second aspect wherein $R^{32}$, $R^{33}$ and $R^{34}$ are as defined in the fourth aspect and $X^2$ is F, Cl, Br, I or $CF_3SO_2$, preferably Br or I;

Suitable catalysts for the purpose of this invention include $(PPh_3)_2PdCl_2$, $(PPh_3)_4Pd$, $Pd(OAc)_2$, $[PdCl(\eta^3\text{-}C_3H_5)]_2$, $Pd_2(dba)_3$, $Pd(dba)_2$ (dba=dibenzylidenacetone), $Pd/P(t\text{-}Bu)_3$.

It will be appreciated that the reaction set out as option a) for the twentieth aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343.

The reaction set out as option b) for the twentieth aspect is a Suzuki reaction which can be carried out according to Suzuki Pure Appl Chem. 1991, 63, 419 or Littke J. Am. Chem. Soc. 2000, 122, 4020

It will be appreciated that the reaction set out as option c) for the twentieth aspect is a Hiyama reaction which can be carried out according to Hatanaka et al. J. Org. Chem. 1988, 53, 918, Hatanaka et al. Synlett, 1991, 845, Tamao et al. Tetrahedron Lett. 1989, 30, 6051 or Denmark et al. Org. Lett. 2000, 2, 565, ibid. 2491.

The twenty first aspect of the invention provides a compound of formula (XIII)

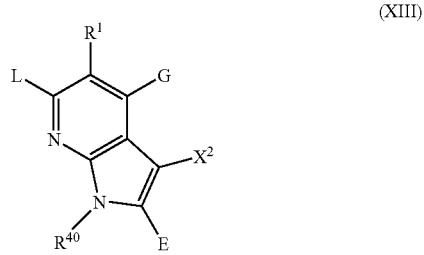

(XIII)

wherein $R^1$, E, G, and L are as defined in the first aspect wherein $X^2$ is as defined in the twentieth aspect; and $R^{40}$ is an amino protecting group as defined in the second aspect with the proviso that when $R^{40}$ is $Si(R^{31})_3$, and $R^1$ is a five-membered heterocyclyl at least one of $R^{31}$ is not $C_{1-6}$ alkyl. The protecting group $R^{40}$ is preferably selected from $R^{31}SO_2$, $R^{31}C(O)$—, or $(R^{31})_2NC(O)$— wherein $R^{31}$ is $C_{1-12}$ alkyl or $C_{6-12}$ aryl, or $R^{31}_3Si$ wherein at least one of $R^{31}$ is $C_{7-12}$ alkyl or $C_{6-12}$ aryl and one or more of the remaining $R^{31}$ groups are independently $C_{1-12}$ alkyl or $C_{6-12}$ aryl.

An intermediate of the twenty first aspect of the invention may be converted into another intermediate of the twenty first aspect. For example, an intermediate compound may undergo a reduction, oxidation, elimination, substitution and/or addition reaction.

The twenty second aspect of the invention provides an alternative process for the introduction of the group $R^2$ to obtain a compound of formula (III) as defined in the third aspect of the invention comprising reaction of a) boronic acid or ester (XIV) or b) stannane (XV) or c) silane (XVI) with $R^2$-Hal in the presence of a suitable palladium catalyst.

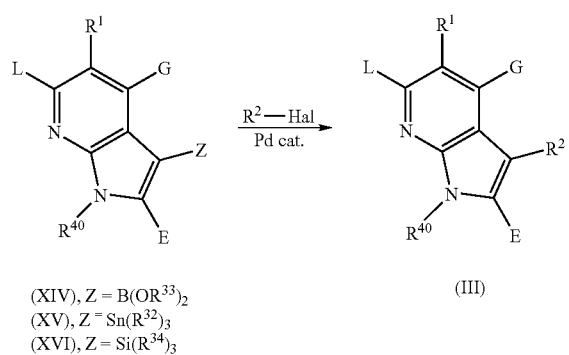

(XIV), Z = B(OR$^{33}$)$_2$
(XV), Z = Sn(R$^{32}$)$_3$
(XVI), Z = Si(R$^{34}$)$_3$ wherein $R^1$, $R^2$, E, G, and L are as defined in the first aspect, wherein $R^{40}$ is as defined in the second aspect.

More preferably $R^{40}$ is silyl, preferably tert-butyldimethylsilyl (TBS), or sulfonamide, most preferably benzenesulfonamide, $(R^{40})_2NSO_2$, and $(R^{40})_2NC(O)$, wherein Hal is I, Br, Cl, F or $CF_3SO_3$, preferably I or Br wherein $R^{32}$ is as defined in the fourth aspect wherein $R^{33}$ is as defined in the fourth aspect wherein $R^{34}$ is as defined in the fourth aspect Suitable catalysts for the purpose of this invention include $(PPh_3)_2PdCl_2$, $(PPh_3)_4Pd$, $Pd(OAc)_2$, $[PdCl(\eta^3-C_3H_5)]_2$, $Pd_2(dba)_3$, $Pd(dba)_2$ (dba=dibenzylidenacetone), Pd/P(t-Bu)$_3$.

The reaction of $R^2$-Hal set out as option a) for the twenty second aspect is a Suzuki reaction which can be carried out according to Suzuki Pure Appl. Chem. 1991, 63, 419 or Littke J. Am. Chem. Soc. 2000, 122, 4020. The boronic ester (XIV) can then be reacted with a halide or triflate ($R^2$-Hal), preferably iodide or bromide in the presence of a palladium catalyst. Suitable catalysts for the purpose of this invention include $(PPh_3)_2PdCl_2$, $(PPh_3)_4Pd$, $Pd_2(dba)_3$, $Pd(dba)_2$ (dba=dibenzylidenacetone), or $Pd(OAc)_2$ It will be appreciated that the reaction of $R^2$-Hal set out as option b) for the twenty second aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343. The stannyl derivative (XV) can be reacted with a halide or triflate ($R^2$-Hal), preferably iodide or bromide, in the presence of a palladium catalyst. Suitable catalysts for the purpose of this invention are those suitable for Stille coupling reaction, for example $PdCl_2(MeCN)_2$, $Pd/P(t-Bu)_3$, $Pd_2(dba)_3$ or $Pd(dba)_2$ (dba=dibenzylidenacetone).

It will be appreciated that the reaction of $R^2$-Hal set out as option c) for the twenty second aspect is a Hiyama reaction which can be carried out according to Hatanaka et al. J. Org. Chem. 1988, 53, 918, Hatanaka et al. Synlett, 1991, 845, Tamao et al. Tetrahedron Lett. 1989, 30, 6051 or Denmark et al. Org. Lett. 2000, 2, 565, ibid. 2491. Compound (XVI) can be reacted with a halide or triflate ($R^2$-Hal), preferably iodide or bromide, in the presence of a palladium catalyst. Suitable catalysts for the purpose of this invention are those suitable for Hiyama coupling reaction for example $[PdCl(\Theta^3-C_3H_5)]_2$, $Pd_2(dba)_3$, or $Pd(dba)_2$ (dba=dibenzylidenacetone)

Compound of formula (XIV) can be formed, for example, from a compound of formula (XIII) by reaction with a strong base such as tert-BuLi followed by trialkylborate B(OR$^{33}$)$_3$.

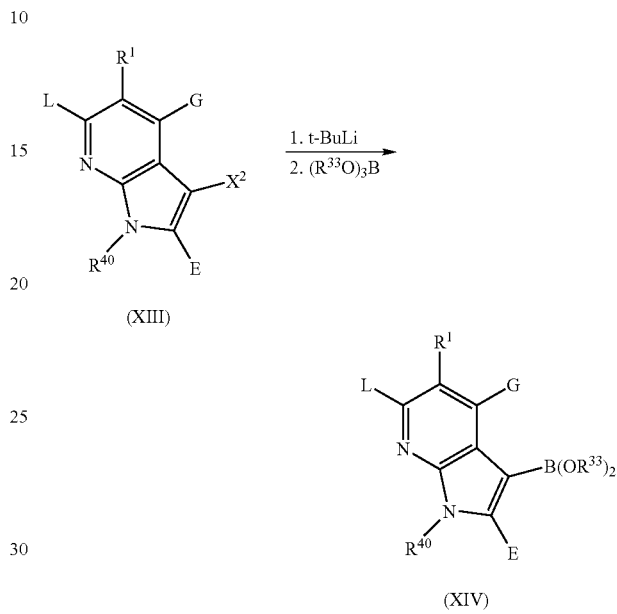

(XIII)

(XIV)

Alternatively, compound (XIV) can be prepared by incubating a compound of formula (XIII) with B(R$^{35}$)$_3$ or $(R^{35})_2B$—B(R$^{35}$)$_2$ wherein each $R^{35}$ is independently hydrogen or OR$^{33}$, wherein $R^{33}$ is as defined in the fourth aspect. Preferably two OR$^{33}$ groups form the group —OC(CH$_3$)$_2$—C(CH$_3$)$_2$O—. Conversion of (XIII) to (XIV) can be catalysed by a palladium catalyst, such as $PdCl_2$ or $PdCl_2$(1,1'-bis(diphenylphosphino)ferrocene).

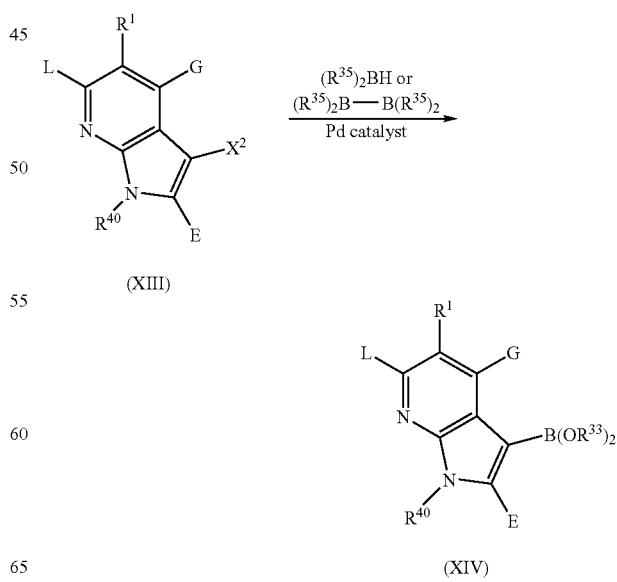

(XIII)

(XIV)

For example, compound (XIII) (E=G=L=hydrogen, X=Br), may be converted into the relevant pinacol boronic ester (XIV).

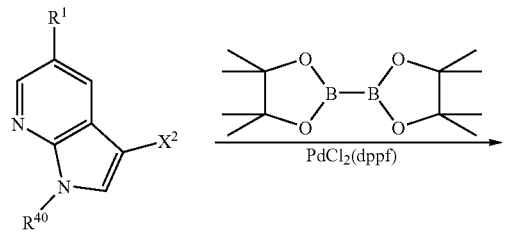

(XIII)

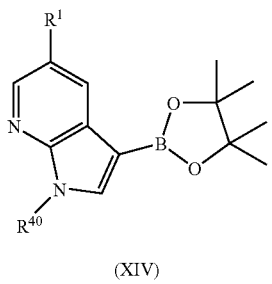

(XIV)

Formation of a compound of formula (XV) from a compound of formula (XIII) can be achieved by reaction with a strong base such as tert-BuLi followed by $(R^{32})_3$Sn-Hal wherein each $R^{32}$ is as defined in the fourth aspect of the invention

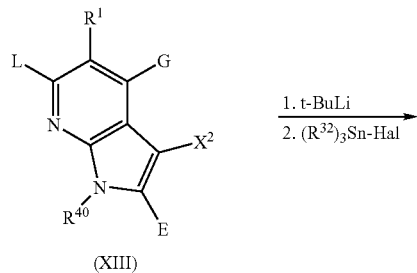

(XIII)

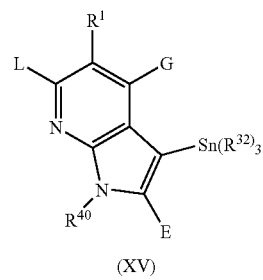

(XV)

Silicon derivative of formula (XVI) may be synthesized from a compound of formula (XIII) by reaction with a strong base such as n-BuLi or tert-BuLi followed by halosilane $(R^{34})_3$Si-Hal or siloxane $[(R^{34})_2SiO]_3$

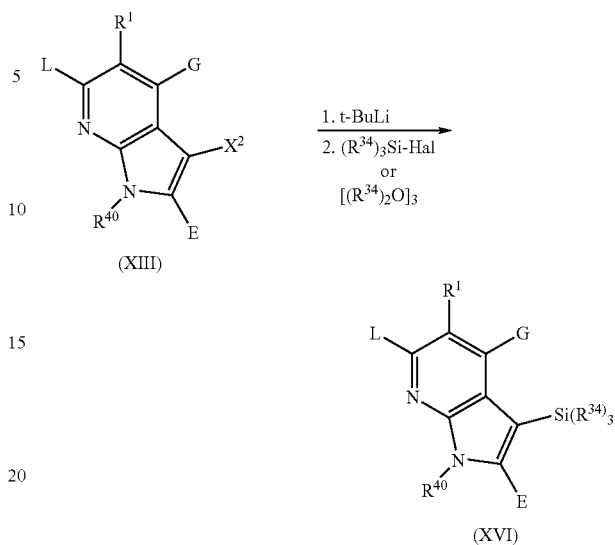

(XIII)

(XVI)

wherein $R^{40}$ is as defined in the second aspect of the invention, and wherein $R^{34}$ is as defined in the fourth aspect of the invention Hal is as defined in the eleventh aspect of the invention $X^2$ is as defined in the fifteenth aspect.

The twenty third aspect of the invention provides a compound of formula (XIV)

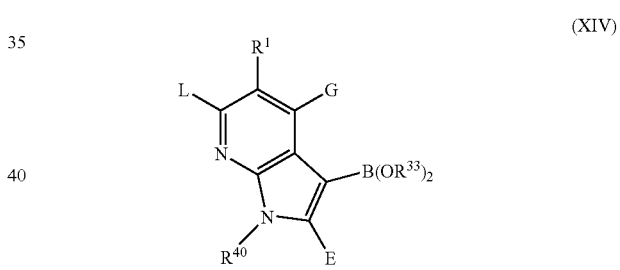

(XIV)

wherein $R^1$, E, G, and L are as defined in the first aspect $R^{40}$ is defined in the second aspect.

$R^{33}$ is defined in the fourth aspect.

The twenty fourth aspect of the invention provides a compound of formula (XV)

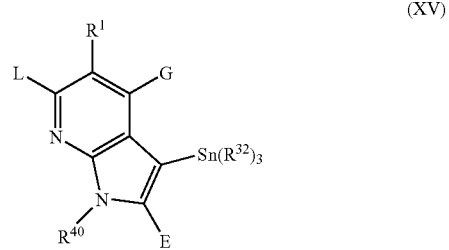

(XV)

wherein $R^1$, E, G, and L are as defined in the first aspect wherein $R^{40}$ is as defined in the second aspect wherein $R^{32}$ is as defined in the fourth aspect The twenty fifth aspect of the invention provides a compound of formula (XVI)

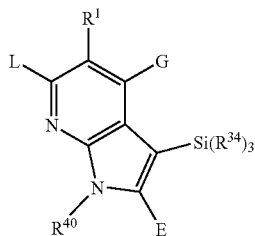

(XVI)

wherein $R^1$, E, G, and L are as defined in the first aspect wherein $R^{40}$ is as defined in the second aspect wherein $R^{34}$ is as defined in the fourth aspect The twenty-sixth aspect of the invention provides a process for the manufacturing of compound of formula (XIII) by the addition of the $R^{40}$ group to a compound of general formula (XVII)

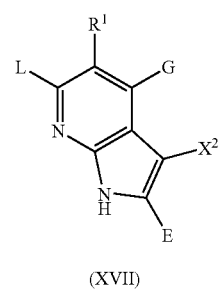 → 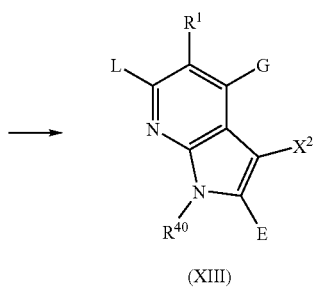

(XVII)         (XIII)

Conditions for the introduction of the protecting group $R^{40}$ will depend upon the protecting group used. Compound (XIII) can be produced by the initial formation of the relevant salt, for example by treatment with BuLi in THF or NaH in DMF, followed by reaction of the salt with an electrophile such as sulfonyl halide, or acid chloride. Alternatively a compound of formula (XIII) can be produced by the direct reaction of compound (XVII) with an electrophile such as benzenesulfonyl halide, preferably benzenesulfonyl chloride. This reaction is preferably carried out in the presence of base (such as sodium hydroxide) and a phase transfer catalyst such as tetra-n-butylammonium bromide or tetra-n-butylammonium hydrogen sulphate.

The twenty-seventh aspect of the invention provides a compound of formula (XVII)

(XVII)

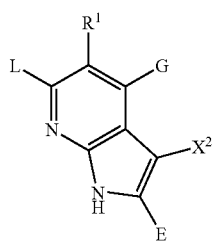

wherein $R^1$, E, G, and L are as defined in the first aspect wherein $X^2$ is as defined in the twentieth aspect An intermediate of the twenty-seventh aspect of the invention may be converted into another intermediate of the twenty-seventh aspect. For example, an intermediate compound may undergo a reduction, oxidation, elimination, substitution and/or addition reaction.

The twenty eighth aspect of the invention provides an alternative process for the introduction of the group $R^2$ to obtain a compound of formula (I) as defined in the first aspect of the invention comprising reaction of a) boronic acid or ester (LIV) or b) stannane (LV) or c) silane (LVI) with $R^2$-Hal in the presence of a suitable palladium catalyst.

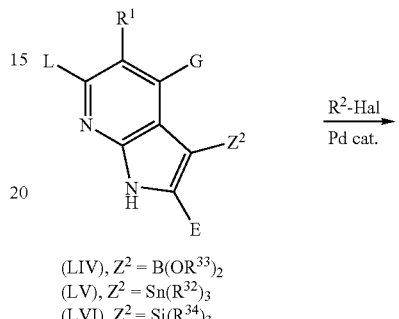

(LIV), $Z^2 = B(OR^{33})_2$
(LV), $Z^2 = Sn(R^{32})_3$
(LVI), $Z^2 = Si(R^{34})_3$

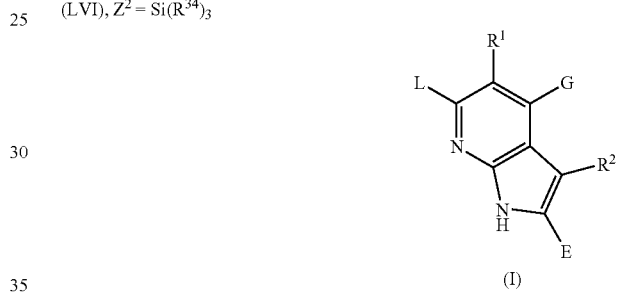

(I)

wherein $R^1$, $R^2$, E, G, and L are as defined in the first aspect, wherein Hal is I, Br, Cl, F or $CF_3SO_3$, preferably I or Br wherein $R^{32}$ is as defined in the fourth aspect wherein $R^{33}$ is as defined in the fourth aspect wherein $R^{34}$ is as defined in the fourth aspect Suitable catalysts for the purpose of this invention include $(PPh_3)_2PdCl_2$, $(PPh_3)_4Pd$, $Pd(OAc)_2$, $[PdCl(\eta^3-C_3H_5)]_2$, $Pd_2(dba)_3$, $Pd(dba)_2$ (dba=dibenzylidenacetone), $Pd/P(t-Bu)_3$.

The reaction of $R^2$-Hal set out as option a) for the twenty eighth aspect is a Suzuki reaction which can be carried out according to Suzuki Pure Appl. Chem. 1991, 63, 419 or Littke J. Am. Chem. Soc. 2000, 122, 4020. The boronic ester (LIV) can then be reacted with a halide or triflate ($R^2$-Hal), preferably iodide or bromide in the presence of a palladium catalyst. Suitable catalysts for the purpose of this invention include $(PPh_3)_2PdCl_2$, $(PPh_3)_4Pd$, $Pd_2(dba)_3$, $Pd(dba)_2$ (dba=dibenzylidenacetone), or $Pd(OAc)_2$ It will be appreciated that the reaction of $R^2$-Hal set out as option b) for the twenty eighth aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343. The stannyl derivative (LV) can be reacted with a halide or triflate ($R^2$-Hal), preferably iodide or bromide, in the presence of a palladium catalyst. Suitable catalysts for the purpose of this invention are those suitable for Stille coupling reaction, for example $PdCl_2(MeCN)_2$, $Pd/P(t-Bu)_3$, $Pd_2(dba)_3$ or $Pd(dba)_2$ (dba=dibenzylidenacetone).

It will be appreciated that the reaction of $R^2$-Hal set out as option c) for the twenty eighth aspect is a Hiyama reaction which can be carried out according to Hatanaka et al. J. Org. Chem. 1988, 53, 918, Hatanaka et al. Synlett, 1991, 845, Tamao et al. Tetrahedron Lett. 1989, 30, 6051 or Denmark et al. Org. Lett. 2000, 2, 565, ibid. 2491. Compound (LVI) can be reacted with a halide or triflate ($R^2$-Hal), preferably iodide or bromide, in the presence of a palladium catalyst. Suitable catalysts for the purpose of this invention are those suitable for Hiyama coupling reaction for example [PdCl($\eta^3$-$C_3H_5$)]$_2$, $Pd_2(dba)_3$, or $Pd(dba)_2$ (dba=dibenzylidenacetone)

Compound of formula (LIV) can be formed, for example, from a compound of formula (XVII) by reaction with a strong base such as tert-BuLi followed by trialkylborate B $(OR^{33})_3$.

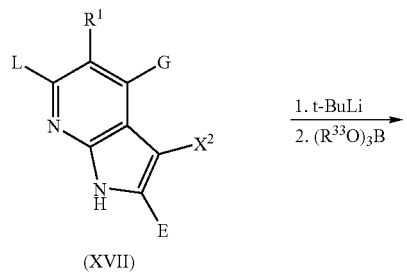

Alternatively, compound (LIV) can be prepared by incubating a compound of formula XVII) with $B(R^{35})_3$ or $(R^{35})_2B$—$B(R^{35})_2$ wherein each $R^{35}$ is independently hydrogen or $OR^{33}$, wherein $R^{33}$ is as defined in the fourth aspect. Preferably two $OR^{33}$ groups form the group —$OC(CH_3)_2$—$C(CH_3)_2O$—. Conversion of (XVII) to (LIV) can be catalysed by a palladium catalyst, such as $PdCl_2$ or $PdCl_2$(1,1'-bis (diphenylphosphino)ferrocene).

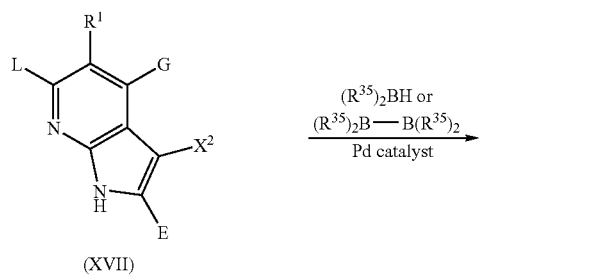

For example, compound (XVII) (E=G=L=hydrogen, X=Br), may be converted into the relevant pinacol boronic ester (LIV).

Formation of a compound of formula (LV) from a compound of formula (XVII) can be achieved by reaction with a strong base such as tert-BuLi followed by $(R^{32})_3$Sn-Hal wherein each $R^{32}$ is as defined in the fourth aspect of the invention Silicon derivative of formula (LVI) may be synthesized from a compound of formula (XVII) by reaction with a strong base such as n-BuLi or tert-BuLi followed by halosilane $(R^{34})_3$Si-Hal or siloxane $[(R^{34})_2SiO]_3$

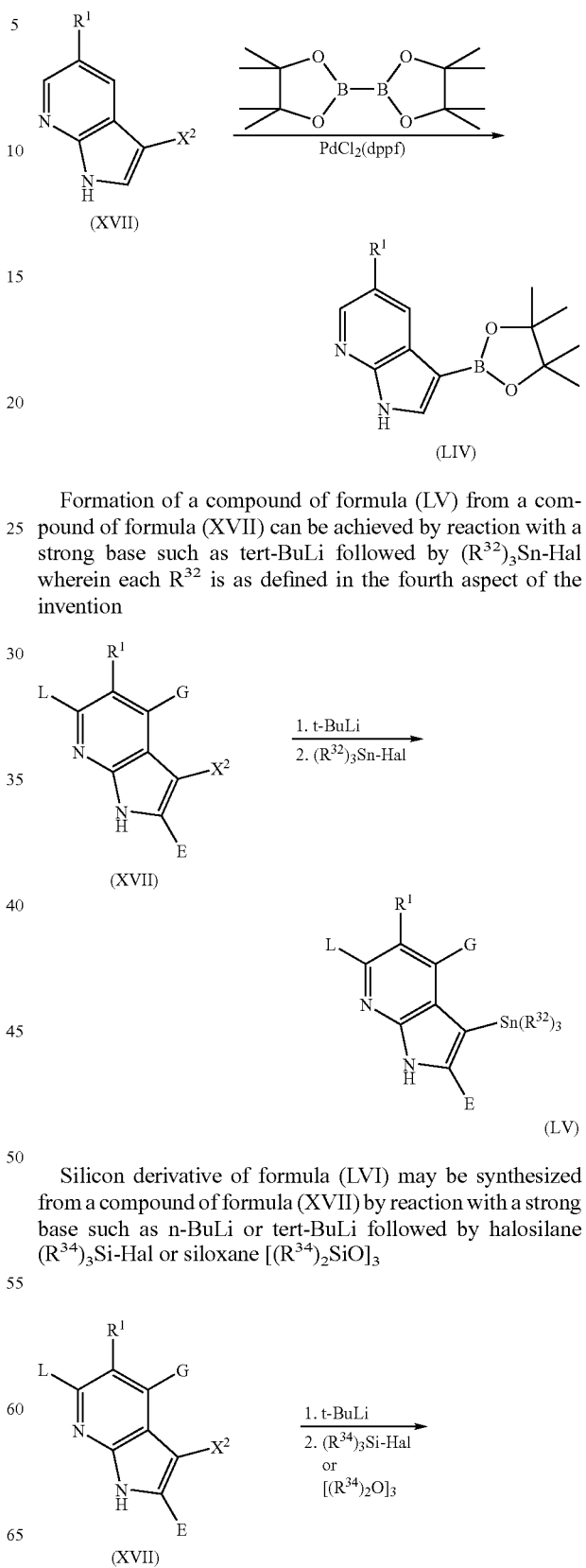

-continued

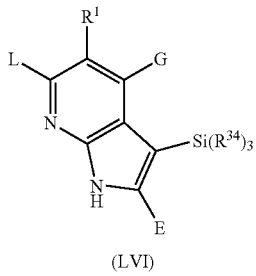
(LVI)

R³⁴ is as defined in the fourth aspect of the invention

Hal is as defined in the twelfth aspect of the invention

X² is as defined in the twentieth aspect.

The twenty ninth aspect of the invention provides a compound of formula (LIV)

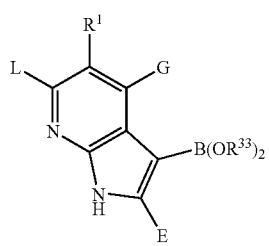
(LIV)

wherein R¹, E, G, and L are as defined in the first aspect

R³³ is defined in the fourth aspect.

The thirtieth aspect of the invention provides a compound of formula (LV)

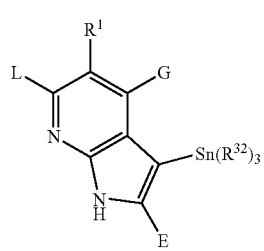
(LV)

wherein R¹, E, G, and L are as defined in the first aspect wherein R³² is as defined in the fourth aspect The thirty first aspect of the invention provides a compound of formula (LVI)

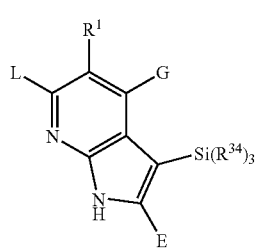
(LVI)

wherein R¹, E, G, and L are as defined in the first aspect wherein R³⁴ is as defined in the fourth aspect The thirty second aspect of the invention provides a process for the production of a compound of formula (XVII) by the introduction of an X² group to a compound of formula (XVIII). Compound (XVII) can be produced from compound (XVIII) by halogenation under anhydrous conditions or by reaction with ICl under basic conditions (such as pyridine or i-Pr₂NEt in a chlorinated solvent such as CH₂Cl₂, CHCl₃, CCl₄) or NBS in an anhydrous solvent such as CH₂Cl₂, CHCl₃, CCl₄). Where X² is iodine, it may preferably be introduced by direct action of I₂ on (XVIII) in the presence of a strong base such as sodium hydroxide or potassium hydroxide in anhydrous solvent such as dimethylformamide.

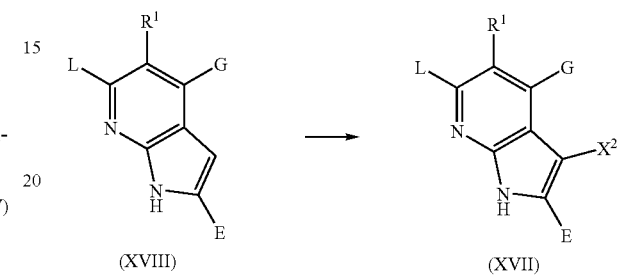

Methods for producing compound of formula (XVIII, E=G=L=hydrogen) are disclosed in GB0207488.8.

Where X² is SO₃CF₃, X² is introduced in a two step process involving oxidation (with for example magnesium monoperphthalate in refluxing acetic acid) or with MoO₅.HMPA) followed by incubation with trifluoromethanesulfonic anhydride in the presence of a non-nucleophilic base such as 2,6-di-t-butyl-4-methylpyridine.

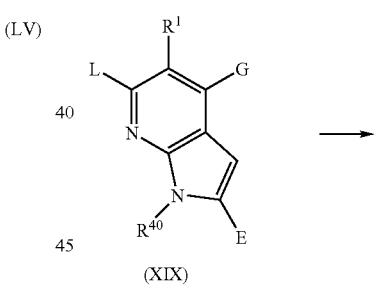
(XIX)

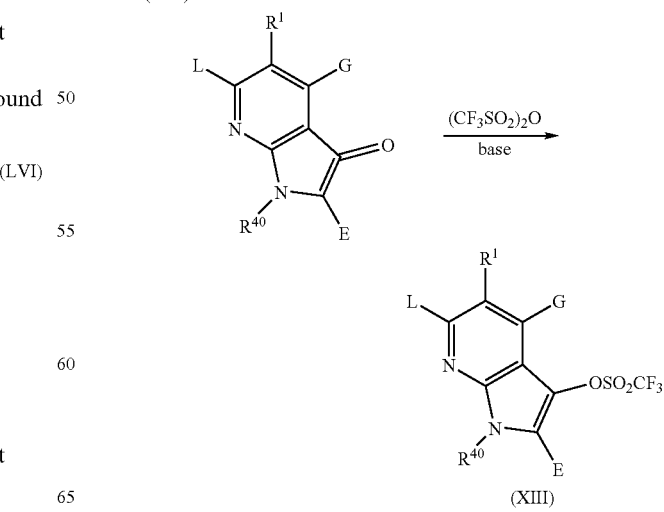
(XIII)

The thirty third aspect of the invention provides a process for the production of a compound of formula (XIII) by the introduction of the X² group to a compound of formula (XIX).

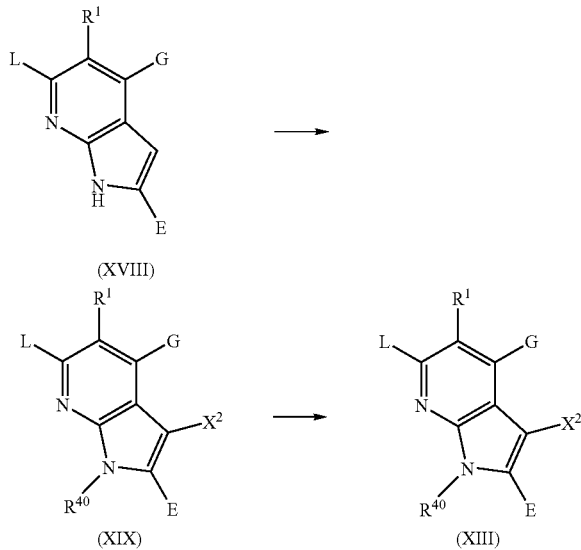

The compound of formula (XIX) is provided by the introduction of a R⁴⁰ group into a compound of formula (XVIII). In particular where R⁴⁰ is a silyl group, introduction of R⁴⁰ occurs prior to the introduction of X².

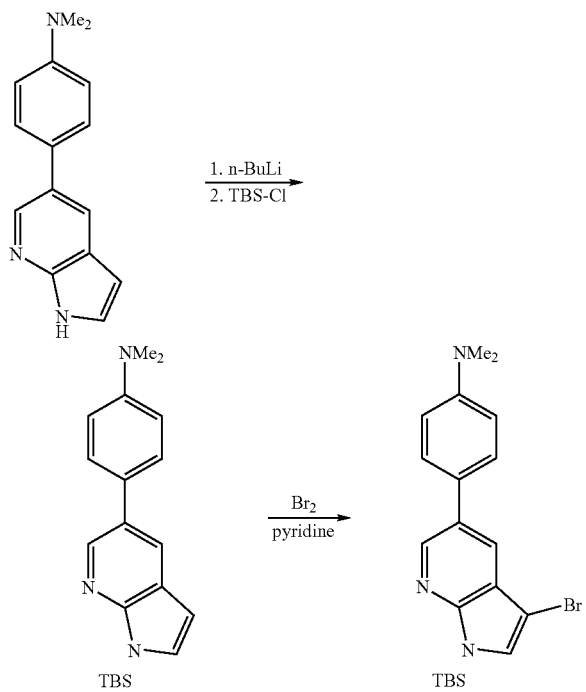

Thus, a skilled person will appreciate that the actual synthetic sequence to prepare compound (XIII) will depend on the type of protecting group R⁴⁰ used.

The thirty fourth aspect of the invention provides a compound of formula (XIX)

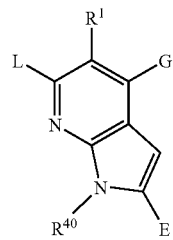

wherein $R^1$, E, G, and L are as defined in the first aspect wherein $R^{40}$ is as defined in the second aspect The thirty fifth aspect of the invention provides a process for the production of a compound of formula (IIIa) containing the 4-substituted oxazole ring by the reaction of aldehyde (XX) with a TOSMIC type reagent (XI).

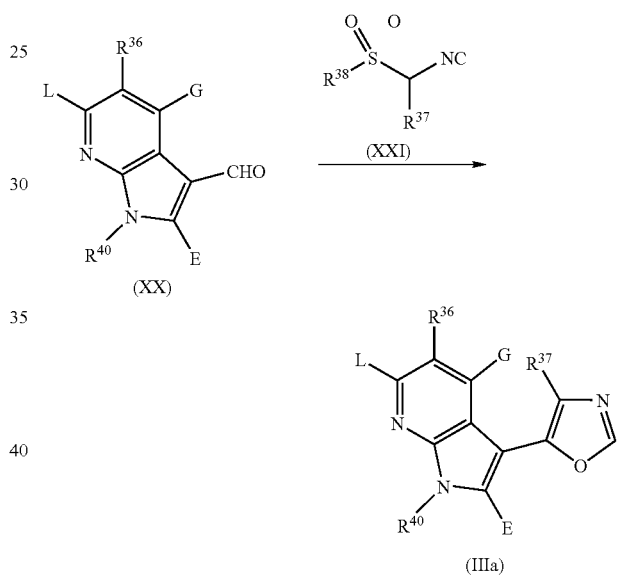

wherein $R^{36}$ is X or $R^1$ wherein $R^1$, E, G, and L are as defined in the first aspect wherein $R^{40}$ is as defined in the second aspect wherein X is as defined in the fourth aspect wherein $R^{37}$ is hydrogen, $C_{1-6}$ alkyl, preferably methyl or ethyl wherein $R^{38}$ is an $C_{6-12}$ aryl, preferably tolyl or phenyl It will be appreciated that the reaction set out for the thirty fifth aspect is a TOSMIC reaction, which has been reviewed by van Leusen, D. and van Leusen A. M. (Organic Reactions 2001, 57, 417), and which can be carried out under conditions similar to those used by Murali Dhar et al. (Bioorg. Med. Chem. Lett. 2002, 12, 3305).

Methods of producing compound (XX) are disclosed in GB 0311313.1.

The thirty sixth aspect of the invention provides a process for the production of a compound of formula (IIIb) containing the 2-substituted oxazole ring by the reaction of aldehyde (XX) with a reagent (XXII).

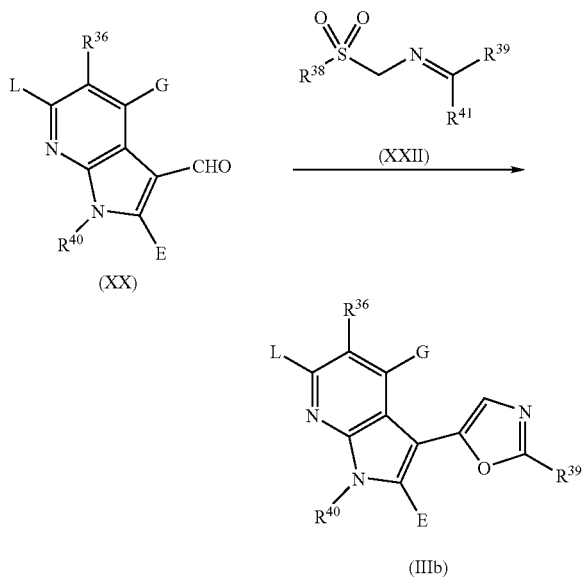

(XX)

(XXII)

(IIIb)

wherein E, G, and L are as defined in the first aspect wherein $R^{40}$ is as defined in the second aspect wherein $R^{36}$ is as defined in the thirty fifth aspect wherein $R^{38}$ is as defined in the thirty fifth aspect wherein $R^{39}$ is a hydrogen, $C_{1-12}$ alkyl, $C_{2-12}$ alkenyl, $C_{2-12}$ alkynyl, haloalkyl, carbocyclyl, heterocyclyl, $(CH_2)_nOR^3$, $(CH_2)_nNR^3{}_2$, $OR^3$, $SR^3$, $NO_2$, $CN$, $NR^3{}_2$, $NR^3COR^3$, $NR^3CONR^3{}_2$, $NR^3COR^3$, $NR^3CO_2R^3$, $CO_2R^3$, $COR^3$, $CONR^3{}_2$, $S(O)_2R^3$, $SONR^3{}_2$, $S(O)R^3$, $SO_2NR^3{}_2$, or $NR^3S(O)_2R^3$ wherein the $C_{1-2}$ alkyl group optionally contains one or more insertions selected from —O—, —N($R^3$)— —S—, —S(O)— and —S(O$_2$)—;

wherein $R^3$ is as defined in the first aspect of the invention wherein $R^{41}$ is $OR^{42}$ or $SR^{42}$ wherein $R^{42}$ is $C_{1-6}$ alkyl, preferably methyl or ethyl The reaction set out for the thirty sixth aspect can be carried out using conditions similar to these described by Houwing et al. (Tetrahedron Lett. 1976, 2, 143).

The thirty seventh aspect of the invention provides a process for the production of a compound of formula (IIIc) containing the triazole ring by the reaction of iminoester (XXIII) with formic acid hydrazide.

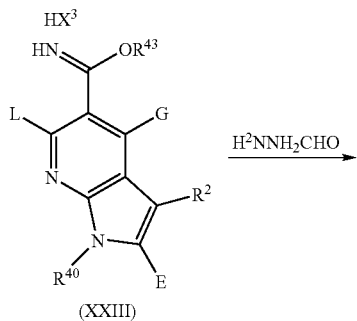

(XXIII)

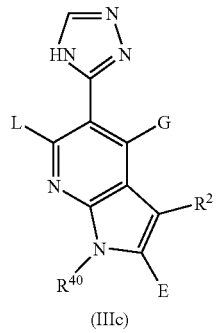

(IIIc)

wherein $R^2$, E, G, and L are as defined in the first aspect wherein $R^{40}$ is as defined in the second aspect wherein $R^{43}$ is $C_{1-6}$ alkyl, preferably methyl or ethyl wherein $X^3$ is F, Cl, Br, I, $HSO_4{}^-$, $CF_3SO_3{}^-$.

The reaction set out for the thirty seventh aspect can be carried out in a suitable solvent such as ethanol in the presence of tertiary amine, preferably triethylamine.

The thirty eighth aspect of the invention provides a compound of formula (XXIII)

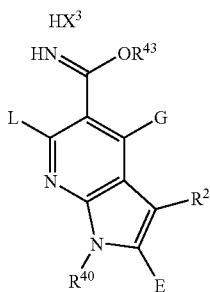

(XXIII)

wherein $R^2$, E, G, and L are as defined in the first aspect wherein $R^{40}$ is as defined in the second aspect wherein $R^{43}$ and $X^3$ are as defined in the thirty seventh aspect The thirty ninth aspect of the invention provides a process for the production of an iminoester of formula (XXIII) by the reaction of nitrile (XXIV) with alcohol $R^{43}OH$ in the presence of mineral acid $HX^3$.

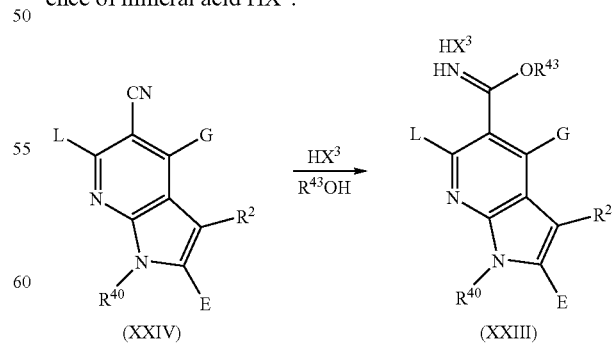

(XXIV)          (XXIII)

wherein $R^2$, E, G, and L are as defined in the first aspect wherein $R^{40}$ is as defined in the second aspect wherein $R^{43}$ and $X^3$ are as defined in the thirty seventh aspect The fortieth aspect of the invention provides a compound of formula (XXIV)

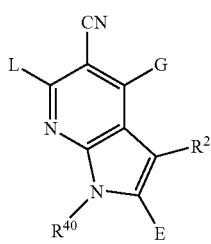

(XXIV)

wherein $R^2$, E, G, and L are as defined in the first aspect wherein $R^{40}$ is as defined in the second aspect The forty first aspect of the invention provides a process for the manufacture of nitrile of formula (XXIV) as defined in the fortieth aspect of the invention comprising a a) reaction of a compound of formula (XXV) with stannane $R^2$—$Sn(R^{32})_3$ in the presence of a palladium catalyst or b) reaction of a compound of formula (XXV) with boronic acid or ester $R^2$—B$(OR^{33})_2$ in a presence of a suitable palladium catalyst or c) reaction of a compound of formula (XXV) with silane $R^2$—Si$(R^{34})_3$ in the presence of a palladium catalyst;

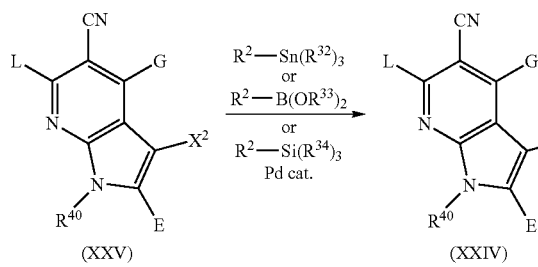

wherein $R^2$, E, G, and L are as defined in the first aspect wherein $R^{40}$ is an amino protecting group as defined in the second aspect wherein $X^2$ is as defined in the twentieth aspect and wherein $R^{32}$, $R^{33}$, and $R^{34}$ are as defined in the fourth aspect Suitable catalysts for the purpose of this invention include $(PPh_3)_2PdCl_2$, $(PPh_3)_4Pd$, $Pd(OAc)_2$, $[PdCl(\eta^3\text{-}C_3H_5)]_2$, $Pd_2(dba)_3$, $Pd(dba)_2$ (dba=dibenzylideneacetone), $Pd/P(t\text{-}Bu)_3$.

It will be appreciated that the reaction set out as option a) for the forty first aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343.

The reaction set out as option b) for the forty first aspect is a Suzuki reaction which can be carried out according to Suzuki Pure Appl. Chem. 1991, 63, 419 or Littke J. Am. Chem. Soc. 2000, 122, 4020

It will be appreciated that the reaction set out as option c) for the forty first aspect is a Hiyama reaction which can be carried out according to Hatanaka et al. J. Org. Chem. 1988, 53, 918, Hatanaka et al. Synlett, 1991, 845, Tamao et al. Tetrahedron Lett. 1989, 30, 6051 or Denmark et al. Org. Lett. 2000, 2, 565, ibid. 2491.

The forty second aspect of the invention provides a compound of formula (XXV)

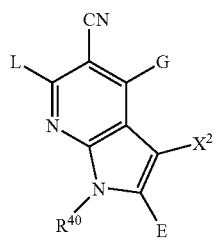

(XXV)

wherein E, G, and L are as defined in the first aspect wherein $R^{40}$ is an amino protecting group as defined in the second aspect wherein $X^2$ is as defined in the twentieth aspect The forty third aspect of the invention provides a process for the manufacture of a compound of formula (XXV) comprising protection of the pyrrole nitrogen in compound (XXVI).

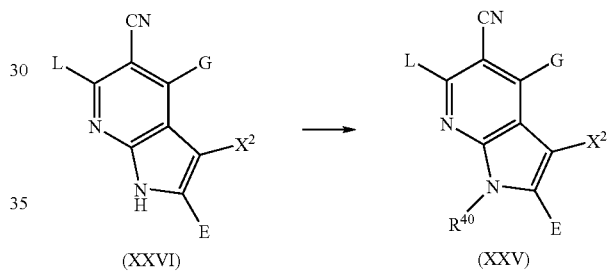

wherein E, G, and L are as defined in the first aspect wherein $X^2$ is as defined in the twentieth aspect wherein $R^{40}$ is as defined in the second aspect of the invention.

The forty fourth aspect of the invention provides a compound of formula

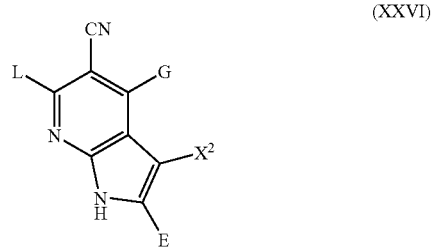

(XXVI)

wherein E, G, and L are as defined in the first aspect wherein $X^2$ is as defined in the twentieth aspect The forty fifth aspect of the invention provides a process for the production of a compound of formula (XXVI) by the introduction of an $X^2$ group to 1H-pyrrolo[2,3-b]pyridine-5-carbonitrile (XXVII)

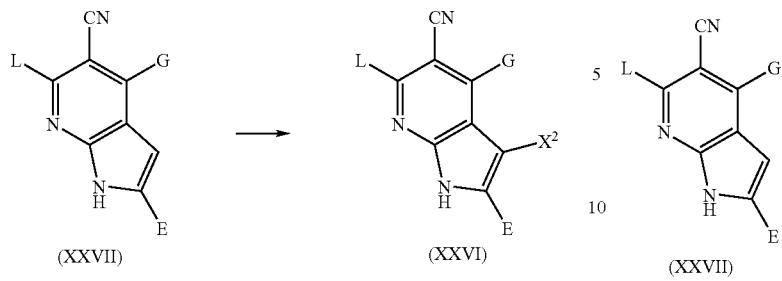

wherein E, G, and L are as defined in the first aspect wherein $X^2$ is as defined in the twentieth aspect Compound (XXVI) can be produced from compound XXVII) by halogenation under anhydrous conditions or by reaction with IC1 under basic conditions (such as pyridine or i-Pr$_2$NEt in a chlorinated solvent such as CH$_2$Cl$_2$, CHCl$_3$, CCl$_4$) or NBS in an anhydrous solvent such as CH$_2$Cl$_2$, CHCl$_3$, CCl$_4$). Where $X^2$ is iodine, it may preferably be introduced by direct action of I$_2$ on (XXVII) in the presence of a strong base such as sodium hydroxide or potassium hydroxide in anhydrous solvent such as dimethylformamide.

Where $X^2$ is SO$_3$CF$_3$, $X^2$ is introduced in a two step process involving oxidation (with for example magnesium monoperphthalate in refluxing acetic acid) or with MoO$_5$.HMPA) followed by incubation with trifluoromethanesulfonic anhydride in the presence of a non-nucleophilic base such as 2,6-di-t-butyl-4-methylpyridine.

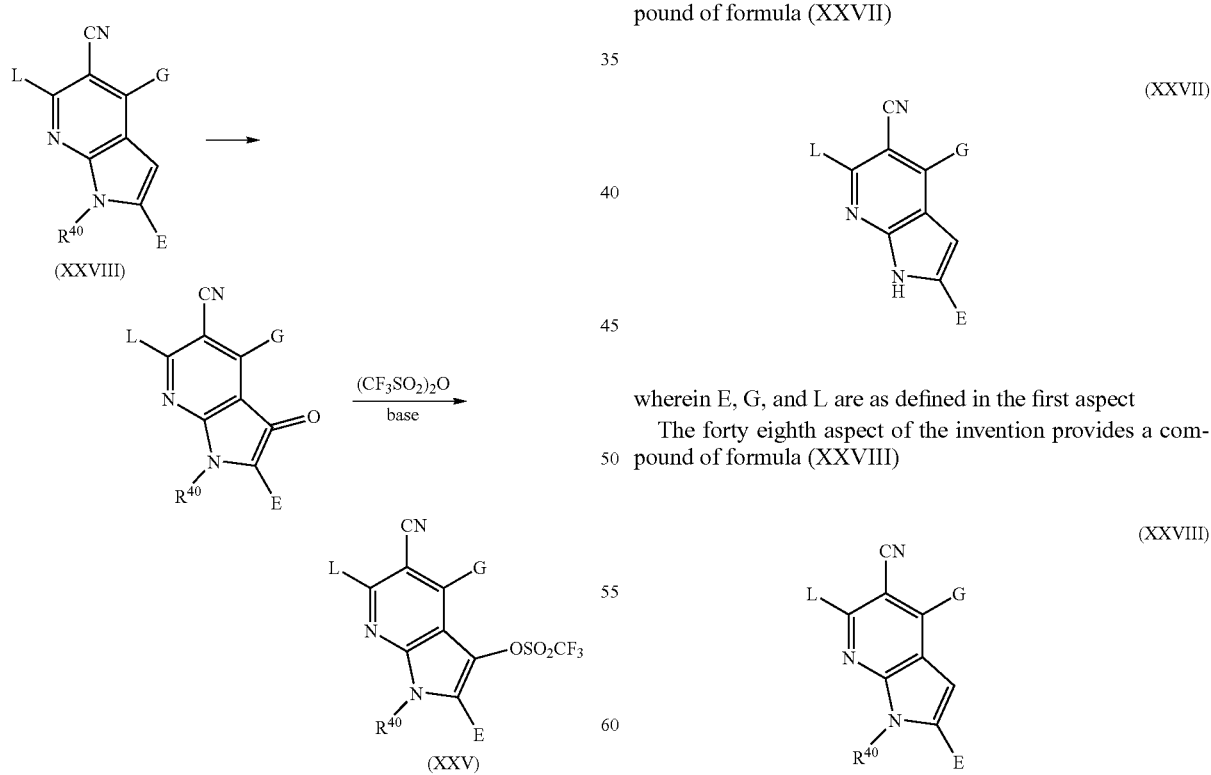

The forty sixth aspect of the invention provides a process for the production of a compound of formula (XXV) by the introduction of the $X^2$ group to a compound of formula (XVIII).

The compound of formula (XXVIII) is provided by the introduction of a $R^{40}$ group into a compound of formula (XXVII). In particular where $R^{40}$ is a silyl group, introduction of $R^{40}$ occurs prior to the introduction of $X^2$.

Thus, a skilled person will appreciate that the actual synthetic sequence to prepare compound (XXV) will depend on the type of protecting group $R^{40}$ used.

The forty seventh aspect of the invention provides a compound of formula (XXVII)

wherein E, G, and L are as defined in the first aspect

The forty eighth aspect of the invention provides a compound of formula (XXVIII)

wherein E, G, and L are as defined in the first aspect wherein $R^{40}$ is an amino protecting group as defined in the second aspect The forty ninth aspect of the invention provides a process for the manufacture of 1H-Pyrrolo[2,3-b]pyridine-5-carbonitrile (XXVIIa) comprising reaction of 5-bromo-1H-pyrrolo[2,3-b]pyridine with Zn(CN)$_2$ in the presence of a suitable palladium catalyst such as Pd(PPh$_3$)$_4$.

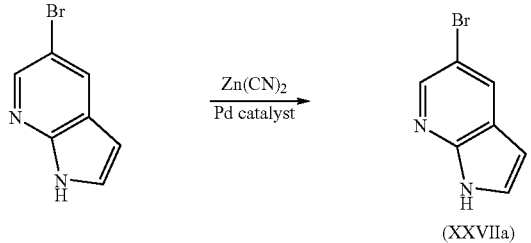

(XXVIIa)

The fiftieth aspect of the invention provides a process for the production of a compound of formula (IIa) containing the triazole ring by the reaction of iminoester (XXIX) with formic acid hydrazide.

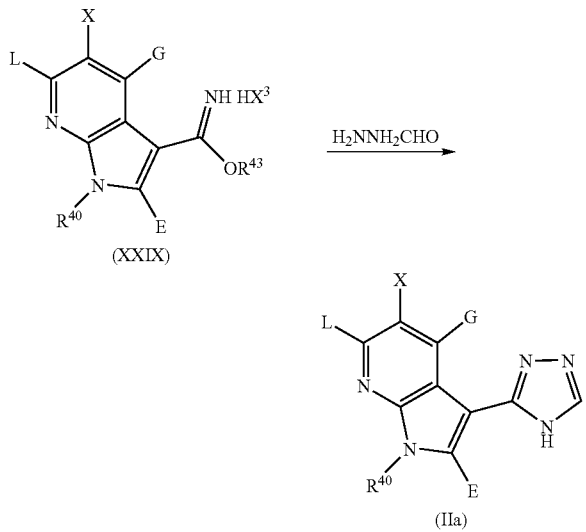

wherein E, G, and L are as defined in the first aspect wherein X is as defined in the fourth aspect wherein R$^{40}$ is as defined in the second aspect wherein R$^{43}$ and X$^3$ are as defined in the thirty seventh aspect The reaction set out for the fiftieth aspect can be carried out in a suitable solvent such as ethanol in the presence of tertiary amine, preferably triethylamine.

The fifty first aspect of the invention provides a compound of formula (XXIX)

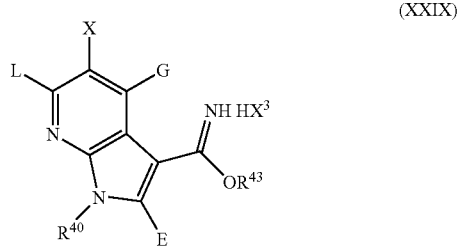

(XXIX)

wherein E, G, and L are as defined in the first aspect wherein X is as defined in the fourth aspect wherein R$^{40}$ is as defined in the second aspect wherein R$^{43}$ and X$^3$ are as defined in the thirty seventh aspect The fifty second aspect of the invention provides a process for the production of iminoester of formula (XXIX) by the reaction of nitrile (XXX) with alcohol R$^{43}$OH in the presence of mineral acid HX$^3$. Preparation of nitrile (XXX, E=G=L=hydrogen) has been disclosed in GB0305144.8.

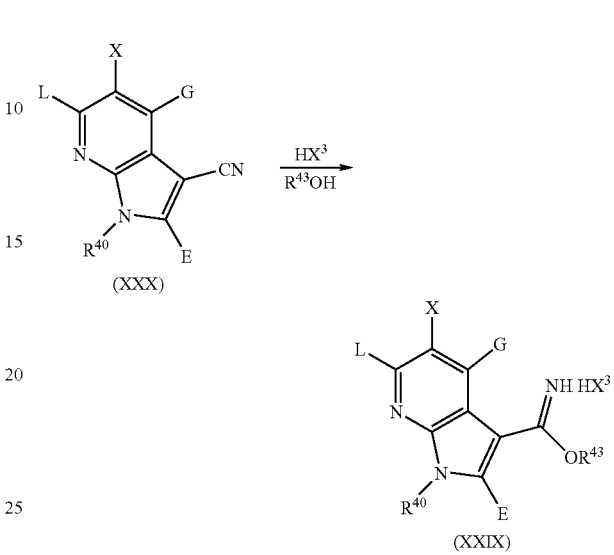

wherein E, G, and L are as defined in the first aspect wherein X is as defined in the fourth aspect wherein R$^{40}$ is as defined in the second aspect wherein R$^{43}$ and X$^3$ are as defined in the thirty seventh aspect The fifty third aspect of the invention provides a process for the manufacture of silicon derivative of formula (XII) as defined in the fifteenth aspect of the invention comprising a a) reaction of a compound of formula (XXXI) with stannane R$^2$—Sn(R$^{32}$)$_3$ in the presence of a palladium catalyst or b) reaction of a compound of formula (XXXI) with boronic acid or ester R$^2$—B(OR$^{33}$)$_2$ in a presence of a suitable palladium catalyst

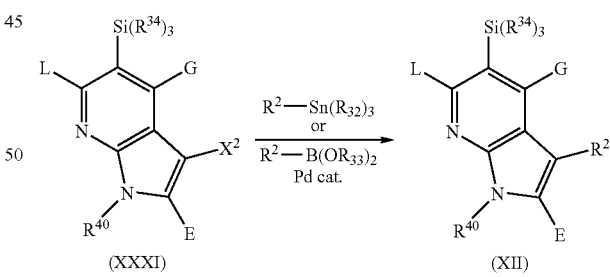

wherein E, G, and L are as defined in the first aspect wherein R$^{40}$ is an amino protecting group as defined in the second aspect wherein X$^2$ is as defined in the twentieth aspect and wherein R$^{32}$, R$^{33}$, and R$^{34}$ are as defined in the fourth aspect Suitable catalysts for the purpose of this invention include (PPh$_3$)$_2$PdCl$_2$, (PPh$_3$)$_4$Pd, Pd(OAc)$_2$, [PdCl(η$^3$-C$_3$H$_5$)]$_2$, Pd$_2$(dba)$_3$, Pd(dba)$_2$ (dba=dibenzylidenacetone), Pd/P(t-Bu)$_3$.

It will be appreciated that the reaction set out as option a) for the fifty third aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343.

The reaction set out as option b) for the fifty third aspect is a Suzuki reaction which can be carried out according to Suzuki Pure Appl. Chem. 1991, 63, 419 or Littke J. Am. Chem. Soc. 2000, 122, 4020

The fifty fourth aspect of the invention provides a compound of formula (XXXI)

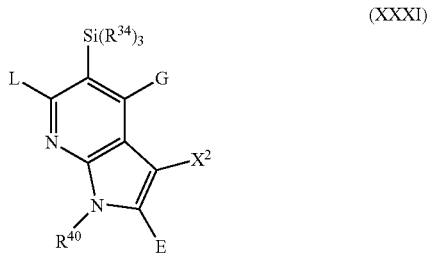

wherein E, G, and L are as defined in the first aspect wherein $R^{40}$ is an amino protecting group as defined in the second aspect wherein $R^{34}$ is defined in the fourth aspect wherein $X^2$ is as defined in the twentieth aspect The fifty fifth aspect of the invention provides a process for the manufacture of a compound of formula (XXXI) comprising protection of the pyrrole nitrogen in compound (XXXII).

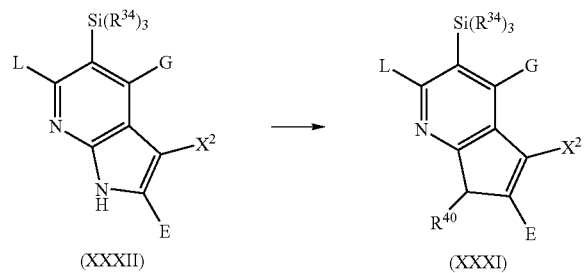

wherein E, G, and L are as defined in the first aspect wherein $X^2$ is as defined in the twentieth aspect wherein $R^{34}$ is defined in the fourth aspect wherein $R^{40}$ is as defined in the second aspect of the invention.

The fifty sixth aspect of the invention provides a compound of formula (XXXII)

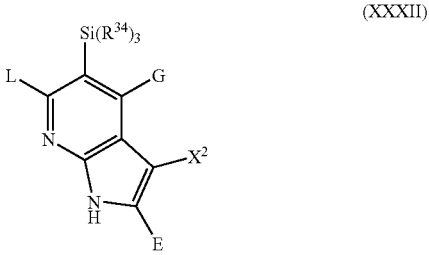

wherein E, G, and L are as defined in the first aspect wherein $R^{34}$ is defined in the fourth aspect wherein $X^2$ is as defined in the twentieth aspect The fifty seventh aspect of the invention provides a process for the production of a compound of formula (XXXII) by the introduction of an $X^2$ group into silicon derivative (XXXII). Preparation of silicon derivative (XXXIII, E=G=L=hydrogen) was disclosed in GB0305142.2.

wherein E, G, and L are as defined in the first aspect wherein $X^2$ is as defined in the twentieth aspect wherein $R^{34}$ is defined in the fourth aspect

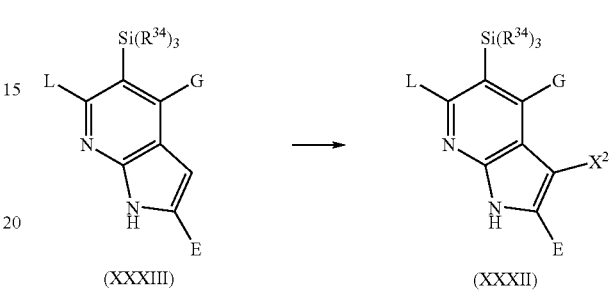

Compound (XXXII) can be produced from compound (XXXIII) by halogenation under anhydrous conditions or by reaction with IC1 under basic conditions (such as pyridine or i-Pr$_2$NEt in a chlorinated solvent such as CH$_2$Cl$_2$, CHCl$_3$, CCl$_4$) or NBS in an anhydrous solvent such as CH$_2$Cl$_2$, CHCl$_3$, CCl$_4$). Where $X^2$ is iodine, it may preferably be introduced by direct action of I$_2$ on (XXXIII) in the presence of a strong base such as sodium hydroxide or potassium hydroxide in anhydrous solvent such as dimethylformamide.

The fifty eighth aspect of the invention provides a process for the production of a compound of formula (XXXI) by the introduction of the $X^2$ group to a compound of formula (XXXIV).

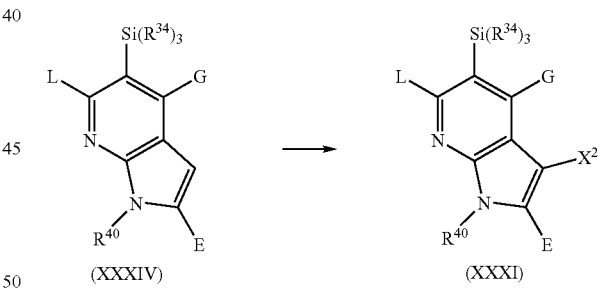

Preparation of silicon derivative (XXXIV, E=GL=hydrogen) was disclosed in GB0305142.2.

Thus, a skilled person will appreciate that the actual synthetic sequence to prepare compound (XXXI) will depend on the type of protecting group $R^{40}$ used.

The fifty ninth aspect of the invention provides a process for the manufacture of intermediate of formula (IIb) as defined in the sixth aspect (II, X=Br) of the invention comprising a a) reaction of a compound of formula (XXXV) with stannane $R^2$—Sn(R$^{32}$)$_3$ in the presence of a palladium catalyst or b) reaction of a compound of formula (XXXV) with boronic acid or ester $R^2$—B(OR$^{33}$) in a presence of a suitable palladium catalyst or c) reaction of a compound of formula (XXXV) with silane $R^2$—Si(R$^{34}$)$_3$ in the presence of a palladium catalyst;

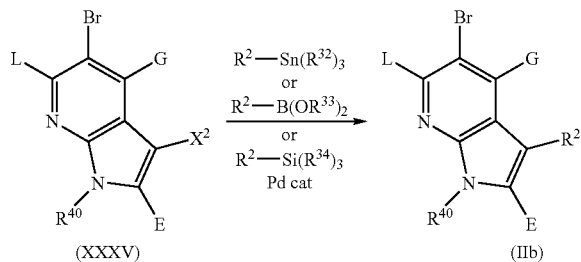 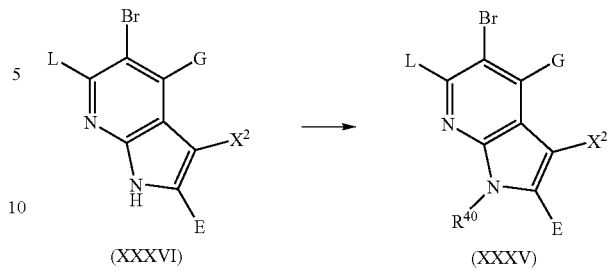

wherein $R^2$, E, G, and L are as defined in the first aspect wherein $R^{40}$ is an amino protecting group as defined in the second aspect wherein $X^2$ is as defined in the twentieth aspect and wherein $R^{32}$, $R^{33}$, and $R^{34}$ are as defined in the fourth aspect Suitable catalysts for the purpose of this invention include $(PPh_3)_2PdCl_2$, $(PPh_3)_4Pd$, $Pd(OAc)_2$, $[PdCl(\eta^3\text{-}C_3H_5]_2$, $Pd_2(dba)_3$, $Pd(dba)_2$ (dba=dibenzylideneacetone), $Pd/P(t\text{-}Bu)_3$.

It will be appreciated that the reaction set out as option a) for the fifty ninth aspect is a Stille reaction, which can be carried out according to Stille Angew. Chem., Int. ed, Engl. 1986, 25, 508; Mitchell Synthesis, 1992, 803, or Littke et al. J. Am. Chem. Soc. 2002, 124, 6343.

The reaction set out as option b) for the fifty ninth aspect is a Suzuki reaction which can be carried out according to Suzuki Pure Appl. Chem. 1991, 63, 419 or Littke J. Am. Chem. Soc. 2000, 122, 4020

It will be appreciated that the reaction set out as option c) for the fifty ninth aspect is a Hiyama reaction which can be carried out according to Hatanaka et al. J. Org. Chem. 1988, 53, 918, Hatanaka et al. Synlett, 1991, 845, Tamao et al. Tetrahedron Lett. 1989, 30, 6051 or Denmark et al. Org. Lett. 2000, 2, 565, ibid. 2491.

The sixtieth aspect of the invention provides a compound of formula (XXXV)

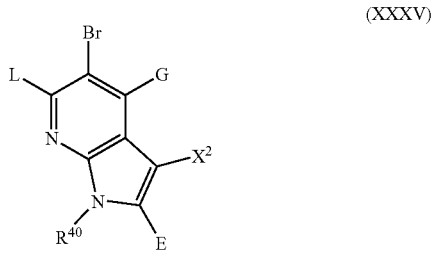

wherein E, G, and L are as defined in the first aspect wherein $R^{40}$ is an amino protecting group as defined in the second aspect wherein $X^2$ is as defined in the twentieth aspect The sixty first aspect of the invention provides a process for the manufacture of a compound of formula (XXXV) comprising protection of the pyrrole nitrogen in compound (XXXVI).

wherein E, G, and L are as defined in the first aspect wherein $X^2$ is as defined in the twentieth aspect wherein $R^{40}$ is as defined in the second aspect of the invention.

The sixty second aspect of the invention provides a compound of formula (XXXVI)

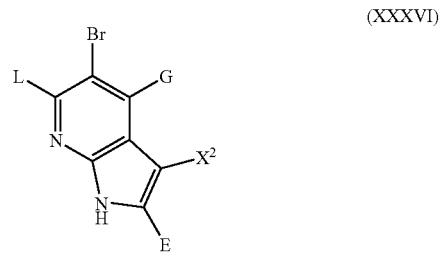

wherein E, G, and L are as defined in the first aspect wherein $X^2$ is as defined in the twentieth aspect The sixty third aspect of the invention provides a process for the production of a compound of formula (XXXVIa) by the introduction of an $X^2$ group to 5-bromo-1H-pyrrolo[2,3-b]pyridine.

wherein $X^2$ is as defined in the twentieth aspect

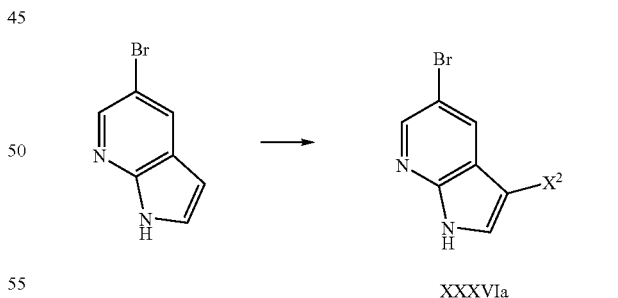

Compound (XXXVIa) can be produced from 5-bromo-1H-pyrrolo[2,3-b]pyridine by halogenation under anhydrous conditions or by reaction with ICl under basic conditions (such as pyridine or i-$Pr_2$NEt in a chlorinated solvent such as $CH_2Cl_2$, $CHCl_3$, $CCl_4$) or NBS in an anhydrous solvent such as $CH_2Cl_2$, $CHCl_3$, $CCl_4$). Where $X^2$ is iodine, it may preferably be introduced by direct action of $I_2$ on 5-bromo-1H-pyrrolo[2,3-b]pyridine in the presence of a strong base such as sodium hydroxide or potassium hydroxide in anhydrous solvent such as dimethylformamide.

Where $X^2$ is $SO_3CF_3$, $X^2$ is introduced in a two step process involving oxidation of (XXXVIIa) (with for example magnesium monoperphthalate in refluxing acetic acid) or with $MoO_5.HMPA$) followed by incubation with trifluoromethanesulfonic anhydride in the presence of a non-nucleophilic base such as 2,6-di-t-butyl-4-methylpyridine.

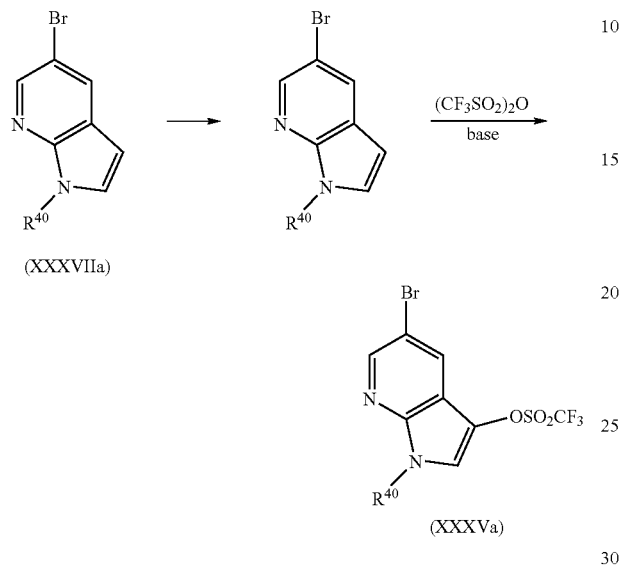

(XXXVIIa)

(XXXVa)

The sixty fourth aspect of the invention provides a process for the production of a compound of formula (XXXV) by the introduction of the $X^2$ group to a compound of formula (XXXV). Preparation of (XXXVII) was disclosed in GB0305142.2.

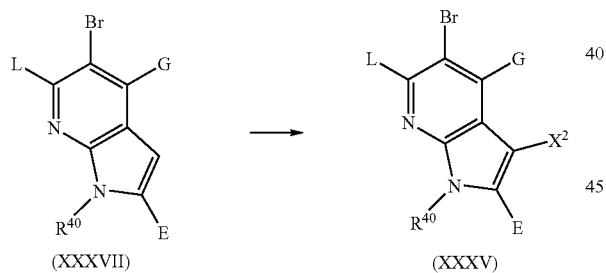

(XXXVII)                (XXXV)

Wherein $X^2$ is as defined in the twentieth aspect, E, G and L are as defined in the first aspect, and $R^2$ is as defined in the second aspect of the invention.

In particular where $R^{40}$ is a silyl group, introduction of $R^{40}$ occurs prior to the introduction of $X^2$.

Thus, a skilled person will appreciate that the actual synthetic sequence to prepare compound (XXXV) will depend on the type of protecting group $R^{40}$ used.

The present invention encompasses one or more compounds as defined in the third, sixth, eighth, tenth, thirteenth, fourteenth, fifteenth, seventeenth, eighteenth, nineteenth, twenty first, twenty third, twenty fourth, twenty fifth, twenty seventh, twenty ninth, thirtieth, thirty first, thirty fourth, thirty eighth, fortieth, forty second, forty fourth, forty seventh, forty eighth, fifty first, fifty fourth, fifty sixth, sixtieth and sixty second aspects of the invention as set out below;

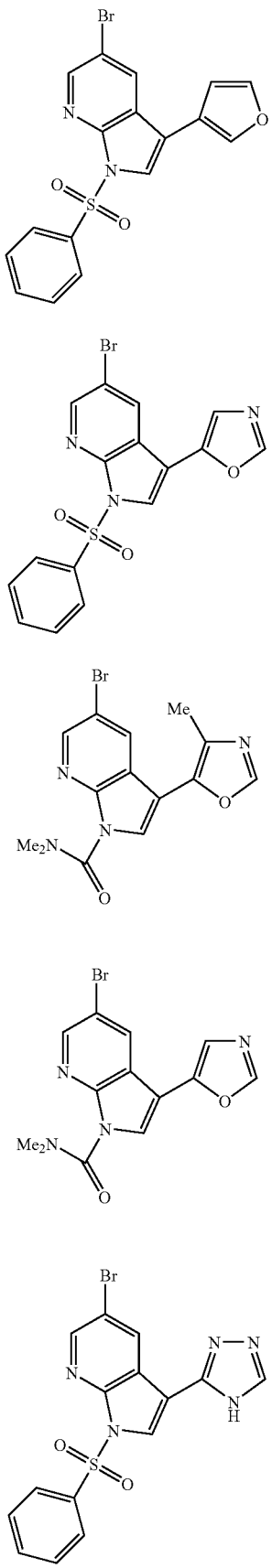

-continued
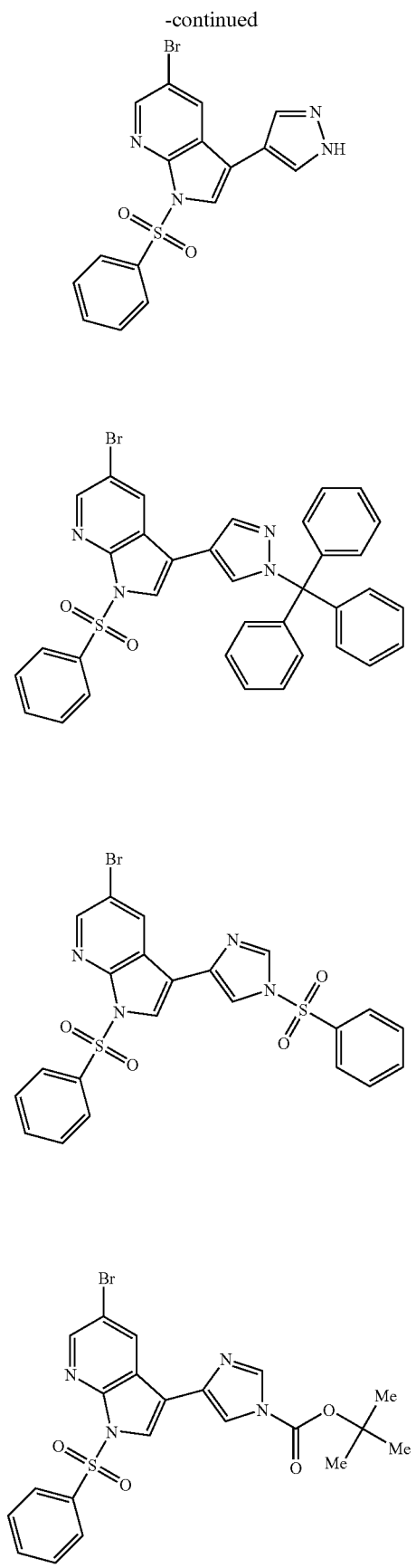
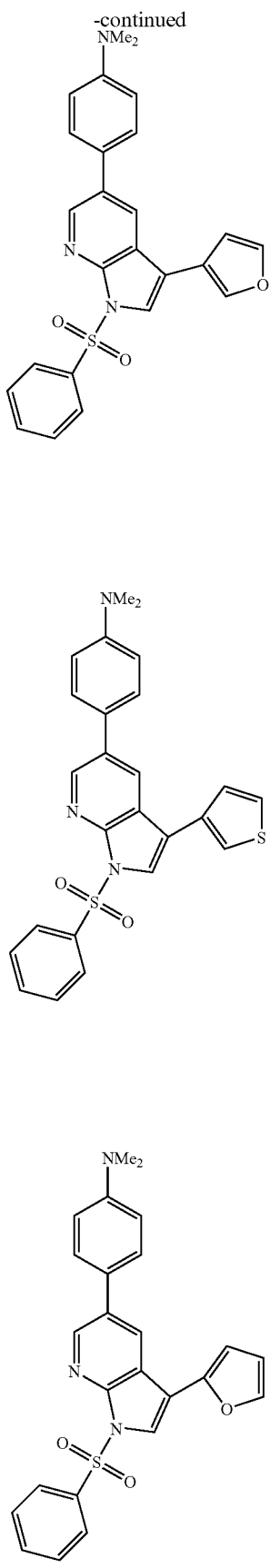

-continued
115
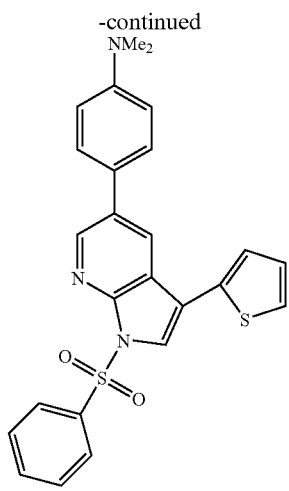
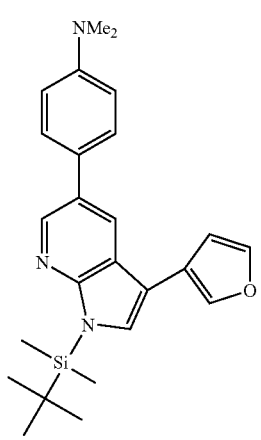
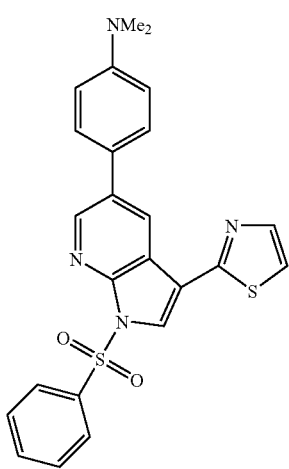
-continued
116
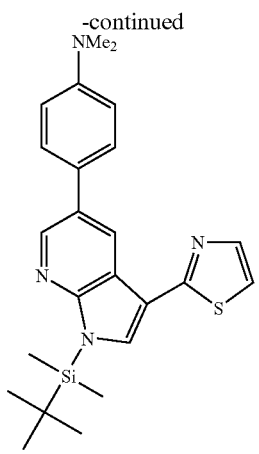
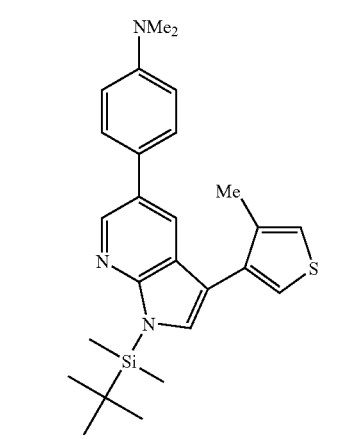
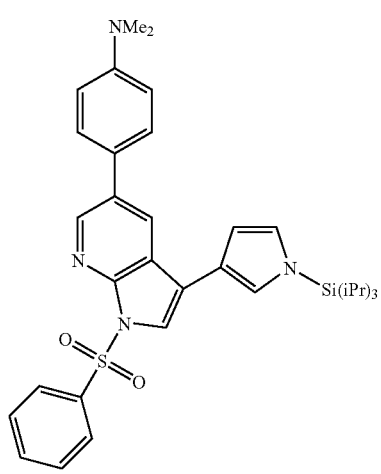

117
-continued
118
-continued
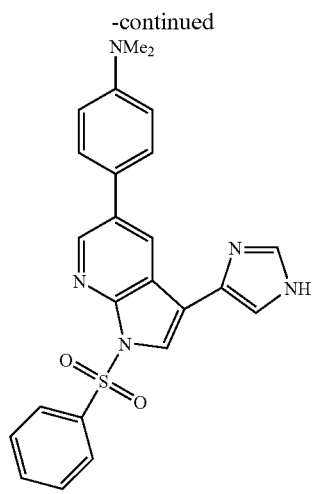
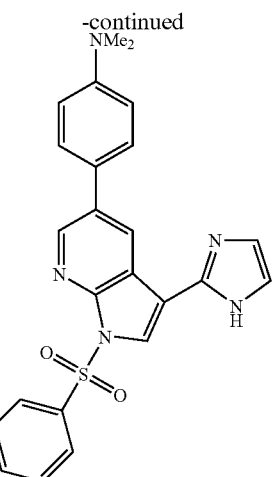
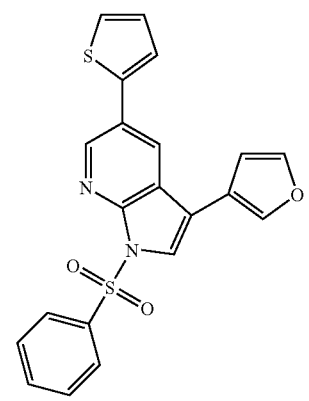
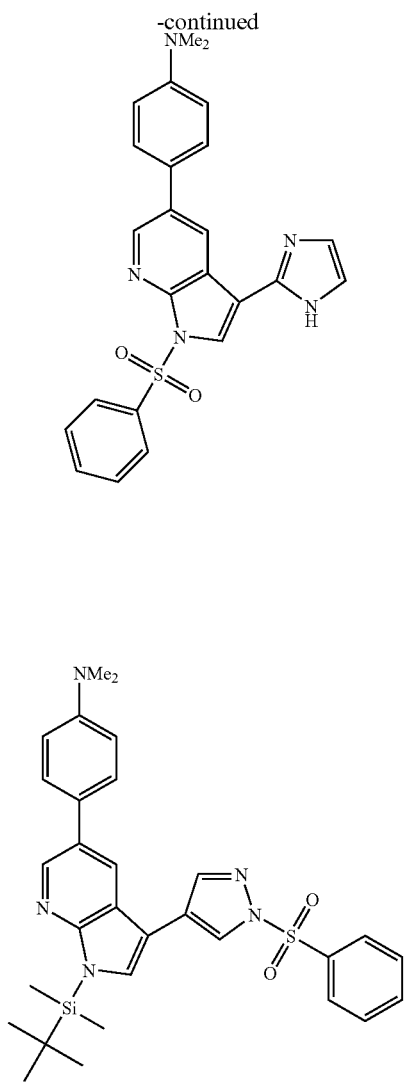
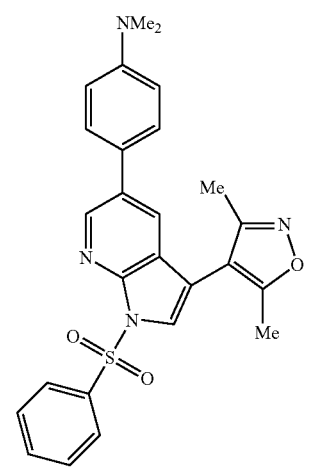
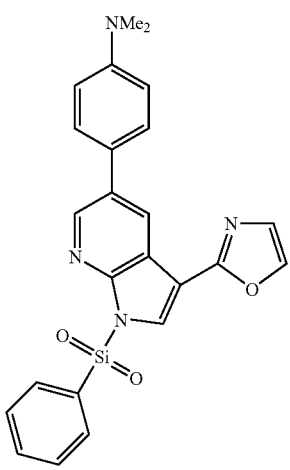

-continued
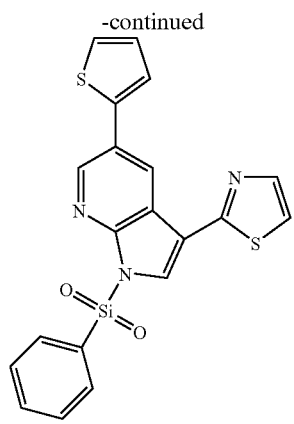
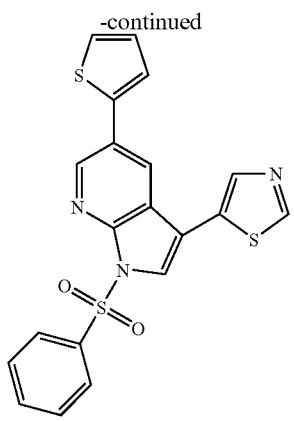
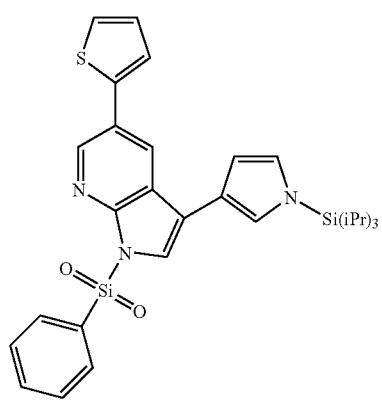
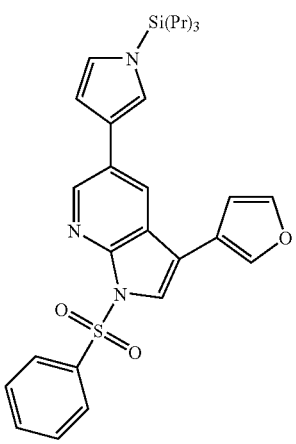
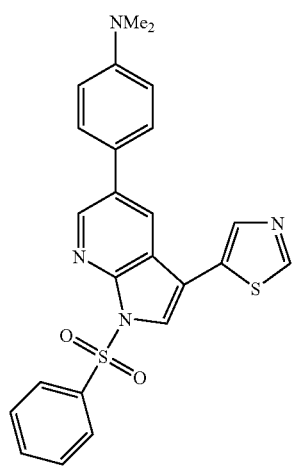
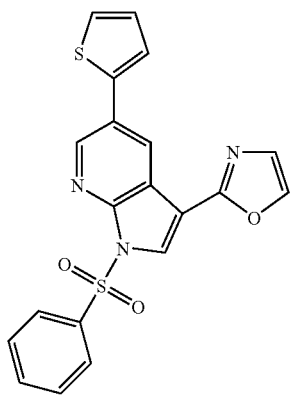

-continued
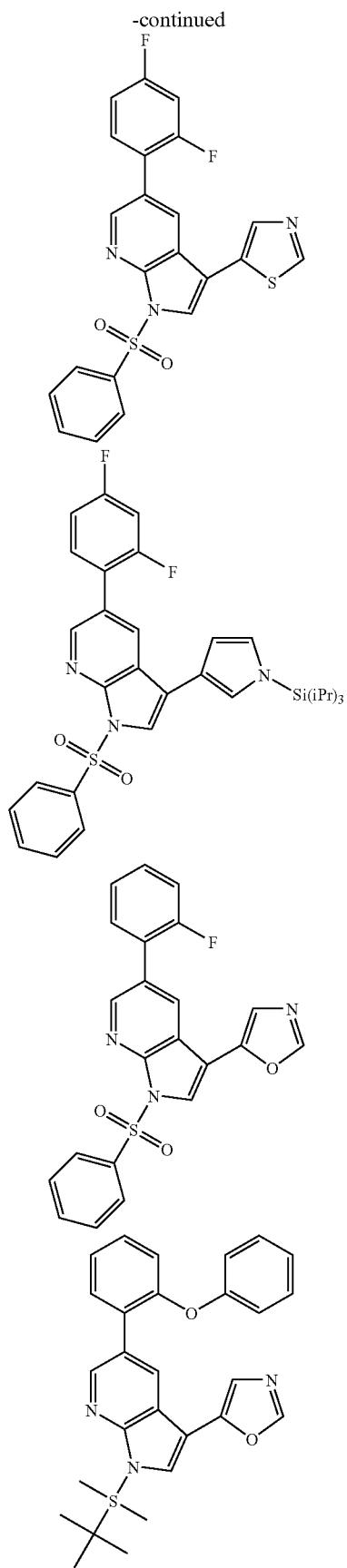
-continued
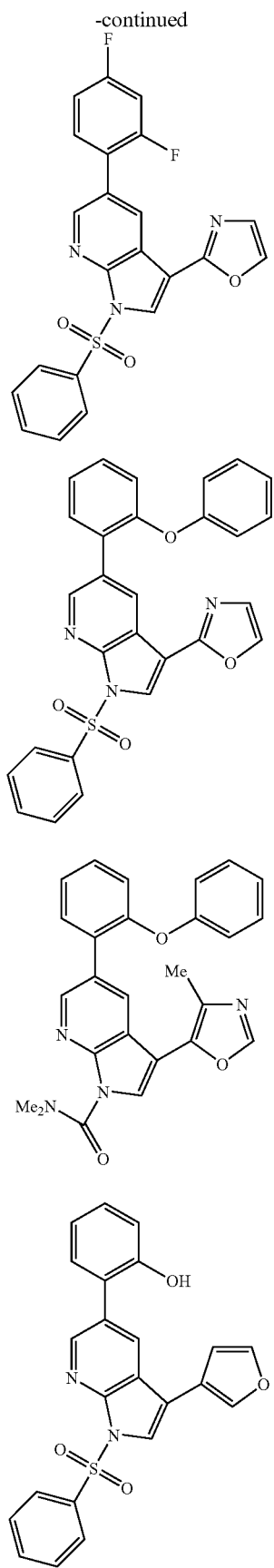

123
-continued
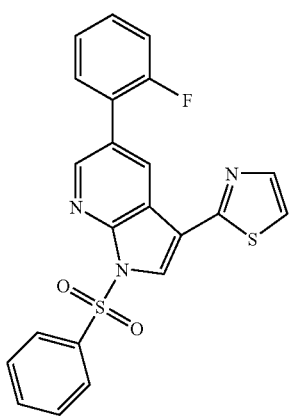
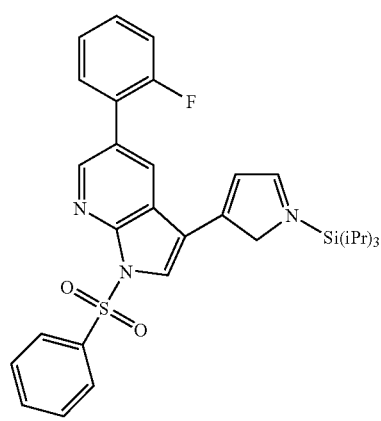
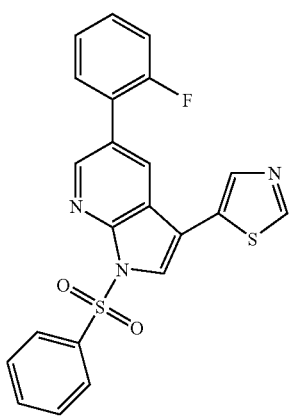
124
-continued
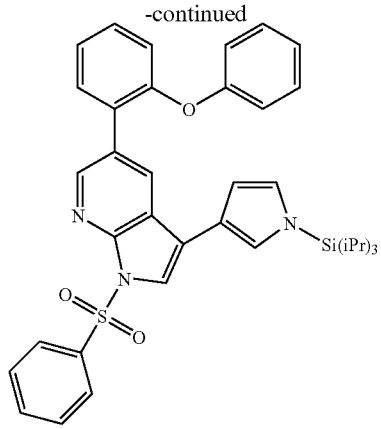
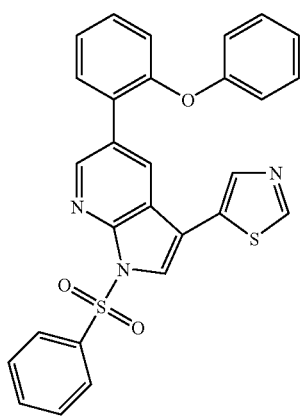
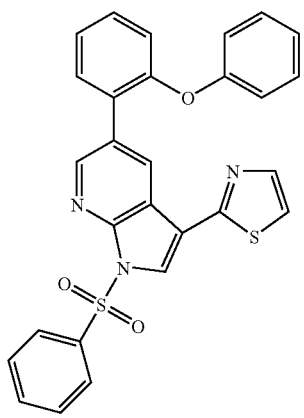

125
-continued
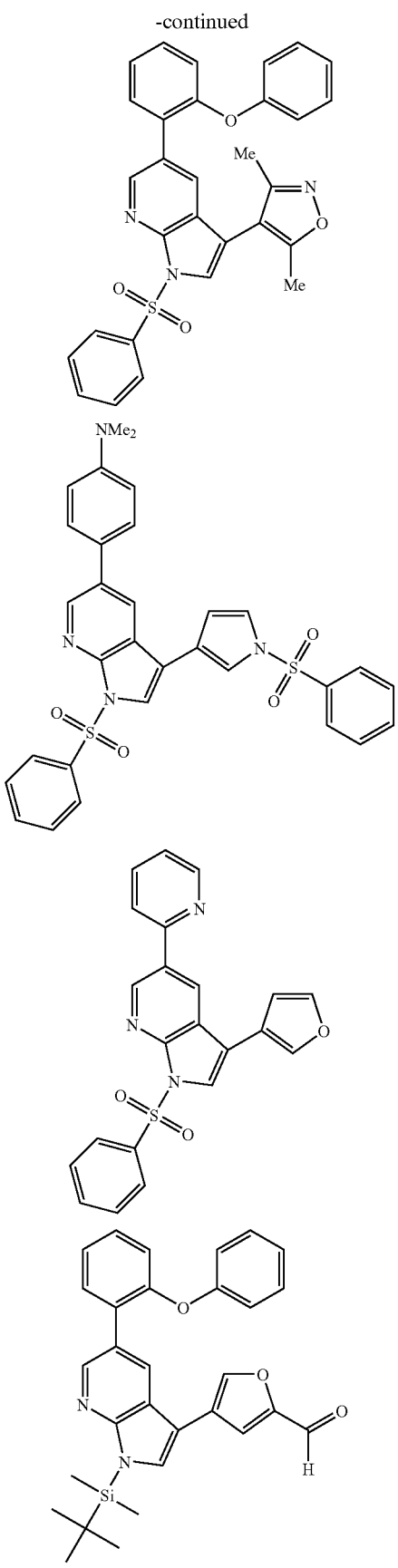
126
-continued
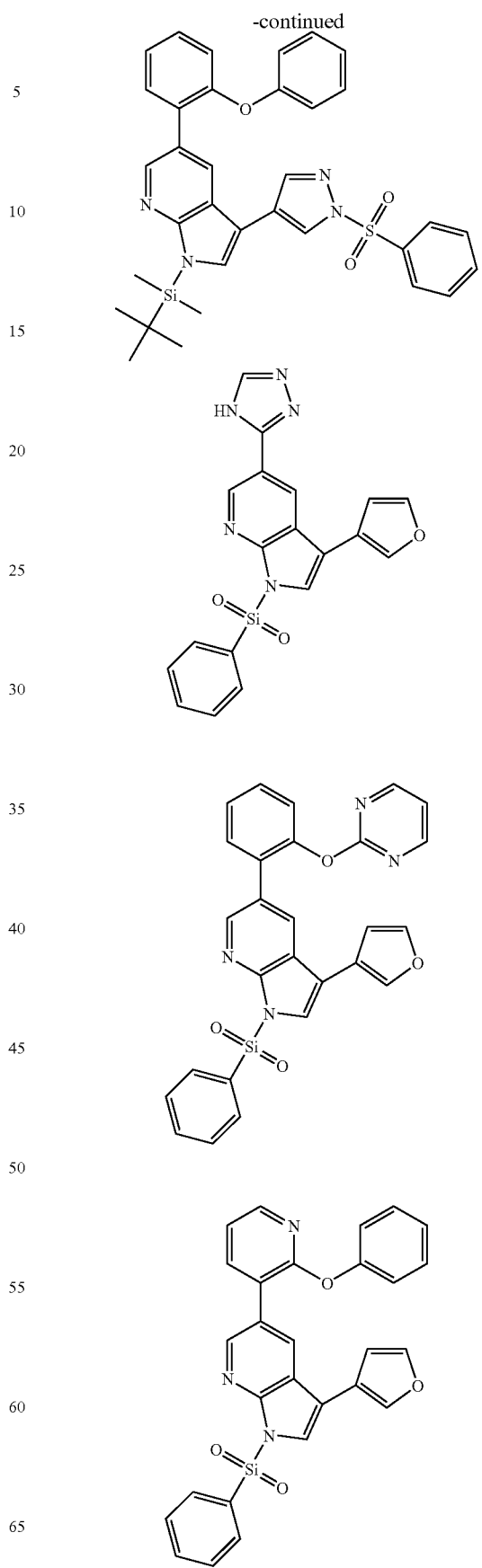

127
-continued
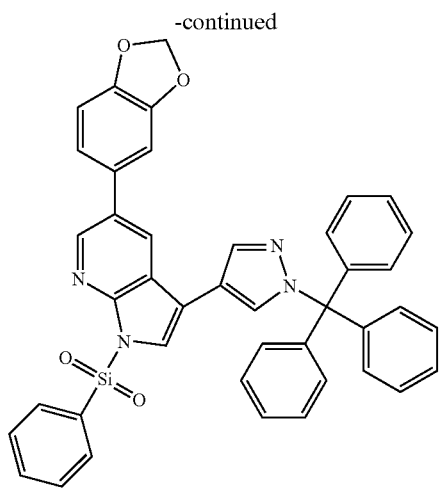
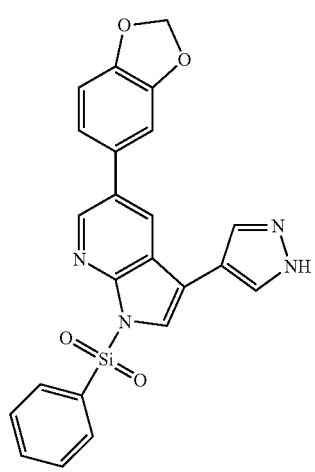
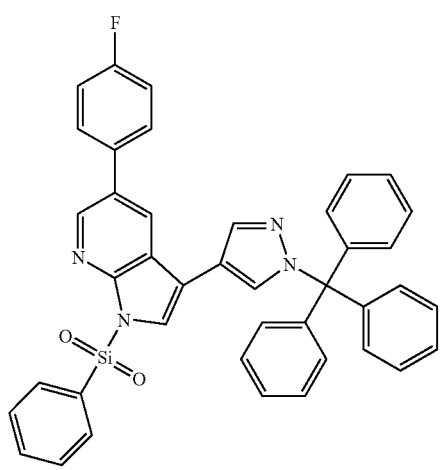
128
-continued
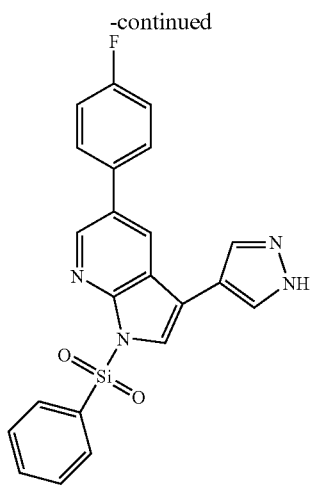
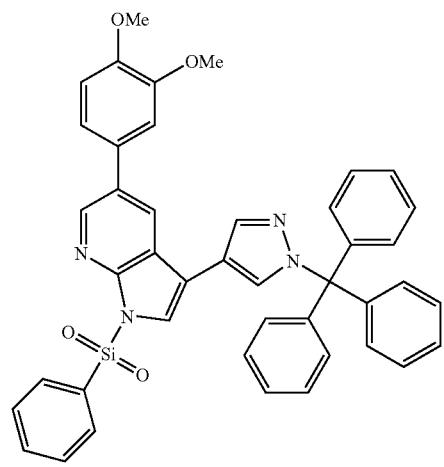
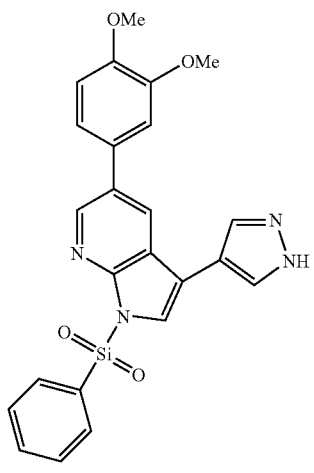

-continued
129
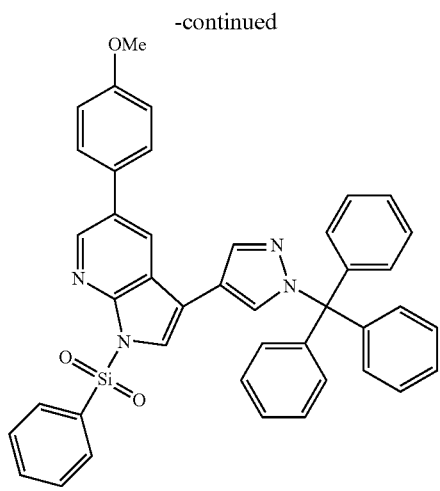
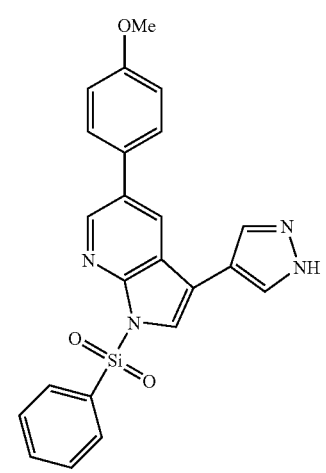
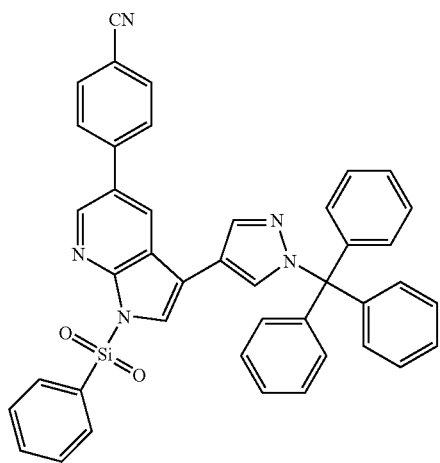
130
-continued
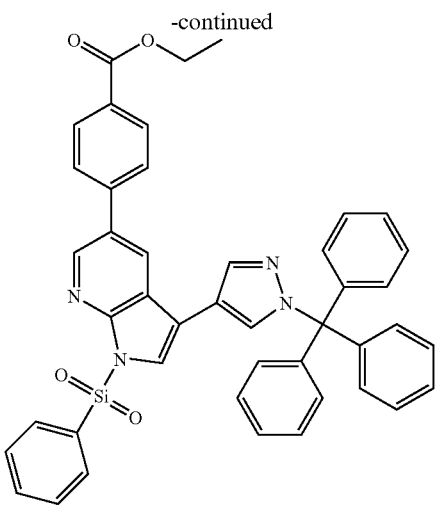
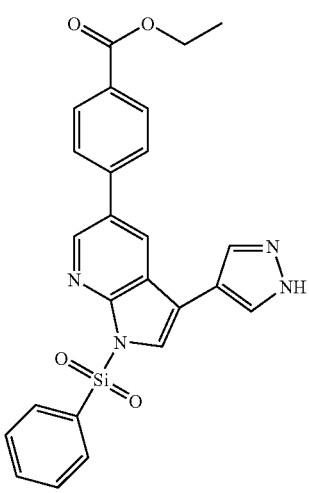
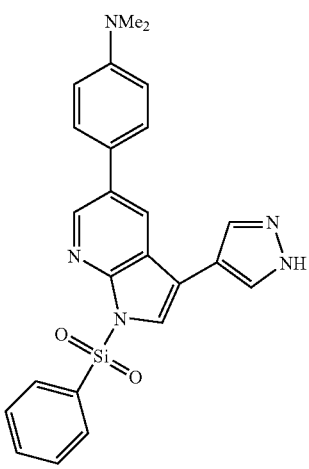

131
-continued
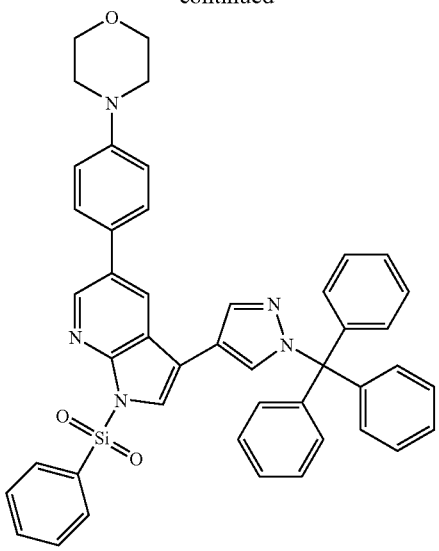
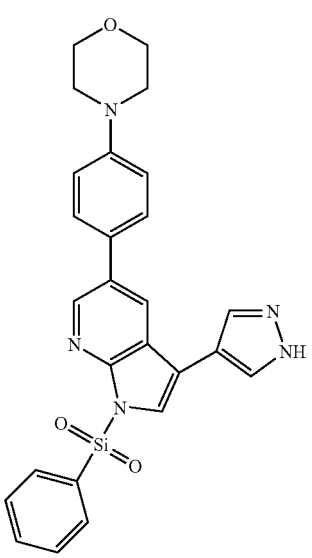
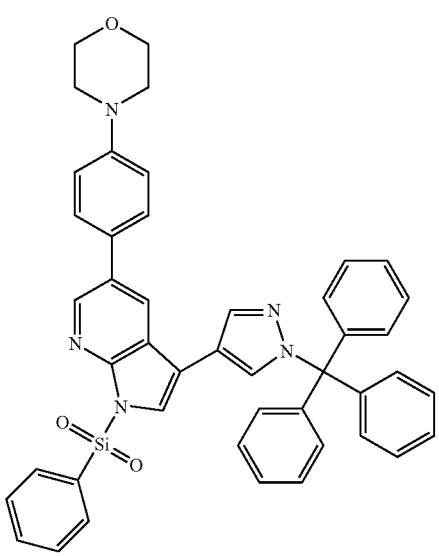
132
-continued
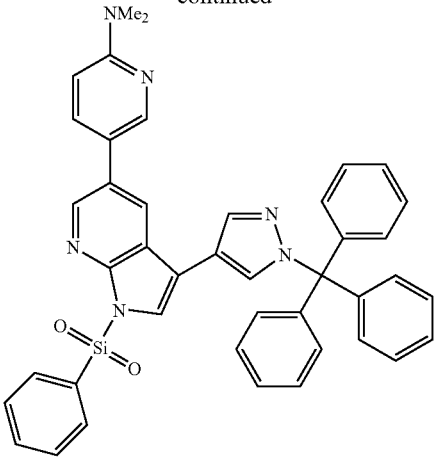
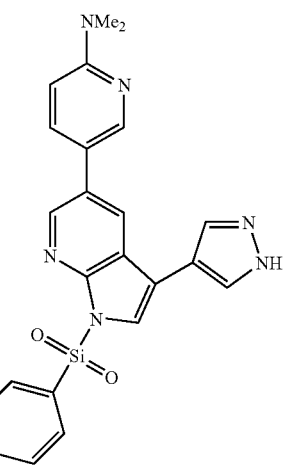
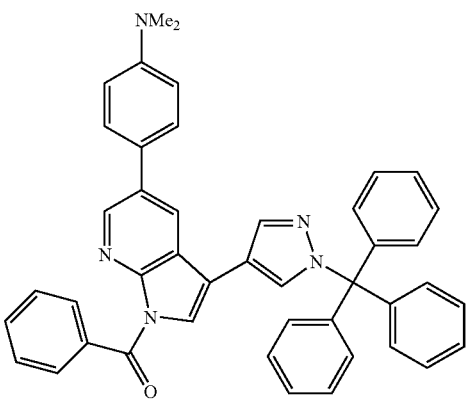

-continued
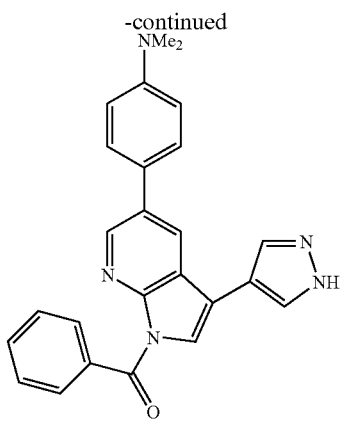
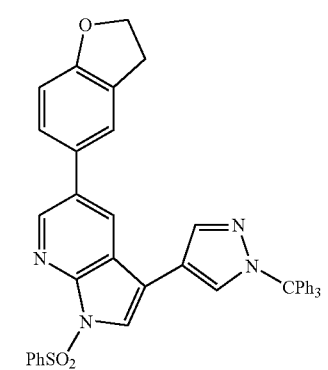
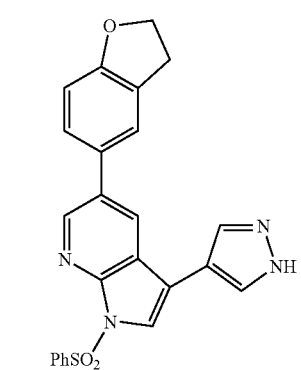
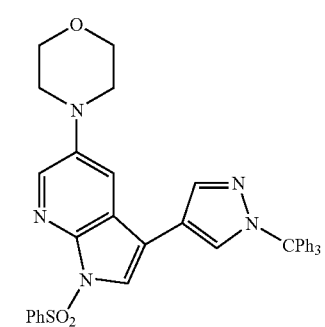
-continued
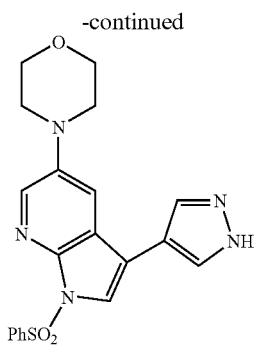
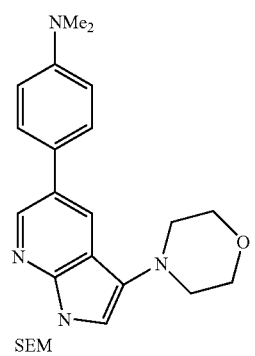
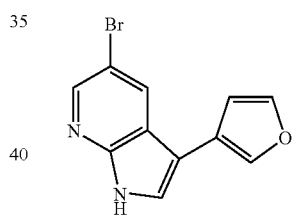 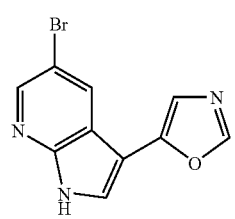
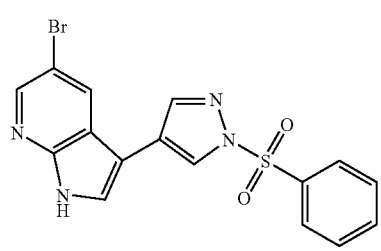
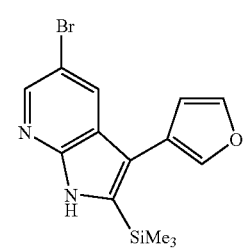

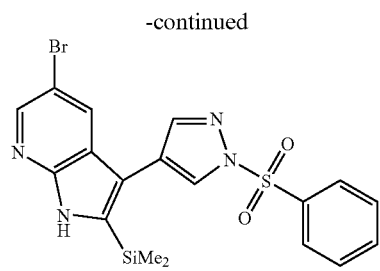
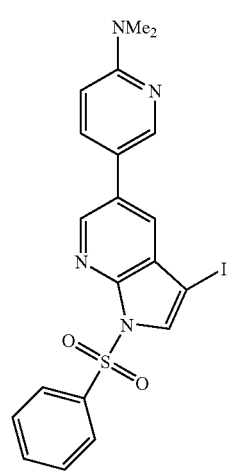
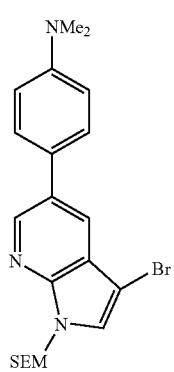
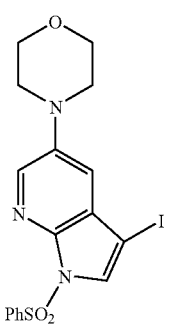
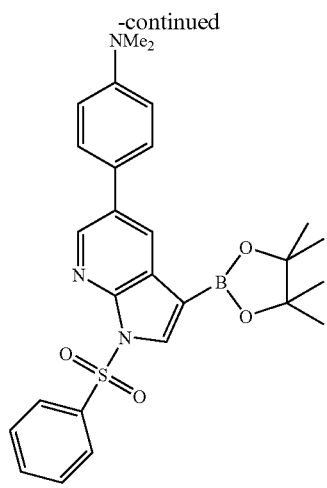
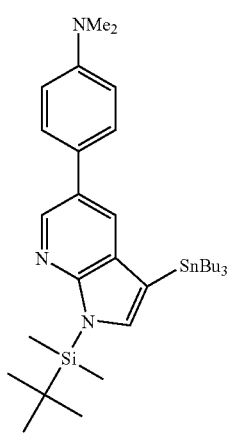
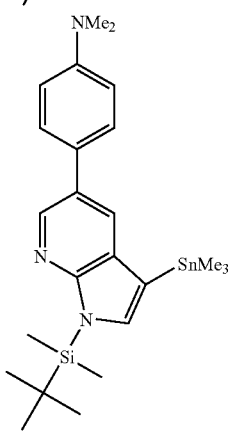
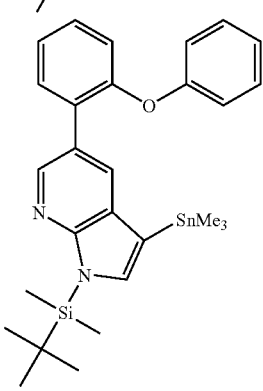

137
-continued
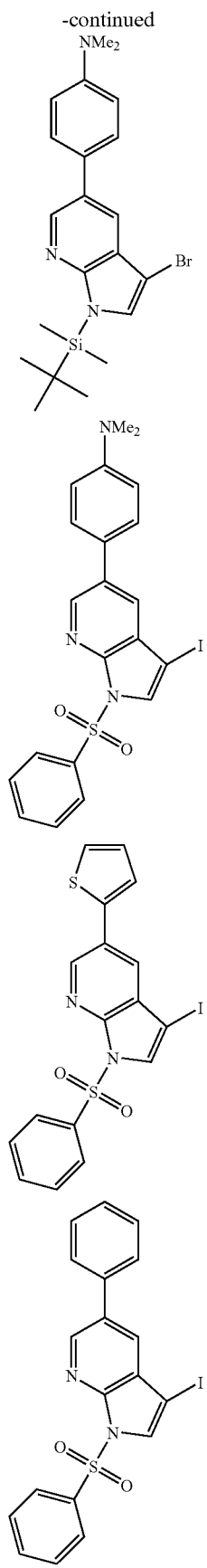
138
-continued
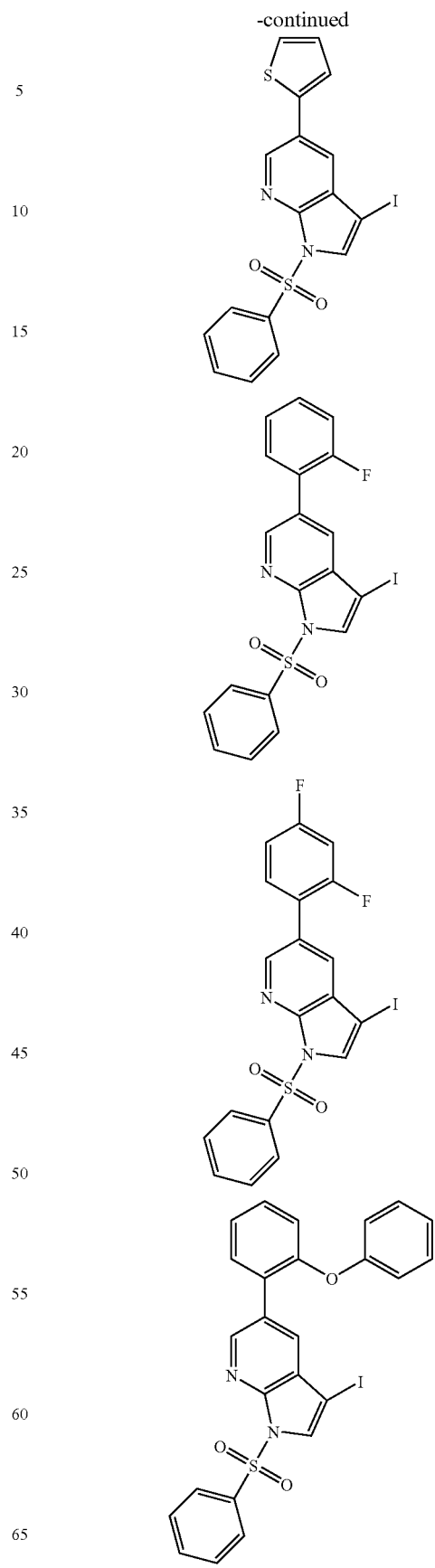

-continued
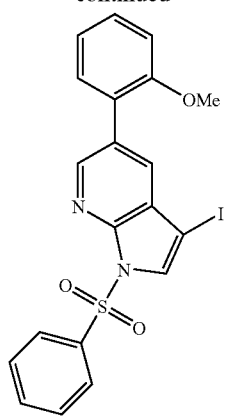
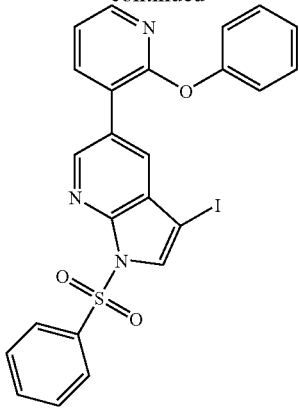
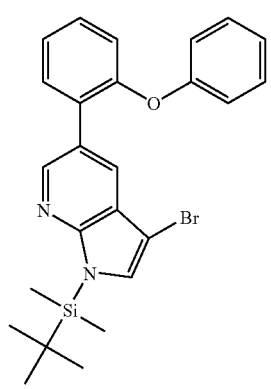
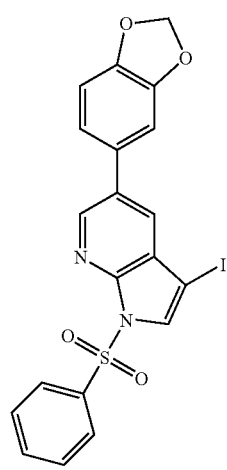
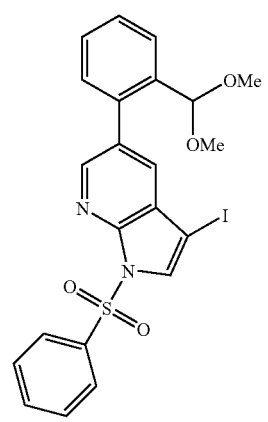
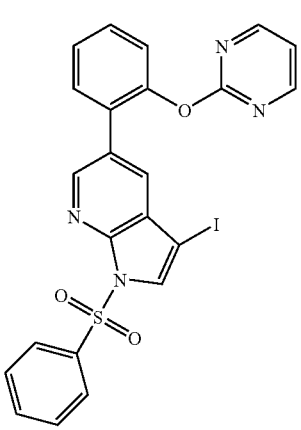
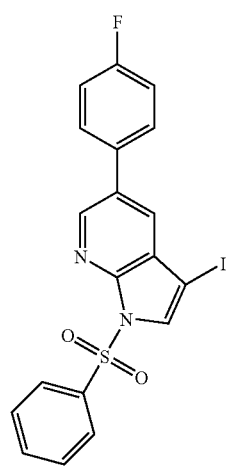

-continued
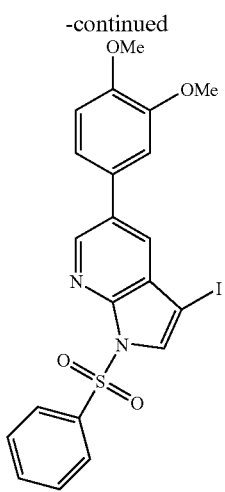
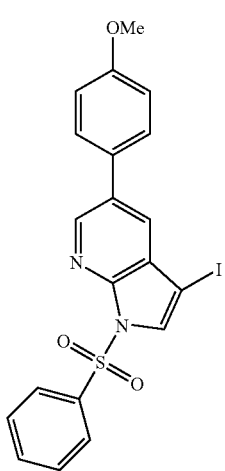
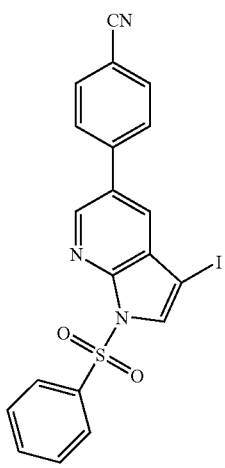
-continued
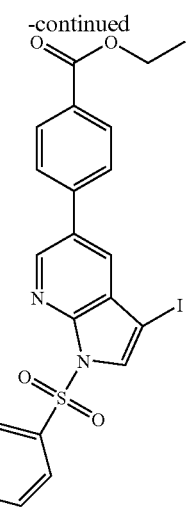
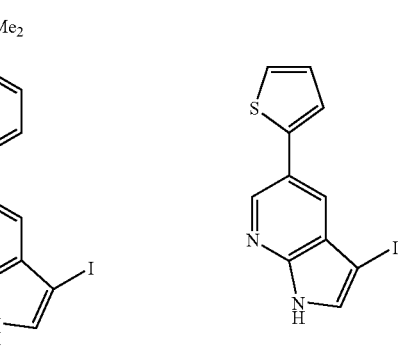

-continued
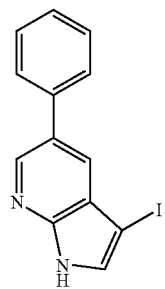 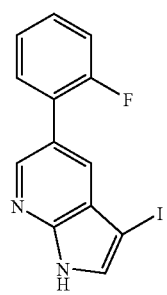 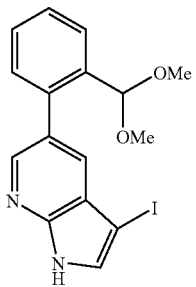 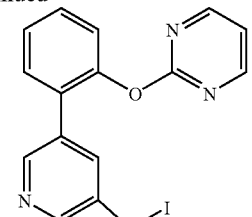
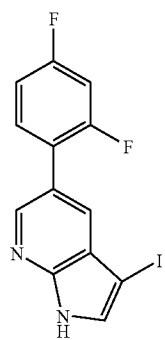 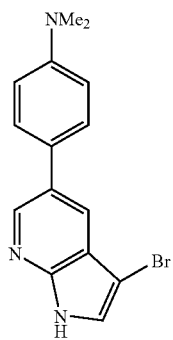 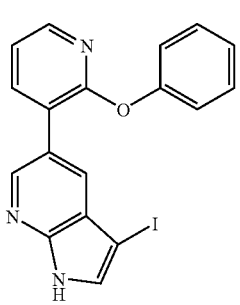 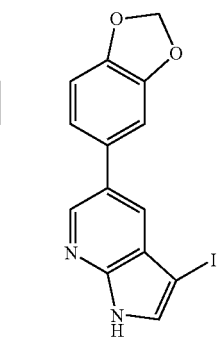
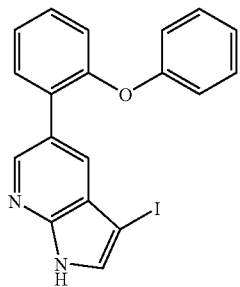 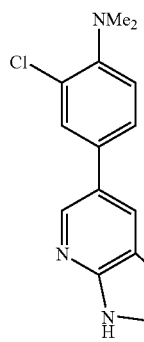 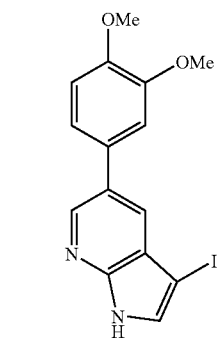
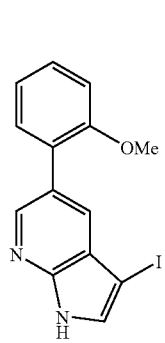 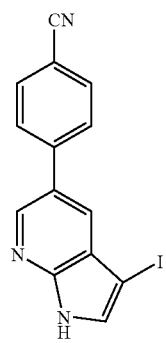 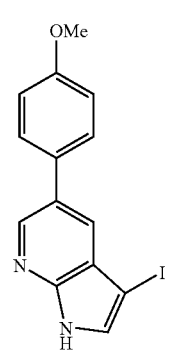 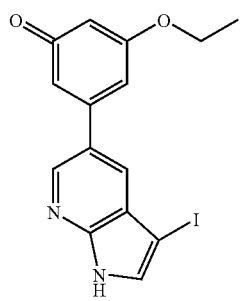

-continued
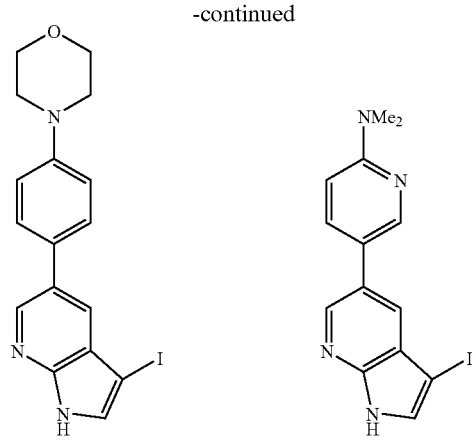
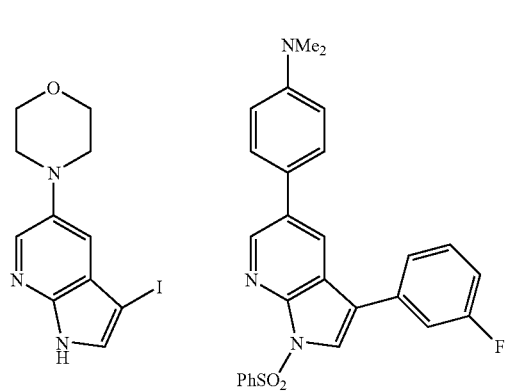
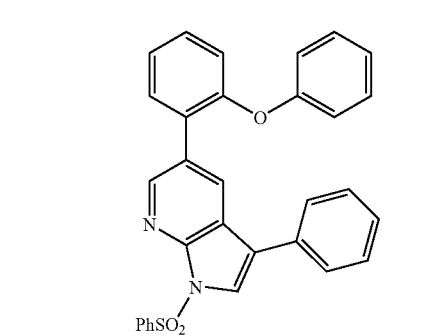
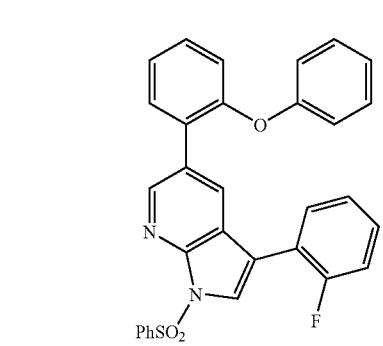
-continued
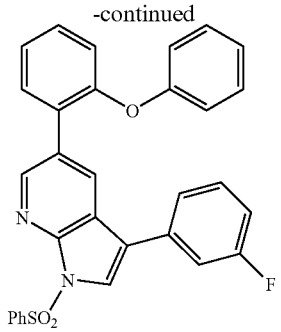
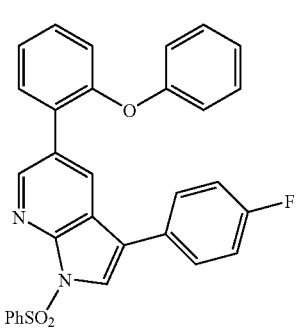
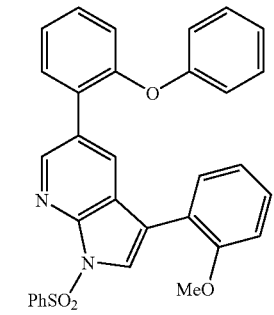
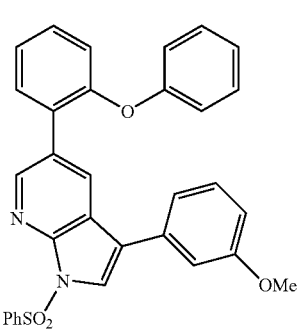

-continued
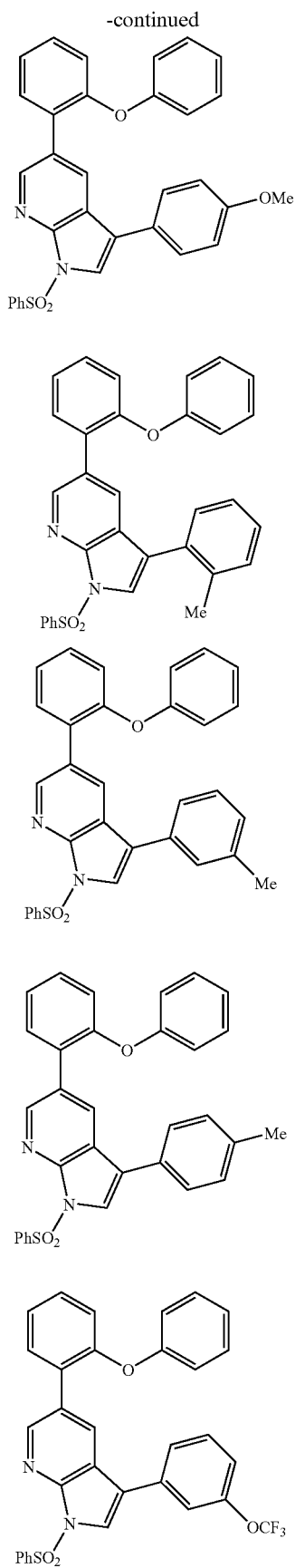
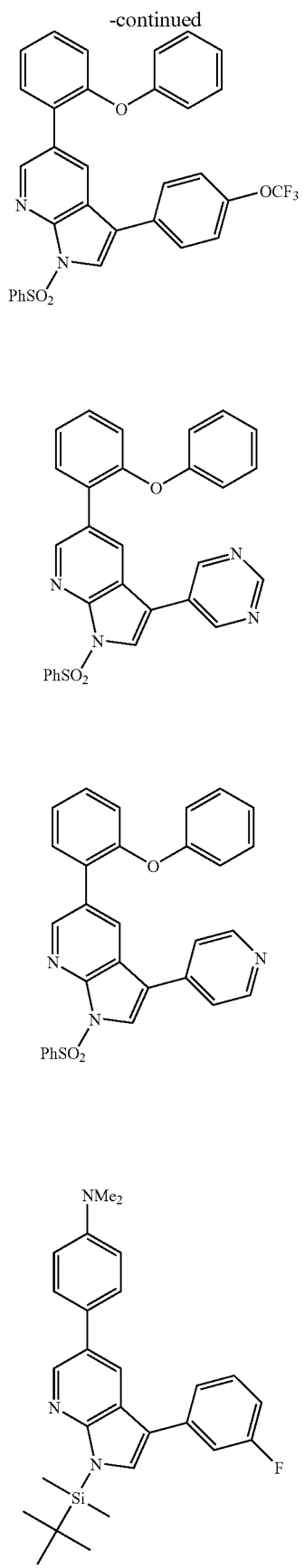

-continued
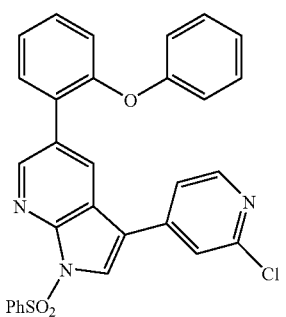
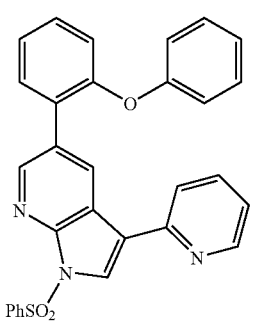
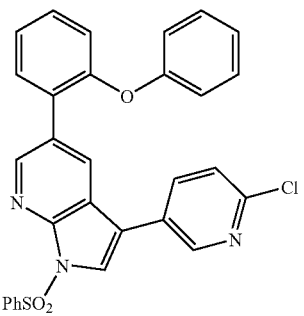
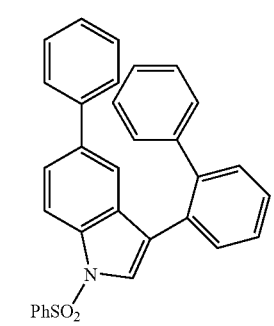
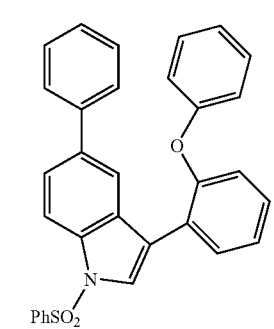
-continued
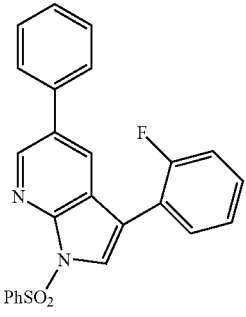
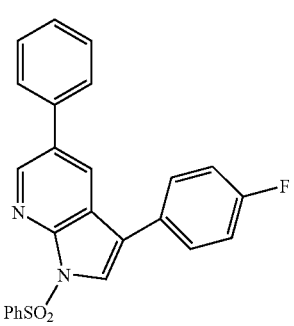
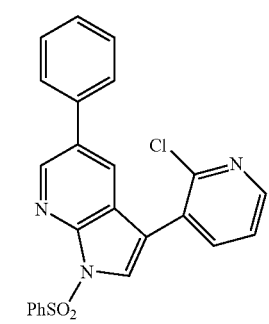
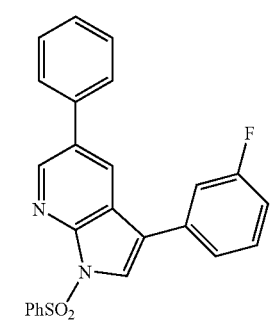

-continued
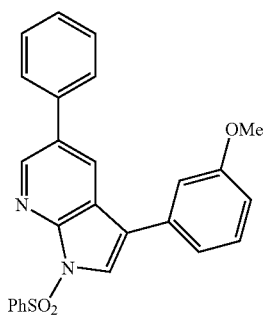
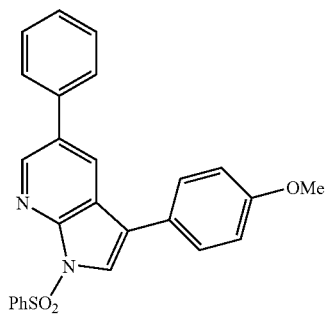
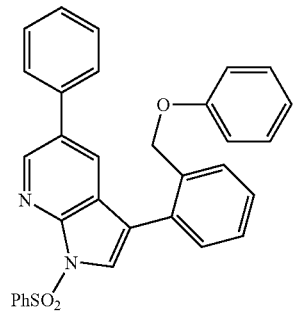
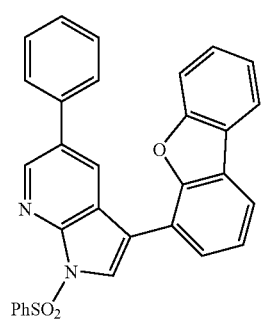
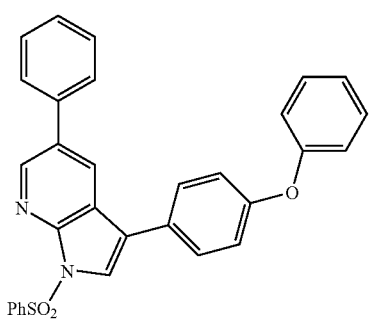
-continued
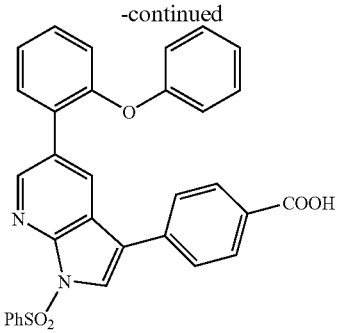
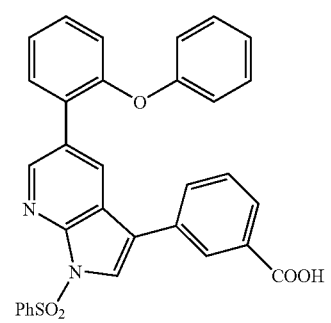
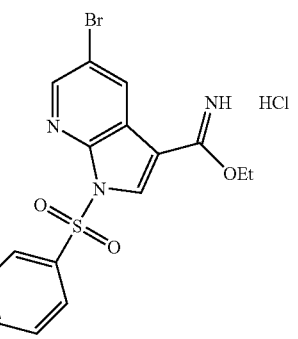
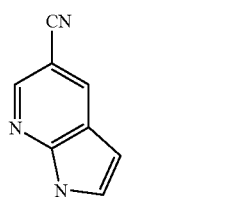 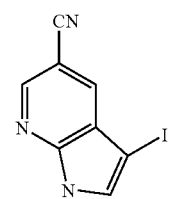
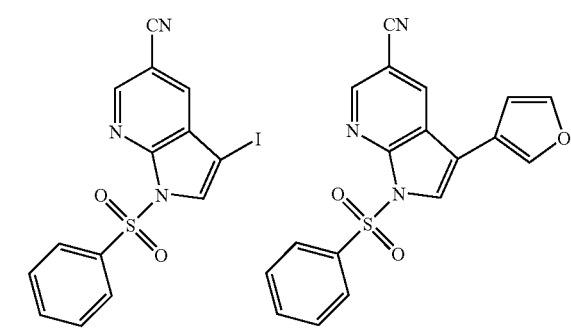

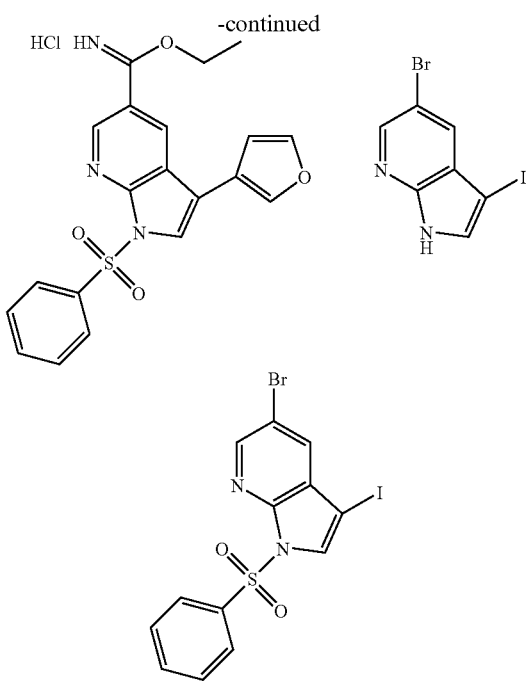

-continued

The present invention also encompasses a process for manufacturing a compound of the first aspect, the process comprising providing a starting material, which is commercially available or can be produced by a method known in the art, converting the starting material to form an intermediate compound of the third, sixth, eighth, tenth, thirteenth, fourteenth, fifteenth, seventeenth, eighteenth, nineteenth, twenty first, twenty third, twenty fourth, twenty fifth, twenty seventh, twenty ninth, thirtieth, thirty first, thirty fourth, thirty eighth, fortieth, forty second, forty fourth, forty seventh, forty eighth, fifty first, fifty fourth, fifty sixth, sixtieth and sixty second aspects aspects using a process as described above or a process known in the art (and optionally converting the intermediate compound so formed into another intermediate compound) and then converting the intermediate compound into a compound of the first aspect using a process as described above or a process known in the art (and optionally converting the compound of the first aspect so formed into another compound of the first aspect).

The sixty fifth aspect of the invention provides a composition comprising a compound according to the first aspect of the invention in combination with a pharmaceutically acceptable carrier, diluent or excipient.

The composition may also comprise one or more additional active agent, such as an anti-inflammatory agent (for example a p38 inhibitor, glutamate receptor antagonist, or a calcium channel antagonist), AMPA receptor antagonist, a chemotherapeutic agent and/or an antiproliferative agent.

Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The composition according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the composition can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve, which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The sixty sixth aspect of the invention provides a process for the manufacture of a composition according to the sixty fifth aspect of the invention. The manufacture can be carried out by standard techniques well known in the art and involves combining a compound according to the first aspect of the invention and the pharmaceutically acceptable carrier or diluent. The composition may be in any form including a tablet, a liquid, a capsule, and a powder or in the form of a food product, e.g. a functional food. In the latter case the food product itself may act as the pharmaceutically acceptable carrier.

The sixty seventh aspect of the present invention relates to a compound of the first aspect, or a composition of the sixty fifth aspect, for use in medicine.

The compounds of the present invention are inhibitors of JNK, such as JNK1, JNK2, or JNK3. In particular, the compounds of the present invention are inhibitors of JNK3. Preferably, the compounds of the present invention inhibit JNK3 selectively (i.e. the compounds of the invention preferably show greater activity against JNK3 than JNK1 and 2). For the purpose of this invention, an inhibitor is any compound, which reduces or prevents the activity of the JNK enzyme.

The compounds are therefore useful for conditions for which inhibition of JNK activity is beneficial. Thus, preferably, this aspect provides a compound of the first aspect, or a composition of the sixty fifth aspect of the present invention, for the prevention or treatment of a JNK-mediated disorder. The compounds of the first aspect of the invention may thus be used for the inhibition of JNK, more preferably for the inhibition of JNK3.

A "JNK-mediated disorder" is any disease or deleterious condition in which JNK plays a role. Examples include neurodegenerative disorder (including dementia), inflammatory disease, a disorder linked to apoptosis, particularly neuronal apoptosis, autoimmune disease, destructive bone disorder, proliferative disorder, cancer, infectious disease, allergy, ischemia reperfusion injury, heart attack, angiogenic disorder, organ hypoxia, vascular hyperplasia, cardiac hypertrophy, thrombin induced platelet aggregation and any condition associated with prostaglandin endoperoxidase synthase-2. The compounds of the present invention may be used for any of these JNK-mediated disorders.

The compounds of the present invention are particularly useful for the prevention or treatment of a neurodegenerative disorder. In particular, the neurodegenerative disorder results from apoptosis and/or inflammation. Examples of neurodegenerative disorders are: dementia; Alzheimer's disease; Parkinson's disease; Amyotrophic Lateral Sclerosis; Huntington's disease; senile chorea; Sydenham's chorea; hypoglycemia; head and spinal cord trauma including traumatic head injury; acute and chronic pain; epilepsy and seizures; olivopontocerebellar dementia; neuronal cell death; hypoxia-related neurodegeneration; acute hypoxia; glutamate toxicity including glutamate neurotoxicity; cerebral ischemia; dementia linked to meningitis and/or neurosis; cerebrovascular dementia; or dementia in an HIV-infected patient.

The neurodegenerative disorder may be a peripheral neuropathy, including mononeuropathy, multiple mononeuropathy or polyneuropathy. Examples of peripheral neuropathy may be found in diabetes mellitus, Lyme disease or uremia; peripheral neuropathy caused by a toxic agent; demyelinating disease such as acute or chronic inflammatory polyneuropathy, leukodystrophies, or Guillain-Barré syndrome; multiple mononeuropathy secondary to a collagen vascular disorder (e.g. polyarteritis nodosa, SLE, Sjögren's syndrome); multiple mononeuropathy secondary to sarcoidosis; multiple mononeuropathy secondary to a metabolic disease (e.g. diabetes or amyloidosis); or multiple mononeuropathy secondary to an infectious disease (e.g Lyme disease or HIV infection).

The compounds of the invention can also be used to prevent or treat disorders resulting from inflammation. These include, for example, inflammatory bowel disorder, bronchitis, asthma, acute pancreatitis, chronic pancreatitis, allergies of various types, and possibly Alzheimer's disease. Autoimmune diseases which may also be treated or prevented by the compounds of the present invention include rheumatoid arthritis, systemic lupus erythematosus, glumerulonephritis, scleroderma, chronic thyroiditis, Graves's disease, autoimmune gastritis, diabetes, autoimmune haemolytis anaemia, autoimmune neutropaenia, thrombocytopenia, atopic dermatitis, chronic active hepatitis, myasthenia gravis, multiple sclerosis, ulcerative colitis, Crohn's disease, psoriasis or graft vs host disease.

A compound of the present invention may be administered simultaneously, subsequently or sequentially with one or more other active agent, such as an anti-inflammatory agent e.g. p38 inhibitor, AMPA receptor antagonist, glutamate receptor antagonist, calcium channel antagonist, a chemotherapeutic agent or an antiproliferative agent. For example, for acute treatment, a p38 inhibitor may be administered to a patient prior to administering a compound of the present invention.

The compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

The sixty eighth aspect of the invention relates to a method of treating or preventing a JNK-mediated disorder in an individual, which method comprises administering to said individual a compound of the first aspect or a composition of the sixty fifth aspect. The active compound is preferably administered in a cumulative effective amount. The individual may be in need of the treatment or prevention. Any of the JNK-mediated disorders listed above in relation to the sixty seventh aspect may be the subject of treatment or prevention according to the sixty eighth aspect. One or more other active agent may be administered to the individual simultaneously, subsequently or sequentially to administering the compound. The other active agent may be an anti-inflammatory agent such as a p38 inhibitor, glutamate receptor antagonist, AMPA receptor antagonist, calcium channel antagonist, a chemotherapeutic agent or an antiproliferative agent, but is preferably p38 inhibitor for acute treatment.

The sixty ninth aspect of the present invention provides the use of a compound of the first aspect in the manufacture of a medicament for the prevention or treatment of a JNK-mediated disorder. The medicament may be used for treatment or prevention of any of the JNK-mediated disorders listed above in relation to the sixty seventh aspect. Again, the compound of the present invention may be administered simultaneously, subsequently or sequentially with one or more other active agent, preferably a p38 inhibitor for acute treatment.

In the seventieth aspect of the invention, there is provided an assay for determining the activity of the compounds of the present invention, comprising providing a system for assaying the activity and assaying the activity of the compound. Preferably the assay is for the JNK inhibiting activity of the compound, more preferably it is for the JNK3-specific inhibiting activity of the compounds. The compounds of the invention may be assayed in vitro, in vivo, in silico, or in a primary cell culture or a cell line. In vitro assays include assays that determine inhibition of either the kinase activity or ATPase activity of activated JNK. Alternatively, in vitro assays may quantitate the ability of a compound to bind JNK and may be measured either by radiolabelling the compound prior to binding, then isolating the inhibitor/JNK complex and determining the amount of the radiolabel bound or by running a competition experiment where new inhibitors are incubated with JNK bound to known radioligands. An example of an assay, which may be used, is Scintillation Proximity Assay (SPA), preferably using radiolabelled ATP. Another example is ELISA. Any type or isoform of JNK may be used in these assays.

In the seventy first aspect, there is provided a method of inhibiting the activity or function of a JNK, particularly JNK3, which method comprises exposing a JNK to a compound or a composition of the first or sixty fifth aspect of the present invention. The method may be performed in a research model, in vitro, in silico, or in vivo such as in an animal model. A suitable animal model may be a kainic acid model in rat or mice, traumatic brain injury model in rat, or MPTP in mice.

All features of each of the aspects apply to all other aspects *mutatis mutandis*.

The invention will now be illustrated by the following non-limiting examples.

EXAMPLES

Synthesis of Example Inhibitor 5

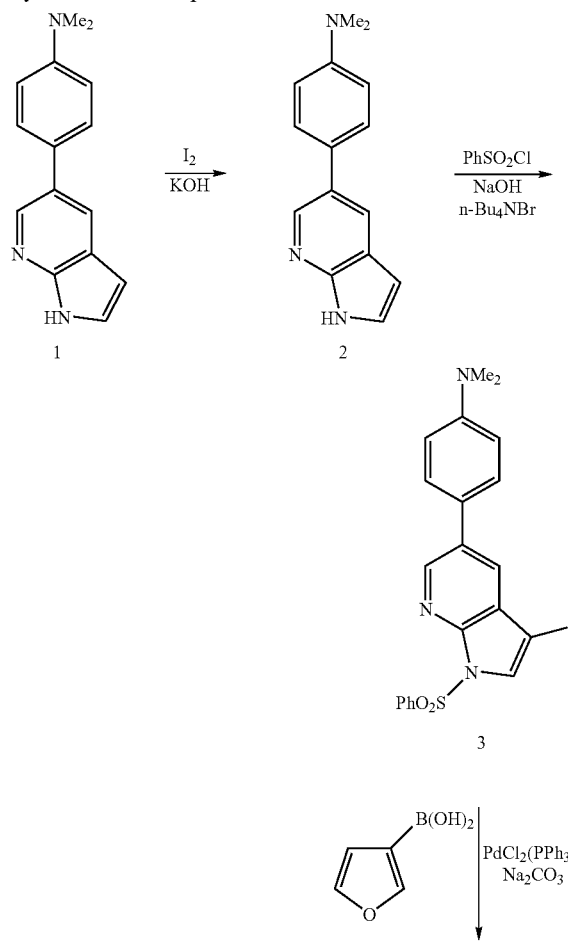

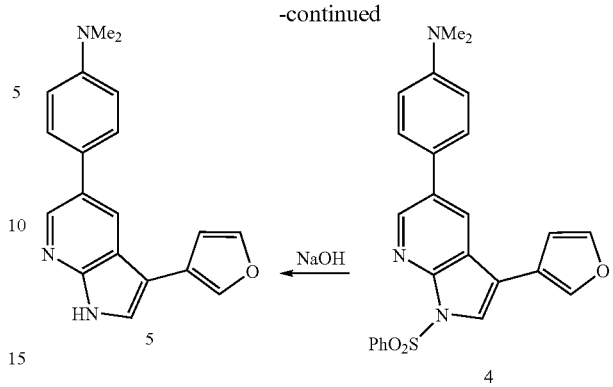

[4-(3-Iodo-1H-pyrrolo[2,3-b]pyridin-5-yl)-phenyl]-dimethyl-amine (2)

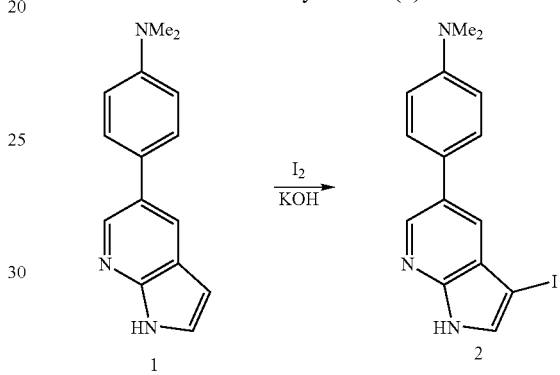

To a solution of 1 (4.08 g, 17.2 mmol) in DMF (43 mL) was added KOH (3.57 g, 63.7 mmol). The reaction mixture was stirred for 20 min, cooled in an ice-bath and treated with iodine (4.37 g, 17.2 mmol) portionwise over 15 min. When the addition was complete the reaction mixture was stirred at r.t. for 0.5 h and poured onto a mixture of water (253 mL) and saturated aqueous $Na_2S_2O_3$ (38 mL). The solid precipitate was filtered off, washed with water, and dried under high vacuum to give 2 as a tan solid (6.06 g, 97%); $^1$H NMR (400 MHz, $CDCl_3$) δ 3.04 (s, 6H), 6.88 (d, J=8.6 Hz, 2H), 7.47 (d, J=2.0 Hz, 1H), 7.58 (d, J=8.6 Hz, 2H), 7.88 (d, J3=1.9 Hz, 1H), 8.58 (d, J=2.0 Hz, 1H), 9.80-10.10 (bs, NH).

[4-(1-Benzenesulfonyl-3-iodo-1H-pyrrolo[2,3-b]pyridin-5-yl)-phenyl]-dimethyl-amine (3)

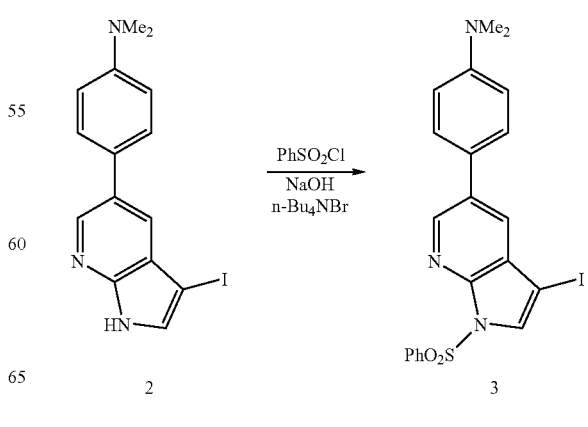

To a solution of 2 (6.00 g, 16.5 mmol) in benzene (100 mL) was added benzenesulfonyl chloride (4.85 mL, 38.0 mmol), tetra-n-butylammonium bromide (2.82 g, 8.76 mmol) and 50% aqueous NaOH (18.5 mL), and the reaction mixture was stirred overnight. The mixture was partitioned between water—benzene. The layers were separated and the aqueous layer was extracted with benzene (5×100 mL). The combined organic extracts were dried (MgSO₄) and concentrated to give orange oil, which solidified on drying in vacuum. The solid was triturated with methanol (200 mL) for 0.5 h, filtered off, and washed with ice-cold methanol (3×50 mL) to give product 3 as a tan solid (5.32 g, 64%); $^1$H NMR (400 MHz, CDCl$_3$) δ 3.01 (s, 6H), 6.81 (d, J=8.9 Hz, 2H), 7.45-7.60 (m, 4H), 7.59 (tt, J=14.8, 2.1 Hz, 1H), 7.74 (d, J=2.1 Hz, 1H), 7.86 (s, 1H), 8.24 (d, J=7.6 Hz, 2H), 8.64 (d, J=2.1 Hz, 1H); MS (CI) m/z 504.10 (MH$^+$).

[4-(1-Benzenesulfonyl-3-furan-3-yl-1H-pyrrolo[2,3-b]pyridin-5-yl)-phenyl]-dimethyl-amine (4)

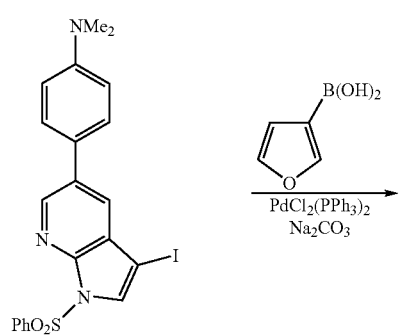

A mixture of 3 (300 mg, 0.596 mmol), EtOH (3.6 mL), toluene (3.6 mL), furan-3-boronic acid (100 mg, 0.894 mmol), 1M aq. Na$_2$CO$_3$ (1.49 mL, 1.49 mmol), LiCl (75.8 mg, 1.79 mmol) and PdCl$_2$(PPh$_3$)$_2$ (41.8 mg, 59.6 μmol) was refluxed for 15 min. The organic layer was separated, brine was added, and the aqueous layer was extracted with AcOEt. The combined organic solutions were concentrated and separated by means of silicagel chromatography using hexane:AcOEt as eluent (in gradient up to 15% AcOEt) to give 4 as an orange foam (205 mg, 78%); $^1$H NMR (400 MHz, CDCl$_3$) δ 3.03 (s, 6H), 6.73 (m, 1H), 6.84 (d, J=8.8 Hz, 2H), 7.45-7.65 (m, 6H), 7.84 (s, 2H), 8.05 (d, J=2.1 Hz, 1H), 8.26 (m, 2H), 8.68 (d, J=2.2 Hz, 1H).

[4-(3-Furan-3-yl-1H-pyrrolo[2,3-b]pyridin-5-yl)-phenyl]-dimethyl-amine (5)

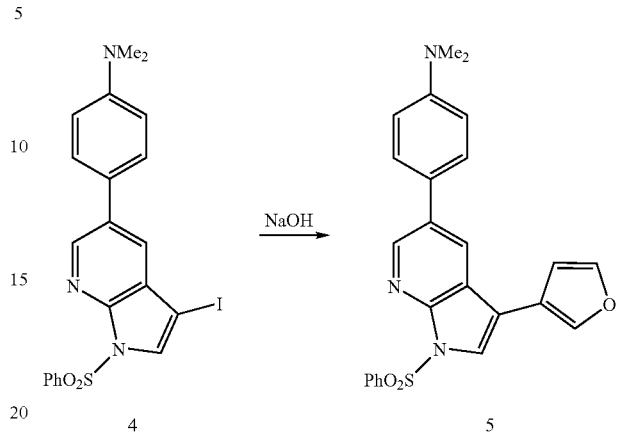

To a solution of 4 (195 mg, 0.44 mmol) in EtOH (9.9 mL), was added 10% aqueous NaOH (5.0 mL), and the reaction mixture heated at 85° C. for 0.5 h. It was then poured onto water (20 mL). The precipitate was filtered off, washed with water, and dried under high vacuum to afford 5 as light yellow solid (110 mg, 82%); $^1$H NMR (400 MHz, CDCl$_3$) δ 3.02 (s, 6H), 6.73 (m, 1H), 6.87 (d, J=8.9 Hz, 2H), 7.49 (d, J=1.8 Hz, 1H), 7.51-7.60 (m, 3H), 7.83 (s, 1H), 8.18 (d, J=1.8 Hz, 1H), 8.59 (d, J=1.8 Hz, 1H), 10.4 (bs, NH); MS (CI) m/z 304.10 (MH$^+$), 345.10 (M+MeCN).

Synthesis of Example Inhibitor 8

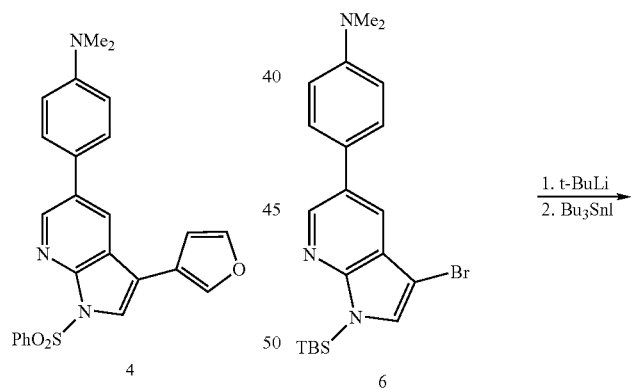

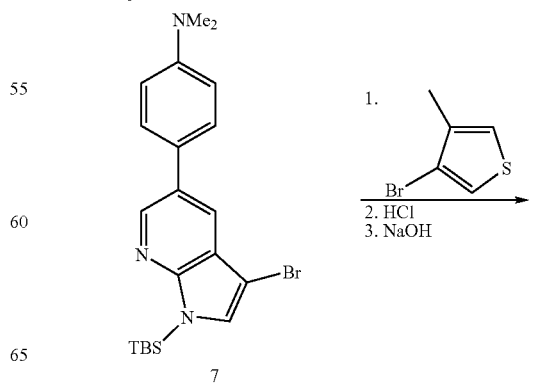

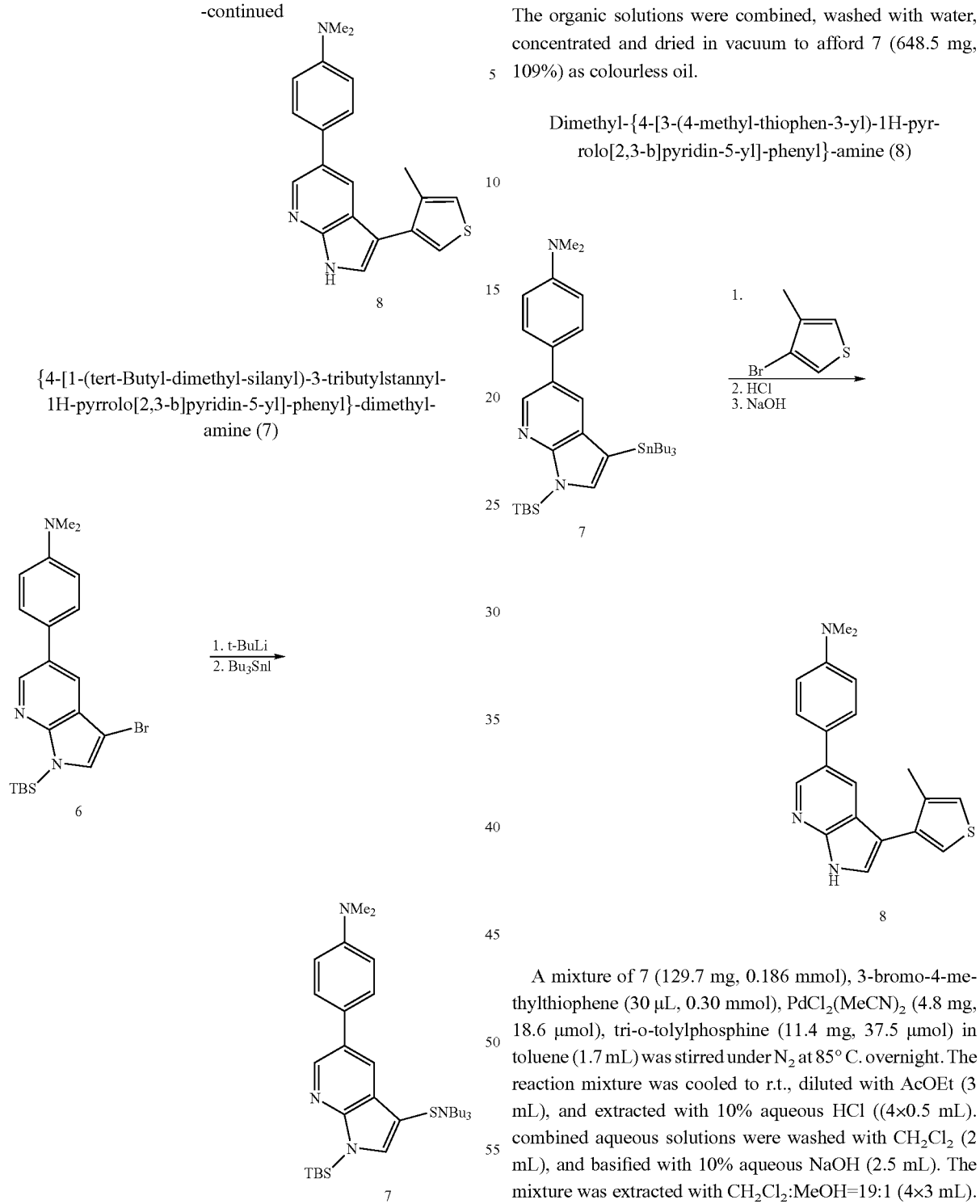

{4-[1-(tert-Butyl-dimethyl-silanyl)-3-tributylstannyl-1H-pyrrolo[2,3-b]pyridin-5-yl]-phenyl}-dimethyl-amine (7)

1.5 M solution of t-BuLi in pentane (1.3 mL, 1.95 mmol) was added dropwise over a period of 3 min to a stirred and cooled (−95° C.) solution of bromide 6 (400 mg, 0.93 mmol) in THF (4.0 mL). After an additional stirring for 10 min at −95° C., tributyltin iodide (319 μL, 1.12 mmol) was added in one portion. The mixture was stirred at −95° C. for 1 h and at r.t. for 1 h. Saturated aqueous NaHCO₃ solution (3 mL) was added, and the mixture was extracted with AcOEt (3×4 mL). The organic solutions were combined, washed with water, concentrated and dried in vacuum to afford 7 (648.5 mg, 109%) as colourless oil.

Dimethyl-{4-[3-(4-methyl-thiophen-3-yl)-1H-pyrrolo[2,3-b]pyridin-5-yl]-phenyl}-amine (8)

A mixture of 7 (129.7 mg, 0.186 mmol), 3-bromo-4-methylthiophene (30 μL, 0.30 mmol), PdCl₂(MeCN)₂ (4.8 mg, 18.6 μmol), tri-o-tolylphosphine (11.4 mg, 37.5 μmol) in toluene (1.7 mL) was stirred under N₂ at 85° C. overnight. The reaction mixture was cooled to r.t., diluted with AcOEt (3 mL), and extracted with 10% aqueous HCl ((4×0.5 mL). combined aqueous solutions were washed with CH₂Cl₂ (2 mL), and basified with 10% aqueous NaOH (2.5 mL). The mixture was extracted with CH₂Cl₂:MeOH=19:1 (4×3 mL). Combined extracts were washed with brine, dried (MgSO₄), and concentrated in vacuum. The residue was purified by preparative TLC using CH₂Cl₂:MeOH=19:1 as eluent to afford 8 (12.9 mg, 21%) as tan solid. ¹H NMR (400 MHz, CDCl₃) δ 2.34 (d, J=1.0 Hz, 3H), 3.01 (s, 6H), 6.85 (d, J=8.9 Hz, 2H), 7.10 (dq, J=3.3, 1.0 Hz, 1H), 7.36 (d, J=3.3 Hz, 1H), 7.41 (d, J=1.2 Hz, 1H), 7.53 (d, J=8.9 Hz, 2H), 8.14 (d, J=2.1 Hz, 1H), 8.59 (d, J=2.1 Hz, 1H), 10.00 (bs, 1H).

Synthesis of Example Inhibitor 15

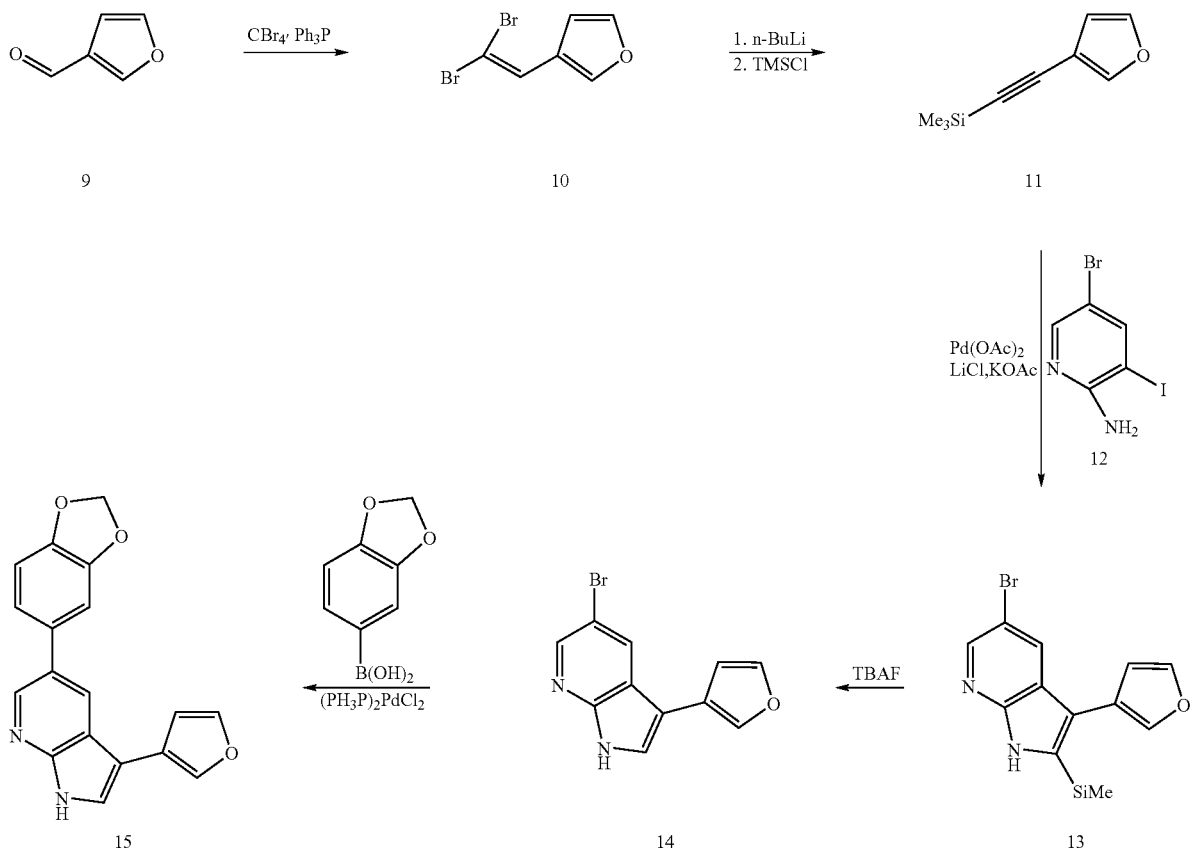

3-(2,2-Dibromo-vinyl)-furan (10)

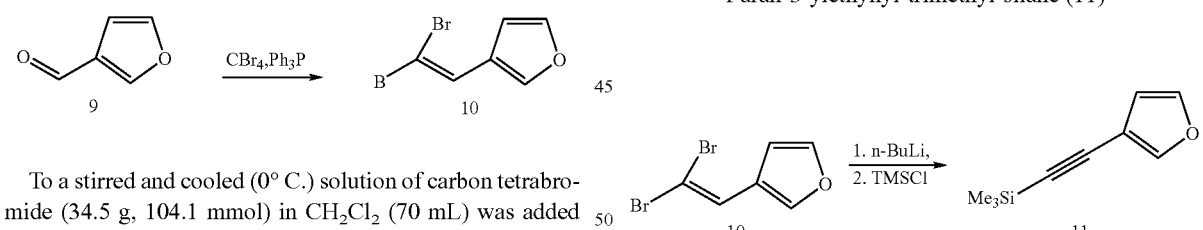

To a stirred and cooled (0° C.) solution of carbon tetrabromide (34.5 g, 104.1 mmol) in CH$_2$Cl$_2$ (70 mL) was added triphenylphosphine (54.6 g, 208.1 mmol) in five equal portions over a period of 5 nm. The resulting dark red solution was stirred for a further 10 min, and a solution of 3-furaldehyde (9) (5 g, 52.0 mmol) in CH$_2$Cl$_2$ (25 mL) was added slowly. The resulting black solution was allowed to warm to r.t. After 5.5 h the mixture was poured into ice-cold pentane and stirred vigourously. The mixture was filtered and the collected solid washed extensively with diethyl ether-ethyl acetate mixture. The combined solutions were washed with saturated aqueous Na$_2$S$_2$O$_3$ (×1), water (×1), 1 M aqueous NaOH, saturated brine (×1), dried (MgSO$_4$), filtered and concentrated. The residue was partially purified by silicagel chromatography (SGC) with hexane as eluent. Appropriate fractions were combined, concentrated and purified by vacuum distillation (150° C./0.5 mm Hg) to afford the dibromo-furan 10 (7.26 g, 55%) as a yellow oil. $^1$H NMR (400 MHz; CDCl$_3$) δ 6.79 (m, 1H), 7.27 (m, 1H), 7.41 (m, 1H) and 7.83 (m, 1H).

Furan-3-ylethynyl-trimethyl-silane (11)

To a stirred and cooled (−78° C.) solution of the dibromo-furan 10 (2.0 g, 7.9 mmol) in THF (20 mL) was added 1.6 M n-BuLi in hexane (10.2 mL, 16.3 mmol) over 3 min. After 1 h the cooling bath bath was removed and the mixture allowed to warm to r.t. Following a further 1.5 h the mixture was cooled back to −78° C. and then TMSCl (3.0 mL, 23.8 mmol) was added dropwise. The mixture was allowed to gradually warm up to r.t. After 19 h the mixture was poured into ice-cold Et$_2$O-saturated aqueous NaHCO$_3$ solution. The organic layer was separated and the aqueous layer extracted with Et$_2$O (2×). The combined organic solutions were dried (MgSO$_4$), filtered and concentrated to afford the crude acetylene 11 (1.83 g) as a yellow oil. This material was used in the next step without purification. $^1$H NMR (400 MHz; CDCl$_3$) inter alia δ 0.23 (s, 9H), 6.44 (m, 1H), 7.34 (m, 1H) and 7.63 (m, 1H).

5-Bromo-3-furan-3-yl-2-trimethylsilanyl-1H-pyrrolo[2,3-b]pyridine (13)

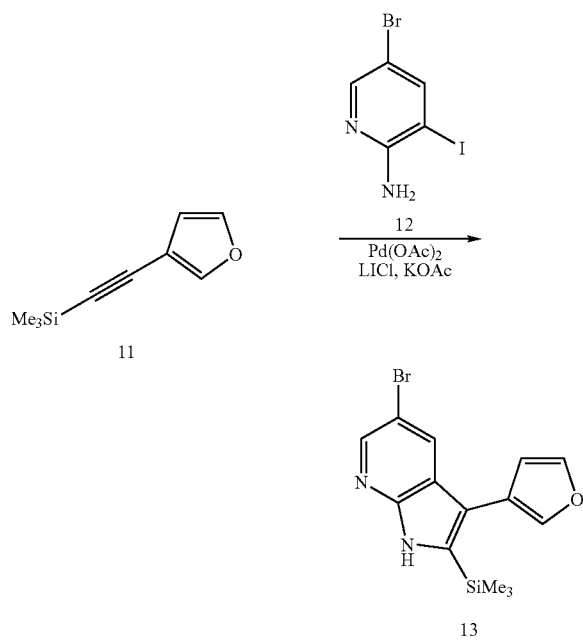

5-Bromo-3-iodo-pyridin-2-ylamine (12) (390 mg, 1.32 mmol; prepared according to WO0196308), crude acetylene 11 (910 mg), LiCl (56 mg, 1.32 mmol), KOAc (259 mg, 2.64 mmol), Pd(OAc)$_2$ (7.4 mg, 0.03 mmol) in DMF (10 mL) were heated in a sealed tube at 100° C. After 19 h the mixture was partitioned between Et$_2$O and saturated aqueous NH$_4$Cl. The organic layer was separated and the aqueous layer was extracted with Et$_2$O (4×). The combined organic solutions were dried (MgSO$_4$) and concentrated. The residual red oil was purified by PTLC with AcOEt:hexane=1:4 as eluent to yield azaindole 13 (97.9 mg, 22%) as an oil. $^1$H NMR (400 MHz; CDCl$_3$) δ 0.32 (s, 9H), 6.53 (d, J=0.9 Hz, 1H), 7.51 (s, 1H), 7.55 (t, J=1.6 Hz, 1H), 7.97 (d, J=1.9 Hz, 1H), 8.34 (d, J=2.1 Hz, 1H), 9.09 (brs, NH).

5-Bromo-3-furan-3-yl-1H-pyrrolo[2,3-b]pyridine (14)

To a stirred solution of azaindole 13 (20.9 mg, 0.06 mmol) in THF (3 mL) was added a 1M solution of TBAF in THF (0.12 mL, 0.12 mmol). After 1.5 h the mixture was concentrated and purified by PTLC with AcOEt as eluent to give azaindole 14 (9.6 mg, 58%) as a white solid. $^1$H NMR (400 MHz; CDCl$_3$) δ 6.67 (m, 1H), 7.44 (d, J=2.4 Hz, 1H), 7.53 (m, 1H), 7.76 (m, 1H), 8.18 (d, J=2.1 Hz, 1H), 8.39 (m, 1H), 9.33 (brs, NH).

5-Benzo[1,3]dioxol-5-yl-3-furan-3-yl-1H-pyrrolo[2,3-b]pyridine (15)

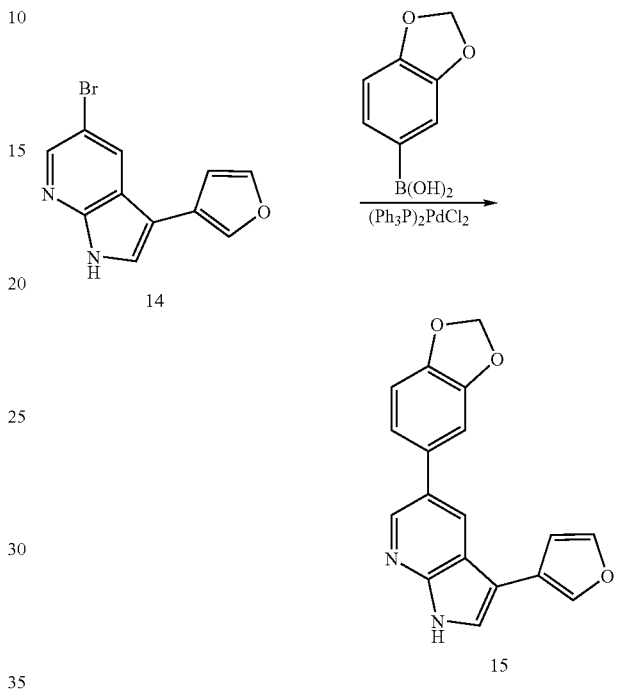

Bromide 14 (17.6 mg, 0.07 mmol), 3,4-(methylenedioxy)phenylboronic acid (16.7 mg, 0.10 mmol), LiCl (8.4 mg, 0.20 mmol), PdCl$_2$(Ph$_3$P)$_2$ (4.6 mg, 0.007 mmol) in 1 M aqueous Na$_2$CO$_3$ (0.17 mL, 0.17 mmol), PhMe (1.5 mL) and EtOH (1.5 mL) was heated at 105° C. After 5 h the mixture was allowed to cool to r.t. and then purified by PTLC with AcOEt:hexane=1:1 as eluent to afford azaindole 15 (15.2 mg, 76%) as a white solid. $^1$H NMR (400 MHz; CDCl$_3$) δ 6.04 (s, 2H), 6.72 (dd, J=0.8 and 1.8 Hz, 1H), 6.94 (dd, J=7.9, 0.3 Hz, 1H), 7.08-7.12 (m, 2H), 7.48 (d, J=2.3 Hz, 1H), 7.54 (t, J=1.6 Hz, 1H), 7.82 (t, J=1.1 Hz, 1H), 8.15 (d, J=2.1 Hz, 1H), 8.52 (d, J=2.1 Hz, 1H), 9.61 (brs, NH).

Synthesis of Example Inhibitor 18

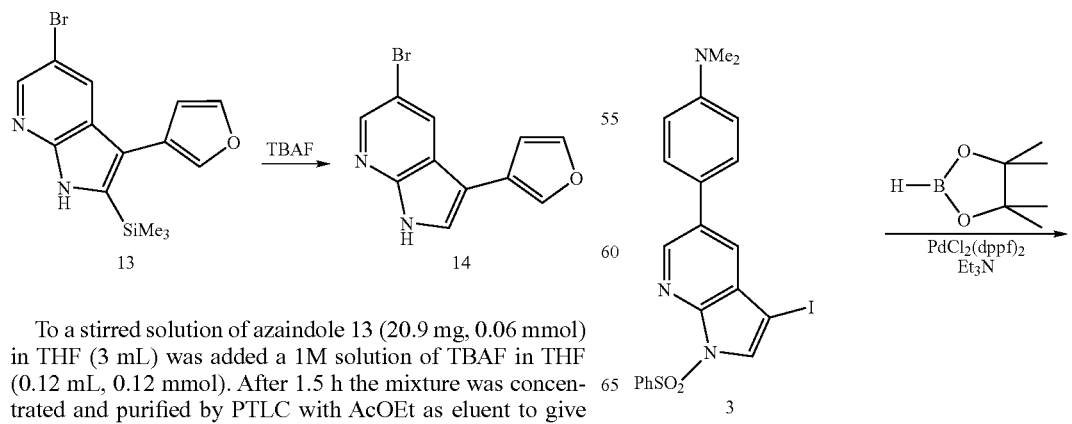

-continued

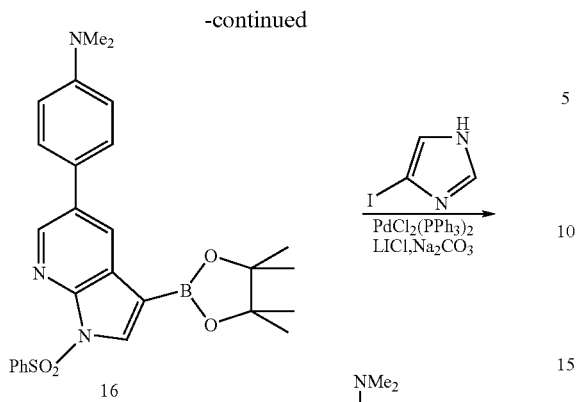

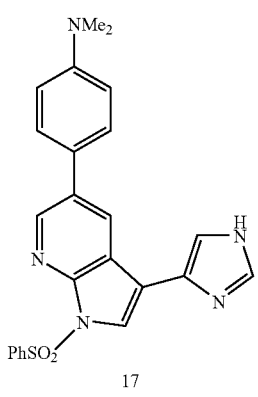

↓ NaOH

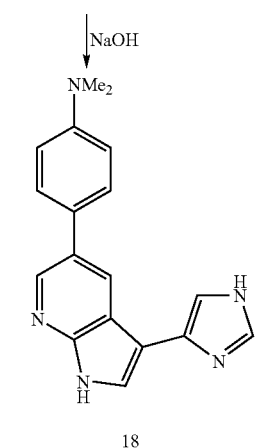

{4-[1-Benzenesulfonyl-3-(4,4,5,5-tetramethyl-[1,3,2]
dioxaborolan-2-yl)-1H-pyrrolo[2,3-b]pyridin-5-yl]-
phenyl}-dimethyl-amine (16)

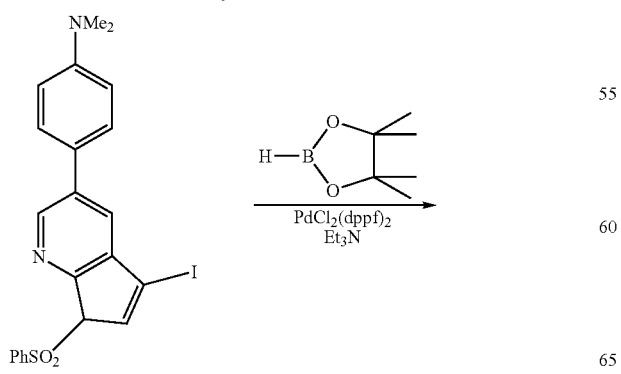

-continued

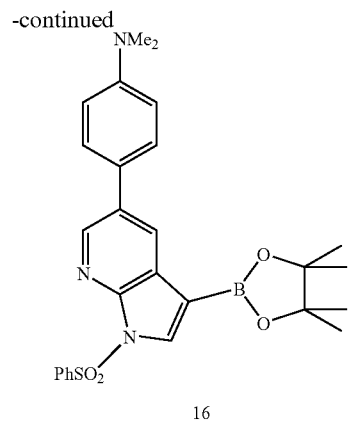

A mixture of 3 (0.50 g, 0.99 mmol), [1,1'-bis(diphenylphosphino) ferrocene dichloropalladium(II).dichloromethane complex [PdCl$_2$(dppf)$_2$.CH$_2$Cl$_2$] (24.3 mg, 0.0298 mmol), triethylamine (415 μL, 2.98 mmol) and 4,4,5,5-tetramethyl-1,3,2-dioxaborolane (221 μL, 1.52 mmol) in dioxane (5.0 mL) was microwaved at 120° C. for 0.5 h. The reaction mixture was cooled, poured onto water (100 mL), extracted with ethyl acetate (4×30 mL), the combined organic extracts washed with brine (30 mL), dried (MgSO$_4$) and concentrated. This gave the product 16 as a brown foam (576 mg, 113%) which was used in the next step without further purification; $^1$H NMR (400 MHz, CDCl$_3$) δ 1.38 (s, 12H), 3.02 (s, 6H), 6.86 (d, J=8.8 Hz, 2H), 7.65-7.45 (m, 5H), 8.16 (s, 1H), 8.26 (d, J=7.4 Hz, 2H), 8.30 (d, J=2.2 Hz, 1H), 8.63 (d, J=2.2 Hz, 1H).

{4-[1-Benzenesulfonyl-3-(1H-imidazol-4-yl)-1H-
pyrrolo[2,3-b]pyridin-5-yl]-phenyl}-dimethyl-
amine (17)

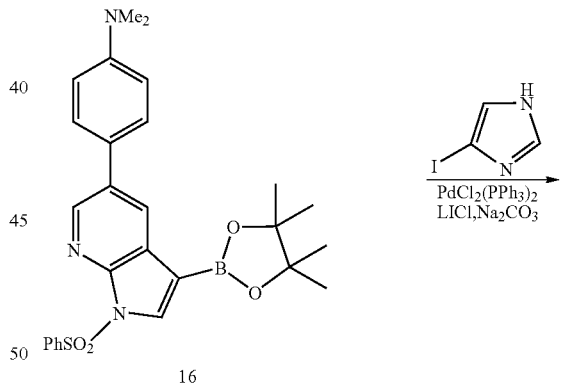

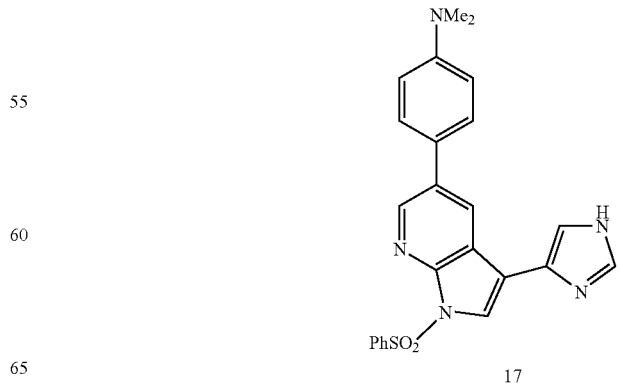

A mixture of 16 (150 mg, 0.298 mmol), 4-iodoimidazole (86.7 mg, 0.447 mmol), dichlorobis(triphenylphosphine)palladium (II) (20.9 mg, 0.0298 mmol), LiCl (37.9 mg, 0.894 mmol), 1M aq. Na$_2$CO$_3$ (0.75 mL, 0.75 mmol) in toluene (1.8 mL) and EtOH (1.8 mL) was microwaved at 120° C. for 15 min. The reaction mixture was cooled, brine (3 mL) was added and the aqueous layer extracted with ethyl acetate (3×5 mL). Sorbent (HM-N, Jones Chromatography) was added, the solvent evaporated and the product purified by silicagel chromatography using MeOH:CH$_2$Cl$_2$ (3:97) (gradient elution) to give product 17 as a brown foam (111 mg, 84%); $^1$H NMR (400 MHz, CDCl$_3$) δ 2.96 (s, 6H), 6.77 (d, J=8.8 Hz, 2H), 7.48-7.35 (m, 5H), 7.52 (t, J=7.6 Hz, 1H), 7.81 (s, 1H), 7.99 (s, 1H), 8.11 (d, J=7.5 Hz, 2H), 8.27 (d, J=2.0 Hz, 1H), 8.61 (d, J=2.1 Hz, 1H).

{4-[3-(1H-Imidazol-4-yl)-1H-pyrrolo[2,3-b]pyridin-5-yl]-phenyl}-dimethyl-amine (18)

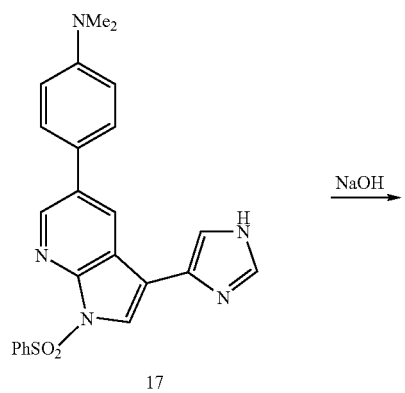

17

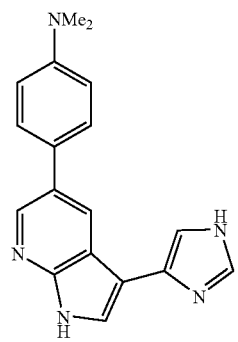

18

To 17 (50 mg, 0.113 mmol) in EtOH (2.5 mL) was added 10% aq. NaOH (1.3 mL) and the reaction mixture was stirred at room temperature for 2 h then at 85° C. for 10 rain. It was cooled and poured onto water (3 mL) and extracted with ethyl acetate (4×5 mL). The combined organic extracts were dried (MgSO$_4$) and concentrated. The residue was purified by preparative LCMS (column LUNA 10μ C18(2) 00G-4253-V0 250×50 mm) using water—acetonitrile (0.1% AcOH) as eluent (in gradient; flow 80 mL/min) to give product 18 as a white solid (9.0 mg, 26%); $^1$H NMR (400 MHz, CDCl$_3$+4 drops CD$_3$OD) δ 2.97 (s, 6H), 6.83 (d, J=8.9 Hz, 2H), 7.27 (d, J=1.0 Hz, 1H), 7.50 (d, J=8.8 Hz, 2H), 7.63 (s, 1H), 7.67 (d, J=1.0 Hz, 1H), 8.24 (d, J=2.1 Hz, 1H), 8.43 (d, J=2.0 Hz, 1H); MS (CI) m/z 304.1 (MH), 345.1 (M+MeCN).

Synthesis of Inhibitor 23

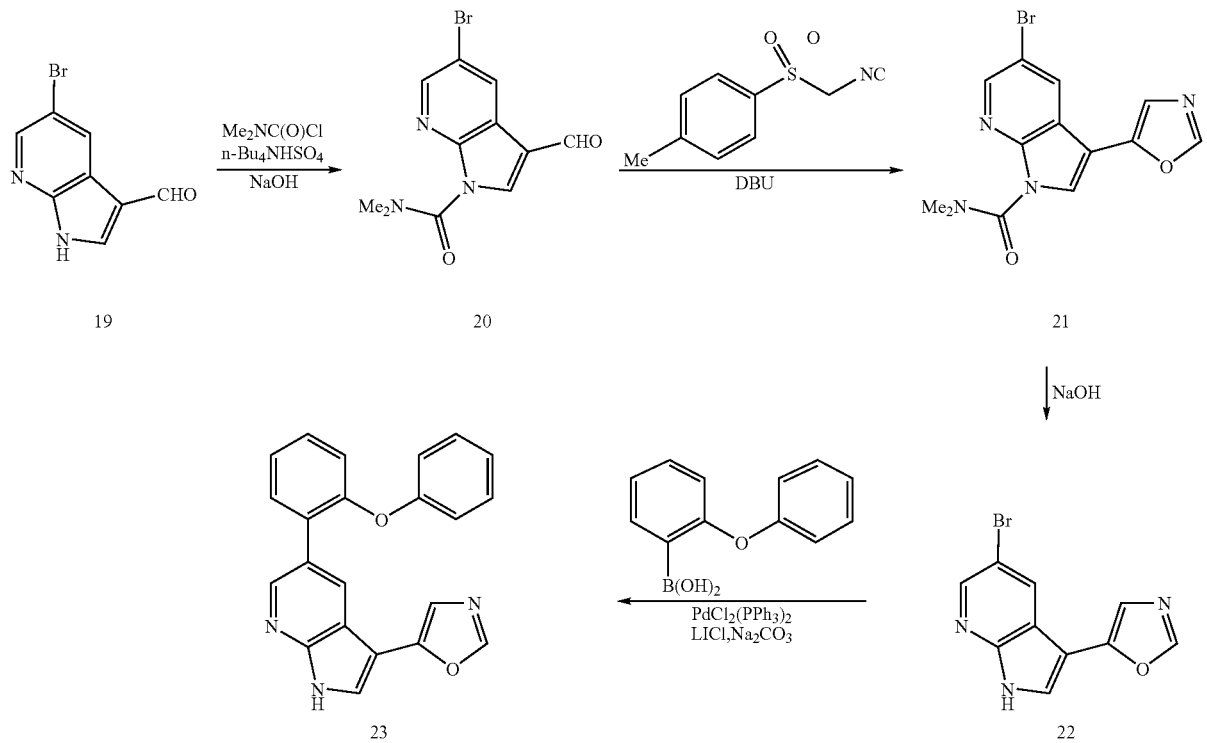

5-Bromo-3-formyl-pyrrolo[2,3-b]pyridine-1-carboxylic acid dimethylamide (20)

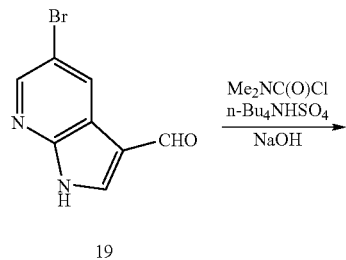

A mixture of 19 (2.01 g, 8.93 mmol; preparation disclosed in GB 0311313.1), dimethylcarbamyl chloride (1.23 mL, 13.4 mmol) and n-Bu$_4$NHSO$_4$ (394 mg, 1.16 mmol) in dichloromethane (50 mL) was treated with 50% aq. NaOH (1.7 mL) and stirred overnight. The reaction mixture was poured onto water (100 mL), the layers separated, the aqueous layer extracted with dichloromethane (3×40 mL). The combined organic extracts were dried (MgSO$_4$) and concentrated to afford 20 as a white solid (2.61 g, 99%) as a mixture of rotamers; $^1$H NMR (400 MHz, CDCl$_3$, major isomer signals quoted) δ 3.40-2.90 (6H), 8.16 (s, 1H), 8.48 (d, J=2.2 Hz, 1H), 8.73 (d, J=2.2 Hz, 1H), 10.01 (s, 1H).

5-Bromo-3-oxazol-5-yl-pyrrolo[2,3-b]pyridine-1-carboxylic acid dimethylamide (21)

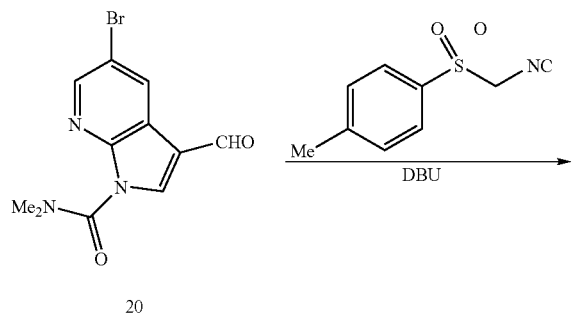

To aldehyde 20 (2.00 g, 6.75 mmol) in 1,2-dimethoxyethane (70 mL) was added tosylmethyl isocyanide (1.58 g, 8.10 mmol) followed by DBU (1.44 g, 9.46 mmol), and the reaction mixture heated at 90° C. overnight. After cooling, sorbent (HM-N, Jones Chromatography) was added and the solvent evaporated. The product was purified by silicagel chromatography using ethyl acetate:hexane (4:6) (gradient elution) to give product 21 as a light orange solid (667 mg, 29%); $^1$H NMR (400 MHz, CDCl$_3$) δ 3.40-2.90 (bs, 6H), 7.32 (s, 1H), 7.86 (s, 1H), 7.96 (s, 1H), 8.32 (d, J=2.2 Hz, 1H), 8.48 (d, J=2.2 Hz, 1H).

5-Bromo-3-oxazol-5-yl-1H-pyrrolo[2,3-b]pyridine (22)

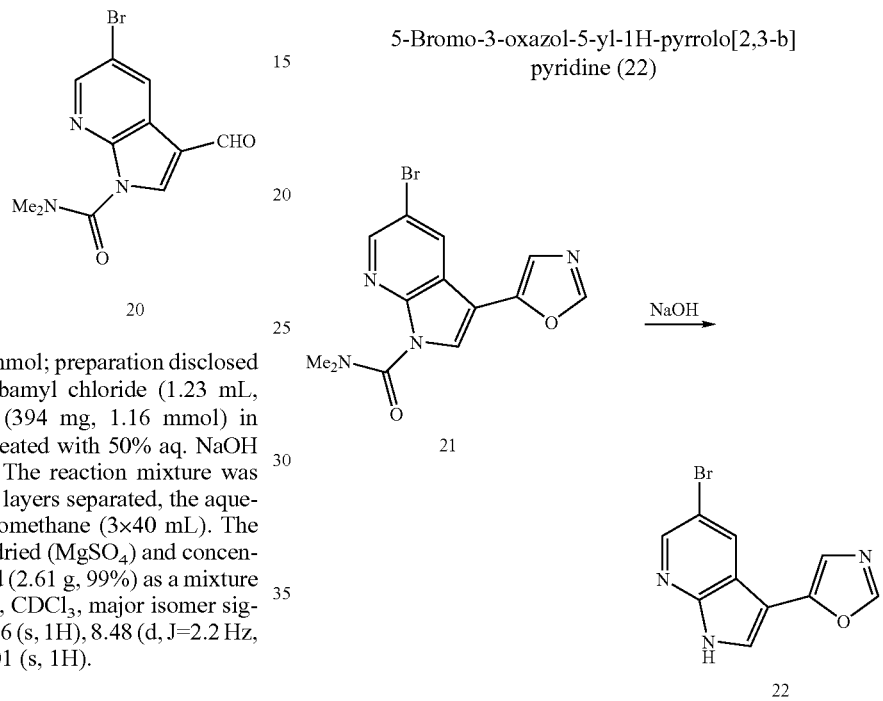

A mixture of 21 (667 mg, 1.99 mmol), EtOH (20 mL) and 10% aq. NaOH (10 mL) was heated at 90° C. for 40 min then cooled and poured onto water (50 mL). The aqueous layer was extracted with ethyl acetate (4×40 mL). The combined organic extracts were washed with brine (30 mL), dried (MgSO$_4$) and concentrated to give 22 as a white solid (477 mg, 91%); $^1$H NMR (400 MHz, CDCl$_3$) δ 7.27 (d, J=2.5 Hz, 1H), 7.67 (d, J=2.5 Hz, 1H), 7.94 (s, 1H), 8.33 (d, J=2.1 Hz, 1H), 8.44 (d, J=2.1 Hz, 1H), 9.30-9.10 (bs, NH).

3-Oxazol-5-yl-5-(2-phenoxy-phenyl)-1H-pyrrolo[2,3-b]pyridine (23)

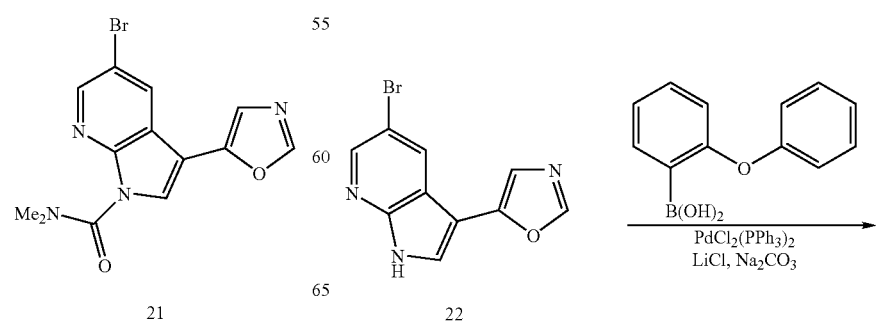

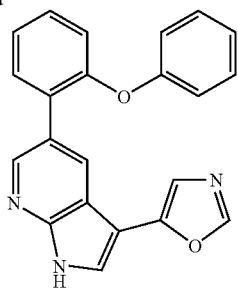

23

A mixture of bromide 22 (300 mg, 1.14 mmol), 2-phenoxyphenylboronic acid (366 mg, 1.71 mmol), PdCl$_2$(PPh$_3$)$_2$ (80.0 mg, 0.114 mmol), LiCl (145 mg, 3.42 mmol) and 1M Na$_2$CO$_3$ (2.85 mL, 2.82 mmol) in toluene (5.4 mL) and EtOH (5.4 mL) was refluxed overnight (105° C. oil bath temp.). The reaction mixture was cooled, and separated between brine (20 mL) and ethyl acetate (30 mL). The aqueous layer was extracted with ethyl acetate (2×30 mL). The combined organic solutions were dried (MgSO$_4$) and concentrated. The resulting solid was dry loaded on a silicagel column. Fractions containing the product were eluted using ethyl acetate:hexane (1:1) (gradient elution) to give a solid which was triturated with ether to give 23 as a white solid (186 mg, 46%); $^1$H NMR (400 MHz, CDCl$_3$) δ 6.94 (dd, J=8.8, 1.0 Hz, 2H), 7.05 (t, J=7.4 Hz, 1H), 7.08 (s, 1H), 7.12 (dd, J=8.1, 1.1 Hz, 1H), 7.33-7.20 (m, 3H), 7.38 (dt, J=9.2, 1.7 Hz, 1H), 7.56 (dd, J=7.6, 1.8 Hz, 1H), 7.64 (d, J=2.4 Hz, 1H), 7.85 (s, 1H), 8.32 (d, J=2.0 Hz, 1H), 8.59 (d, J=2.0 Hz, 1H), 9.35-9.20 (bs, NH).

Synthesis of Example Inhibitor 29

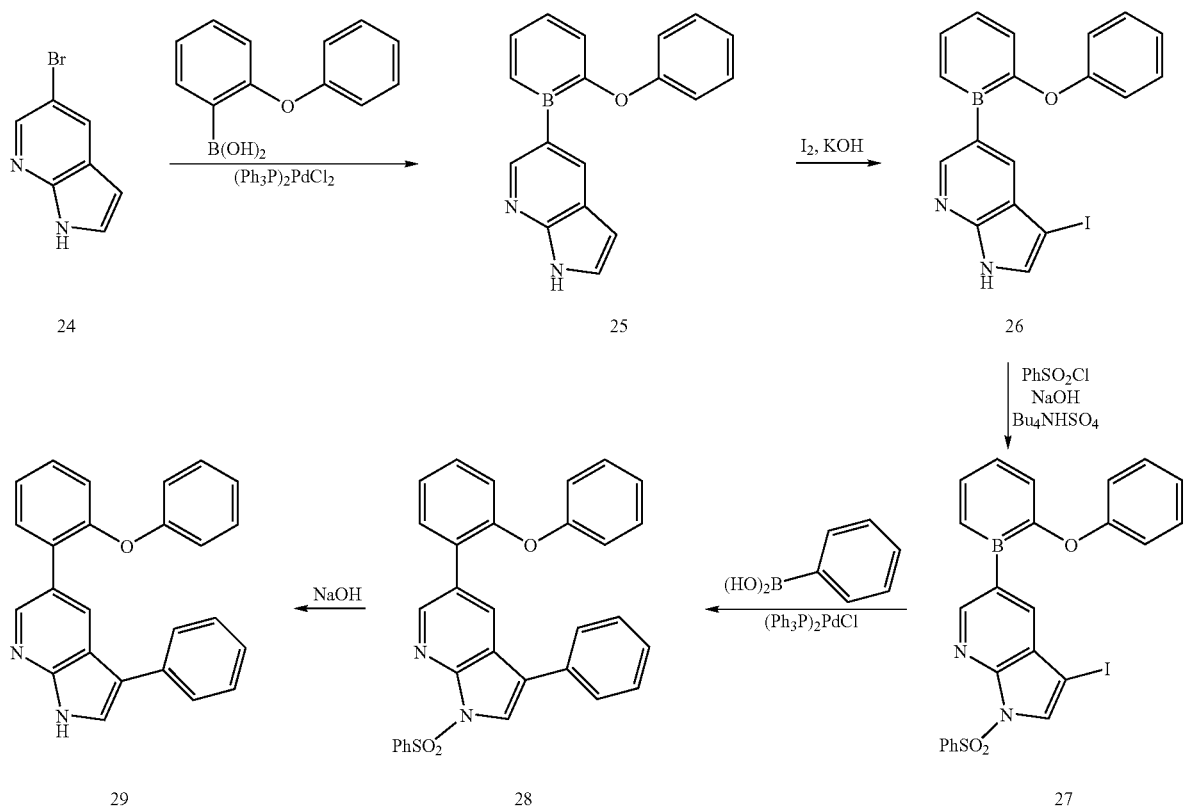

5-(2-Phenoxy-phenyl)-1H-pyrrolo[2,3-b]pyridine (25)

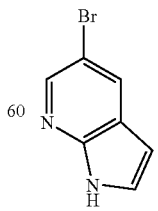
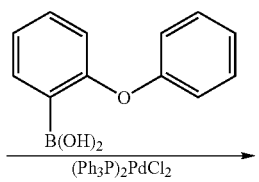

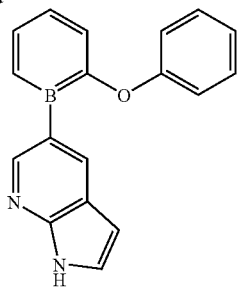

25

To a solution of the 5-bromoazaindole 24 (15.0 g, 76.1 mmol) in toluene (360 mL) and EtOH (360 mL) was added LiCl (9.68 g, 228.4 mmol), dichlorobis(triphenylphosphine) palladium (II) (5.34 g, 7.6 mmol), 2-phenoxyphenylboronic acid (24.44 g, 114.2 mmol) and 1 M sodium carbonate (190 mL, 190 mmol). After 4 h, the mixture was allowed to cool to room temperature and the phases separated. The aqueous layer was washed with EtOAc (3×) and the combined organic extracts dried (MgSO$_4$), filtered and evaporated. The resulting residue was purified by silicagel chromatography [gradient elution, hexanes to hexanes-EtOAc (1:1)] to afford product 25 (18.30 g, 84%) as a cream-coloured solid. $^1$H NMR (400 MHz, CDCl$_3$) δ 6.51 (dd, J=3.5, 2.0 Hz, 1H), 6.92-6.96 (m, 2H), 7.01 (t, J=7.4 Hz, 1H), 7.05 (dd, J=8.1, 1.2 Hz, 1H), 7.22-7.28 (m, 3H), 7.30-7.34 (m, 2H), 7.52 (dd, J=7.5, 1.8 Hz, 1H), 8.13 (d, J=2.0 Hz, 1H), 8.52 (d, J=2.0 Hz, 1H), 9.82 (bs, 1H).

3-Iodo-5-(2-phenoxy-phenyl)-1H-pyrrolo[2,3-b]pyridine (26)

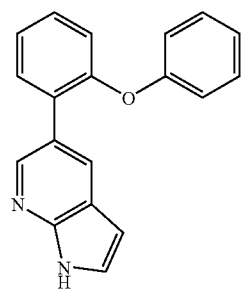

25

I$_2$, KOH →

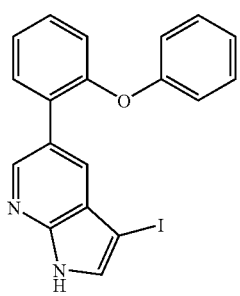

26

To a solution of the azaindole 25 (18.30 g, 63.9 mmol) in DMF (100 mL) was added KOH (13.27 g, 236.5 mmol) in a single portion. After 0.5 h, iodine (16.18 g, 63.9 mmol) was added in portions over a 3 min. period. After a further 1 h the reaction was quenched by the addition of a solution of sodium thiosulfate (70 g) in H$_2$O (400 mL). The semisolid was filtered off, dissolved in dichloromethane. The solution and washed with saturated brine (1×), dried (MgSO$_4$), and concentrated to afford the iodide 26, which was used directly in the next step without further purification. $^1$H NMR (400 MHz; CDCl$_3$) δ6.92-6.95 (m, 2H), 7.01 (tt, J=7.3, 1.0 Hz, 1H), 7.08 (dd, J=8.1, 1.3 Hz, 1H), 7.23-7.30 (m, 3H), 7.36 (dt, J=7.3, 1.8 Hz, 1H), 7.40 (s, H), 7.54 (dd, J=7.6, 1.8 Hz, 1H), 7.93 (d, J=2.0 Hz, 1H), 8.54 (d, J=2.0 Hz, 1H) and 11.06 (bs, 1H).

1-Benzenesulfonyl-3-iodo-5-(2-phenoxy-phenyl)-1H-pyrrolo[2,3-b]pyridine (27)

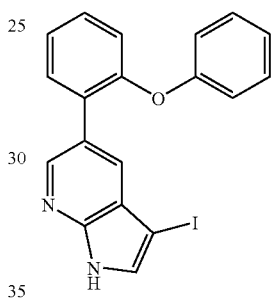

26

PhSO$_2$Cl
NaOH
───────→
Bu$_4$NHSO$_4$

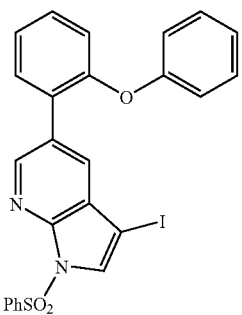

27

To a solution of the crude azaindole 26 (prepared in the previous step) in dichloromethane (373 mL) was sequentially added, benzenesulfonyl chloride (12.6 mL, 99.1 mmol), 50% aqueous sodium hydroxide (12.2 mL) and tetrabutylammonium hydrogen sulfate (2.82 g, 8.3 mmol). After 2 h stirring the mixture was partitioned between dichloromethane and saturated brine. The organic extract was dried (MgSO$_4$), filtered and concentrated to afford the azaindole 27 (24.2 g, 68% from 25) as a tan coloured solid. $^1$H NMR (400 MHz; CDCl$_3$) δ 6.89-6.92 (m, 2H), 7.01-7.05 (m, 2H), 7.22-7.28 (m, 3H), 7.33-7.37 (m, 1H), 7.45 (dd, J=7.6, 2.0 Hz, 1H), 7.47-7.52 (m, 2H), 7.60 (tt, J=7.6, 1.3 Hz, 1H), 7.84 (d, J=2.0 Hz, 1H), 7.85 (s, 1H), 8.20-8.22 (m, 2H) and 8.64 (d, J=2.0 Hz, 1H).

1-Benzenesulfonyl-5-(2-phenoxy-phenyl)-3-phenyl-1H-pyrrolo[2,3-b]pyridine (28)

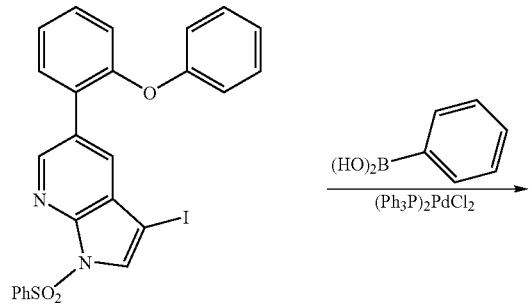

27

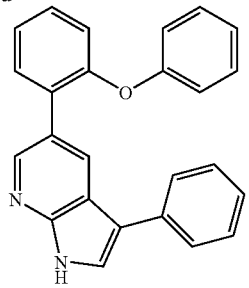

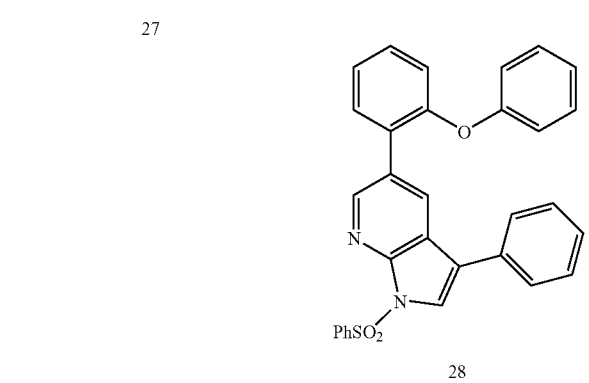

28

To a solution of the iodide 27 (2.00 g, 3.62 mmol) in toluene (40 mL) and EtOH (40 mL) was added lithium chloride (0.46 g, 10.86 mmol), dichlorobis(triphenylphosphine) palladium (II) (0.127 g, 0.18 mmol), phenylboronic acid (0.662 g, 5.43 mmol) and 1 M sodium carbonate (9.05 mL, 9.05 mmol). The mixture was refluxed under $N_2$ (oil bath temp. 105° C.) for 2.5 h and then concentrated in vacuo. The resulting residue was co-evaporated once from xylene and purified by silicagel chromatography (gradient elution, hexanes to dichloromethane) to afford the azaindole 28 (1.16 g, 64%) as pale yellow solid. $^1$H NMR (400 MHz; CDCl$_3$) δ6.91-6.94 (m, 2H), 7.04-7.08 (m, 2H), 7.22-7.30 (m, 3H), 7.31-7.41 (m, 4H), 7.44-7.53 (m, 5H), 7.60 (tt, J=7.4, 1.3 Hz, 1H), 7.87 (s, 1H), 8.23-8.26 (m, 3H) and 8.66 (d, J=1.9 Hz, 1H).

5-(2-Phenoxy-phenyl)-3-phenyl-1H-pyrrolo[2,3-b]pyridine (29)

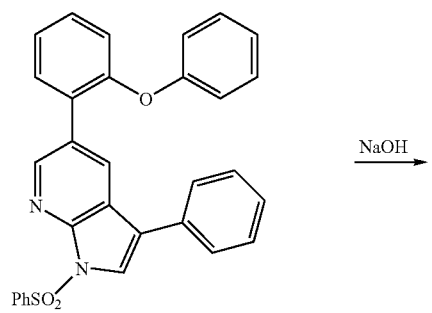

28

-continued

29

To a solution of azaindole 28 (1.16 g, 2.31 mmol) in EtOH (70 mL) was added a 10% sodium hydroxide solution (8.5 mL), and the mixture was heated at 105° C. After 1 h, the mixture was allowed to cool to r.t. and partitioned between chloroform and saturated brine. The aqueous layer was extracted with chloroform (3×), and the combined organic extracts dried (MgSO$_4$), filtered and concentrated. The residue was purified by silicagel chromatography (gradient elution, hexanes to 5% EtOAc in dichloromethane) to afford a yellow solid which was washed with cold Et$_2$O to furnish azaindole 29 (0.546 g, 65%) as a cream coloured solid. $^1$H NMR (400 MHz; CDCl$_3$) δ6.95-6.98 (m, 2H), 7.04 (tt, J=7.4, 1.0 Hz, 1H), 7.11 (dd, J=8.1, 1.2 Hz, 1H), 7.25-7.31 (m, 4H), 7.35-7.41 (m, 3H), 7.54-7.57 (m, 4H), 8.41 (d, J=2.0 Hz, 1H), 8.58 (d, J=2.0 Hz, 1H), 10.78 (bs, 1H).

Synthesis of Example Inhibitor 32

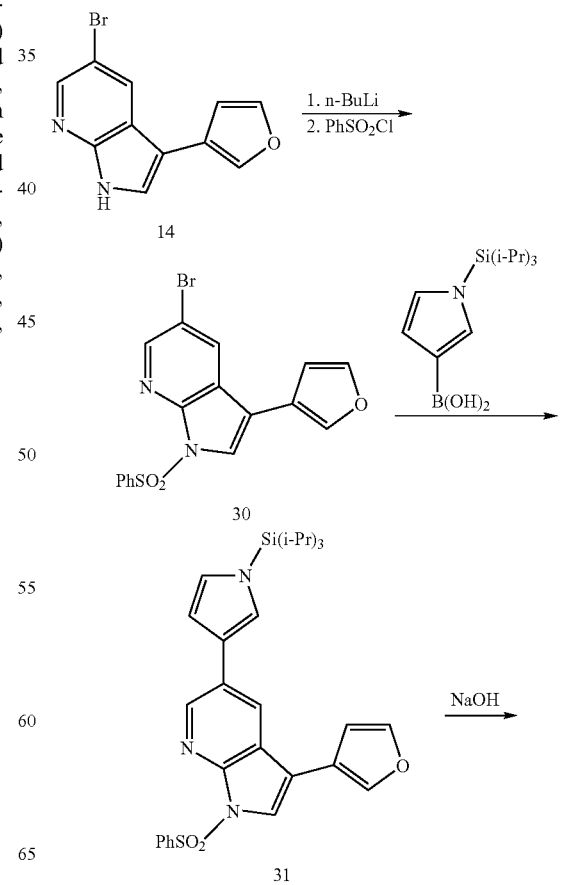

-continued

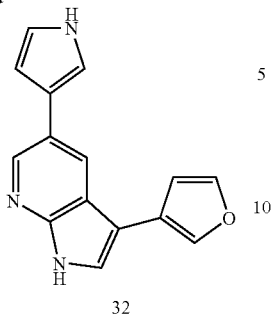
32

1-Benzenesulfonyl-5-bromo-3-furan-3-yl-1H-pyrrolo[2,3-b]pyridine (30)

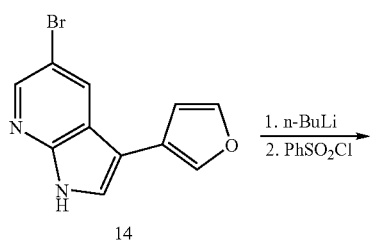

To a stirred and cooled (−78° C.) suspension of azaindole 14 (100.0 mg, 0.38 mmol) in THF (0.75 mL) was added a 2.5 M solution of n-BuLi in hexane (0.182 mL, 0.456 mmol) over a period of 5 min. The brown solution was stirred at −78° C. for 0.5 h. Benzenesulfonyl chloride (58.4 μL, 0.456 mmol) was added dropwise. The mixture was allowed to warm up to r.t. overnight, partitioned between saturated aqueous NaHCO$_3$—AcOEt. The aqueous layer was extracted with AcOEt (5×). Combined organic solutions were dried (MgSO$_4$), concentrated and purified by silicagel chromatography with CH$_2$Cl$_2$:AcOEt as eluent (in gradient) to give protected azaindole 30 (101.3 mg, 66%) as a tan solid. $^1$H NMR (400 MHz; CDCl$_3$) δ 6.66 (dd, J=1.0, 1.8 Hz, 1H), 7.48-7.63 (m, 3H), 7.55 (t, J=1.8 Hz, 1H), 7.76 (m, 1H), 7.83 (s, 1H), 8.08 (d, J=2.1 Hz, 1H), 8.17-8.21 (m, 2H), 8.49 (d, J=2.1 Hz, 1H).

1-Benzenesulfonyl-3-furan-3-yl-5-(1-triisopropylsilanyl-1H-pyrrol-3-yl)-1H-pyrrolo[2,3-b]pyridine (31)

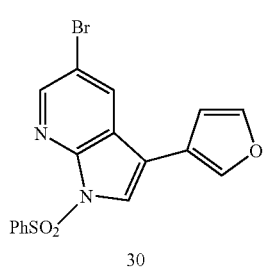 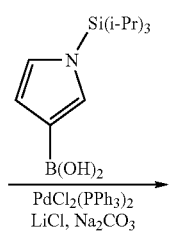

-continued

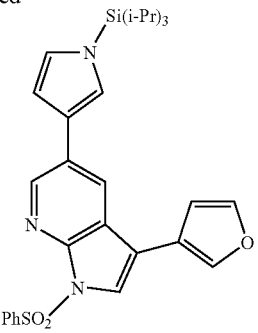
31

A mixture of 30 (31.6 mg, 0,078 mmol), 1-triisopropylsilanyl-1H-pyrrole-3-boronic acid (31 mg, 0.12 mmol), PdCl$_2$(PPh$_3$)$_2$ (6 mg, 7.8 μmol), LiCl (10 mg, 0.24 mmol), aqueous 1.0 M Na$_2$CO$_3$ (200 μL, 0.2 mmol), EtOH (0.47 mL) and toluene (0.47 mL) were heated at 85° C. over weekend. After cooling the organic layer was separated and purified by PTLC using AcOEt:hexane=3:7 as eluent to give the product 31 as a colourless oil (15.3 mg, 36%). $^1$H NMR (400 MHz, CDCl$_3$) δ 1.13 (d, J=7.5 Hz, 18H), 1.49 (septet, J=7.5 Hz, 3H), 6.60 (dd, J=2.7, 1.5 Hz, 1H), 6.71 (dd, J=1.8, 0.79 Hz, 1H), 6.84 (t, J=2.5 Hz, 1H), 7.05 (t, J=1.7 Hz, 1H), 7.48 (t, J=8.0 Hz, 2H), 7.56 (m, 2H), 7.78 (s, 1H), 7.83 (s, 1H), 7.99 (d, J=2.0 Hz, 1H), 8.20 (m, 1H), 8.23 (s, 1H), 8.68 (d, J=2.0 Hz, 1H).

3-Furan-3-yl-5-(1H-pyrrol-3-yl)-1H-pyrrolo[2,3-b]pyridine (32)

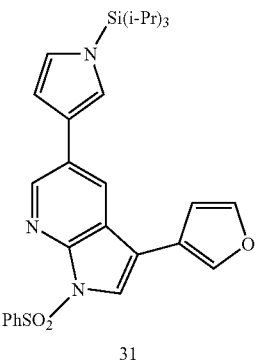

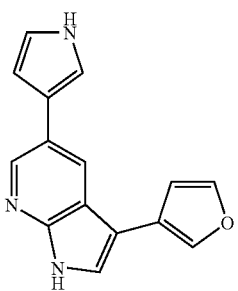

A mixture of 31 (15.3 mg, 0.28 μmol), EtOH (1.0 mL) and 10% aq. NaOH (0.5 mL) were heated at 110° C. for 40 min then cooled and poured onto saturated aqueous NaHCO$_3$ (5 mL) and extracted with ethyl acetate (4×10 mL). The combined organic extracts were dried (MgSO$_4$), concentrated and the residue purified by PTLC using 5% MeOH in CH$_2$Cl$_2$ to give the pure product as a solid (4.15 mg, 59%); $^1$H NMR (400 MHz, CDCl$_3$) δ 6.60 (d, J=1.6 Hz, 1H), 6.72 (s, 1H), 6.92 (dd, J=4.7, 2.5 Hz, 1H), 7.15 (d, J=2.0 Hz, 1H), 7.41 (d, J=2.3 Hz, 1H), 7.54 (s, 1H), 7.82 (s, 1H), 8.15 (d, J=1.7 Hz, 1H), 8.37 (bs, NH), 8.57 (d, J=1.8 Hz, 1H), 8.96 (bs, NH).

Synthesis of Example Inhibitor 34

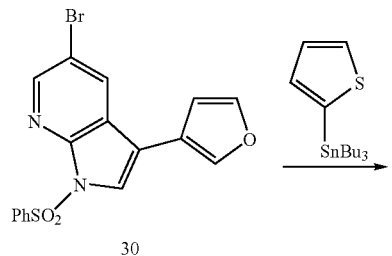

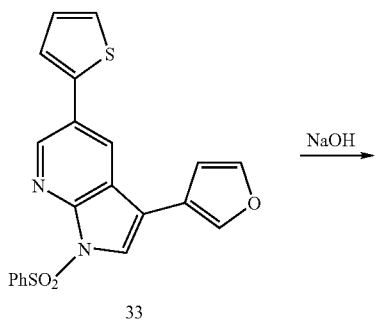

1-Benzenesulfonyl-3-furan-3-yl-5-thiophen-2-yl-1H-pyrrolo[2,3-b]pyridine (33)

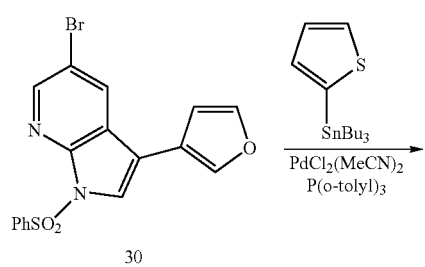

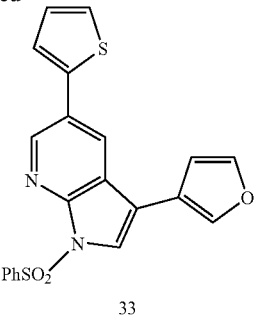

A mixture of bromide 30 (40.3 mg, 0.1 mmol), tributylthiophen-2-yl-stannane (62 μL, ca 0.2 mmol), PdCl$_2$.(MeCN)$_2$ (3.6 mg, 0.014 mmol), and tri-o-tolyl-phosphane (6.6 mg, 0.022 mmol) in toluene (0.9 mL) was stirred under N$_2$ for 2 h. The reaction mixture was cooled and separated by PTLC with CH$_2$Cl$_2$ as eluent to afford 33 (31.7 mg, 78%) as yellowish solid. $^1$H NMR (400 MHz; CDCl$_3$) δ 6.71 (dd, J=2.0, 1.0 Hz, 1H), 7.12 (dd, J=5.1, 3.6 Hz, 1H), 7.32 (dd, J=3.6, 1.2 Hz, 1H), 7.35 (dd, J=5.1, 1.2 Hz, 1H), 7.48-7.63 (m, 4H), 7.82 (m, 1H), 7.84 (s, 1H), 8.09 (d, J=2.2 Hz, 1H), 8.22-8.26 (m, 2H), 8.73 (d, J=2.2 Hz, 1H).

3-Furan-3-yl-5-thiophen-2-yl-1H-pyrrolo[2,3-b]pyridine (34)

To a solution of 33 (28.3 mg, 0.0696 mmol) in EtOH (1.4 mL), was added 10% aqueous NaOH (0.67 mL), and the reaction mixture refluxed (oil bath 110° C.) for 0.5 h. The mixture was diluted with water (1.4 mL), and stirred for an additional 0.5 h at r.t. The precipitate was filtered off, washed with water, and dried under high vacuum to afford 34 as tan solid (15.8 mg, 85%); $^1$H NMR (400 MHz; CDCl$_3$) δ 6.72 (dd, J=1.8, 0.8 Hz, 1H), 7.14 (dd, J=5.1, 3.6 Hz, 1H), 7.32-7.36 (m, 2H), 7.48 (d, J=2.5 Hz, 1H), 7.55 (t, J=1.7 Hz, 1H), 7.82 (m, 1H), 8.23 (dd, J=2.0, 0.4 Hz, 1H), 8.65 (d, J=2.0 Hz, 1H), 9.67 (bs, 1H).

Synthesis of Example Inhibitor 41

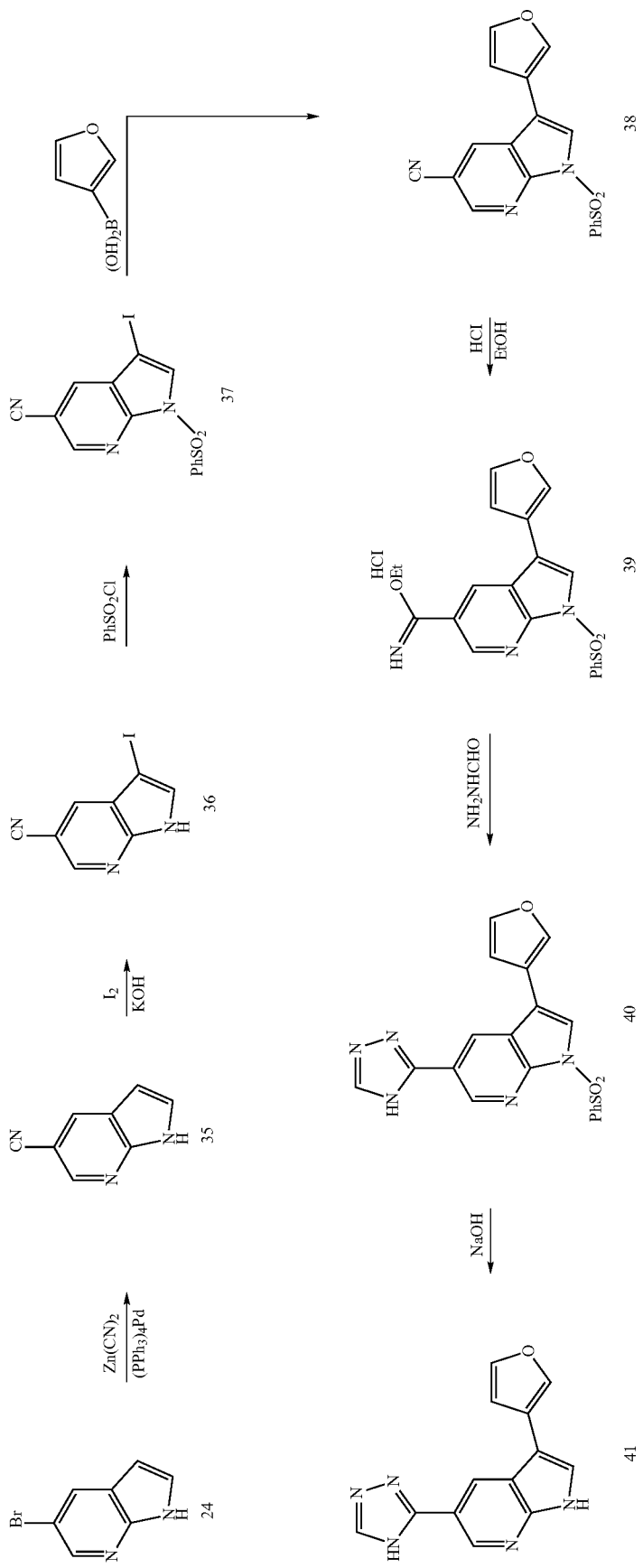

1H-Pyrrolo[2,3-b]pyridine-5-carbonitrile (35)

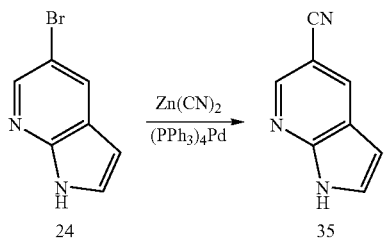

A mixture of bromide 24 (10.0 g, 50.8 mmol), ZnCl₂ (3.58 g, 30.5 mmol), and Pd(PPh₃)₄ (3.52 g, 3.05 mmol) in DMF (110 mL) was heated at 80° C. overnight. The solvent was evaporated and the residue separated by silicagel chromatography (100 g column) using hexane:ethyl acetate as eluent (gradient elution). The resulting solid was partitioned between water (200 mL)/CH₂Cl₂ (100 mL) and the aqueous phase extracted with more CH₂Cl₂ (4×100 mL). The combined organic extracts were dried (MgSO₄) and concentrated to give the product as a white solid (5.48 g, 75%), which was used for subsequent reactions without further purification.

3-Iodo-1H-pyrrolo[2,3-b]pyridine-5-carbonitrile (36)

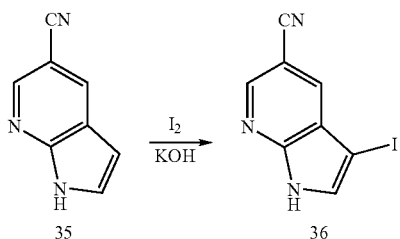

To a solution of 35 (3.0 g, 21.0 mmol) in DMF (53 mL) was added KOH (4.35 g, 77.5 mmol, pellets) and the reaction mixture stirred for 20 min., cooled to 0° C., and treated with iodine (5.32 g, 21.0 mmol). It was stirred at room temperature for 50 min then poured onto a mixture of water (306 mL)/sat. aqueous Na₂S₂O₃ (46 mL). The resulting solid was filtered off and washed with water (2×) to give 36 (3.57 g, 63%) as creamy solid; ¹H NMR (400 MHz, DMSO) δ 7.96 (s), 8.25 (s), 8.64 (s), 12.74 (NH).

1-Benzenesulfonyl-3-iodo-1H-pyrrolo[2,3-b]pyridine-5-carbonitrile (37)

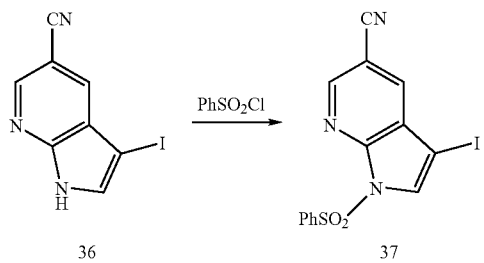

A mixture of iodide 36 (3.50 g, 13.0 mmol), PhSO₂Cl (2.49 mL, 19.5 mmol), n-Bu₄NHSO₄ (0.57 g, 1.69 mmol) in CH₂Cl₂ (77 mL) was treated with 50% aq. NaOH (2.46 mL) then stirred for 40 min. It was then poured onto water (250 mL), the aqueous phase extracted with more CH₂Cl₂ (3×60 mL) and the combined organic extracts dried (MgSO₄) and concentrated. Methanol was added to the resulting solid and the mixture stirred for 0.5 h. The solid was filtered off and washed with more methanol (2×) to afford iodide 37 as a white solid (4.00 g, 75%); ¹H NMR (400 MHz, CDCl₃) δ 7.46 (t, J=5.7 Hz, 2H), 7.59 (tt, J=7.5, 2.0 Hz, 1H), 7.93 (d, J=1.9 Hz, 1H), 7.95 (s, 1H), 8.16 (m, 2H), 8.60 (d, J=2.0 Hz, 1H).

1-Benzenesulfonyl-3-furan-3-yl-1H-pyrrolo[2,3-b]pyridine-5-carbonitrile (38)

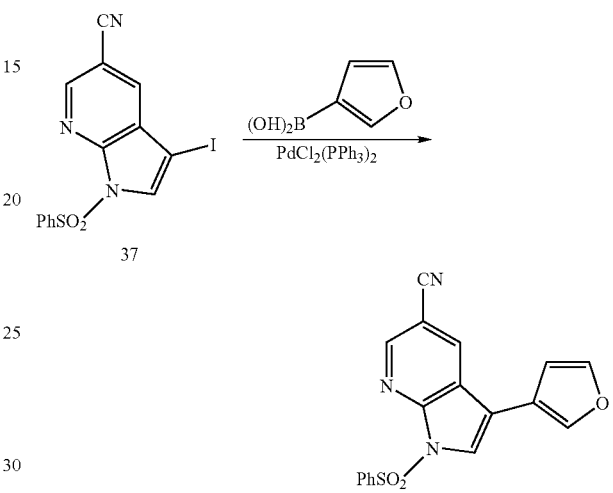

A mixture of iodide 37 (2.00 g, 4.89 mmol), furan-3-boronic acid (820 mg, 7.33 mmol), PdCl₂(PPh₃)₂ (343 mg, 0.49 mmol), LiCl (622 mg, 14.7 mmol), 1.0 M aqueous Na₂CO₃ (12.2 mL, 12.2 mmol), EtOH (23 mL) and toluene (23 mL) were refluxed for 50 min. After cooling the layers were separated, brine was added to the aqueous layer and extracted with ethyl acetate (3×50 mL). The combined organic extracts were dried (MgSO₄) and concentrated. The resulting solid was purified by silicagel chromatography using 30% ethyl acetate in hexane (gradient elution) to give 38 as an orange solid (1.23 g, 72%);

¹H NMR (400 MHz, CDCl₃) δ 6.60 (dd, J=1.90, 0.9 Hz, 1H), 7.47 (t, J=7.0, 1.3 Hz, 2H), 7.50 (t, J=1.6 Hz, 1H), 7.57 (tt, J=7.4, 1.2 Hz, 1H), 7.70 (m, 1H), 7.89 (s, 1H), 8.16 (m, 2H), 8.19 (d, J=1.9 Hz, 1H), 8.62 (d, J=2.0 Hz, 1H).

1-Benzenesulfonyl-3-furan-3-yl-1H-pyrrolo[2,3-b]pyridine-5-carboximidic acid ethyl ester hydrochloride salt (39)

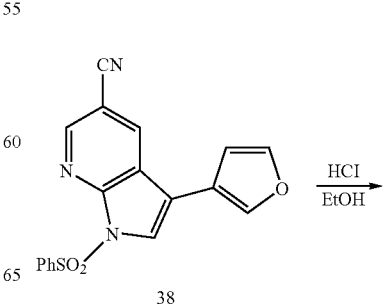

-continued

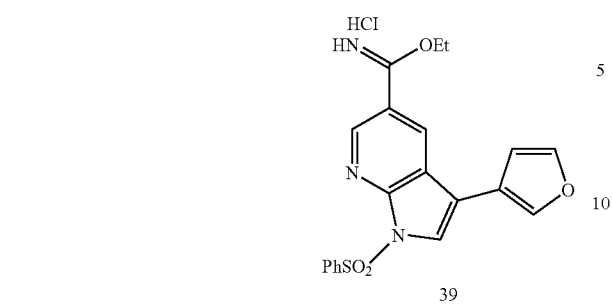

39

Gaseous HCl was bubbled through an ice-cold and stirred suspension of 38 (300 mg, 0.86 mmol) in EtOH (31 mL) for 20 min and the resulting mixture stirred at room temperature overnight. It was then filtered to remove small amount of black solid and the solvent evaporated to give the product 39 as a red/brown solid (331 mg, 89%).

1-Benzenesulfonyl-3-furan-3-yl-5-(4H-[1,2,4]triazol-3-yl)-1H-pyrrolo[2,3-b]pyridine (40)

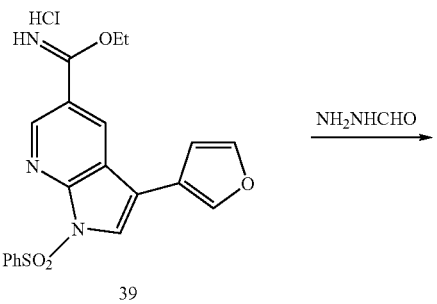

39

NH$_2$NHCHO →

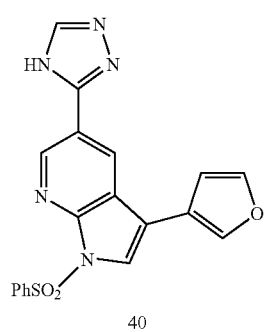

40

A mixture of 39 (300 mg, 0.70 mmol), formic hydrazide (209 mg, 3.47 mmol) and Et$_3$N (759 μM, 6.95 mmol) in EtOH (10.4 mL) was heated at 75° C. overnight. After cooling, the solvent was evaporated and the residue purified by silicagel chromatography using 80% ethyl acetate in hexane (gradient elution) then preparative TLC (1 mm plates, EtOAc eluent) to give 40 as a white solid (132.6 mg, 76%); $^1$H NMR (400 MHz, CDCl$_3$+2 drops CD$_3$OD) δ 6.71 (m, 1H), 7.40-7.70 (m, 5H), 7.84 (s, 1H), 7.93 (t, J=1.0 Hz, 1H), 8.10-8.30 (m, 3H), 8.63 (d, J=2.0 Hz, 1H), 9.10 (bs, NH); MS (CI) m/z 391.9 (MH$^+$), 433.1 (M+MeCN).

3-Furan-3-yl-5-(4H-[1,2,4]triazol-3-yl)-1H-pyrrolo[2,3-b]pyridine (41)

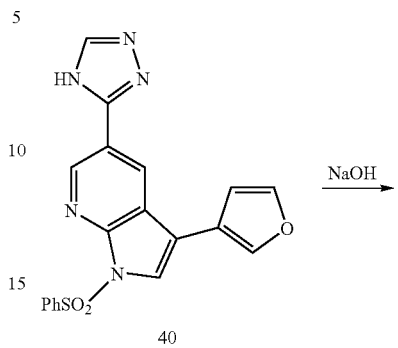

40

NaOH →

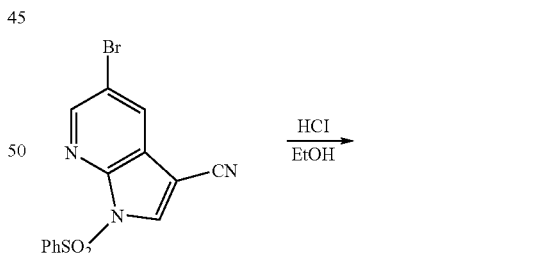

41

A mixture of 40 (60 mg, 0.15 mmol), EtOH (1.54 mL) and 10% aq. NaOH (767 μL) were heated at 90° C. for 45 min then cooled and poured onto water (11 mL) and extracted with ethyl acetate (4×10 mL). The combined organic extracts were dried (MgSO$_4$), concentrated and the residue purified by preparative LCMS (column LUNA 10μ C18(2) 00G-4253-V0 250×50 mm) using water—acetonitrile (0.1% AcOH) as eluent (in gradient; flow 80 mL/min) to give the product as a white solid (10.7 mg, 28%); $^1$H NMR (400 MHz, CDCl$_3$+2 drops CD$_3$OD) δ 6.70 (d, J=1.0 Hz, 1H), 7.45 (s, 1H), 7.49 (t, J=1.5 Hz, 1H), 7.89 (s, 1H), 8.16 (bs, 1H), 8.75 (d, J=1.9 Hz, 1H), 8.92 (s, 1H).

Synthesis of Example Bromide 44

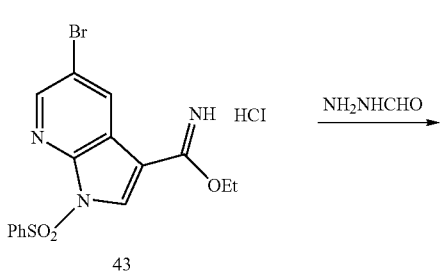

42

HCl / EtOH →

43

NH$_2$NHCHO →

1-Benzenesulfonyl-5-bromo-1H-pyrrolo[2,3-b]pyridine-3-carboximidic acid ethyl ester hydrochloride salt (42)

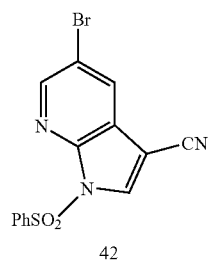

42

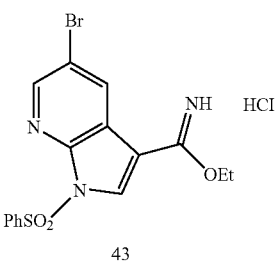

43

To an ice-cold solution of 42 (200 mg, 0.55 mmol; preparation disclosed in GB 0315732.8) in EtOH (20 mL) was bubbled gaseous HCl for 20 min. and the reaction mixture stirred at room temperature overnight. The solvent was evaporated and the residue dried under high vacuum overnight to give 43 as a white solid (229 mg, 93%).

1-Benzenesulfonyl-5-bromo-3-(4H-[1,2,4]triazol-3-yl)-1H-pyrrolo[2,3-b]pyridine (44)

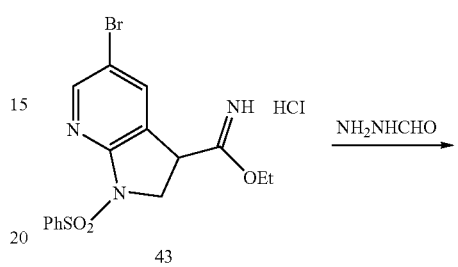

43

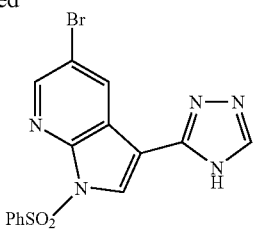

44

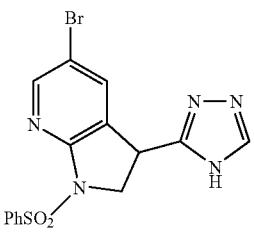

44

A mixture of 43 (215 mg, 0.48 mmol), formic hydrazide (145 mg, 2.42 mmol), Et₃N (528 µL, 4.83 mmol) in EtOH (7.2 mL) was stirred overnight at 75° C. Sorbent (HM-N, Jones chromatography) was added to the mixture and the solvent evaporated. The product was purified by silica gel chromatography using hexane:ethyl acetate (in gradient) to give 44 as a white solid (110 mg, 56%). $^1$H NMR (400 MHz, CDCl₃+2 drops CD₃OD) δ 7.92 (s, 1H), 8.00 (m, 6H), 8.28 (d, J=2.2 Hz, 1H), 8.71 (d, J=2.2 Hz, 1H).

Synthesism of Example Inhibitor 50

191 192
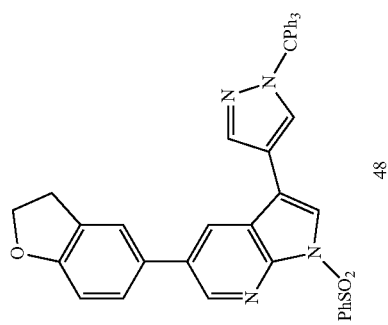
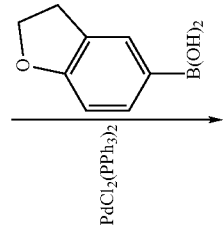
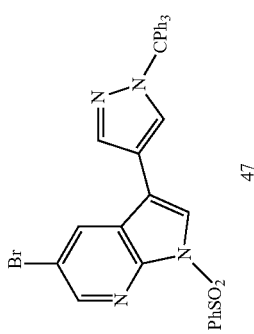
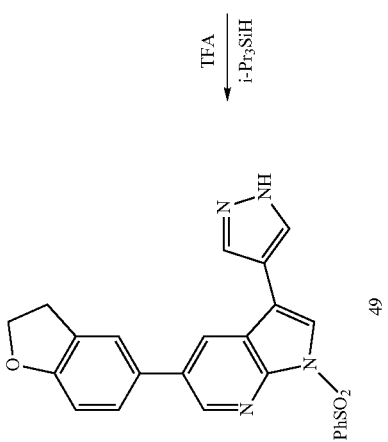
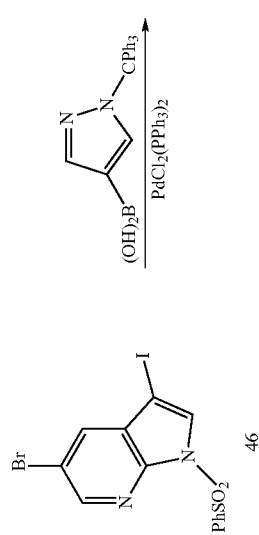
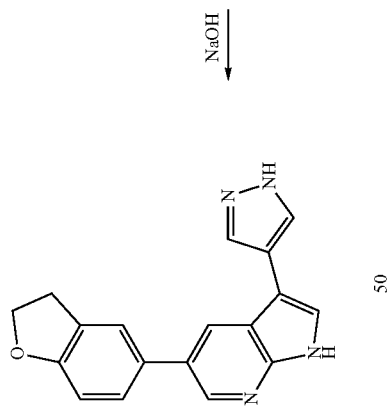
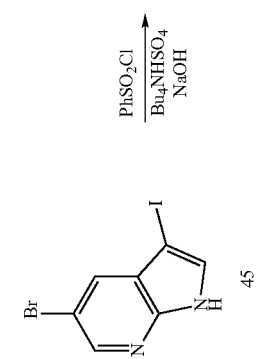
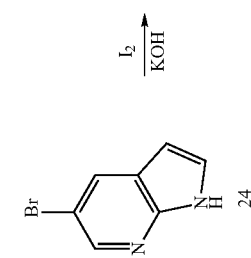

5-Bromo-3-iodo-1H-pyrrolo[2,3-b]pyridine (45)

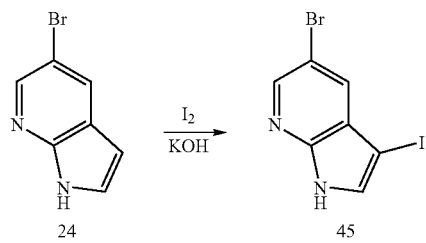

To a solution of bromide 24 (10.00 g, 51 mmol) in DMF (330 mL) was added KOH (10.70 g, 191 mmol, pellets) and the reaction mixture was stirred for about 20 min. The mixture was then cooled in an ice-bath and iodine (11.55 g, 45.62 mmol) was added portionwise over 10 min. When the addition was complete the reaction mixture was stirred at room temperature for 3.5 h, diluted with EtOAc (500 mL) and washed with saturated brine solution (500 mL). The aqueous layer was extracted with EtOAc (4×200 mL), The combined organic solutions were dried (MgSO$_4$) and concentrated to afford 45 as a pale yellow solid (15.62 g, 95%); $^1$H NMR (400 MHz, DMSO) δ 7.78 (s, 1H), 7.84 (d, J=2.2 Hz, 1H), 7.93 (bs, NH), 8.29 (d, J=2.0 Hz, 1H).

1-Benzenesulfonyl-5-bromo-3-iodo-1H-pyrrolo[2,3-b]pyridine (46)

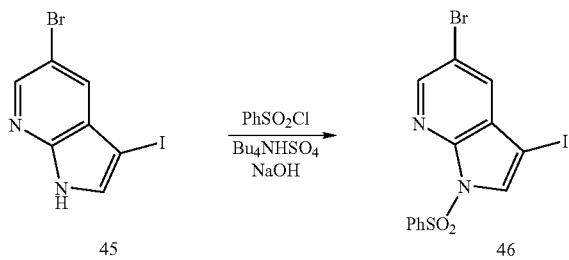

To a cooled solution of 45 (15.00 g, 46.6 mmol) in CH$_2$Cl$_2$ (210 mL) was added benzenesulfonyl chloride (9.18 mL, 71.8 mmol), 50% aq NaOH (13.04 mL) and Bu$_4$NHSO$_4$ (2.35 g, 6.94 mmol). The mixture was allowed to warm to ambient temperature and stirred for 2 h 45 min. The mixture was diluted with CH$_2$Cl$_2$ (200 mL) and washed with saturated brine solution (200 mL). The aqueous layer was extracted with CH$_2$Cl$_2$ (2×200 mL), the combined organics were dried (MgSO$_4$) and concentrated to afford a pale yellow solid. The solid was stirred vigorously with cold methanol for 1 h and the resulting precipitate was filtered off and dried under vacuum to afford 46 as a white solid (20.90 g, 97%); $^1$H NMR (400 MHz, CDCl$_3$) δ7.49 (t, J=15.5, 7.4 Hz, 2H), 7.60-7.64 (m, 1H), 7.81 (d, J=2.2 Hz, 1H), 7.87 (s, 1H), 8.17-8.19 (m, 2H), 8.45 (d, J=2.1 Hz, 1H).

1-Benzenesulfonyl-5-bromo-3-(1-trityl-1H-pyrazol-4-yl)-1H-pyrrolo[2,3-b]pyridine (47)

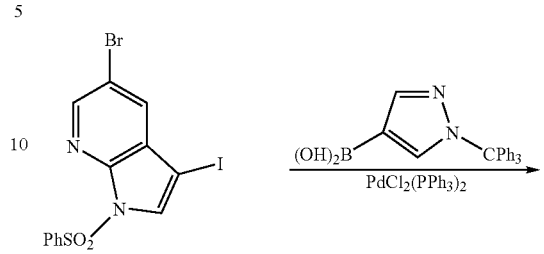

A mixture of 46 (1 g, 2.16 mmol), EtOH (14 mL), toluene (14 mL), 1-trityl-1H-pyrazole-4-boronic acid (767 mg, 2.16 mmol), 1M aq. Na$_2$CO$_3$ (5.4 mL, 5.4 mmol), LiCl (275 mg, 6.5 mmol) and PdCl$_2$(PPh$_3$)$_2$ (75 mg, 0.108 mmol) was refluxed for 1 h 45 min. The reaction mixture was concentrated to afford a pale yellow solid. The solid was purified by silicagel chromatography (Si 50 g column) using 30% ethyl acetate in hexane as eluent (gradient elution) to give the product 47 (798 mg, 57%) as a pale yellow solid; $^1$H NMR (400 MHz, CDCl$_3$) δ 7.18-7.23 (m, 6H), 7.33-7.37 (m, 9H), 7.47 (t, J=15.6, 7.4 Hz, 2H), 7.57-7.60 (m, 2H), 7.74 (s, 1H), 7.91 (s, 1H), 7.95 (d, J=2.1 Hz, 1H), 8.15-8.18 (m, 2H), 8.46 (d, J=2.2 Hz, 1H).

1-Benzenesulfonyl-5-(2,3-dihydro-benzofuran-5-yl)-3-(1-trityl-1H-pyrazol-4-yl)-1H-pyrrolo[2,3-b]pyridine (48)

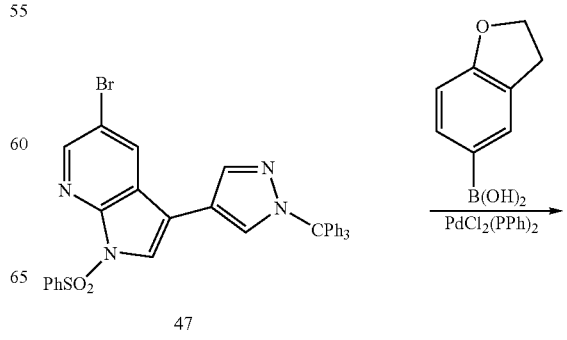

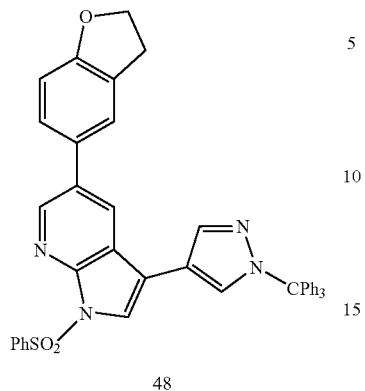

48

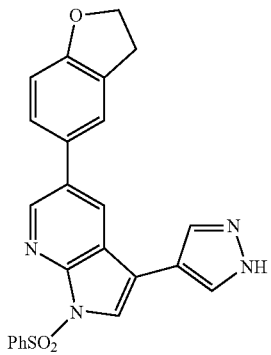

49

A mixture of 47 (200 mg, 0.308 mmol), EtOH (1.5 mL), toluene (1.5 mL), 2,3-dihydrobenzofuran-5-boronic acid (50 mg, 0.308 mmol), 1M aq. Na$_2$CO$_3$ (0.48 mL, 0.48 mmol), LiCl (25 mg, 0.619 mmol) and PdCl$_2$(PPh$_3$)$_2$ (15 mg, 0.021 mmol) was refluxed for 1 h 40 min. The reaction mixture was concentrated to afford a pale yellow solid, which was purified by silicagel chromatography using 30% ethyl acetate in hexane as eluent (gradient elution) to give the product 48 (187 mg, 86%) as a pale yellow solid; $^1$H NMR (400 MHz, CDCl$_3$) δ 3.27 (t, J=17.2, 8.6 Hz, 2H), 4.61 (t, J=17.4, 8.7 Hz, 2H), 6.86 (d, J=8.2 Hz, 1H), 7.19-7.23 (m, 7H), 7.33-7.36 (m, 10H), 7.45 (t, J=15.3, 7.26 Hz, 2H), 7.54-7.58 (m, 1H), 7.65 (s, 1H), 7.74 (s, 1H), 7.89 (d, J=2.1 Hz, 1H), 7.97 (s, 1H), 8.19-8.21 (m, 2H), 8.60 (d, J=2.1 Hz, 1H).

To a solution of 48 (187 mg, 0.270 mmol) in CH$_2$Cl$_2$ (2 mL) was added triisopropylsilane (0.14 mL), TFA (0.73 mL) and distilled water (6 drops). The mixture was stirred at room temperature for 1 h 30 min. The reaction was quenched and made neutral by addition of aqueous saturated NaHCO$_3$ and diluted with EtOAc (200 mL) and water (100 mL). The aqueous layer was extracted further with CH$_2$Cl$_2$ (150 mL), the organic solutions were combined, dried (MgSO$_4$) and concentrated to afford a light brown oily solid. Purification by preparative TLC (EtOAc) afforded 49 (45 mg, 38%) as an off white solid; $^1$H NMR (400 MHz, CDCl$_3$+1 drop CD$_3$OD) δ 2.62 (t, J=17.7, 8.6 Hz, 2H), 3.96 (t, J=17.3, 8.6 Hz, 2H), 6.22 (d, J=8.2 Hz, 1H), 6.65 (t, J=8.0, 2.4 Hz, 2H), 6.76 (s, 1H), 6.84-6.88 (m, 2H), 6.93-6.96 (m, 1H), 7.19 (s, 1H), 7.27 (s, 1H), 7.41 (s, 1H), 7.56 (d, J=7.9 Hz, 2H), 7.97 (s, 1H).

1-Benzenesulfonyl-5-(2,3-dihydro-benzofuran-5-yl)-3-(1H-pyrazol-4-yl)-1H-pyrrolo[2,3-b]pyridine (49)

5-(2,3-dihydro-benzofuran-5-yl)-3-(1H-pyrazol-4-yl)-1H-pyrrolo[2,3-b]pyridine (50)

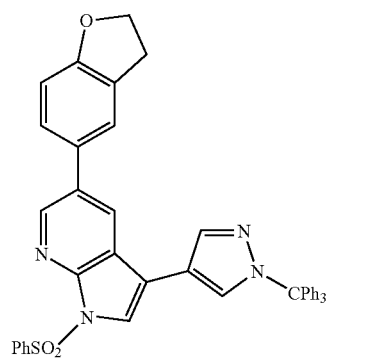

48

TFA
i-Pr$_3$SiH
⟶

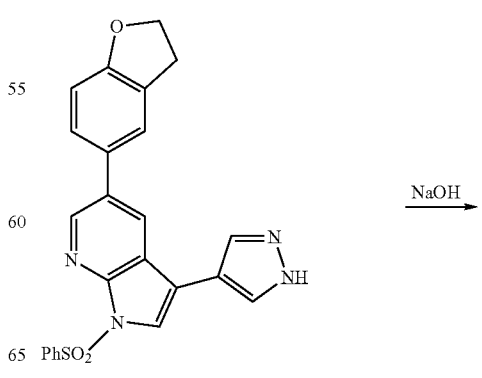

49

NaOH
⟶

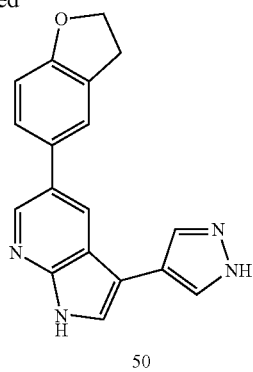

50

To 49 (45 mg, 0.10 mmol) in EtOH (3 mL) was added 10% aq. NaOH (1.25 mL) and the reaction mixture was heated at 85° C. for 1 h. The mixture was concentrated to afford a yellow solid. Purification by preparative LCMS (column LUNA 10μ C18(2) 00G-4253-V0 250×50 mm) using water—acetonitrile (0.1% AcOH) as eluent (in gradient; flow 80 mL/min) afforded the product 50 (16 mg, 53%) as a white solid; $^1$H NMR (400 MHz, CD$_3$OD) δ 3.24 (t, J=17.4, 8.7 Hz, 2H), 4.55 (t, J=17.4, 8.7 Hz, 2H), 6.80 (d, J=8.2 Hz, 1H), 7.36 (d, J=8.2 Hz, 1H), 7.50 (s, 1H), 7.58 (s, 1H), 7.98 (s, 2H), 8.24 (s, 1H), 8.38 (s, 1H).

Synthesis of Example 3,5-Disubstituted 7-Azaindole Derivative (58)

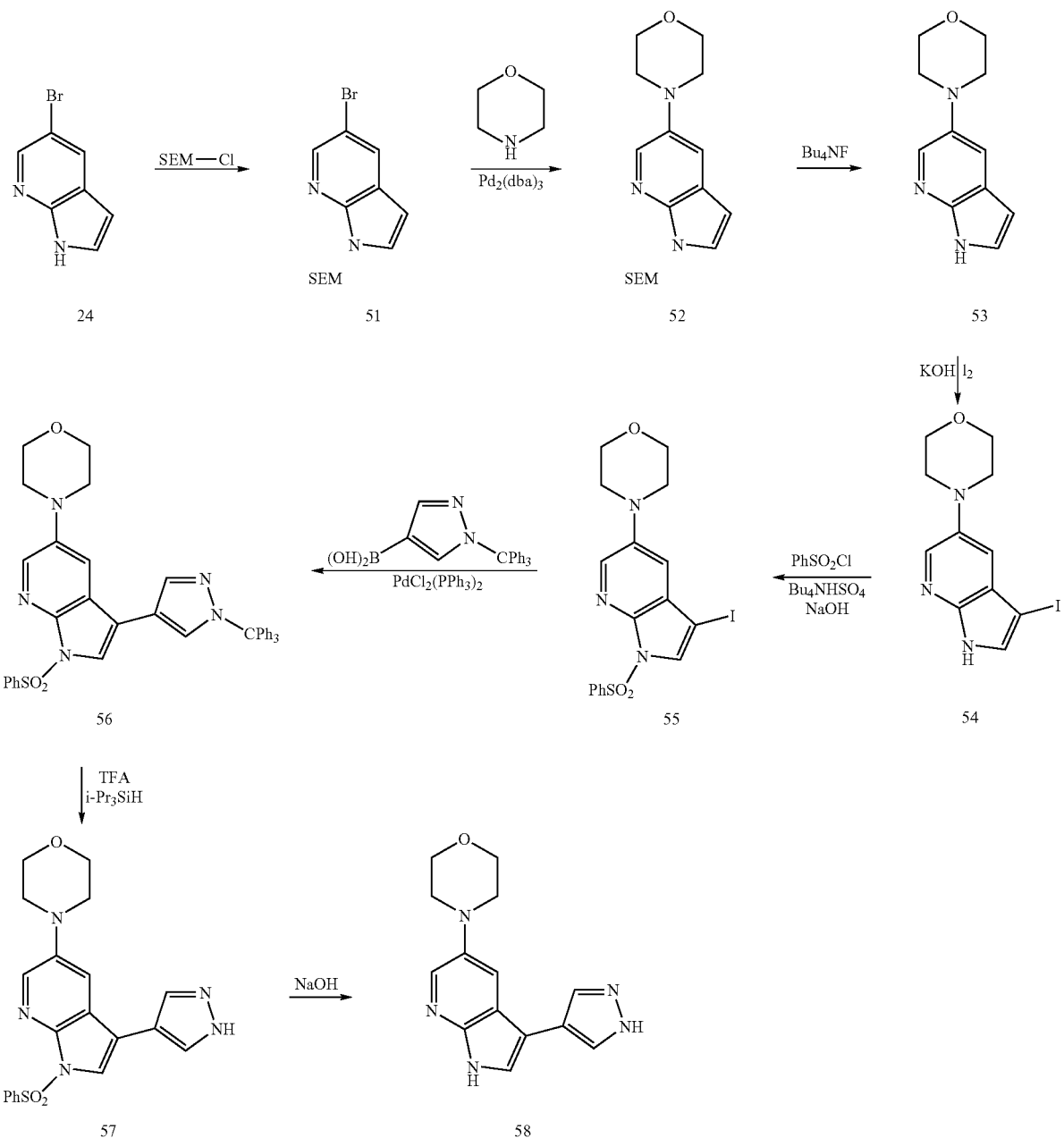

5-Bromo-1-(2-trimethylsilanylethoxymethyl)-1H-pyrrolo[2,3-b]pyridine (51)

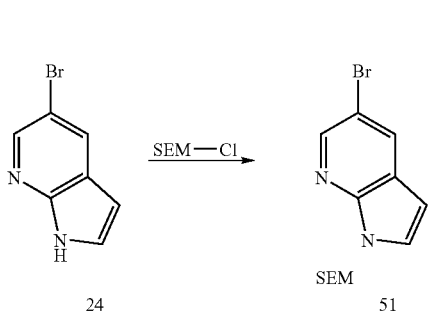

Sodium hydride (60% suspension in oil, 0.305 g, 7.63 mmol) was added to a stirred solution of 5-bromo-7-azaindole 24 (1.00 g, 5.08 mmol) in DMF (10 mL). After the mixture was stirred for 30 min, 2-(trimethylsilyl)ethoxymethyl chloride (SEM-Cl; 1.35 mL, 7.63 mmol) was added. The mixture was stirred for 2.5 days and poured into brine and extracted with AcOEt. The organic layer was washed with brine twice, dried (MgSO$_4$), and concentrated. The residue was purified by means of SGC with hexane:AcOEt as eluent to afford 51 (1.50 g, 90%) as a tan syrup. $^1$H NMR (400 MHz, CDCl$_3$) δ 0.00 (s, 9H), 0.94-0.99 (m, 2H), 3.53-3.61 (m, 2H), 5.71 (s, 2H), 6.53 (d, J=0.36 Hz, 1H), 7.42 (d, J=0.36 Hz, 1H), 8.09 (d, J=0.22 Hz, 1H), 8.42 (d, J=0.22 Hz, 1H).

5-Morpholin-4-yl-1-(2-trimethylsilanylethoxymethyl)-1H-pyrrolo[2,3-b]pyridine (52)

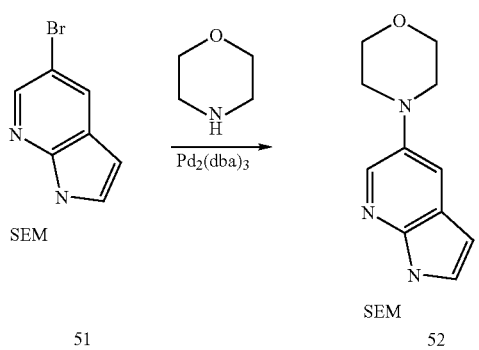

A mixture of 51 (1.48 g, 4.52 mmol), morpholine (0.473 mL, 5.43 mmol), Pd$_2$(dba)$_3$ (0.083 g, 0.090 mmol), Xantphos (0.157 g, 0.271 mmol) and t-BuONa (0.652 g, 6.78 mmol) in toluene (15 mL) was heated at 100° C. for 2.5 hours. The mixture was cooled and poured into brine and extracted with AcOEt. The organic layer was washed with brine, dried (MgSO$_4$), and concentrated. The residue was purified by means of SGC with hexane: AcOEt as eluent to afford 52 (0.81 g, 54%) as a tan syrup. $^1$H NMR (400 MHz, CDCl$_3$) δ 0.00 (s, 9H), 0.94-1.00 (m, 2H), 3.18-3.23 (m, 4H), 3.57-3.63 (m, 2H), 3.96-4.02 (m, 4H), 5.70 (s, 2H), 6.50 (d, J=0.35 Hz, 1H), 7.38 (d, J=0.35 Hz, 1H), 7.55 (d, J=0.26 Hz, 1H), 8.24 (d, J=0.26 Hz, 1H).

5-Morpholin-4-yl-1H-pyrrolo[2,3-b]pyridine (53)

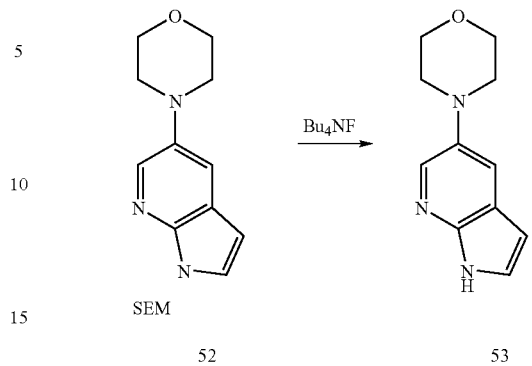

Ethylenediamine (0.090 mL, 1.35 mmol) and 1M solution of TBAF in THF (2.70 mL, 2.70 mmol) were added to a solution of 52 (0.300 g, 0.90 mmol) in THF (5 mL). The mixture was stirred at 60° C. for 6 hours. More 1.0 M TBAF solution (1.80 ml, 1.80 mmol) was added and stirring was continued at 60° C. for 42 hours. The mixture was cooled, and poured into saturated aqueous NaHCO$_3$ solution and extracted with AcOEt. The organic layer was washed with brine, dried (MgSO$_4$), and concentrated to afford a tan solid. The solid was recrystallized from AcOEt to afford 53 (0.065 g) as a pale yellow crystalline solid. The mother liquors were concentrated and successively purified by means of SGC with AcOEt: MeOH as eluent and preparative TLC with CH$_2$Cl$_2$: MeOH as eluent to afford additional 53 (0.060 g, total yield: 0.125 g, 68%) as a pale yellow solid. $^1$H NMR (400 MHz, CDCl$_3$) δ 3.05-3.09 (m, 4H), 3.83-3.87 (m, 4H), 6.36 (dd, J=0.35, 0.20 Hz, 1H), 7.22 (dd, J=0.33, 0.25 Hz, 1H), 7.45 (d, J=0.25 Hz, 1H), 8.07 (d, J=0.25 Hz, 1H), 8.97 (bs, 1H).

3-Iodo-5-morpholin-4-yl-1H-pyrrolo[2,3-b]pyridine (54)

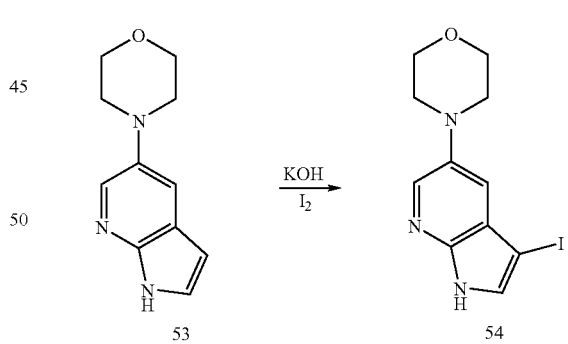

To a stirred solution of 53 (0.096 g, 0.47 mmol) in DMF (2 mL) was added solid KOH (85%, 0.112 g, 1.69 mmol). After 20 min iodine (0.132 g, 0.52 mmol) was added in one portion. After stirring for 1 hour the mixture was cooled with ice-water bath, and water (10 mL) followed by saturated aqueous Na$_2$S$_2$O$_3$ solution (2 mL) were added. The precipitate was filtered off, washed with water and dried to afford 54 (0.102 g, 66%) as a brown solid. $^1$H NMR (400 MHz, CDCl$_3$) δ 3.11-3.15 (m, 4H), 3.85-3.89 (m, 4H), 7.19 (d, J=0.26 Hz, 1H), 7.33 (d, J=0.24 Hz, 1H), 8.08 (d, J=0.26 Hz, 1H), 9.81 (bs, 1H).

1-Benzenesulfonyl-3-iodo-5-morpholin-4-yl-1H-pyrrolo[2,3-b]pyridine (55)

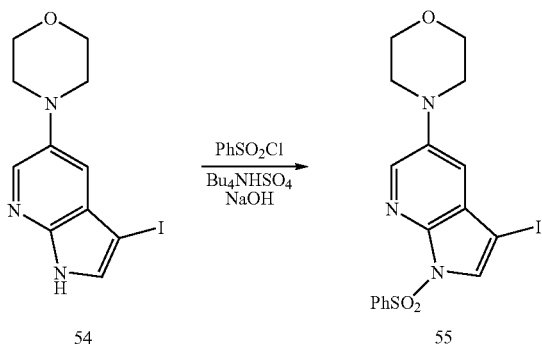

Tetrabutylammonium hydrogen sulfate (0.020 g, 0.059 mmol), benzenesulfonyl chloride (0.055 mL, 0.43 mmol) and 50% aqueous NaOH solution (0.20 mL) were added to a solution of 54 (0.095 g, 0.29 mmol) in CH$_2$Cl$_2$ (3 mL). After stirring for 2 hours, the mixture was poured into saturated aqueous NaHCO$_3$ solution and extracted with CH$_2$Cl$_2$ three times. The combined organic solutions were washed with saturated aqueous NaHCO$_3$ solution, dried (MgSO$_4$), and concentrated to afford a tan syrup. MeOH was added to the syrup and the mixture was cooled in an ice bath. The precipitate was filtered off, washed with MeOH and dried to afford 55 (0.088 g) as a brown solid. The filtrate was concentrated and purified by means of preparative TLC with hexane:AcOEt as eluent to afford additional 55 (0.016 g, total yield: 0.104 g, 77%) as a brown solid. $^1$H NMR (400 MHz, CDCl$_3$) δ 3.08-3.12 (m, 4H), 3.80-3.84 (m, 4H), 7.00 (d, J=0.26 Hz, 1H), 7.38-7.44 (m, 2H), 7.48-7.54 (m, 1H), 7.72 (s, 1H), 8.08-8.11 (m, 2H), 8.12 (d, J=0.26 Hz, 1H).

1-Benzenesulfonyl-5-morpholin-4-yl-3-(trityl-1H-pyrazol-4-yl)-1H-pyrrolo[2,3-b]pyridine (56)

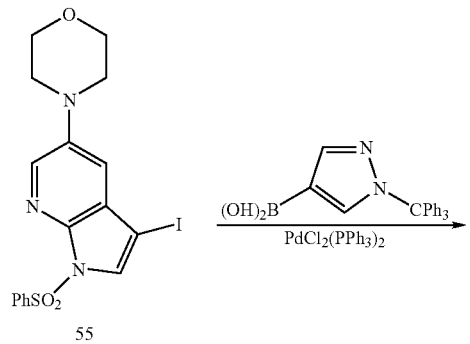

A mixture of iodide 55 (0.083 g, 0.18 mmol), (1-trityl-1H-pyrazol-4-yl)boronic acid (0.094 g, 0.27 mmol), PdCl$_2$(PPh$_3$)$_2$ (0.012 g, 0.017 mmol), LiCl (0.022 g, 0.52 mmol) and 1.0 M aqueous Na$_2$CO$_3$ solution (0.442 mL, 0.442 mol) in EtOH (2 mL)-toluene (2 mL) was stirred at 105° C. for 2 hours. The mixture was cooled and the organic layer was poured into water and extracted with AcOEt. The organic extract was washed with brine, dried (MgSO$_4$), and concentrated to afford a syrup. The syrup was purified by means of preparative TLC with hexane:AcOEt as eluent to afford 56 (0.093 g, 81%) as a tan syrup. $^1$H NMR (400 MHz, CDCl$_3$) δ 2.97-3.02 (m, 4H), 3.77-3.82 (m, 4H), 7.11-7.16 (m, 6H), 7.24-7.29 (m, 8H), 7.35-7.40 (m, 2H), 7.44-7.49 (m, 1H), 7.51 (d, J=0.08 Hz, 1H), 7.61 (s, 1H), 7.86 (d, J=0.08 Hz, 1H), 8.06-8.09 (m, 2H), 8.13 (d, J=0.26 Hz, 1H).

1-Benzenesulfonyl-5-morpholin-4-yl-3-(1H-pyrazol-4-yl)-1H-pyrrolo[2,3-b]pyridine (57)

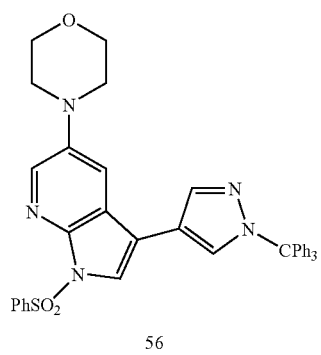

Triisopropylsilane (0.058 mL, 0.28 mmol), trifluoroacetic acid (TFA, 0.2 mL) and water (0.02 mL) were added to a solution of 56 (0.093 g, 0.14 mmol) in CH$_2$Cl$_2$ (2 mL). After string for 15 minutes, the pH of the mixture was adjusted to pH 7-8 with saturated aqueous NaHCO$_3$ and product was extracted with CH$_2$Cl$_2$ twice. The combined organic solutions was dried (MgSO$_4$) and concentrated to afford a tan syrup. Hexane:AcOEt (1:1) solution of was added to the syrup and the mixture was cooled with ice-water bath. The precipitate was filtered off, washed with hexane and dried to afford 57 (0.037 g, 63%) as a brown solid. $^1$H NMR (400 MHz, CDCl$_3$) δ 3.06-3.10 (m, 4H), 3.80-3.84 (m, 4H), 7.34 (d, J=0.27 Hz, 1H), 7.39-7.44 (m, 2H), 7.48-7.53 (m, 1H), 7.68 (s, 1H), 7.79 (bs, 1H), 8.09-8.13 (m, 2H), 8.18 (d, J=0.27 Hz, 1H).

5-Morpholin-4-yl-3-(1H-pyrazol-4-yl)-1H-pyrrolo[2,3-b]pyridine (58)

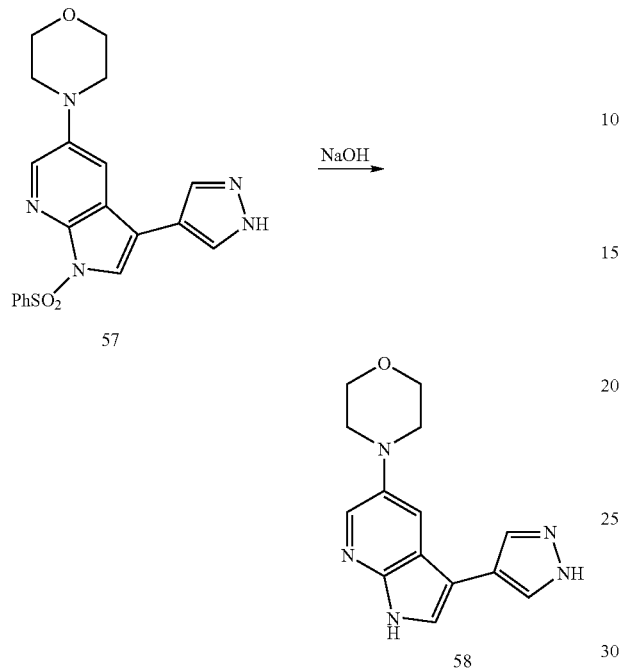

A mixture of 57 (0.031 g, 0.076 mmol) and 10% aqueous NaOH solution (1 mL) in EtOH (2 mL) was stirred at 90° C. for 1 hour. The mixture was cooled and evaporated to afford a tan syrup. The syrup was dissolved with CH$_2$Cl$_2$ and the solution was washed with brine. The aqueous layer was extracted twice with CH$_2$Cl$_2$. The combined extracts were dried (MgSO$_4$) and concentrated to afford a syrup, which was purified by means of preparative TLC with CH$_2$Cl$_2$:MeOH as eluent to afford 58 (0.016 g, 78%) as a pale brown solid. $^1$H NMR (400 MHz, CD$_3$OD) δ 3.13-3.17 (m, 4H), 3.85-3.89 (m, 4H), 7.51 (s, 1H), 7.74 (d, J=0.26 Hz, 1H), 7.93 (bs, 2H), 8.06 (d, J=0.26 Hz, 1H).

Synthesis of Example 3,5-Disubstituted 7-Azaindole Derivative 62

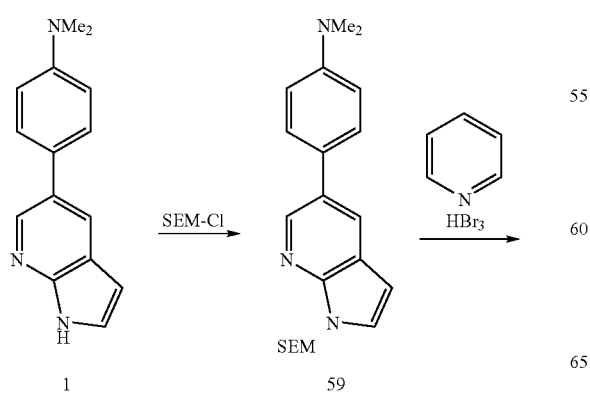

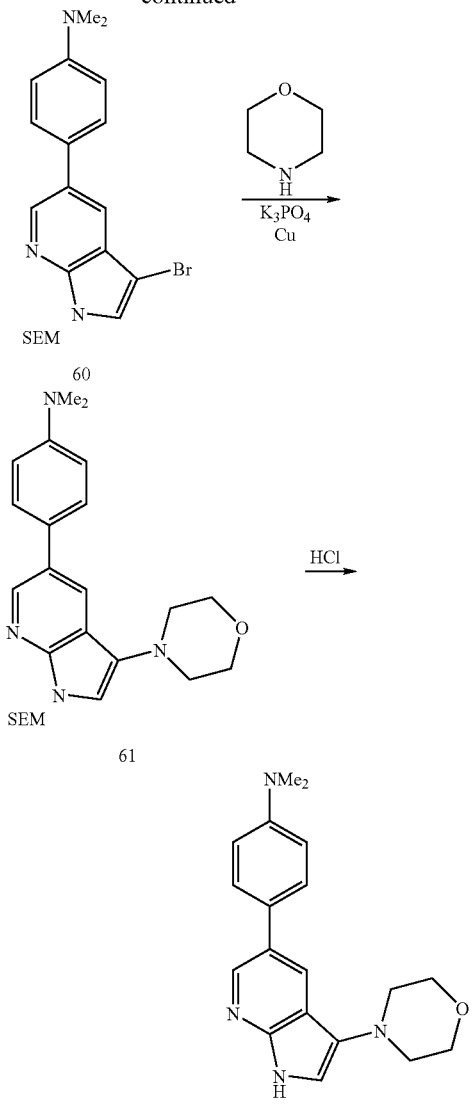

Dimethyl-[4-[1-(2-trimethylsilanylethoxymethyl)-1H-pyrrolo[2,3-b]pyridine-5-yl]phenyl]amine (59)

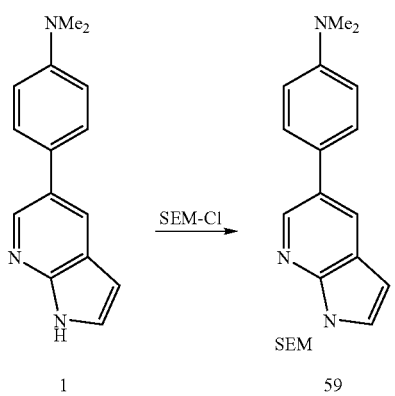

Sodium hydride (60% suspension in oil; 0.253 g, 6.33 mmol) was added to a stirred solution of 1 (1.00 g, 4.21 mmol)

in DMF (10 mL). After stirring for 30 min, 2-(trimethylsilyl)ethoxymethyl chloride (1.12 mL, 6.32 mmol) was added. The mixture was stirred for 5 hours, poured into brine and extracted with AcOEt. The organic extracts was washed twice with brine, dried (MgSO$_4$), and concentrated. The residue was purified by means of SGC with hexane:AcOEt as eluent to afford 59 (1.30 g, 84%) as a white solid. $^1$H NMR (400 MHz, CDCl$_3$) δ 0.00 (s, 9H), 0.95-1.02 (m, 2H), 3.07 (s, 6H), 3.59-3.67 (m, 2H), 5.75 (s, 2H), 6.59 (d, J=0.36 Hz, 1H), 6.88-6.93 (m, 2H), 7.40 (d, J=0.36 Hz, 1H), 7.56-7.61 (m, 2H), 8.09 (d, J=0.21 Hz, 1H), 8.61 (d, J=0.21 Hz, 1H).

[4-[3-Bromo-1-(2-trimethylsilanylethoxymethyl)-1H-pyrrolo[2,3-b]pyridine-5-yl]phenyl]dimethylamine (60)

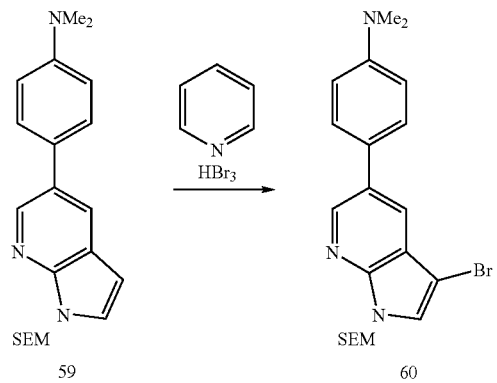

Pyridine (0.180 mL, 2.23 mmol) and pyridinium tribromide (0.832 g, 2.34 mmol) were added to a stirred and cooled (−70° C.) solution of 59 (0.820 g, 2.23 mmol) in CH$_2$Cl$_2$ (10 mL). The mixture was stirred at −70° C. for 30 min., poured into saturated aqueous NaHCO$_3$ solution and extracted with CH$_2$Cl$_2$. The organic extract was washed with brine, dried (MgSO$_4$), and concentrated. The residue was purified by means of SGC with hexane:AcOEt as eluent to afford 60 (0.700 g, 70%) as a pale yellow solid. $^1$H NMR (400 MHz, CDCl$_3$) δ 0.00 (s, 9H), 0.94-1.01 (m, 2H), 3.07 (s, 6H), 3.58-3.64 (m, 2H), 5.71 (s, 2H), 6.88-6.93 (m, 2H), 7.43 (s, 1H), 7.56-7.62 (m, 2H), 8.01 (d, J=0.21 Hz, 1H), 8.62 (d, J=0.21 Hz, 1H).

Dimethyl-[4-[3-morpholin-4-yl-1-(2-trimethylsilanylethoxymethyl)-1H-pyrrolo[2,3-b]pyridin-5-yl]phenyl]amine (61)

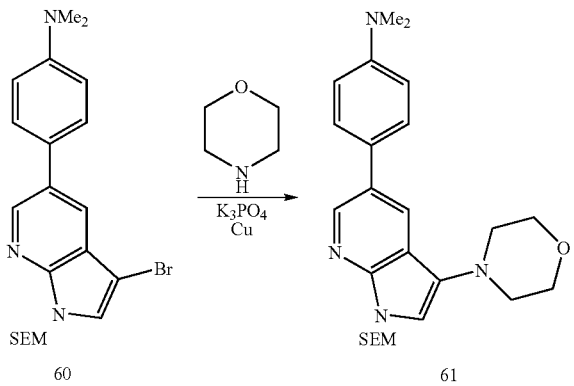

A mixture of 60 (0.055 g, 0.12 mmol), morpholine (0.021 mL, 0.24 mmol), tri-potassium phosphate monohydrate (0.057 g, 0.25 mmol), and copper (powder) (0.00078 g, 0.012 mmol) in N,N-dimethylethanolamine (1 mL) was heated at 120° C. for 2 days. The mixture was cooled and poured into brine and extracted with AcOEt. The organic layer was washed with brine twice, dried (MgSO$_4$), concentrated, and purified by means of preparative TLC with hexane:AcOEt as eluent to afford 61 (0.0096 g, 17%) as a tan syrup. $^1$H NMR (400 MHz, CDCl$_3$) δ 0.00 (s, 9H), 0.88-0.95 (m, 2H), 3.01 (s, 6H), 3.07-3.14 (m, 4H), 3.51-3.57 (m, 2H), 3.91-3.97 (m, 4H), 5.63 (s, 2H), 6.82-6.88 (m, 3H), 7.48-7.53 (m, 2H), 8.00 (d, J=0.21 Hz, 1H), 8.52 (d, J=0.21 Hz, 1H).

Dimethyl-[4-(3-morpholin-4-yl-1H-pyrrolo[2,3-b]pyridine-5-yl)phenyl]amine (62)

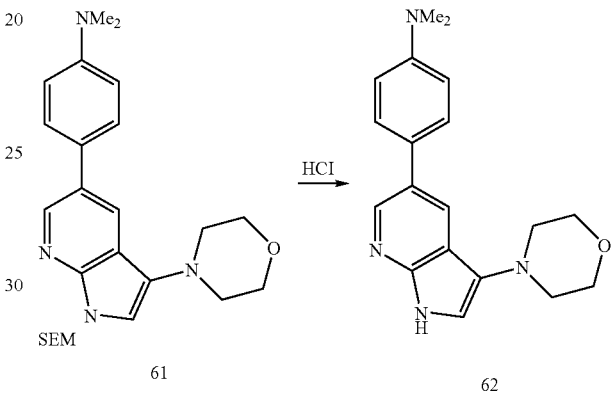

A mixture of 61 (0.017 g, 0.038 mmol), 10% hydrochloric acid (1 mL), and ethanol (1 mL) was heated at 80° C. for 30 minutes. The mixture was cooled and poured into saturated NaHCO$_3$ solution and extracted with AcOEt. The organic extract was dried (MgSO$_4$), concentrated and purified by means of preparative TLC with CH$_2$Cl$_2$:methanol as eluent to afford 62 (0.0047 g, 39%) as a tan solid. $^1$H NMR (400 MHz, CDCl$_3$) δ 2.94 (s, 6H), 3.02-3.06 (m, 4H), 3.86-3.90 (m, 4H), 6.75-6.81 (m, 3H), 7.42-7.47 (m, 2H), 7.97 (d, J=0.21 Hz, 1H), 8.44 (d, J=0.21 Hz, 1H), 8.74 (bs, 1H).

Synthesis of 2,3,5-Trisubstituted Azaindole 63

2-Methyl-5-(2-phenoxy-phenyl)-3-phenyl-1H-pyrrolo[2,3-b]pyridine (63)

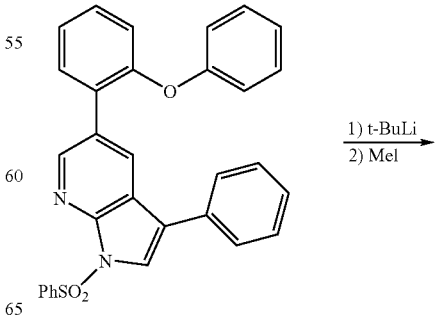

-continued

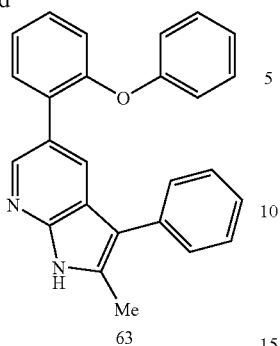

63

To a stirred and cooled (−78° C.) solution of the azaindole 28 (80 mg, 0.16 mmol) in dry THF (2 mL) was added a 1.5 M solution of tert-butyllithium in pentane (0.13 mL, 0.19 mmol) dropwise. After 0.6 h, methyl iodide (0.10 mL, 1.61 mmol) was added dropwise and the reaction mixture allowed to slowly warm to room temperature. Following a further 22.5 h the mixture was diluted with EtOAc and saturated NaHCO$_3$ solution and partitioned. The aqueous layer was washed with EtOAc (3×). The combined organic extracts were dried (MgSO$_4$), filtered and concentrated. The product was purified by PTLC using hexanes-EtOAc=4:1 as eluent to afford the desired azaindole 63 (4.4 mg, 7.3%). $^1$H NMR (400 MHz; CDCl$_3$) δ 3.94 (s, 3H), 6.93-6.96 (m, 2H), 7.01-7.05 (m, 1H), 7.08 (dd, J=1.3 and 8.1 Hz, 1H), 7.22-7.29 (m, 3H), 7.33-7.39 (m, 4H), 7.50-7.54 (m, 3H), 8.35 (d, J=2.0 Hz, 1H) and 8.57 (d, J=2.0 Hz, 1H). MS (CI) m/z 377 (MH$^+$).

Biological Activity

JNK1, JNK2, JNK3—SPA Assay

1. Compound is dissolved in DMSO to a convenient concentration and this is diluted in 10% DMSO to a five times concentrate of the desired starting concentration (frequently 1:100).
2. 10 µl of 500 mM EDTA is added to alternative wells of the Opti-plate row, which will receive kinase reaction plus DMSO. This creates the negative control.
3. For the JNK2 and JNK3 assay, compounds are prepared in six 2-fold dilutions with water and each concentration is tested in duplicate. For the JNK1 assay compounds are prepared in four 5-fold dilutions with water which are tested in triplicate. Controls are treated identically.
4. 20 µl per well of each compound concentration is transferred to an Opti-plate, in duplicate.
5. 30 µl (JNK2/3 SPA) or 50 µl (JNK1 SPA) of substrate solution (25 mM HEPES pH 7.5, 10 mM magnesium acetate with 3.33 µM ATP (JNK2/3) or 2 µM ATP (JNK1), approximately 7.5 kBq [γ-$^{33}$P] ATp, GST-c-Jun, in water) is added to each well.
6. 50 µl (JNK2/3 SPA) or 30 µl (JNK1 SPA) of kinase solution (JNK in 25 mM HEPES pH 7.5, 10 mM Mg Acetate) is added to each well.

| Kinase | Kinase per well (µg) | GST-c-Jun per well (µg) |
|---|---|---|
| JNK1 | 0.25 | 1 |
| JNK2 | 0.2 | 1.2 |
| JNK3 | 0.16 | 1.2 |

7. The plate is incubated for 30 minutes at room temperature.
8. 100 µl of bead/stop solution is added to each well (5 mg/ml glutathione-PVT-SPA beads, 40 mM ATP in PBS).
9. Plates are sealed and incubated for 30 minutes at room temperature, centrifuged for 10 minutes at 2500 g and counted.
10. The IC$_{50}$ values are calculated as the concentration of the compound being tested at which the phosphorylation of c-Jun is decreased to 50% of the control value. Example IC$_{50}$ values for the compounds of this invention are given in Table 1.

p38 ELISA

Active p38 kinase (100 ng; Upstate) was added to 2 µg GST-ATF2 substrate (NEB) in 250 mM Hepes pH 7.5/100 mM MgAc/50 µM ATP (final) in the presence or absence of compounds in 50 µl. The mixture was incubated at 30° C. for 1 hour, and then diluted with 200 µl PBS-Tween (0.05%). From this, duplicate volumes of 100 µl were added to a Reacti-Bind glutathione coated plate (Pierce) and incubated for 1 hour. After washing 3 times with PBS-Tween (0.05%), rabbit anti-phospho-ATF2 (Thr71) antibody (NEB) was added at 1:500, and incubated for another hour at room temperature. After 3 additional washes with PBS-Tween (0.05%), 100 g of anti-rabbit IgG alkaline phosphatase-conjugated secondary antibody (Sigma) was added at 1:1000, the reaction was incubated for a further hour, washed 3 times, and then phosphatase substrate (Sigma) was added (100 µl per well; 3 tablets in 5 ml water). After incubation in the dark at 37° C. for 1 hour, the reaction mixture was transferred to a clear 96 well plate, and the absorbance at 405 nm was read.

The IC$_{50}$ values are calculated as the concentration of the compound being tested at which the phosphorylation of ATF2 is decreased to 50% of the control value. Example IC$_{50}$ values for the compounds of this invention are given in Table 1 (last column).

TABLE 1

IC$_{50}$ values for selected compounds against JNK1, JNK2, JNK3, and p38 MAP kinase

| Compound | JNK3 IC$_{50}$ (nM) | JNK2 IC$_{50}$ (nM) | JNK1 IC$_{50}$ (nM) | p38 IC$_{50}$ (nM) |
|---|---|---|---|---|
|  | <500 | <500 | <500 | >10,000 |

TABLE 1-continued

IC$_{50}$ values for selected compounds against JNK1, JNK2, JNK3, and p38 MAP kinase

| Compound | JNK3 IC$_{50}$ (nM) | JNK2 IC$_{50}$ (nM) | JNK1 IC$_{50}$ (nM) | p38 IC$_{50}$ (nM) |
|---|---|---|---|---|
| | <500 | <500 | <500 | >10,000 |
| | <500 | | | |
| | <500 | <500 | <500 | >10,000 |
| | <500 | | | |
| | <500 | | | |
| | <500 | | | |

The invention claimed is:

1. A compound of formula (I):

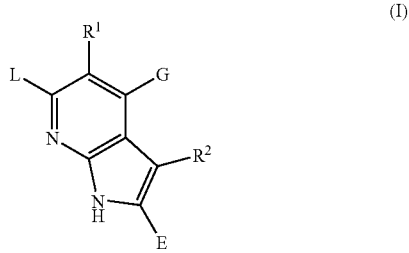

or a pharmaceutically acceptable salt thereof, wherein $R^1$ is an optionally substituted carbocyclyl, $R^2$ is an optionally substituted five membered heterocyclyl group, E is hydrogen, halogen, cyano, $C_{1-6}$ alkoxy or $C_{1-6}$ alkyl, G is hydrogen, halogen, cyano, $C_{1-6}$ alkoxy or $C_{1-6}$ alkyl, and L is hydrogen, halogen, cyano, $C_{1-6}$ alkoxy or $C_{1-6}$ alkyl;

wherein $R^1$ is optionally fused to a partially saturated, unsaturated or fully saturated five to seven membered ring containing zero heteroatoms, and each substitutable carbon atom in $R^1$, including the optional fused ring, is optionally and independently substituted by one or more of halogen, $C_{1-12}$ alkyl, $C_{2-12}$ alkenyl, $C_{2-12}$ alkynyl, haloalkyl, carbocyclyl, heterocyclyl, $(CH_2)_nOR^3$, $(CH_2)_nNR^3{}_2$, $OR^3$, $SR^3$, $NO_2$, CN, $NR^3{}_2$, $NR^3COR^3$, $NR^3CONR^3{}_2$, $NR^3COR^3$, $NR^3CO_2R^3$, $CO_2R^3$, $COR^3$, $CONR^3{}_2$, $S(O)_2R^3$, $SONR^3{}_2$, $S(O)R^3$, $SO_2NR^3{}_2$, or $NR^3S(O)_2R^3$ wherein the $C_{1-12}$ alkyl group optionally contains one or more insertions selected from —O—, —N($R^3$)—, —S—, —S(O)— and —S(O$_2$)—; and each saturated carbon in the optional fused ring is further optionally and independently substituted by =O, =S, NNR$^4{}_2$, =N—OR$^4$, =NNR$^4$COR$^4$, =NNR$^4$CO$_2$R$^4$, =NNSO$_2$R$^4$, or =NR$^4$; and each substitutable nitrogen atom in $R^1$ is optionally substituted by $R^5$, $COR^5$, $SO_2R^5$ or $CO_2R^5$;

wherein n is 1 to 6;

wherein $R^3$ is hydrogen, $C_{1-12}$ alkyl, carbocyclyl or heterocyclyl, optionally substituted by one or more of $C_{1-6}$ alkyl, carbocyclyl, heterocyclyl, halogen, $C_{1-6}$ haloalkyl, $OR^6$, $SR^6$, $NO_2$, CN, $NR^6R^6$, $NR^6COR^6$, $NR^6CONR^6R^6$, $NR^6COR^6$, $NR^6CO_2R^6$, $CO_2R^6$, $COR^6$, $CONR^6{}_2$, $S(O)_2R^6$, $SONR^6{}_2$, $S(O)R^6$, $SO_2NR^6R^6$, $NR^6S(O)_2R^6$, wherein the $C_{1-12}$ alkyl group optionally incorporates one or two insertions selected from the group consisting of —O—, —N($R^6$)—, —S(O)— and —S(O$_2$)—, wherein each $R^6$ may be the same or different and is as defined below;

wherein two $R^3$ in $NR^3{}_2$ may optionally form a partially saturated, unsaturated or fully saturated five to seven membered ring containing one to three heteroatoms, optionally and independently substituted by one or more of $C_{1-6}$ alkyl, halogen, $C_{1-6}$ haloalkyl, $OR^6$, $SR^6$, $NO_2$, CN, $NR^6R^6$, $NR^6COR^6$, $NR^6CONR^6R^6$, $NR^6COR^6$, $NR^6CO_2R^6$, $CO_2R^6$, $COR^6$, $CONR^6{}_2$, $S(O)_2R^6$, $SONR^6{}_2$, $S(O)R^6$, $SO_2NR^6R^6$, $NR^6S(O)_2R^6$, wherein the $C_{1-6}$ alkyl group optionally incorporates one or two insertions selected from the group consisting of —O—, —N($R^6$)—, —S(O)— and —S(O$_2$)—, wherein each $R^6$ may be the same or different and is as defined below;

wherein $R^4$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^6$, $SR^6$, $NO_2$, CN, $NR^6R^6$, $NR^6COR^6$, $NR^6CONR^6R^6$, $NR^6COR^6$, $NR^6CO_2R^6$, $CO_2R^6$, $COR^6$, $CONR^6{}_2$, $S(O)_2R^6$, $S(O)R^6$, $SO_2NR^6R^6$, $NR^6S(O)_2R^6$, wherein the $C_{1-12}$ alkyl group optionally incorporates one or two insertions selected from the group consisting of —O—, —N($R^6$)—, —S(O)— and —S($O_2$)—, wherein each $R^6$ may be the same or different and is as defined below;

wherein $R^5$ is hydrogen, $C_{6-12}$ aryl, $C_{1-6}$ alkyl or $C_{1-6}$ haloalkyl;

wherein $R^6$ is hydrogen, $C_{1-6}$ alkyl, or $C_{1-6}$ haloalkyl;

and wherein $R^2$ is a five-membered heterocyclyl group containing from 1 to 4 heteroatoms independently selected from N, S or O, wherein at least one heteroatom is N and wherein the optionally substituted five-membered heterocyclyl group is optionally fused to a partially saturated, unsaturated or fully saturated five to seven membered ring containing zero to three heteroatoms, and each substitutable carbon or heteroatom in $R^2$ including the optional fused ring, is optionally and independently substituted by one or more of halogen, $C_{1-12}$ alkyl, $C_{2-12}$ alkenyl, $C_{2-12}$ alkynyl, haloalkyl, carbocyclyl, heterocyclyl, $(CH_2)_nOR^7$, $(CH_2)_nNR^7_2$, $OR^7$, $SR^7$, $NO_2$, CN, $NR^7_2$, $NR^7COR^7$, $NR^7CONR^7_2$, $NR^7COR^7$, $NR^7CO_2R^7$, $CO_2R^7$, $COR^7$, $CONR^7_2$, $S(O)_2R^7$, $SONR^7_2$, $S(O)R^7$, $SO_2NR^7_2$, or $NR^7S(O)_2R^7$ wherein the $C_{1-12}$ alkyl group optionally contains one or more insertions selected from —O—, —N($R^7$)— —S—, —S(O)— and —S($O_2$)—; and each saturated carbon in the optional fused ring is further optionally and independently substituted by =O, =S, $NNR^8_2$, =N—$OR^8$, =$NNR^8COR^8$, =$NNR^8CO_2R^8$, =$NNSO_2R^8$, or =$NR^8$; and each substitutable nitrogen atom in $R^2$ is optionally substituted by $R^9$, $COR^9$, $SO_2R^9$ or $CO_2R^9$; wherein n is 1 to 6;

wherein $R^{10}$ is hydrogen, $C_{1-6}$ alkyl, or $C_{1-6}$ haloalkyl;

wherein $R^7$ is hydrogen, $C_{1-12}$ alkyl, carbocyclyl or heterocyclyl, optionally substituted by one or more of $C_{1-6}$ alkyl, carbocyclyl, heterocyclyl, halogen, $C_{1-6}$ haloalkyl, $OR^{11}$, $SR^{11}$, $NO_2$, CN, $NR^{11}R^{11}$, $NR^{11}COR^{11}$, $NR^{11}CONR^{11}R^{11}$, $NR^{11}COR^{11}$, $NR^{11}CO_2R^{11}$, $CO_2R^{11}$, $COR^{11}$, $CONR^{11}_2$, $S(O)_2R^{11}$, $SONR^{11}_2$, $S(O)R^{11}$, $SO_2NR^{11}R^{11}$, $NR^{11}S(O)_2R^{11}$, wherein the $C_{1-12}$ alkyl group optionally incorporates one or two insertions selected from the group consisting of —O—, —N($R^{11}$)—, —S(O)— and —S($O_2$)—, wherein each $R^{11}$ may be the same or different and is as defined below;

wherein two $R^7$ in $NR^7_2$ may optionally form a partially saturated, unsaturated or fully saturated five to seven membered ring containing one to three heteroatoms, optionally and independently substituted by one or more of $C_{1-6}$ alkyl, halogen, $C_{1-6}$ haloalkyl, $OR^{11}$, $SR^{11}$, $NO_2$, CN, $NR^{11}R^{11}$, $NR^{11}COR^{11}$, $NR^{11}CONR^{11}R^{11}$, $NR^{11}COR^{11}$, $NR^{11}CO_2R^{11}$, $CO_2R^{11}$, $COR^{11}$, $CONR^{11}_2$, $S(O)_2R^{11}$, $SONR^{11}_2$, $S(O)R^{11}$, $SO_2NR^{11}R^{11}$, $NR^{11}S(O)_2R^{11}$, wherein the $C_{1-6}$ alkyl group optionally incorporates one or two insertions selected from the group consisting of —O—, —N($R^{11}$)—, —S(O)— and —S($O_2$)—, wherein each $R^{11}$ may be the same or different and is as defined below;

wherein $R^8$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^{11}$, $SR^{11}$, $NO_2$, CN, $NR^{11}R^{11}$, $NR^{11}COR^{11}$, $NR^{11}CONR^{11}R^{11}$, $NR^{11}COR^{11}$, $NR^{11}CO_2R^{11}$, $CO_2R^{11}$, $COR^{11}$, $CONR^{11}_2$, $S(O)_2R^{11}$, $S(O)R^{11}$, $SO_2NR^{11}R^{11}$, $NR^{11}S(O)_2R^{11}$, wherein the $C_{1-12}$ alkyl group optionally incorporates one or two insertions selected from the group consisting of —O—, —N($R^{11}$)—, —S(O)— and —S($O_2$)—, wherein each $R^{11}$ may be the same or different and is as defined below;

wherein $R^9$ is hydrogen, $C_{6-12}$ aryl, $C_{1-6}$ alkyl or $C_{1-6}$ haloalkyl; and wherein $R^{11}$ is hydrogen, $C_{1-6}$ alkyl, or $C_{1-6}$ haloalkyl.

2. A compound of formula (I) as claimed in claim 1, wherein $R^1$ is an optionally substituted five or six membered carbocyclyl group wherein the carbocyclyl group is optionally fused to one or more unsaturated rings.

3. A compound as claimed in claim 1 wherein $R^1$ is selected from optionally substituted phenyl, cyclohexyl furan, and naphthaline.

4. A compound as claimed in claim 1 wherein $R^1$ is substituted with one or more of $OR^{12}$, halogen, $C_{1-6}$ alkyl, $C_{2-6}$ alkenyl, $C_{2-6}$ alkynyl, haloalkyl, $C_{1-6}$ alkylaryl, $C_{1-6}$ alkylheterocyclyl, $(CH_2)_nOR^{12}$, $(CH_2)_nNR^{12}_2$, $SR^{12}$, $NO_2$, CN, $NR^{12}_2$, $NHC(O)R^{12}$, $NHS(O)_2R^{12}$, $CO_2R^{12}$, $COR^{12}$, $CONR^{12}_2$, $S(O)_2R^{12}$, $S(O)R^{12}$ or $SO_2NR^{12}_2$; wherein $R^{12}$ is hydrogen, $C_{1-4}$ alkyl or aryl, or heterocyclyl, and n is 1, 2, 3, 4, 5 or 6.

5. A compound of formula (I) as claimed in claim 1 wherein $R^2$ is selected from optionally substituted imidazole, isoxazole, isothiazole, oxazole, oxadiazole, oxathiazole, pyrazole, pyrrole, tetrazole, thiadiazole, thiatriazole, thiazole or triazole.

6. A compound as claimed in claim 1 wherein $R^2$ is a group

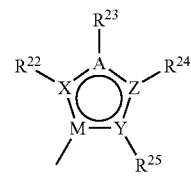

wherein A, X, Y or Z are independently selected from N, O, C, S and M is C or N, wherein one, two, three or four of A, X, Y, Z and M is N other than C;

$R^{22}$, $R^{23}$, $R^{24}$ or $R^{25}$ are independently selected from a lone electron pair, hydrogen, halogen, $C_{1-12}$ alkyl, haloalkyl, $OR^{26}$, $SR^{26}$, $NO_2$, CN, $NR^{26}_2$, $NR^{26}CONR^{26}_2$, $NR^{26}COR^{26}$, $NR^{26}CO_2R^{26}$, $(CH_2)_nOR^{26}$, $(CH_2)_nNR^{26}_2$, $CO_2R^{26}$, $COR^{26}$, $CONR^{26}_2$, $S(O)_2R^{26}$, $SONR^{26}_2$, $S(O)R^{26}$, $SO_2NR^{26}_2$, or $NHS(O)_2R^{26}$;

wherein n is 1 to 6;

or wherein any two of $R^{22}$, $R^{23}$, $R^{24}$ or $R^{25}$ may optionally form a partially saturated, unsaturated or fully saturated five to seven membered ring containing zero to three heteroatoms, each saturated carbon in the optional fused ring is further optionally and independently substituted with one or more of halogen, $C_{1-12}$ alkyl, $C_{2-12}$ alkenyl, $C_{2-12}$ alkynyl, haloalkyl, carbocyclyl, heterocyclyl, $OR^{26}$, $SR^{26}$, $NO_2$, CN, $NR^{26}_2$, $NR^{26}CONR^{26}_2$, $NR^{26}COR^{26}$, $NR^{26}CO_2R^{26}$, $(CH_2)_nOR^{26}$, $(CH_2)_nNR^{26}_2$, $CO_2R^{26}$, $COR^{26}$, $CONR^{26}_2$, $S(O)_2R^{26}$, $SONR^{26}_2$, $S(O)R^{26}$, $SO_2NR^{26}_2$, or $NR^{26}S(O)_2R^{26}$; and each saturated carbon in the optional fused ring is further optionally and independently substituted by =O, =S, $NNR^{27}_2$, =N—$OR^{27}$, =$NNR^{27}COR^{27}$, =$NNR^{27}CO_2R^{27}$, =$NNSO_2R^{27}$, or =$NR^{27}$; and each substitutable nitrogen atom in $R^1$ is optionally substituted by $R^{28}$, $COR^{28}$, $SO_2R^{28}$ or $CO_2R^{28}$;

wherein n is 1 to 6;

wherein $R^{26}$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^{29}$, $SR^{29}$, $NO_2$, CN, $NR^{29}R^{29}$, $NR^{29}CONR^{29}R^{29}$, $NR^{29}COR^{29}$, $NR^{29}CO_2R^{29}$, $CO_2R^{29}$, $COR^{29}$, $CONR^{29}_2$, $S(O)_2R^{29}$, $SONR^{29}_2$, $S(O)R^{29}$, $SO_2NR^{29}R^{29}$, $NR^{29}S(O)_2R^{29}$, wherein the $C_{1-12}$ alkyl group optionally incorporates one or two insertions selected from the group consisting of —O—, —N($R^{29}$)—, —S(O)— and —S($O_2$)—, wherein each $R^{29}$ may be the same or different and is as defined below;

wherein $R^{27}$ is hydrogen, $C_{1-12}$ alkyl, carbocyclyl or heterocyclyl, optionally substituted by one or more of $C_{1-6}$ alkyl, halogen, $C_{1-6}$ haloalkyl, $OR^{29}$, $SR^{29}$, $NO_2$, CN, $NR^{29}R^{29}$, $NR^{29}COR^{29}$, $NR^{29}CONR^{29}R^{29}$, $NR^{29}CO_2R^{29}$, $CO_2R^{29}$, $COR^{29}$, $CONR^{29}_2$, $S(O)_2R^{29}$, $S(O)R^{29}$, $SO_2NR^{29}R^{29}$, $NR^{29}S(O)_2R^{29}$, wherein the $C_{1-12}$ alkyl group optionally incorporates one or two insertions selected from the group consisting of —O—, —N($R^{29}$)—, —S(O)— and —S($O_2$)—, wherein each $R^{29}$ may be the same or different and is as defined below;

wherein $R^{28}$ is hydrogen, $C_{1-6}$ alkyl, $C_{1-6}$ haloalkyl or $C_{6-12}$ aryl; and wherein $R^{29}$ is hydrogen, $C_{1-6}$ alkyl, or $C_{1-6}$ haloalkyl.

7. A compound of formula (I) as claimed in claim 6 wherein $R^{22}$, $R^{23}$, $R^{24}$ or $R^{25}$ are independently selected from a lone electron pair, hydrogen, halogen, $C_{1-6}$ alkyl, haloalkyl, $OR^{30}$, $SR^{30}$, CN, $NR^{30}_2$, $NR^{30}COR^{30}$, $CO_2R^{30}$, $COR^{30}$, $CONR^{30}_2$, $S(O)_2R^{30}$, or $S(O)R^{30}$;

wherein $R^{30}$ is hydrogen, $C_{1-4}$ alkyl, or carbocyclyl.

8. A compound of formula (I) selected from the group consisting of:

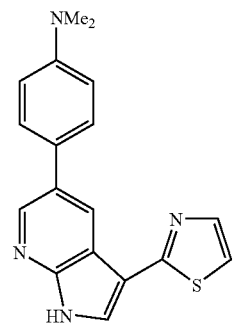

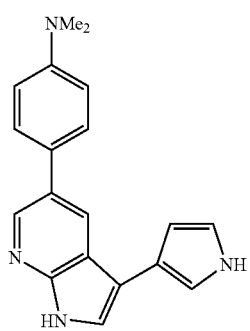

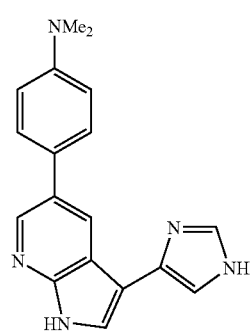

-continued

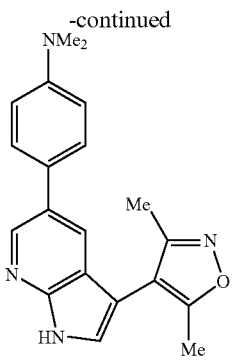

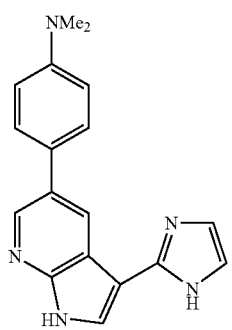

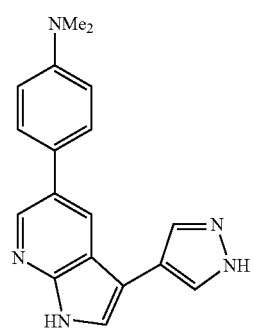

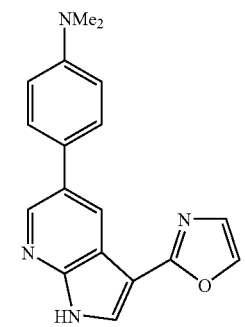

-continued
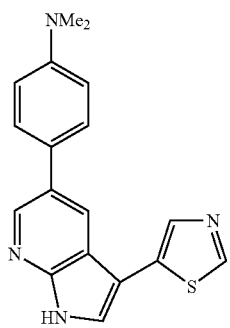
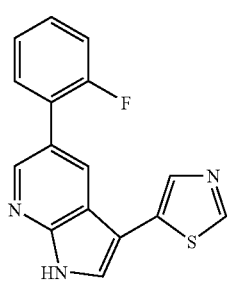
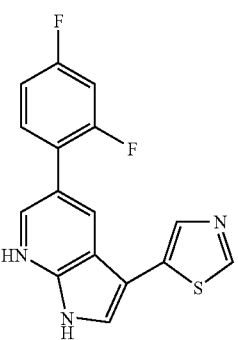
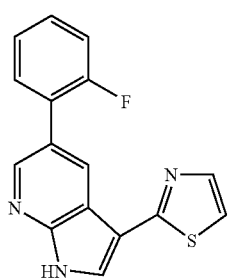
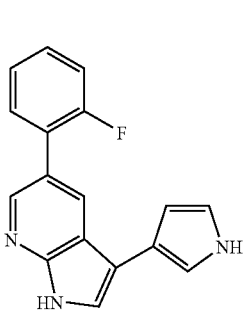
-continued
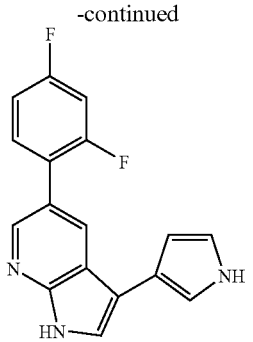
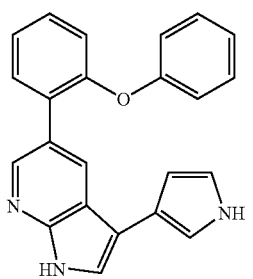
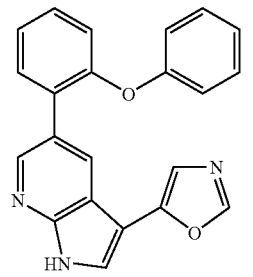
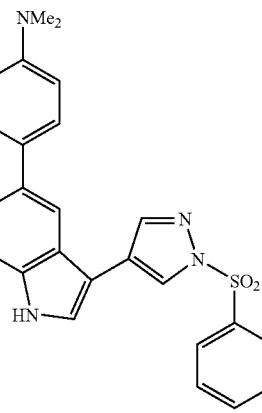

-continued

-continued
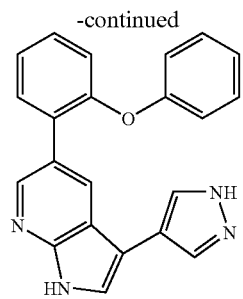
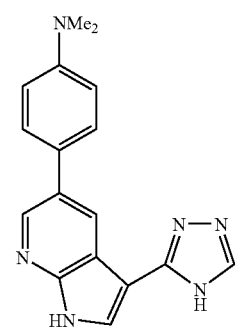
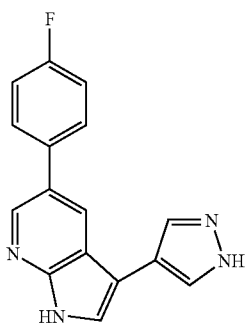
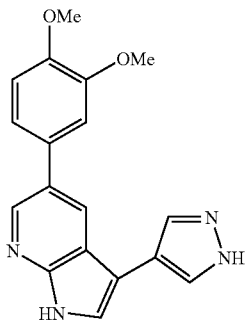
-continued
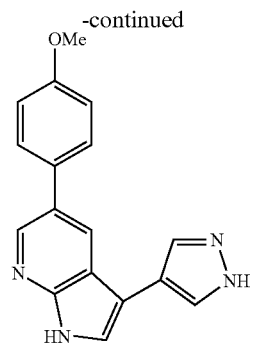
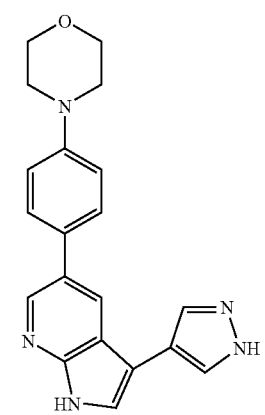
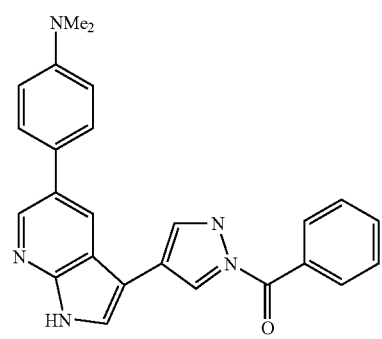
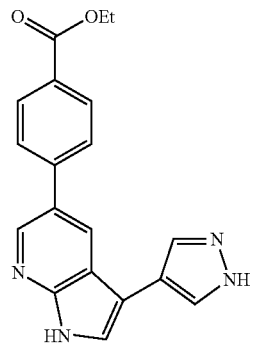

221                                                222
-continued                                         -continued
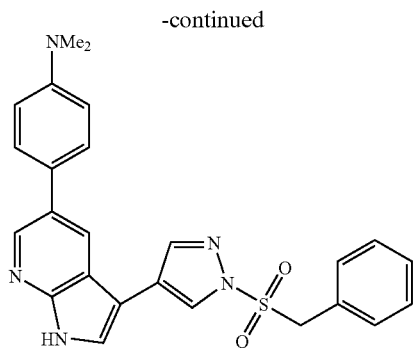
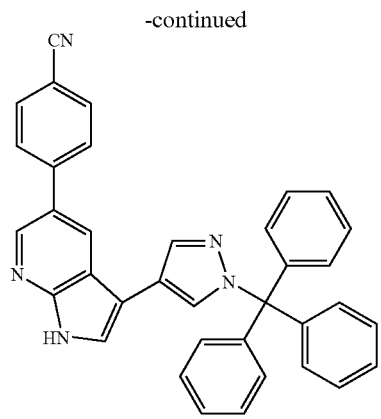
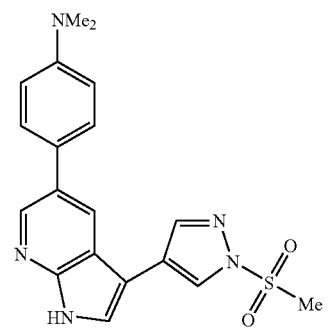
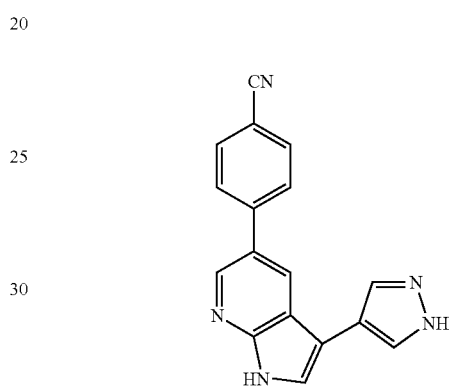
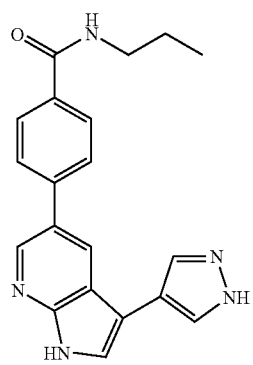
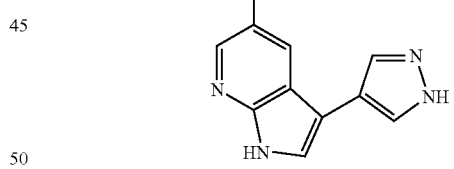
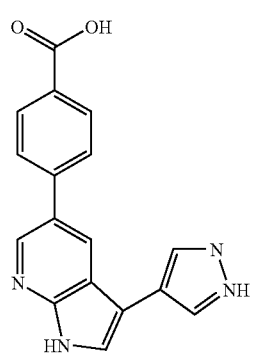
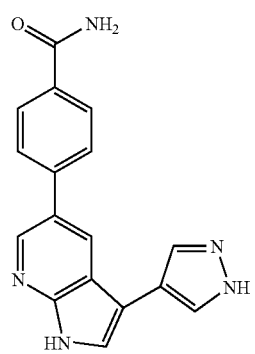

223
-continued
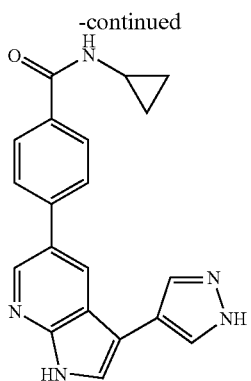
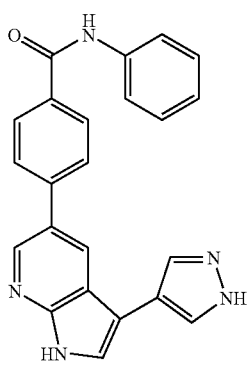
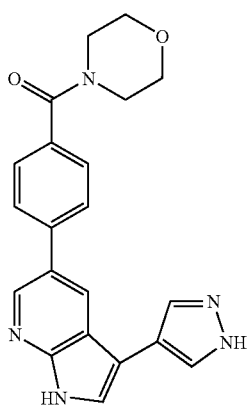
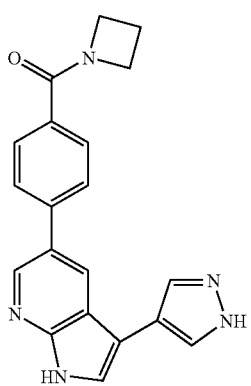
224
-continued
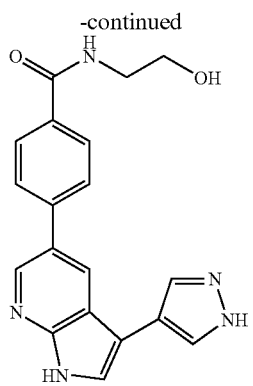
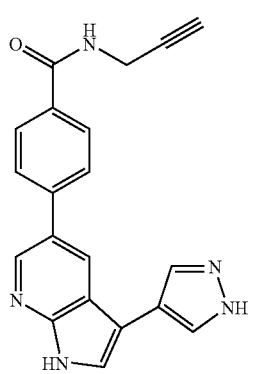
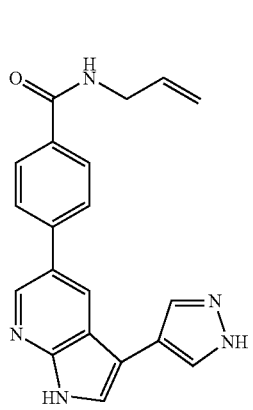
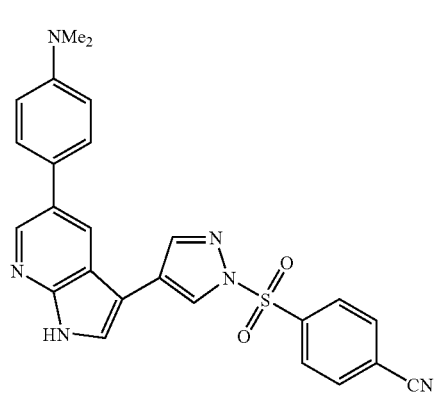

-continued
225
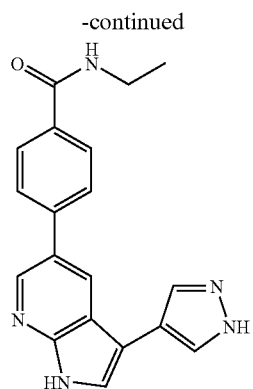
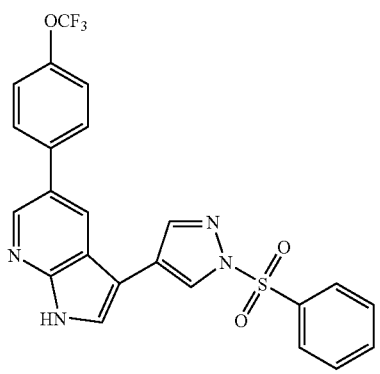
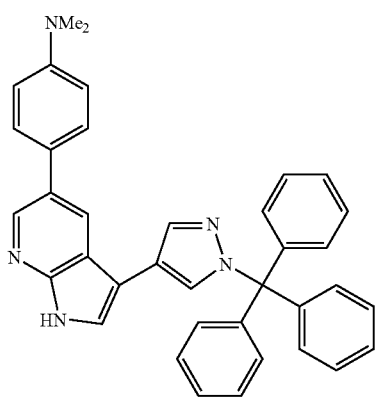
226
-continued
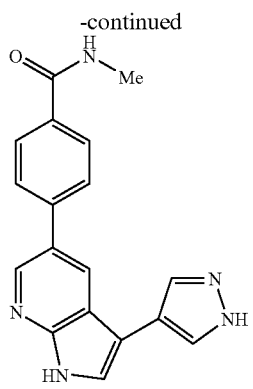
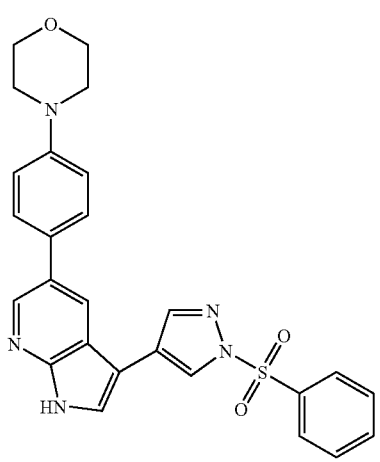

227
-continued
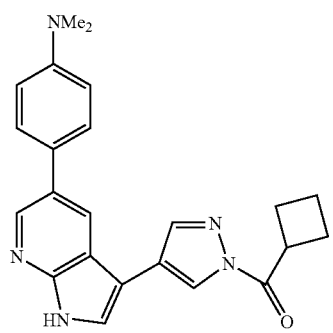
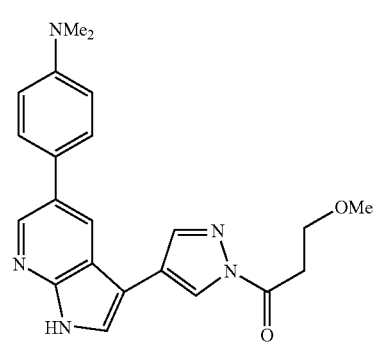
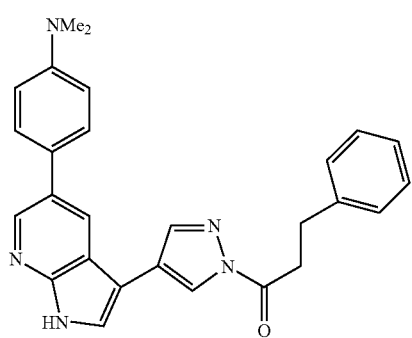
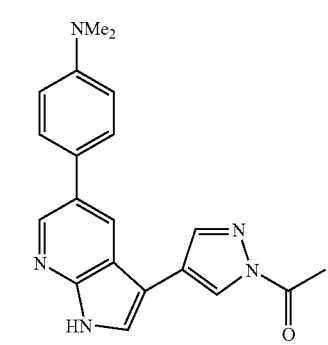
228
-continued
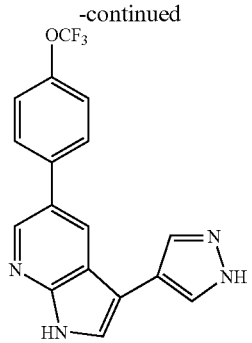
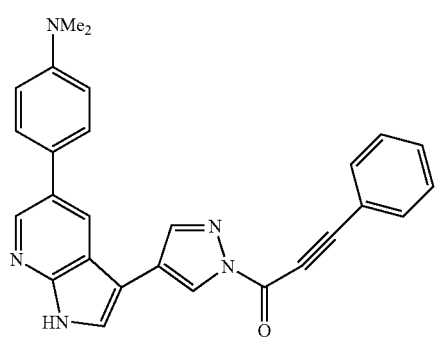
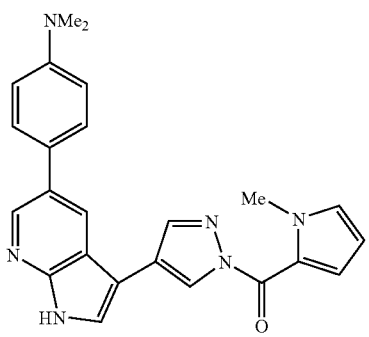
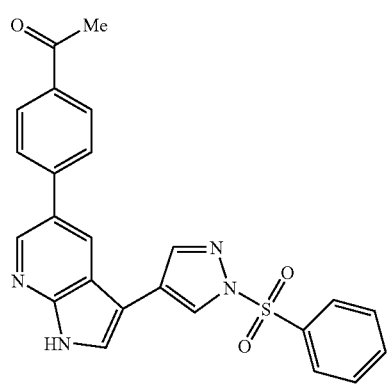

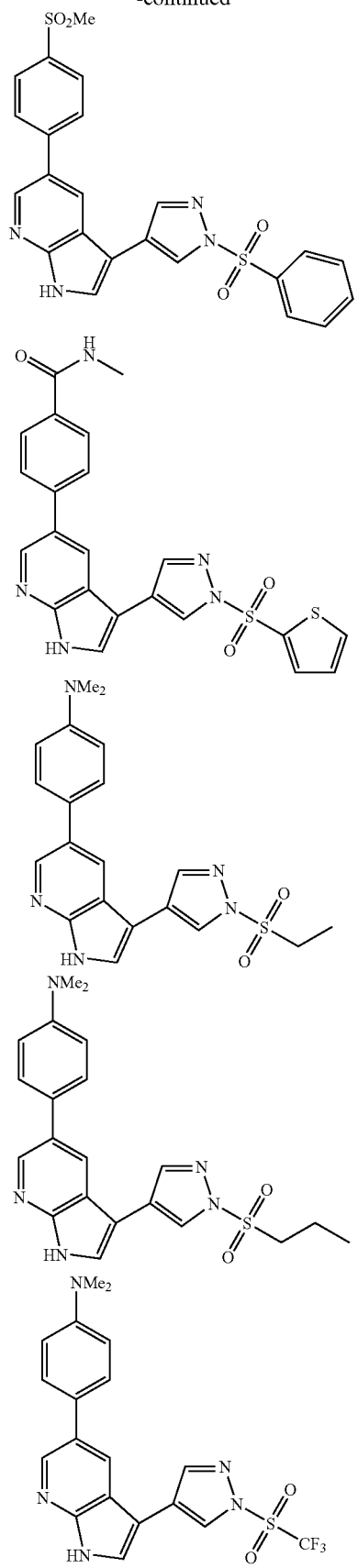
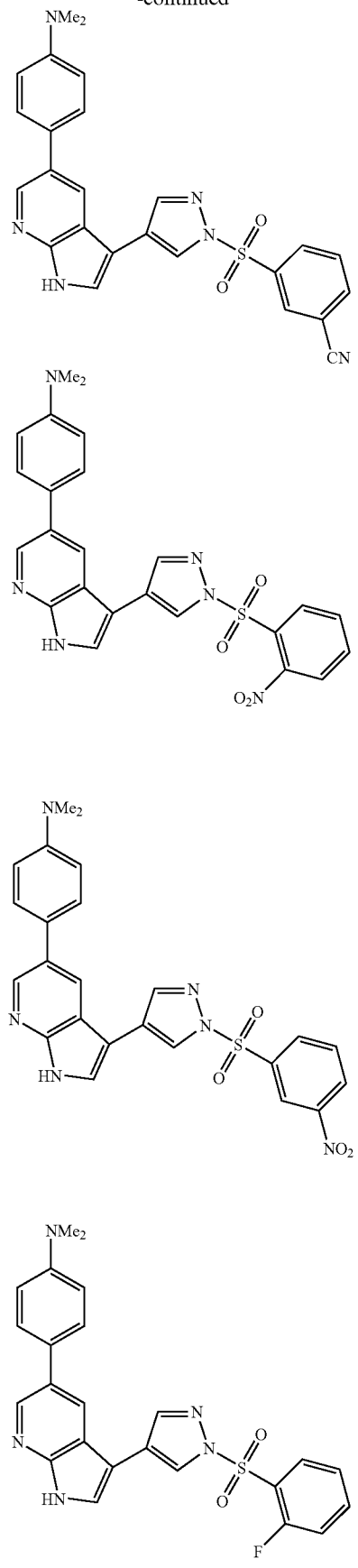

-continued
231
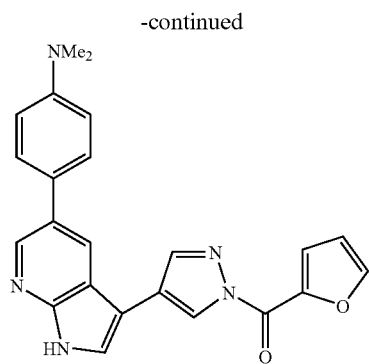
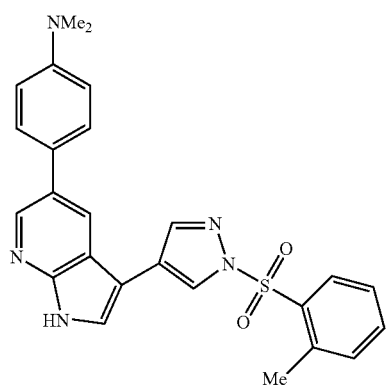
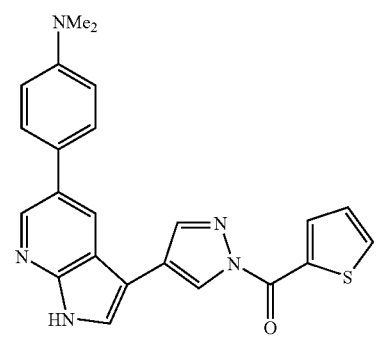
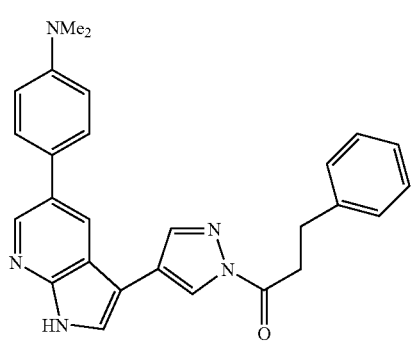
232
-continued
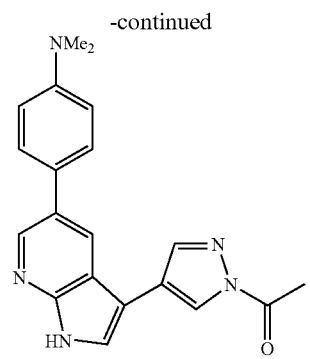
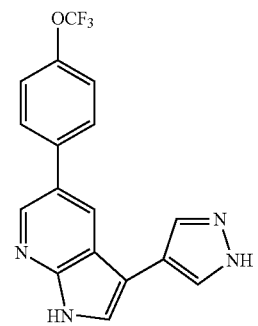
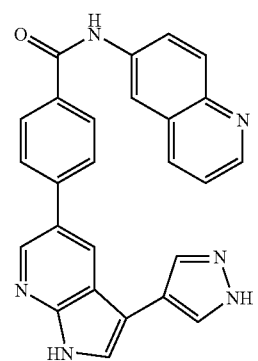
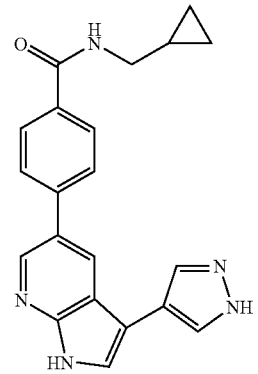

233                                    234
-continued                             -continued
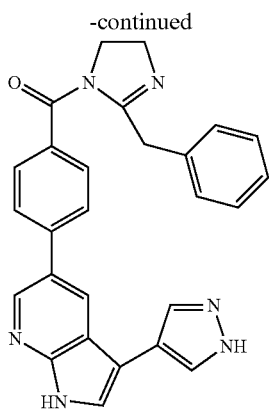                   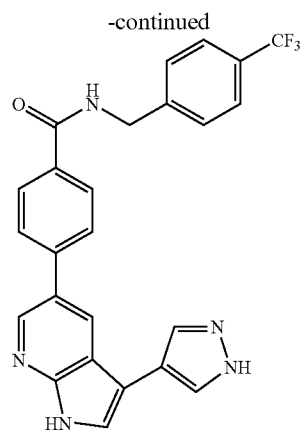
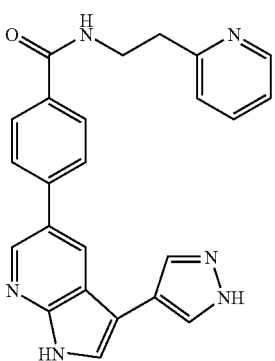                   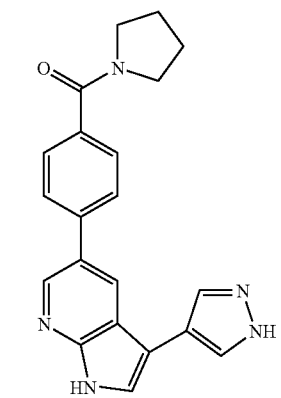
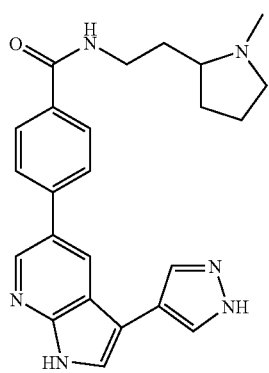                   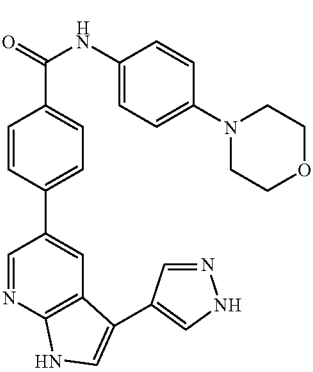
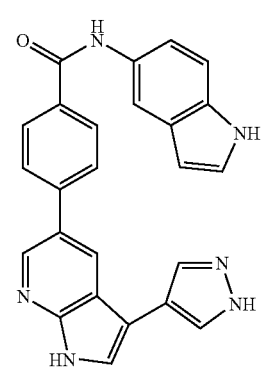                   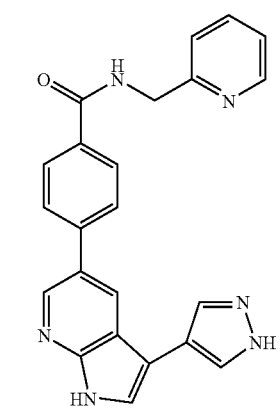

235
-continued
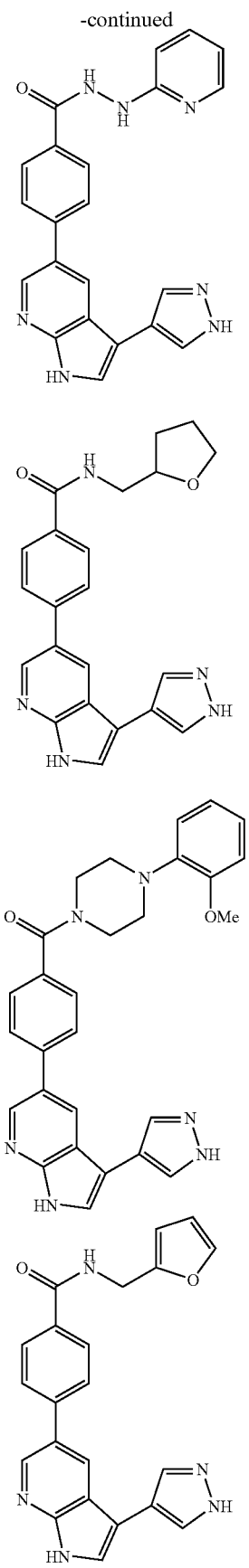
236
-continued
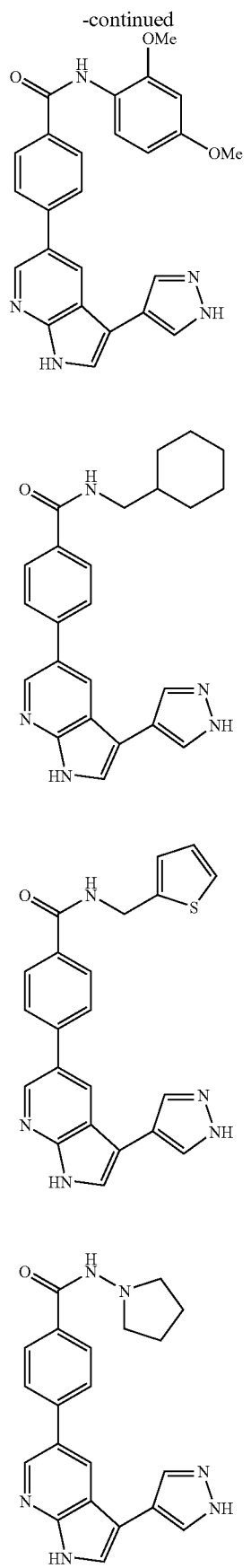

237
-continued
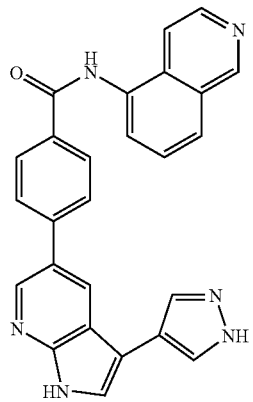
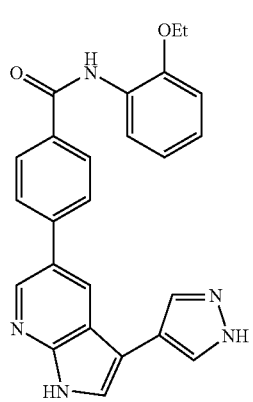
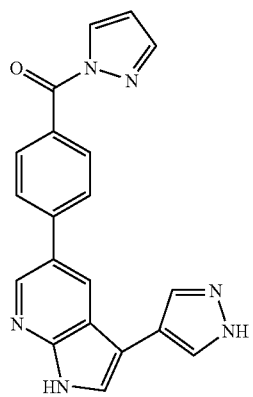
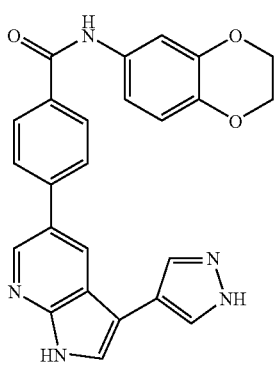
238
-continued
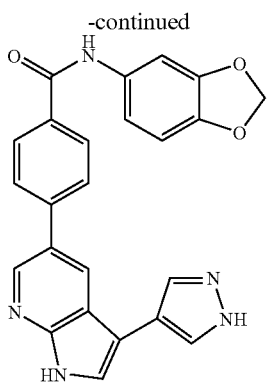
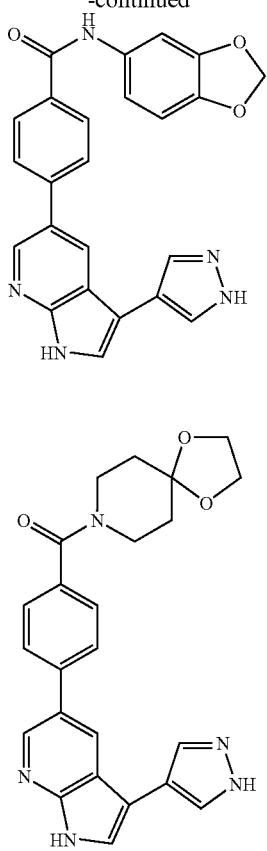
and 9. A process for the manufacture of a compound of formula (I) as claimed in claim 1 comprising removal of group $R^{40}$ from an intermediate (III)

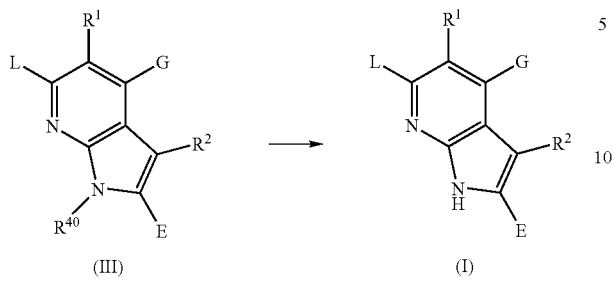

(III)     (I)

wherein $R^1$, $R^2$, E, G, and L are as defined in claim 1, and $R^{40}$ is an amino protecting group.

10. A process as claimed in claim 9 wherein $R^{40}$ is $R^{31}SO_2$, $R^{31}C(O)$, $R^{31}_3Si$, $R^{31}OCH_2$, $(R^{31})_2NSO_2$, $(R^{31})_2NC(O)$, $R^{31}OC(O)$, $R^{31}(R^{31}O)CH$, $R^{31}CH_2CH_2$, $R^{31}CH_2$, $PhC(O)CH_2$, $CH_2=CH$, $ClCH_2CH_2$, $Ph_3C$, $Ph_2(4\text{-pyridyl})C$, $Me_2N$, $HO-CH_2$, $R^{31}OCH_2$, $(R^{31})_3SiOCH_2$, $(R^{31}O)_2CH$, t-BuOC(O)CH_2$, $Me_2NCH_2$, or tetrahydropyranylamine, wherein $R^{31}$ is $C_{1-6}$ alkyl or $C_{6-12}$ aryl.

11. A compound of formula (III)

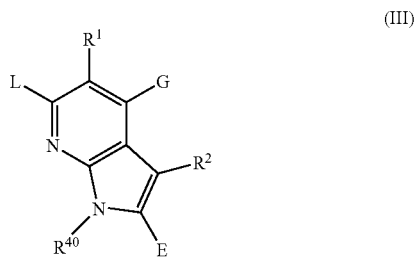

(III)

wherein $R^1$, $R^2$, E, G, and L are as defined in claim 1 and $R^{40}$ is a nitrogen protecting group selected from $R^{31}SO_2$, $R^{31}C(O)$, $R^{31}_3Si$, $R^{31}OCH_2$, $(R^{31})_2NSO_2$, $(R^{31})_2NC(O)$, $R^{31}OC(O)$, $R^{31}(R^{31}O)CH$, $R^{31}CH_2CH_2$, $R^{31}CH_2$, $PhC(O)CH_2$, $CH_2=CH$, $ClCH_2CH_2$, $Ph_3C$, $Ph_2(4\text{-pyridyl})C$, $Me_2N$, $HO-CH_2$, $R^{31}OCH_2$, $(R^{31})_3SiOCH_2$, $(R^{31}O)_2CH$, t-BuOC(O)CH_2$, $Me_2NCH_2$ and tetrahydropyranylamine, wherein $R^{31}$ is $C_{1-6}$ alkyl or $C_{6-12}$ aryl.

12. A process for the manufacture of a compound of formula (III) comprising a) reaction of a compound of formula (II) with stannane $R^1-Sn(R^{32})_3$ in the presence of a palladium catalyst or b) reaction of a compound of formula (II) with boronic acid or ester $R^1-B(OR^{33})_2$ in a presence of a suitable palladium catalyst or c) reaction of a compound of formula (II) with silane $R^1-Si(R^{34})_3$ in the presence of a palladium catalyst;

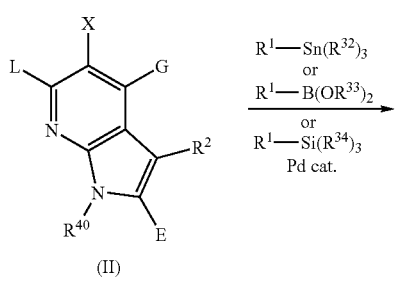

(II)

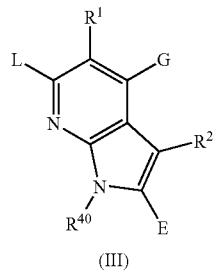

(III)

wherein $R^1$, $R^2$, E, G, and L are as defined in claim 1 and $R^{40}$ is a nitrogen protecting group selected from $R^{31}SO_2$, $R^{31}C(O)$, $R^{31}_3Si$, $R^{31}OCH_2$, $(R^{31})_2NSO_2$, $(R^{31})_2NC(O)$, $R^{31}OC(O)$, $R^{31}(R^{31}O)CH$, $R^{31}CH_2CH_2$, $R^{31}CH_2$, $PhC(O)CH_2$, $CH_2=CH$, $ClCH_2CH_2$, $Ph_3C$, $Ph_2(4\text{-pyridyl})C$, $Me_2N$, $HO-CH_2$, $R^{31}OCH_2$, $(R^{31})_3SiOCH_2$, $(R^{31}O)_2CH$, t-BuOC(O)CH_2$, $Me_2NCH_2$ and tetrahydropyranylamine, wherein $R^{31}$ is $C_{1-6}$ alkyl or $C_{6-12}$ aryl, X is F, Cl, Br, I or $CF_3SO_3$, and $R^{32}$ is independently $C_{1-6}$ alkyl;

$R^{33}$ is independently hydrogen or $C_{1-6}$ alkyl or wherein two $R^{33}$ groups together optionally form a five, six or seven membered ring with the boron and oxygen atoms, wherein the ring is optionally substituted with one or more $C_{1-6}$ alkyl group and $R^{34}$ is independently $C_{1-6}$ alkyl, F, or OH.

13. A process as claimed in claim 12 wherein the catalyst is $(PPh_3)_2PdCl_2$, $(PPh_3)_4Pd$, $Pd(OAc)_2$, $[PdCl(\eta^3\text{-}C_3H_5)]_2$, $Pd_2(dba)_3$, $Pd(dba)_2$ (dba=dibenzylideneacetone), or $Pd/P(t\text{-}Bu)_3$.

14. A process for the manufacture of a compound of formula (I) as claimed in claim 1 comprising a) reaction of a compound of formula (IV) with stannane $R^1-Sn(R^{32})_3$ in the presence of a palladium catalyst or b) reaction of a compound of formula (IV) with boronic acid or ester $R^1-B(OR^{33})_2$ in a presence of a suitable palladium catalyst or c) reaction of a compound of formula (IV) with silane $R^1-Si(R^{34})_3$ in the presence of a palladium catalyst;

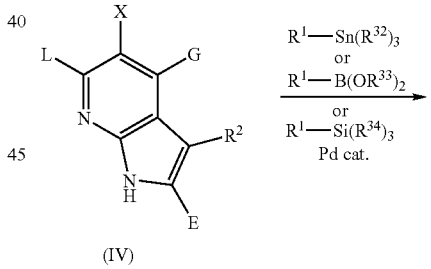

(IV)

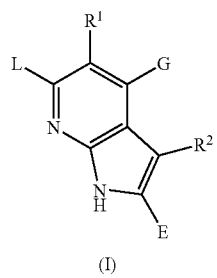

(I)

wherein $R^1$ and $R^2$, E, G, and L are as defined in any one of claims 1 to 8,
wherein X is F, Cl, Br, I or $CF_3SO_3$,
and wherein $R^{32}$ is independently $C_{1-6}$ alkyl;
wherein $R^{33}$ is independently hydrogen or $C_{1-6}$ alkyl or wherein two $R^{33}$ groups together optionally form a five, six or seven membered ring with the boron and oxygen atoms, wherein the ring is optionally substituted with one or more $C_{1-6}$ alkyl group;
and wherein $R^{34}$ is independently $C_{1-6}$ alkyl, F, or OH.

15. A process as claimed in claim 14 wherein the catalyst is $(PPh_3)_2PdCl_2$, $(PPh_3)_4Pd$, $Pd(OAc)_2$, $[PdCl(\eta^3-C_3H_5)]_2$, $Pd_2(dba)_3$, $Pd(dba)_2$ (dba=dibenzylidenacetone), or $Pd/P(t-Bu)_3$.

16. A process for the production of a compound of formula (III) comprising reaction of a) boronic acid or ester (X) or b) stannane (XI) or c) silane (XII) with $R^1$-Hal in the presence of a suitable palladium catalyst,

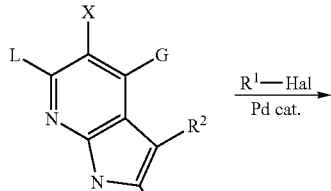

(X), $Z^2 = B(OR^{33})_2$
(XI), $Z^2 = Sn(R^{32})_3$
(XII), $Z^2 = Si(R^{34})_3$

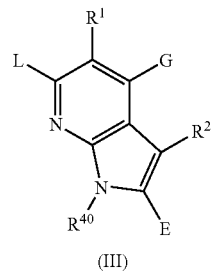

(III)

wherein $R^1$, $R^2$, E, G, and L are as defined in claim 1,
wherein $R^{40}$ is $R^{31}SO_2$, $R^{31}C(O)$, $R^{31}_3Si$, $R^{31}OCH_2$, $(R^{31})_2NSO_2$, $(R^{31})_2NC(O)$, $R^{31}OC(O)$, $R^{31}(R^{31}O)CH$, $R^{31}CH_2CH_2$, $R^{31}CH_2$, $PhC(O)CH_2$, $CH_2$=CH, $ClCH_2CH_2$, $Ph_3C$, $Ph_2(4\text{-pyridyl})C$, $Me_2N$, HO—$CH_2$, $R^{31}OCH_2$, $(R^{31})_3SiOCH_2$, $(R^{31}O)_2CH$, $t\text{-}BuOC(O)CH_2$, $Me_2NCH_2$, or tetrahydropyranylamine,
wherein $R^{31}$ is $C_{1-6}$ alkyl or $C_{6-12}$ aryl,
wherein Hal is I, Br, Cl, F or $CF_3SO_3$, and
wherein $R^{32}$ is independently $C_{1-6}$ alkyl;
$R^{33}$ is independently hydrogen or $C_{1-6}$ alkyl or wherein two $R^{33}$ groups together optionally form a five, six or seven membered ring with the boron and oxygen atoms, wherein the ring is optionally substituted with one or more $C_{1-6}$ alkyl group and $R^{34}$ is independently $C_{1-6}$ alkyl, F, or OH.

17. A process as claimed in claim 16 wherein the catalyst is $(PPh_3)_2PdCl_2$, $(PPh_3)_4Pd$, $Pd(OAc)_2$, $[PdCl(\eta^3-C_3H_5)]_2$, $Pd_2(dba)_3$, and/or $Pd(dba)_2$ (dba=dibenzylidenacetone), or $Pd/P(t-Bu)_3$.

18. A process for the production of a compound of formula (I) comprising reaction of a) boronic acid or ester (L) or b) stannane (LI) or c) silane (LII) with $R^1$-Hal in the presence of a suitable palladium catalyst,

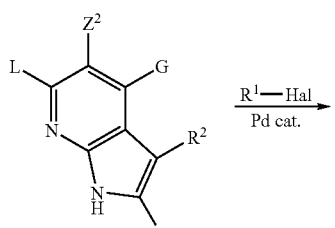

(L), $Z^2 = B(OR^{33})_2$
(LI), $Z^2 = Sn(R^{32})_3$
(LII), $Z^2 = Si(R^{34})_3$

-continued

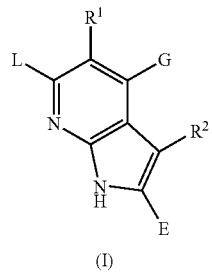

(I)

wherein $R^1$, $R^2$, E, G, and L are as defined in claim 1,
wherein Hal is I, Br, Cl, F or $CF_3SO_3$, and
wherein $R^{32}$ is independently $C_{1-6}$ alkyl;
$R^{33}$ is independently hydrogen or $C_{1-6}$ alkyl or wherein two $R^{33}$ groups together optionally form a five, six or seven membered ring with the boron and oxygen atoms, wherein the ring is optionally substituted with one or more $C_{1-6}$ alkyl group and $R^{34}$ is independently $C_{1-6}$ alkyl, F, or OH.

19. A process as claimed in claim 18 wherein the catalyst is $(PPh_3)_2PdCl_2$, $(PPh_3)_4Pd$, $Pd(OAc)_2$, $[PdCl(\eta^3-C_3H_5)]_2$, $Pd_2(dba)_3$, $Pd(dba)_2$ (dba=dibenzylidenacetone), and/or $Pd/P(t-Bu)_3$.

20. A process for the manufacture of an intermediate of formula (III) comprising a) reaction of a compound of formula (XIII) with stannane $R^2$—$Sn(R^{32})_3$ in the presence of a palladium catalyst or b) reaction of a compound of formula (XIII) with boronic acid or ester $R^2$—$B(OR^{33})_2$ in a presence of a suitable palladium catalyst or c) reaction of a compound of formula (XIII) with silane $R^2$—$Si(R^{34})_3$ in the presence of a palladium catalyst;

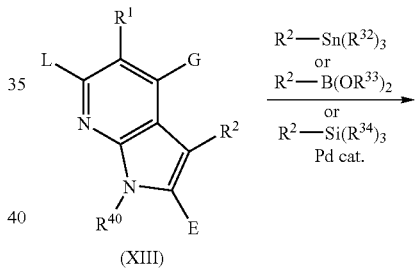

(XIII)

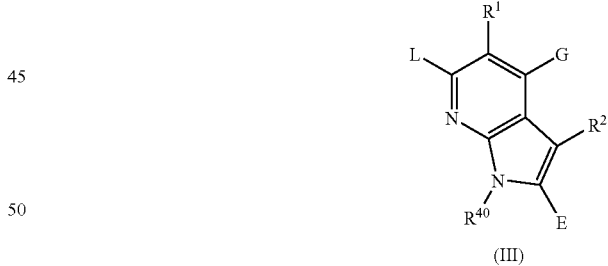

(III)

wherein $R^1$, $R^2$, E, G, and L are as defined in claim 1,
wherein $R^{40}$ is $R^{31}SO_2$, $R^{31}C(O)$, $R^{31}_3Si$, $R^{31}OCH_2$, $(R^{31})_2NSO_2$, $(R^{31})_2NC(O)$, $R^{31}OC(O)$, $R^{31}(R^{31}O)CH$, $R^{31}CH_2CH_2$, $R^{31}CH_2$, $PhC(O)CH_2$, $CH_2$=CH, $ClCH_2CH_2$, $Ph_3C$, $Ph_2(4\text{-pyridyl})C$, $Me_2N$, HO—$CH_2$, $R^{31}OCH_2$, $(R^{31})_3SiOCH_2$, $(R^{31}O)_2CH$, $t\text{-}BuOC(O)CH_2$, $Me_2NCH_2$, or tetrahydropyranylamine,
wherein $R^{31}$ is $C_{1-6}$ alkyl or $C_{6-12}$ alkyl,
$R^{32}$ is independently $C_{1-6}$ alkyl;
$R^{33}$ is independently hydrogen or $C_{1-6}$ or wherein two $R^{33}$ groups together optionally form a five, six or seven membered ring with the boron and oxygen atoms, wherein the ring is optionally substituted with one or more $C_{1-6}$ alkyl group and $R^{34}$ is independently $C_{1-6}$ alkyl, F, or OH, and $X^2$ is F, Cl, Br, I or $CF_3SO_3$.

21. A process as claimed in claim 20 wherein the catalyst is (PPh₃)₂PdCl₂, (PPh₃)₄Pd, Pd(OAc)₂, [PdCl(η³-C₃H₅)]₂, Pd₂(dba)₃, Pd(dba)₂ (dba=dibenzylidenacetone), and/or Pd/P(t-Bu)₃.

22. A process for the production of a compound of formula (III) comprising reaction of a) boronic acid or ester (XIV) or b) stannane (XV) or c) silane (XVI) with R²-Hal in the presence of a suitable palladium catalyst,

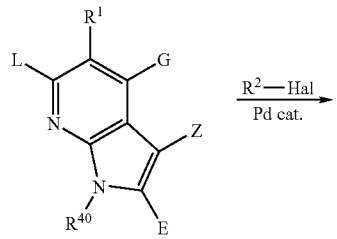

(XIV), Z = B(OR³³)₂
(XV), Z = Sn(R³²)₃
(XVI), Z = Si(R³⁴)₃

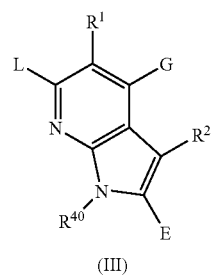

(III)

wherein R¹, R², E, G, and L are as defined in claim 1,
wherein R⁴⁰ is R³¹SO₂, R³¹C(O), R³¹₃Si, R³¹OCH₂, (R³¹)₂NSO₂, (R³¹)₂NC(O), R³¹OC(O), R³¹(R³¹O)CH, R³¹CH₂CH₂, R³¹CH₂, PhC(O)CH₂, CH₂=CH, ClCH₂CH₂, Ph₃C, Ph₂(4-pyridyl)C, Me₂N, HO—CH₂, R³¹OCH₂, (R³¹)₃SiOCH₂, (R³¹O)₂CH, t-BuOC(O)CH₂, Me₂NCH₂, or tetrahydropyranylamine,
wherein R³¹ is C₁₋₆ alkyl or C₆₋₁₂ aryl,
Hal is I, Br, Cl, F or CF₃SO₃,
and R³³ is independently hydrogen or C₁₋₆ alkyl or wherein two R³³ groups together optionally form a five, six or seven membered ring with the boron and oxygen atoms, wherein the ring is optionally substituted with one or more C₁₋₆ alkyl group and R³⁴ is independently C₁₋₆ alkyl, F, or OH.

23. A process as claimed in claim 22 where the catalyst is (PPh₃)₂PdCl₂, (PPh₃)₄Pd, Pd(OAc)₂, [PdCl(η³-C₃H₅)]₂, Pd₂(dba)₃, Pd(dba)₂ (dba=dibenzylidenacetone), and/or Pd/P(t-Bu)₃.

24. A process for the production of a compound of formula (I) comprising reaction of a) boronic acid or ester (LIV) or b) stannane (LV) or c) silane (LVI) with R²-Hal in the presence of a suitable palladium catalyst,

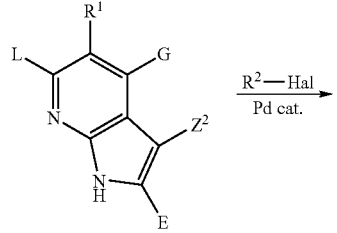

(LIV), Z² = B(OR³³)₂
(LV), Z² = Sn(R³²)₃
(LVI), Z² = Si(R³⁴)₃

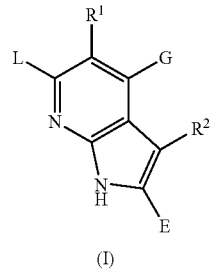

(I)

wherein R¹, R², E, G, and L are as defined in claim 1,
wherein Hal is I, Br, Cl, F or CF₃SO₃, and
wherein R³² is independently C₁₋₆ alkyl;
R³³ is independently hydrogen or C₁₋₆ alkyl or wherein two R³³ groups together optionally form a five, six or seven membered ring with the boron and oxygen atoms, wherein the ring is optionally substituted with one or more C₁₋₆ alkyl group and R³⁴ is independently C₁₋₆ alkyl, F, or OH.

25. A process as claimed in claim 24 wherein the catalyst is (PPh₃)₂PdCl₂, (PPh₃)₄Pd, Pd(OAc)₂, [PdCl(η³-C₃H₅)]₂, Pd₂(dba)₃, Pd(dba)₂ (dba=dibenzylidenacetone), and/or Pd/P(t-Bu)₃.

26. A compound selected from the group consisting of:

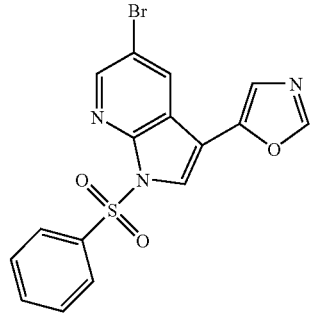

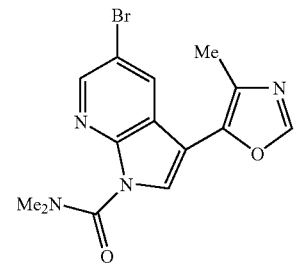

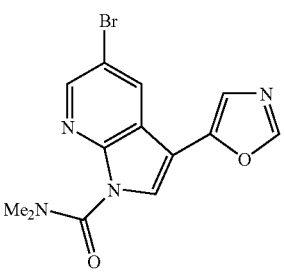

245
-continued
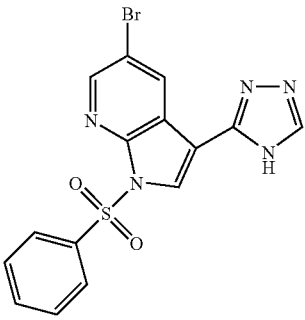
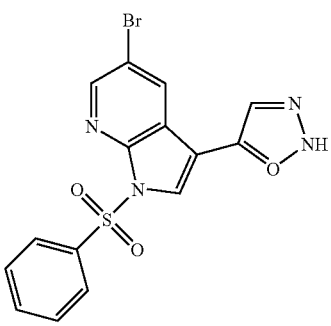
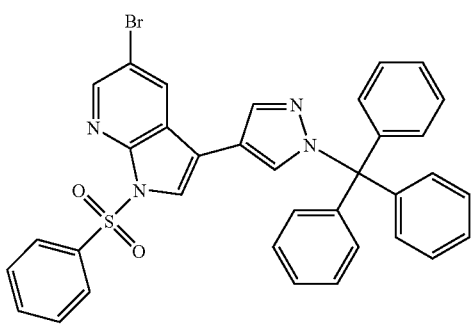
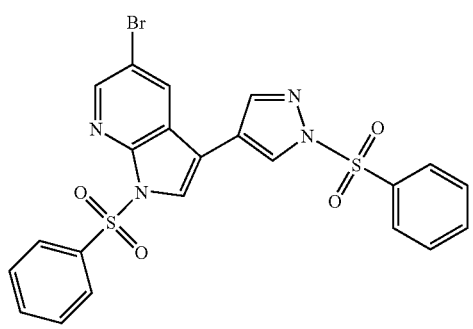
246
-continued
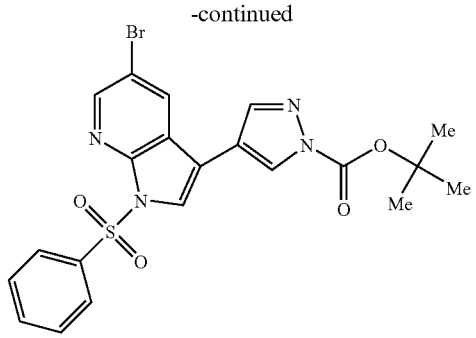
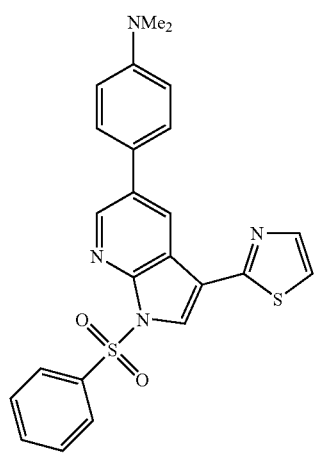
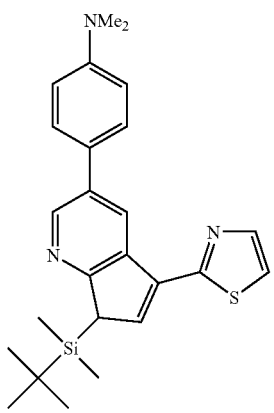
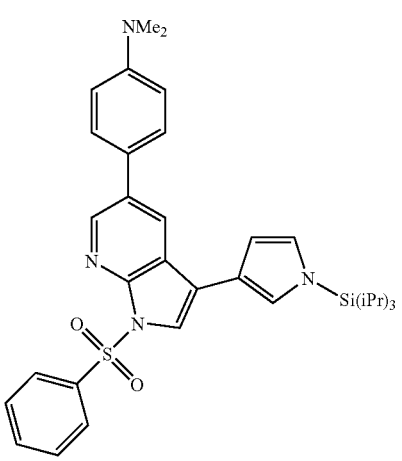

247
-continued
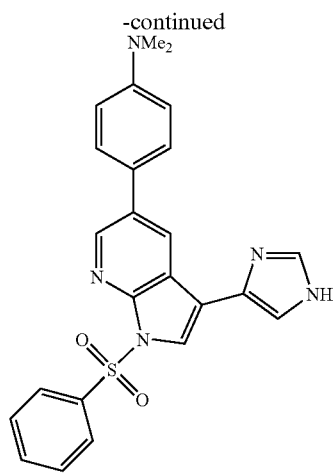
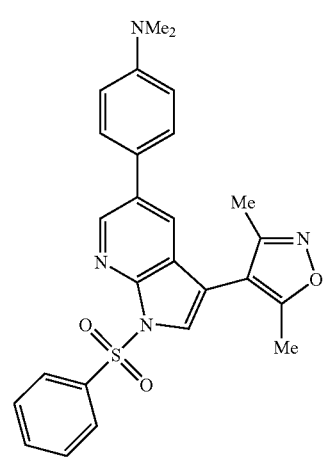
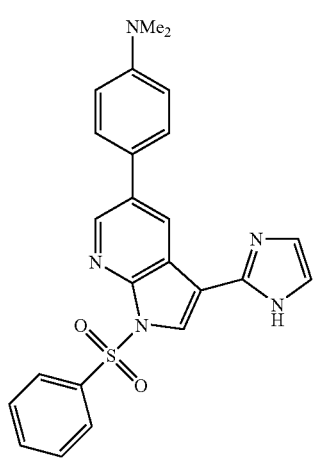
248
-continued
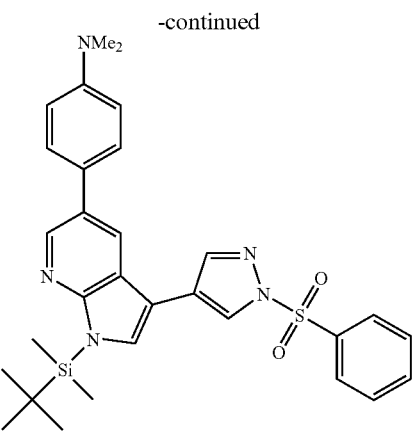
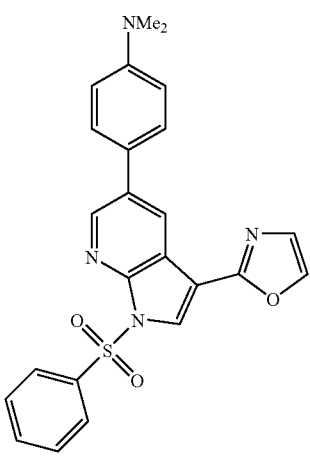
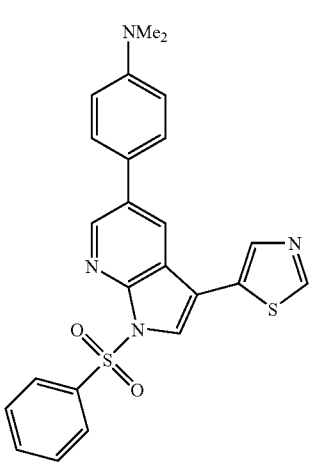

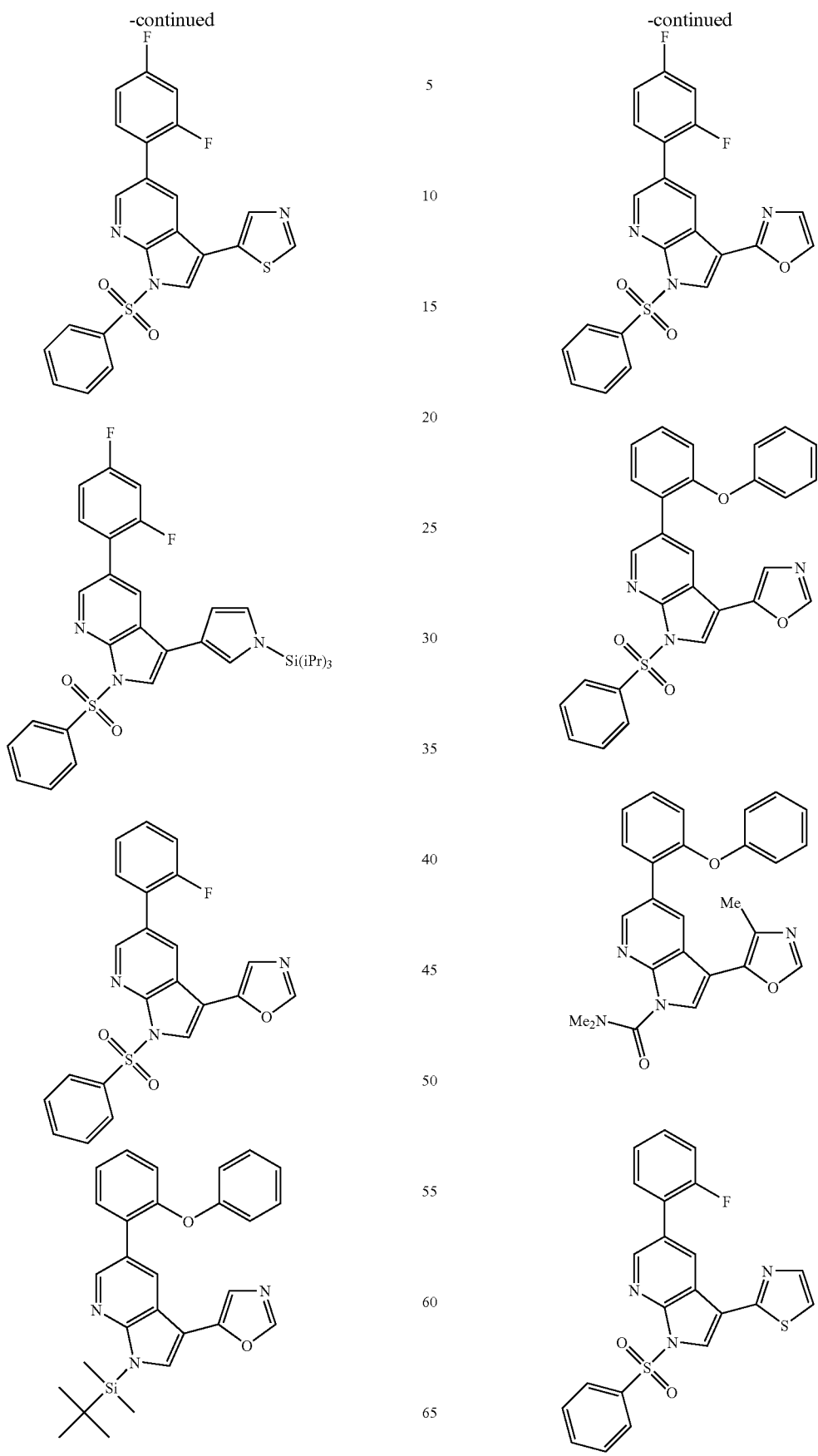

251
-continued
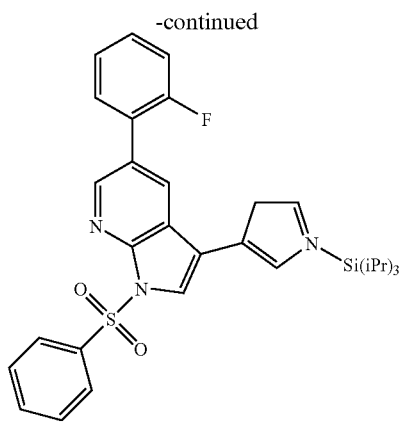
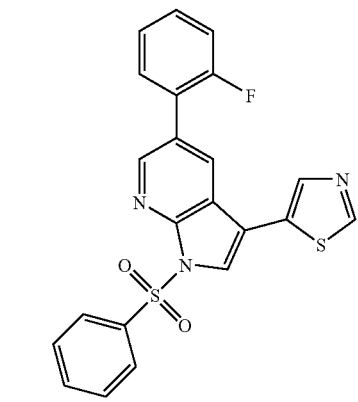
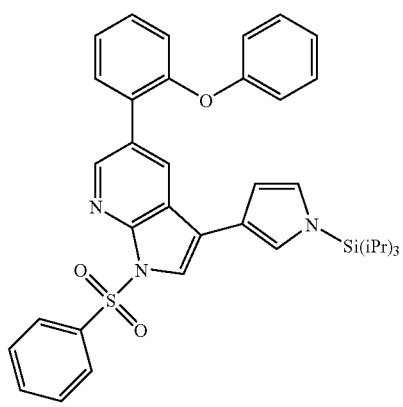
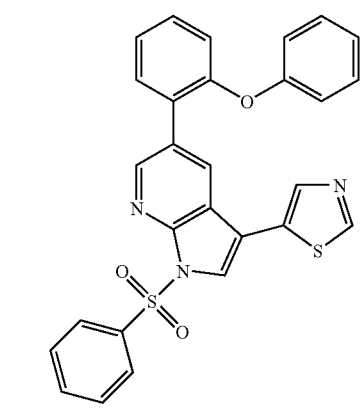
252
-continued
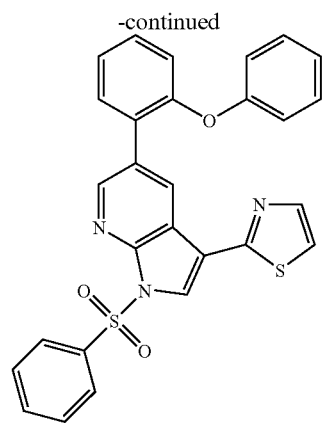
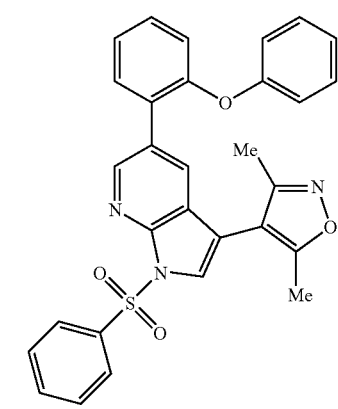
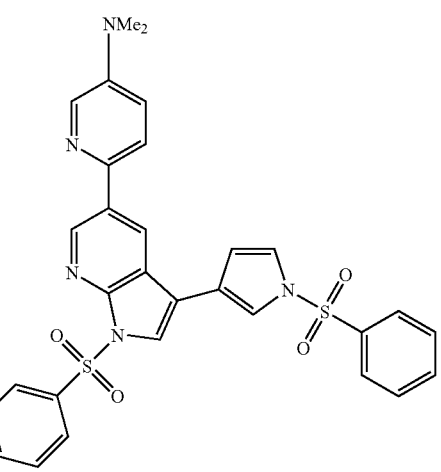

253
-continued
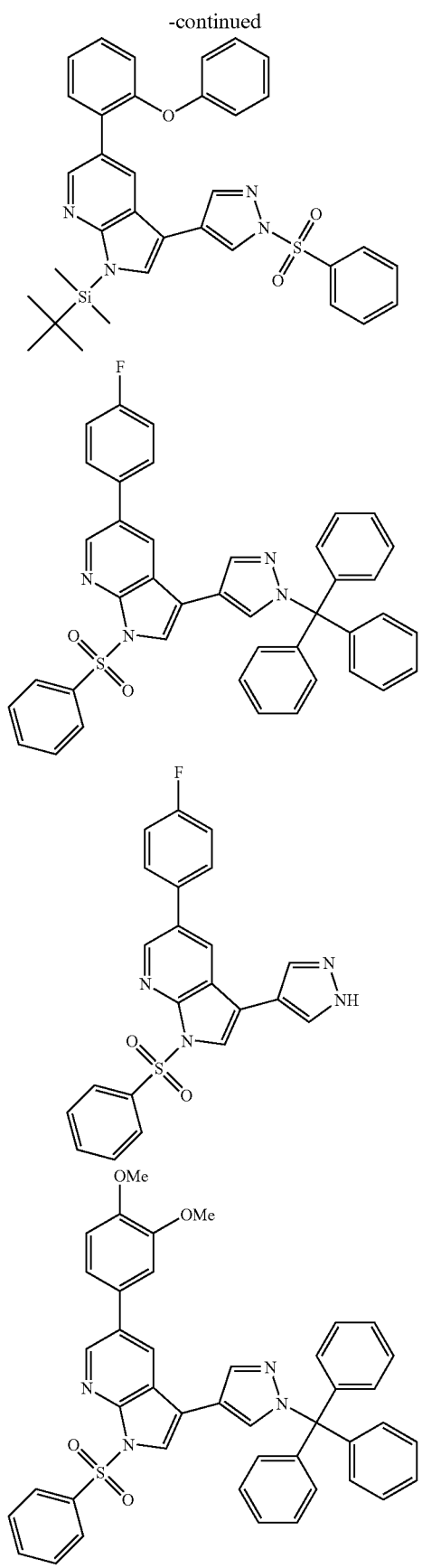
254
-continued
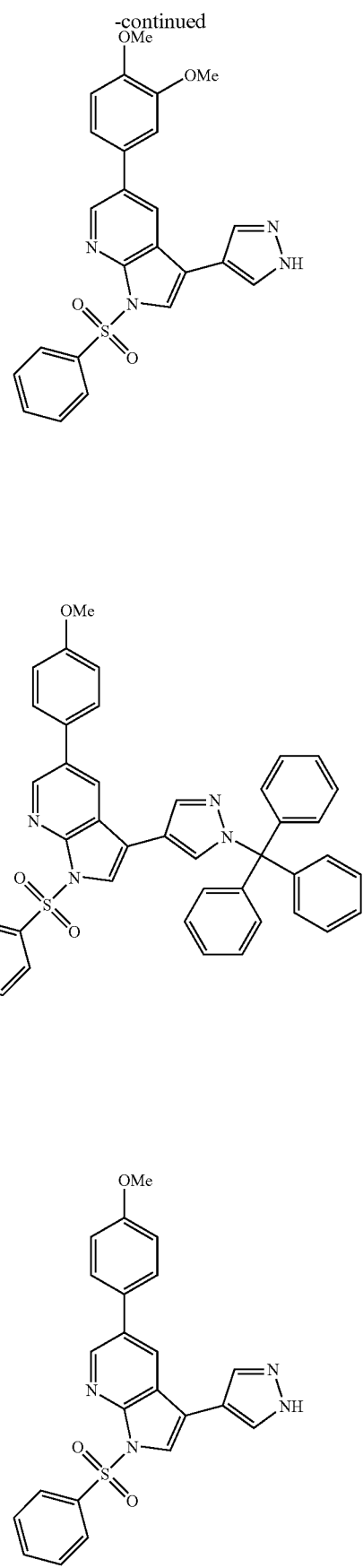

255
-continued
256
-continued
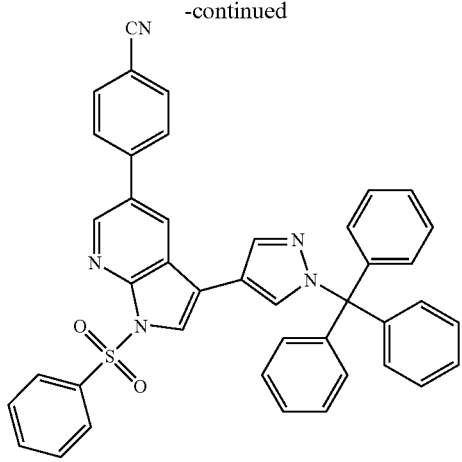

-continued

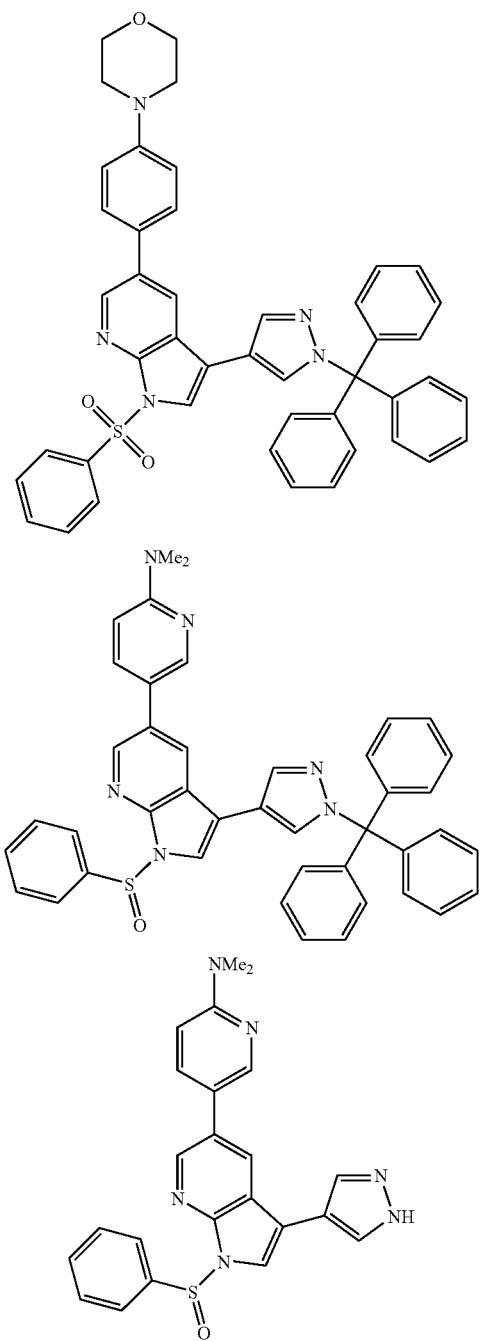

-continued

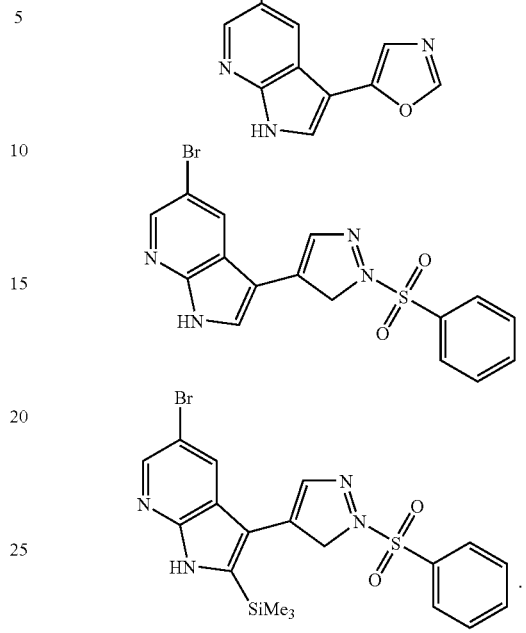

27. The compound of as claimed in claim 1, wherein each n is 1, 2 or 3.

28. The compound of as claimed in claim 1, wherein each substitutable carbon or hetero-atom in $R^2$ is optionally and independently substituted by one or more of $C_{1-6}$ alkyl, $OR^{10}$, $SR^{10}$, $NO_2$, $CN$, $NR^{10}{}_2$, $NR^{10}COR^{10}$, $NR^{10}CONR^{10}{}_2$, $NR^{10}COR^{10}$, $NHCO_2R^{10}$, $CO_2R^{10}$, $COR^{10}$, $CONR^{10}{}_2$, $S(O)_2R^{10}$, $SONR^{10}{}_2$, $S(O)R^{10}$, $SO_2NR^{10}{}_2$, or $NR^{10}S(O)_2R^{10}$.

29. The compound of as claimed in claim 4, wherein $R^{12}$ is phenyl or pyridine.

30. The compound of as claimed in claim 6, wherein each n is 1, 2 or 3.

31. The compound of as claimed in claim 6, wherein $R^2$ is imidazole, isoxazole, isothiazole, oxazole, oxadiazole, oxatriazole, pyrazole, pyrrole, tetrazole, thiadiazole, thiatriazole, thiazole or triazole.

32. The compound of as claimed in claim 7, wherein $R^{30}$ is methyl, ethyl or phenyl.

33. The compound of as claimed in claim 12, wherein X is I or Br.

34. The compound of as claimed in claim 14, wherein $R^{33}$ is hydrogen or both $R^{33}$ groups form the group —$C(CH_3)_2$—$C(CH_3)_2$.

* * * * *